US008629097B2

(12) United States Patent
Jo et al.

(10) Patent No.: US 8,629,097 B2
(45) Date of Patent: Jan. 14, 2014

(54) MACROMOLECULE TRANSDUCTION DOMAINS AND METHODS FOR IDENTIFICATION AND USES THEREOF

(75) Inventors: Dae Woong Jo, Gwangju (KR); Jae Sun Ko, Gwangju (KR); Jin Sook Kim, Gwangju (KR); Kyung Mi Park, Yeosu-si (KR); Jin Kyung Song, Gwangju (KR); Jung Hee Lim, Gunsan-si (KR); Thi Thuy Nga Do, Hwasun-gun (KR); Thi Lan Phuong Do, Hwasun-gun (KR); Minh Tam Duong, Hwasun-gun (KR)

(73) Assignee: Procell Therapeutics Inc., Seoul (KR)

( * ) Notice: Subject to any disclaimer, the term of this patent is extended or adjusted under 35 U.S.C. 154(b) by 661 days.

(21) Appl. No.: 12/524,935

(22) PCT Filed: Jan. 29, 2008

(86) PCT No.: PCT/KR2008/000525
§ 371 (c)(1),
(2), (4) Date: Jul. 29, 2009

(87) PCT Pub. No.: WO2008/093982
PCT Pub. Date: Aug. 7, 2008

(65) Prior Publication Data
US 2010/0197598 A1 Aug. 5, 2010

Related U.S. Application Data

(60) Provisional application No. 60/887,060, filed on Jan. 29, 2007.

(51) Int. Cl.
*C07K 7/04* (2006.01)
*C07K 7/08* (2006.01)
*C07K 7/06* (2006.01)

(52) U.S. Cl.
USPC .......................................... 514/1.2; 530/327

(58) Field of Classification Search
CPC ............... C07K 7/04; C07K 7/06; C07K 7/08
USPC .................................. 514/21.5; 530/300, 327
See application file for complete search history.

(56) References Cited

U.S. PATENT DOCUMENTS

| 5,807,746 | A  | 9/1998  | Lin et al.  |
| 6,248,558 | B1 | 6/2001  | Lin et al.  |
| 6,432,680 | B1 | 8/2002  | Lin et al.  |
| 6,835,810 | B2 | 12/2004 | Hwu         |
| 7,101,844 | B2 | 9/2006  | Kim et al.  |
| 7,166,692 | B2 | 1/2007  | Karas       |
| 2003/0077289 | A1 | 4/2003 | Wang      |
| 2004/0043463 | A1 | 3/2004 | Rao       |
| 2006/0106197 | A1 | 5/2006 | Karas     |
| 2007/0154437 | A1 | 7/2007 | Rao et al. |

FOREIGN PATENT DOCUMENTS

| WO | WO 95/34295 A1 | 12/1995 |
| WO | WO 99/49879 A1 | 10/1999 |
| WO | 03 097671      | 11/2003 |

OTHER PUBLICATIONS

Snyder, E.L., and Dowdy, S.F. "Recent advances in the use of protein transduction domains for the delivery of peptides, proteins and nucleic acids in vivo.," Expert Opin. Drug. Deliv. 2:43-51 (2005).*
Kabouridis, P.S., "Biological applications of protein transduction technology," Trends in Biotechnology 21(11):498-503 (2003).*
Hirokawa, T., et al. "SOSUI: classification and secondary structure prediction system for membrane proteins," Bioinformatics Applications Note 14(4):378-379 (1998).*
UniProtKB/TrEMBL Accession No. F9CXY9, accessed at http://www.uniprot.org/uniprot/F9CXY9, on Feb. 6, 2012.*
Pappalardo, et al. "Vaccine protocols optimization: In silico experiences," Biotechnology Advances 28:82-93 (2010).*
Bachmann et al., "Vaccine delivery: a matter of size, geometry, kinetics and molecular patterns," Nature Reviews Immunology 10:787-796 (2010).*
Manning et al., "Stability of protein pharmaceuticals: an update," Pharm. Research 27:544-575 (2010).*
Pfeifer, et al., "Gene therapy: promises and problems," Ann. Rev. Genomics Hum. Genet. 2:177-211 (2001).*
Kontinen, et al., "A gene (prsA) of *Bacillus subtilis* involed in a novel, late stage of protein export," Mol. Microbiol. 5:1273-1283 (1991).*
Office Action issued Nov. 12, 2010, in Australia Patent Application No. 2008211854.
Sébastien Deshayes, et al., "Insight into the Mechanism of Internalization of the Cell-Penetrating Carrier Peptide Pep-1 through Conformational Analysis", Biochemistry, vol. 43, 2004, pp. 1449-1457.
Jehangir S. Wadia, et al., "Protein transduction techonology", Current Opinion in Biotechonology, vol. 13, 2002, pp. 52-56.
Ho, A. et al., "Synthetic Protein Transduction Domains: Enhanced Transduction Potential In Vitro and In Vivo[1]", Cancer Research, vol. 61, pp. 474-477 (2001).
Joliot, A. et al., "Transduction Peptides: From Technology to Physiology", Nature Cell Biology, vol. 6, No. 3, pp. 189-196 (2004).
Pooga, M. et al., "Cell Penetration by Transportan", The FASEB Journal, vol. 12, No. 1, pp. 67-77 (1998).
Elliott, G. et al., "Intercellular Trafficking and Protein Delivery by a Herpesvirus Structural Protein", Cell, vol. 88, No. 2, pp. 223-233 (1997).
Jo, D. et al., "Intracellular Protein Therapy With SOCS3 Inhibits Inflammation and Apoptosis", Nature Medicine, vol. 11, No. 8, pp. 892-898 (2005).

(Continued)

*Primary Examiner* — Christina Bradley
*Assistant Examiner* — Kristina M Hellman
(74) *Attorney, Agent, or Firm* — Oblon, Spivak, McClelland, Maier & Neustadt, L.L.P.

(57) ABSTRACT

The present invention discloses novel macromolecule transduction domain (MTD) peptides which facilitate the traverse of a biologically active molecule across the cell membrane. Also disclosed are polynucleotides encoding the MTD peptides, methods of identifying the MTD peptides; methods of genetically engineering a biologically active molecule to have cell permeability by using the MTD peptides, methods of importing a biologically active molecule into a cell by using the MTD peptides, and uses thereof.

19 Claims, 114 Drawing Sheets

(56) References Cited

OTHER PUBLICATIONS

Veach, R. A. et al., "Receptor/Transporter-Independent Targeting of Functional Peptides Across the Plasma Membrane", The Journal of Biological Chemistry, vol. 279, No. 12, pp. 11425-11431 (2004).

Jo, D. et al., "Epigenetic Regulation of Gene Structure and Function With a Cell-Permeable Cre Recombinase", Nature Biotechnology, vol. 19, pp. 929-933 (2001).

Wadia, J. S. et al., "Modulation of Cellular Function by TAT Mediated Transduction of Full Length Proteins", Current Protein and Peptide Science, vol. 4, No. 2, pp. 97-104 (2003).

Christiaens, B. et al., "Membrane Interaction and Cellular Internalization of Penetratin Peptides", Eur. J. Biochem., vol. 271, pp. 1187-1197 (2004).

Hawiger, J., "Noninvasive Intracellular Delivery of Functional Peptides and Proteins", Current Opinion in Chemical Biology, vol. 3, pp. 89-94 (1999).

Wadia, J. S. et al., "Transducible TAT-HA Fusogenic Peptide Enhances Escape of TAT-Fusion Proteins After Lipid Raft Macropinocytosis", Nature Medicine, vol. 10, No. 3, pp. 310-315 (2004).

Console, S. et al., "Antennapedia and HIV Transactivator of Transcription (TAT) "Protein Transduction Domains" Promote Endocytosis of High Molecular Weight Cargo Upon Binding to Cell Surface Glycosaminoglycans", The Journal of Biological Chemistry, vol. 278, No. 37, pp. 35109-35114 (2003).

Jo, D. et al., "Cell Cycle-Dependent Transduction of Cell-Permeant Cre Recombinase Proteins", Journal of Cellular Biochemistry, vol. 89, pp. 674-687 (2003).

Morris, M. C. et al., "A Peptide Carrier for the Delivery of Biologically Active Proteins Into Mammalian Cells", Nature Biotechnology, vol. 19, pp. 1173-1176 (2001).

Lin, Q. et al., "Enhanced Cell-Permeant Cre Protein for Site-Specific Recombination in Cultured Cells", BMC Biotechnology, vol. 4, No. 25, pp. 1-13 (2004).

Extended European Search Report issued Jun. 22, 2011, in European Patent Application No. 08712219.8.

Susan Michaelis et al., "Effects of Signal Sequence Mutations on the Kinetics of Alkaline Phosphatase Export to the Periplasm in *Escherichia coli*", Journal of Bacteriology, vol. 167, No. 1, Jul. 1986, pp. 160-167.

\* cited by examiner

Fig. 1a-1

| Red: hydrophobic A/a<br>Black: hydrophilic A/a<br>Green: nonpolar A/a<br>Blue: basic A/a<br>No: No helix structure | | | HRSS: Hydrophobic Region of Signal Sequence<br>Helix: Bird's eye view of peptide structure (determined by SOSUI program)<br>SOSUI analysis requires at least 20 amino acids-length peptide. To make 20 A/a-length, additional A/a derived from N-terminals of EGFP was added to the end of the peptide.<br>The numbers of HRSS represent the amino acid number of the origin protein.<br>The number of preliminarily modified and finally modified sequences represents the amino acid-length of the peptide. | | | | |
|---|---|---|---|---|---|---|---|
| # | Origin | Hydropathy | HRSS<br>(Candidate Domain) | Helix | Preliminarily<br>modified Sequences | Helix | finally modified<br>Sequences | Helix |
| JO-01 | CAC04038 putative NLP/P60-family secreted protein [Streptomyces coelicolorA3(2)]. | | 7<br>VLTTTAVTVVCAITVL<br>AAPG 25 | 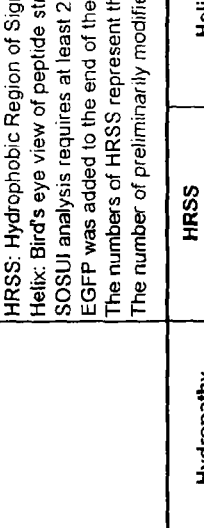 | VLAVVVCAIVLAAP 14 | No | AVVVCAIVLAAP 12 | No |
| JO-02 | NP_057021 phosphatidylinositol glycan, class T precursor [Homo sapiens]. | | 1<br>MAAAMPLALLVLLLL<br>GPGGWCLA 23 | | AAAPLALLVLLLLGP LA 17 | | PLALLVLLLLGP 12 | No |
| JO-03 | NP_072171 chorionic somatomammotropin hormone 2 isoform 3 [Homo sapiens]. | | 1<br>MAAGSRTSLLLAFAL<br>LCLPWLQE 23 | | AAGLLLAFALLCLP 14 | No | LLLAFALLCLP 11 | 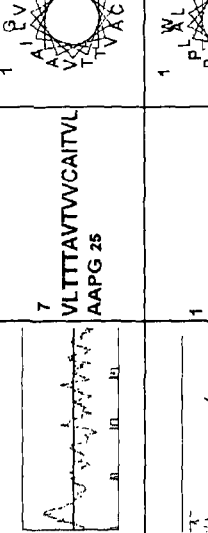 |

Fig. 1a-2

| | | | | | |
|---|---|---|---|---|---|
| JO-04 | NP_932156 nudix-type motif 9 isoforma [Homo sapiens]. | LLGKALAAVSLSLAL ASVTIRSS 27 | | LLGALAAVLLALA 13 | |
| JO-05 | NP_057327 NAD(P)H:quinone oxidoreductase type 3, polypeptide A2 | TSPVLLASLGVGLVT LLGLAVGS 27 | | PVLLALGVGLVLLGL AV 17 | |
| JO-06 | CAD55300 putative secreted protein. [Streptomyces coelicolor | WIAGAAAAVLLAAG GITYAVAGD 30 | | AAAAVLLAAGGIAVA 15 | AAAAVLLAA 9 |

Fig. 1a-3

| | | | | | | |
|---|---|---|---|---|---|---|
| JO-07 | NP_629514 secreted protein [Streptomyces coelicolor A3(2)]. | | LALTVCGIWAVVVIG LFVFGL 25 | | IVVAVVVI 8 | No |
| JO-08 | CAB57190 putative secreted chitin binding protein [Streptomyces coelicolor A3(2)]. | | TAALIGAVLAPVVAV SLPA 25 | No | AALIGAVLAPVVAVL PA 17 | AVLAPVVAV 9 |
| JO-09 | CAB51015 putative secreted protein [Streptomyces coelicolor A3(2)]. | | QFLAVCGLPVVALLA TALFAPLP 31 | | LAVCGLPVVALLAAL APLP 19 | LAVCGLPVVALLA 13 |

| | | | | | | |
|---|---|---|---|---|---|---|
| JO-10 | NP_625021 glycosyl hydrolase (secreted protein) [Streptomyces coelicolor] | 14 | LLVALGGAVVAAPV AAAVAPHAL 36 | | LLVALGGAVVAAPV AAAVAP 20 | | LLGGAVVAAPVAAAV AP 16 | |
| JO-11 | NP_630686 secreted protein [Streptomyces coelicolor A3(2)]. | 15 | RLLLVLAVLLAVLTP TAPEALA 36 | No | LLLVLAVLLAVLPAP ALA 18 | | LLLVLAVLLAVLP 13 | |
| JO-12 | NP_057329 dehydrogenase/ reductase (SDR family) member 8 [Homo sapiens]. | 4 | LLDILLLLPLLIVCSLE SFVKLF 26 | | LLILLLLPLLIVL 13 | | LLLLLLLPLLIV 12 | |

| # | Origin | Hydropathy | HRSS (Candidate Domain) | Helix | Preliminarily modified Sequences | Helix | finally modified Sequences | Helix |
|---|---|---|---|---|---|---|---|---|
| JO-13 | NP_639877 putative secreted protein [Streptomyces coelicolor A3(2)] | | SVLRGLAAAALAVLP LTVSTPAH 26 | | VLGLAAAALAVLPLV PA 17 | | LAAAALAVLPL 11 | No |
| JO-14 | NP_699201 protease inhibitor 16 precursor [Homo sapiens]. | | CSFLMLLPLLLLLV ATTGPVG 26 | | FLMLLPLLLLLVAP VG 17 | | FLMLLPLLLLLVA 14 | |
| JO-15 | NP_639871 putative secreted protein [Streptomyces coelicolor A3(2)]. | | ALTASAATAAAAL GLAAAVPAQ 28 | | ALAAAAAAALGLA AAVPA 19 | | AAAAAALGLAAAVP A 15 | |

Fig. 1b-2

| | | | | | |
|---|---|---|---|---|---|
| JO-16 | CAB85250 putative secreted protein [Neisseria meningitidis Z2491]. | LLLAALLLIAFAAVKL VLLQW 27 | (helical wheel) | LLLAALLLIAFAAVLV LL 18 | (helical wheel) | LLLAALLLIAFAAV 14 | (helical wheel) |
| JO-17 | NP_626397 small secreted hydrophilic protein [Streptomyces coelicolor A3[2]] | MAALAAVVLIPLGIAA TSFAL 27 | (helical wheel) | MAALAAVVLIPLGIA A 16 | (helical wheel) | ALAAVVLIPLGIAA 14 | No |
| JO-18 | CAB57190 putative secreted chitin binding protein [Streptomyces coelicolor] | TAALIGAVLAPVVAV SLPA 25 | No | AALIGAVLAPVVAVL PA 17 | (helical wheel) | AALIGAVLAPVVAV 14 | (helical wheel) |

Fig. 1b-3

| | | | | | | |
|---|---|---|---|---|---|---|
| JO-19 | NP_626007 secreted cellulose-binding protein [Streptomyces coelicolor] | [plot] | AAAVAVAGLAPLAL 23 10 | No | AAAVAVAGLAPLAL 14 | No | AAGIAVAIAAIVPLA 15 | [helical wheel] |
| JO-20 | NP_625632 secreted protein [Streptomyces coelicolor A3(2)] | [plot] | GAAGIAVAIAAIVPLA DPAPA 26 6 | No | AAGIAVAIAAIVPLA 15 | No | IAVAIAAIVPLA 12 | No |
| JO-21 | CAC31790 putative secreted protein [Mycobacterium leprae] | [plot] | GLAANVAMAAAATV LAAPALA 25 5 | [helical wheel] | LAAVAMAAAAVLAA PALA 18 | [helical wheel] | VAMAAAAVLAAPAL A 15 | [helical wheel] |

Fig. 1b-4

| | | | | | | |
|---|---|---|---|---|---|---|
| JO-22 | CAB38593putative secreted protein [Streptomyces coelicolor A3(2)]. | [hydropathy plot] | LAAVGAALALGVAA APAQAAPA 11 32 | [helical wheel] | LAAVGAALALGVAA APAAAPA 21 | [helical wheel] | AALALGVAAAPAAA PA 16 | [helical wheel] |
| JO-23 | NP_630266secreted Protein [Streptomyces coelicolor A3(2)]. | [hydropathy plot] | LASVLTVLLTVLLPL VPAWPAAG 5 27 | [helical wheel] | LLLALLLAAGLVLVP 15 | [helical wheel] | LAVLVLLVLLP 11 | No |
| JO-24 | NP_630165secreted Protein [Streptomyces coelicolor A3(2)]. | [hydropathy plot] | TAARTVAVLAPVLF ALQFFAPS 5 27 | [helical wheel] | ALVAVAVAVVALLGV A 16 | [helical wheel] | VVAVLAPVL 9 | [helical wheel] |
| JO-25 | NC_003888secreted Protein [Streptomyces coelicolor A3(2)]. | [hydropathy plot] | AAPAALLLPLLLLLP LTGCDRLA 11 33 | [helical wheel] | LLLIIVLLIVPALVIA 16 | [helical wheel] | AALLLPLLLLLP 12 | No |

Fig. 1c-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-26 | NP_627363secreted Protein [Streptomyces coelicolor A3(2)]. | 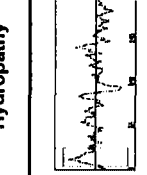 | ALAVGAAVAALLVIG GSVWAVTA 40 18 | 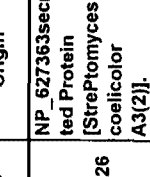 | ALVLCLALAAAVVPA 15 | 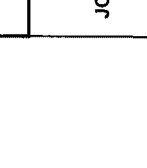 | PAAVAALLVI 10 | No |
| JO-27 | NP_631288secreted Protein [Streptomyces coelicolor A3(2)]. | 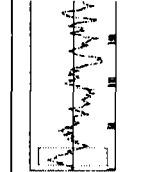 | SVRAYSLLIAALLPLS ACGIPET 26 4 | 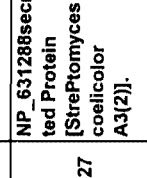 | AAPVPPAALALLLVA 15 | 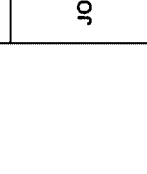 | LLIAALLP 8 | No |
| JO-28 | NP_630325secreted Protein [Streptomyces coelicolor A3(2)]. | 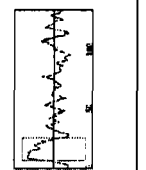 | TRALSAAVLLGLAA APAAADSS 26 4 | 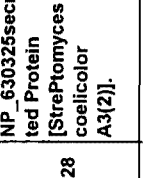 | IVALLLVPLVLAIAAV L 17 | 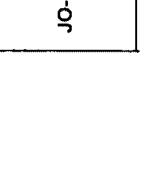 | AAVVLLPLAAAP 12 | No |

Fig. 1c-2

| | | | | | |
|---|---|---|---|---|---|
| JO-29 | NP_631289 secreted Protein [Streptomyces coelicolor A3(2)]. | LWAAAAAALTLVGA APAAAQAAP 29 | IVALLLVPLVLAIAAV L 17 | AAAAAALLVP 10 | No |
| JO-30 | CAB51015 Putative secreted Protein [Streptomyces coelicolor A3(2)]. | QFLAVCGLPVVALLA TALFAPLP 31 | LAVLPVVALLAALFA P 16 | LPVVALLA 8 | |
| JO-31 | NP_629515 chitinase C (secreted Protein) [Streptomyces coelicolor | AAALAATLALPLAGL VGLA 25 | PPLVLAALVACIIVLI 16 | AAALAAPLALP 11 | No |

Fig. 1c-3

| | | | | | | |
|---|---|---|---|---|---|---|
| JO-32 | NP_940995 C1q and tumor necrosis factor related Protein 1 isoform 1 [Homo saPIens]. | QGLLLAYCLLLAFAS GLVLSRVP 28 | | LALAVLAAALLAVAP A 16 | No | LLLALLLAA 9 |
| JO-33 | NP_854150 POSSIBLE CONSERVED SECRETED PROTEIN [Mycobacterium] | MKALVAVSAVAVVA LLGVSSAQ 22 | | LGLPPLLLLALAGGA A 16 | No | AVAVVALL 8 |
| JO-34 | NP_630361 Probable secreted Protein [StrePtomyces coelicolor A3(2)]. | LTLLIVLLIGVPAGYL VISANQ 29 | | LVPLGALALVVAFPA A 16 | No | LLLIiVLLIVP 11 | No |

Fig. 1c-4

| | | | | | |
|---|---|---|---|---|---|
| JO-35 | P39790 Extracellular metalloProtease Precursor. | 12 FAYLTVLCLALAAAV SFGVPAK 33 | [helical wheel] | PAVIGVAAVVAAAA 15 | [helical wheel] | LALAAAVP 9 | No |
| JO-36 | CAA19252 Putative liPoProtein [StrePtomyces coelicolor A3(2)]. | 13 AAPRSVPPARALAG LLLVTALAL 35 | No | ALPLLPLLLLVGALL 15 | [helical wheel] | PAALALLLVA 10 | No |
| JO-37 | NP_62568Slarge secreted Protein [StrePtomyces coelicolor A3(2)]. | 12 IVALLLVPLVSLTAIW AFATVLT 34 | [helical wheel] | PIGVLVVVLGLAVL AL 17 | [helical wheel] | IVALLLVPLVLAIAAV L 17 | [helical wheel] |
| JO-38 | NP_62568Slarge secreted Protein [StrePtomyces coelicolor A3(2)]. | 12 IVALLLVPLVSLTAIW AFATVLT 34 | [helical wheel] | VLVGAAAVPVLVAA G 15 | [helical wheel] | IVALLLVP 8 | [helical wheel] |

Fig. 1d-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-39 | NP_625685large secreted Protein [StrePtomyces coelicolor A3(2)]. | 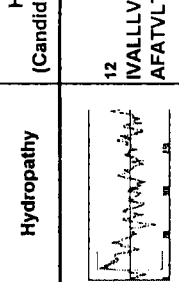 | 12 IVALLLVPLVSLTAIW AFATVLT 34 |  | LAVLVLLVLLPLVPA 15 |  | PLVLAIAAVL 10 |  |
| JO-40 | NP_808800 golgi PhosPhoProtein 2 [Homo saPiens]. |  | 12 KSPPLVLAALVACIIV LGFNYWI 34 | 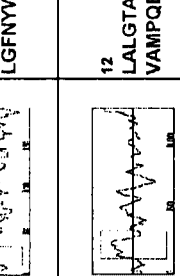 | VVAVLAPVLFAL 12 | No | PLVLAALVA 9 | No |
| JO-41 | NP_626993secre ted Protein [StrePtomyces coelicolor A3(2)]. |  | 12 LALGTAVLSAAALLA VAMPQEAQ 34 |  | AALLPLLLLLPL 13 | No | AAALLAVA 8 | No |

Fig. 1d-2

| | | | | | | |
|---|---|---|---|---|---|---|
| JO-42 | NP_004863 thymic dendritic cell-derived factor 1 [Homo saPiens]. | [plot] | 13 QLGLPPLLLLTMALA GGSGTASA 35 | No | ALAVGAAVAALLVI 14 | [helical wheel] | PLLLLALA 8 | [helical wheel] |
| JO-43 | NP_631398 secreted Protein [StrePtomyces coelicolor A3(2)]. | [plot] | 14 LTVPLGALALVVAFP ATA 31 | No | LLIAALLPL 9 | [helical wheel] | ALALVVA 7 | [helical wheel] |
| JO-44 | NP_627373Peni cillin-binding Protein (secreted Protein) [StrePtomyces | [plot] | 15 KPAVIGSVAAVVVAG AGFGAYAM 37 | [helical wheel] | LAAVVLLGLAAAPAA 15 | No | VAAVVVAA 8 | [helical wheel] |

Fig. 1d-3

| | | | | | | |
|---|---|---|---|---|---|---|
| JO-45 | NP_056226 sulfatase modifying factor 2 [Homo saPiens]. | | 2 ARHGLPLLPLLSLLV GAWLKLG 23 | helical wheel | WAAAAAALLVGAAP A 15 | No | PLLPLLLV 9 | No |
| JO-46 | NP_854998 Conserved hypothetical secreted protein [Mycobacterium] | | 4 PMIGMVVLVVVLGLA VLALSYRL 26 | helical wheel | LAVCGLPVVALLA 13 | No | VVLVVVLPLAVLA 13 | No |
| JO-47 | NP_627512 secreted Protein [StrePtomyces coelicolor A3(2)]. | | 23 VLVGAAAVPVMLVA AGC 39 | No | AAAVAVAGLAPLAL 14 | helical wheel | AAAVPVLVAA 10 | No |

Fig. 1d-4

| | | | | | |
|---|---|---|---|---|---|
| JO-48 | NP_110448 phospholipase A2, group XIIA [Homo sapiens]. |  MALLSRPALTLLLL MAAVVRCQ 23 |  | ALLPALLLLLAAVV 15 |  | PALLLLLAAVV 12 | No |
| JO-49 | NP_003245 tissue inhibitor of metalloproteinase 1 precursor [Homo sapiens]. |  MAPFEPLASGILLLL WLIAPSRA 23 |  | APPLAILLLLIAPA 15 |  | PLAILLLLIAP 12 | No |
| JO-50 | NP_002978 small inducible cytokine A17 precursor [Homo sapiens]. | 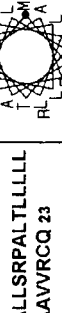 MAPLKMLALVTLLL GASLQHIHA 23 | No | APLLALVLLLALIA 14 | 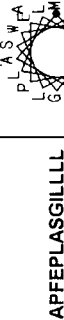 | PLLALVLLLALIA 13 | No |
| JO-51 | NP_001012495 stromal cell derived factor 1 isoform gamma precursor [Mus musculus]. |  MDAKVVAVLALVLA ALCISDGK 22 |  | AVVAVLALVLAALI 14 |  | VVAVLALVLAAL 12 | No |

Fig. 1e-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-52 | NP_775628 ficolin 3 isoform 2 precursor [Homo sapiens]. | 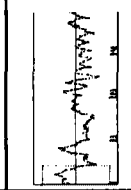 | MDLLWILPSLWLLLL GGPACLK 22 | 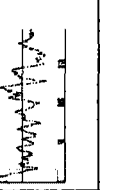 | LLILPLLLLLPAL 13 | No | PLLLLLPAL 9 | No |
| JO-53 | NP_624483 secreted protein [Streptomyces coelicolor A3(2)]. | 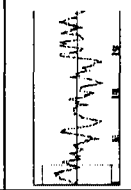 | MFRHLAAVATALAV VTVTPVEAT 23 | 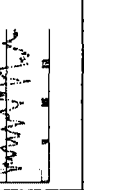 | LAAVAALAVVVPVA 14 | No | LAAVAALAVVVP 12 | No |
| JO-54 | NP_997465 HERV-FRD provirus ancestral Env polyprotein [Homo sapiens]. | 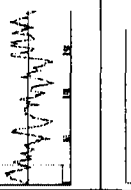 | MGLLLLVLILTPSLA AY 17 | No | LLLLVLILPLAA12 | No | LLLLVLILPLAA 12 | No |

Fig. 1e-2

| | | | | | | |
|---|---|---|---|---|---|---|
| JO-55 | NP_854234 posible conserved secreted protein [Mycobacterium bovis] | [hydropathy plot] | 1 MKGTKLAVVVGMTV AAVSLAA Fig. 1e-3
| | | | | | |
|---|---|---|---|---|---|
| JO-58 | P05067Amyloid beta A4 protein precursor (APP) (Alzheimer disease amyloid | 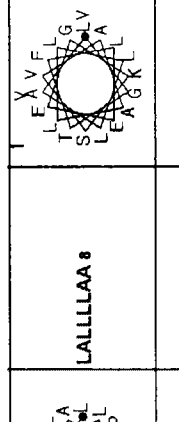 | 1 MLPGLALLLLAAWT ARALEVPTD 23 | No | LPLALLLLAAAALVP 15 | 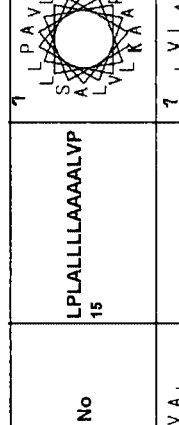 | LALLLLAA 8 | 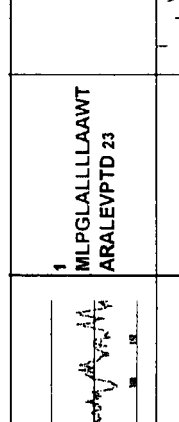 |
| JO-59 | NP_004878 small inducible cytokine B14 precursor [Homo sapiens]. | 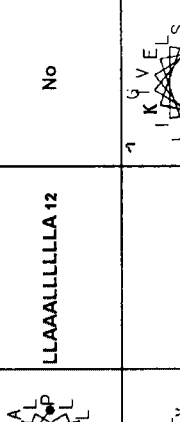 | 10 PVSMRLLAAALLLLL LALYTAR 31 |  | PVLLAAILLLLLL A 16 | 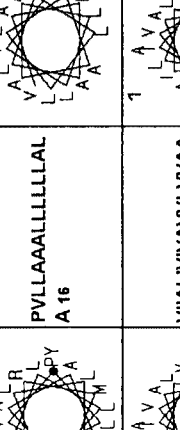 | LLAAALLLLLA 12 | No |
| JO-60 | NP_626589Secre ted protein [Streptomyces coelicolor A3(2)] | 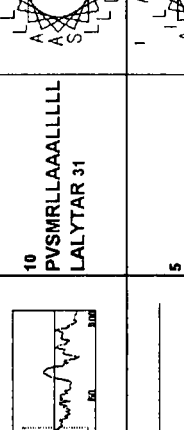 | 5 VIIALIVIVAVVLVVAA VLALR 26 |  | VIIALIVIVAVVLVVAA VLAL 21 | 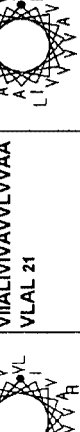 | VIIALIVIVA 10 |  |

Fig. 1e-4

| | | | | | | |
|---|---|---|---|---|---|---|
| JO-61 | NP_626589 secreted protein [Streptomyces coelicolor A3(2)] | | VIIALIVIVAVVLVVAA VLALR 26 | | VIIALIVIVAVVLVVAA VLAL 21 | No | VVLVVAAVLAL 11 | No |
| JO-62 | NP_856548 SOLUBLE SECRETED ANTIGEN MPB53 [Mycobacterium] | | VSPIKAFADGIVAVAI AVVLMFG 28 | | VPIAAVAVAIAVVL 14 | | VAVAIAVVL 9 | |
| JO-63 | NP_629854 secreted protein [Streptomyces coelicolor A3(2)]. | | PLIVVAAAVVAVGA GLAVWATA 31 | | AALLALLLAALPAAA LLLAA 15 | | PLIVVAAAVVAV 13 | No |
| JO-64 | AAB59058 lambda receptor protein [Escherichia coli]. | | KLPLAVAVAAGVMS AQAMAVDF 28 | | LPLAVAVAAVAAAV 14 | No | PLAVAVAAVAA 11 | No |

Fig. 1f-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-65 | NP_825185 NLP/P60-family secreted protein [Streptomyces avermitilis MA-4680]. | | LTMAAIALVCAVTVL GAPGAAHA 30 | | LAAIALVAVVLAPAA A 16 | No | AAIALVAVVL 10 | |
| JO-66 | NP_626568 secreted protein [Streptomyces coelicolor A3(2)]. | | AAALAAIAVIGAATAP AVAA 28 | | AAALAAIAVIAAAPAV AA 18 | | AAALAAIAVI 10 | No |
| JO-67 | NP_626568 secreted protein [Streptomyces coelicolor A3(2)]. | | AAALAAIAVIGAATAP AVAA 28 | | AAALAAIAVIAAAPAV AA 18 | No | AAAPAVAA 8 | No |

Fig. 1f-2

| | | | | | | |
|---|---|---|---|---|---|---|
| JO-68 | NP_625639 secreted protein [Streptomyces coelicolor A3(2)] | 7 GAGALLASLLLAALP FTAEAAES 29 | No | PLIVVVAAAVVAVAL A VAAV 19 | (helical wheel) | LLLAALP 7 | No |
| JO-69 | CAC32053 putative secreted protein [Mycobacterium leprae] | 6 ALLSAVVCAAWATL ILAPIGAAA 28 | (helical wheel) | AVVAAALILAPI 12 | No | ALLAVVAA 8 | (helical wheel) |
| JO-70 | NP_630954 secreted protein [Streptomyces coelicolor A3(2)] | 6 AVVGVVFLSPILLAG AGMVLVSS 28 | (helical wheel) | AVVVVLPILLAA 12 | No | AVVVVLPILL 10 | (helical wheel) |

Fig. 1f-3

| | | | | | | |
|---|---|---|---|---|---|---|
| JO-71 | P97300 Neuroplastin precursor (Stromal cell-derived receptor 1) (SDR-1). | [plot] | 6 LPGALALSLLLVSGS LLPGPGA 27 | No | ALALLLLVLLPPA 13 | No | ALALLLLVP 9 | No |
| JO-72 | AAA41949 Rat parotid gland acidic proline-rich protein mRNA, complete CDS | [plot] | 1 MLVVLLTAALLVLSS AHGSDEEV 23 | [helical wheel] | LVVLLAALLVL 11 | No | LVVLLAALLVL 11 | No |
| JO-73 | AAA17887 Drosophila melanogaster spatzle (spz) gene | [plot] | 1 MMTPMWISLFKVLLL LFAFFAT 22 | [helical wheel] | PILVLLLLA 9 | [helical wheel] | PVLLLLA 7 | [helical wheel] |

Fig. 1f-4

| | | | | | | |
|---|---|---|---|---|---|---|
| JO-74 | NP_627867 conserved secreted protein [Streptomyces coelicolor A3(2)] | [plot] | AVSALAGLVLAGSAL AVVNAAPA 30 | [helical wheel] | LVLAALAVVAAPA 13 | No | ALAVVAAP 8 | No |
| JO-75 | NP_631283 secreted protein [Streptomyces coelicolor A3(2)]. | [plot] | FLIAGVIVALLAVFTV VRAVRIV 30 | [helical wheel] | VIVALLAVVVAV 12 | No | VIVALLAV 8 | [helical wheel] |
| JO-76 | NP_003231 endometrial bleeding associated factor preproprotein | [plot] | MWPLWLCWALWVL PLAGPGAALT 23 | [helical wheel] | PLLALVLPLAP 11 | No | ALVLPLAP 8 | No |
| JO-77 | CAB76313 putative secreted protein [Streptomyces coelicolor A3(2)]. | [plot] | MVLCAVALLILAVSL VGGND 20 | [helical wheel] | AVALLILAV 9 | [helical wheel] | AVALLILAV 9 | [helical wheel] |

Fig. 1g-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-78 | P07198 Xenopsin precursor [Contains: Xenopsin precursor | | 1 MYKGIFLCVLLAVICA NSLATPS 23 | | VLLAVIALAP 10 | | VLLAVIP 7 | |
| JO-79 | NP_631293secre ted protein [Streptomyces coelicolor A3(2)]. | | 13 SGALAVWLIVAAVVV VAVLIGAF 35 | | LIVAAVVVAVLI 13 | | LIVAAVVVAVLI 13 | |
| JO-80 | NP_626373secre ted protein [Streptomyces coelicolor A3(2)]. | | 16 VYGVASAVVAATT GTLALASPG 38 | | AVVVAALALAP 11 | No | AVVVAAP 7 | No |

Fig. 1g-2

| | | | | | | |
|---|---|---|---|---|---|---|
| JO-81 | NP_624952 secreted cellulose-binding protein [Streptomyces coelicolor A3(2)] | | 18 ATTLVLSTLAAVLLT LIPWSGTA 40 | | LAAVLLLIPA 10 | No | LAAVLLLIP 9 | No |
| JO-82 | NP_009104 protease, serine, 23 precursor [Homo sapiens]. | | 2 AGIPGLLFLLFFLLCA VGQVSPY 24 | | IPLLLLLAVVP 12 | No | LLLLLAVVP 10 | |
| JO-83 | AAK63068 phytotoxic protein PcF precursor [Phytophthora cactorum]. | | 2 NFKTCPAVALVAVVA TVATAEDP 24 | | PAVALVAVVAVAP 13 | No | AVALVAVVAVA 11 | No |

Fig. 1g-3

| | | | | | |
|---|---|---|---|---|---|
| JO-84 | NC_003903Strep tomyces coelicolor A3(2) plasmid SCP1, complete sequence. | 2 VTSVLRGLVAALLAV LSITASTP 24 | | LVAALLAVLIAP 12 | No | LVAALLAVL 9 | |
| JO-85 | NP_629842pepti de transport system secreted peptide binding protein [Streptomyces] | 20 RLLAAAGAGALLLA SGAVAPSVA 42 | | ALLLAAVAP 9 | No | LLAAAAALLLA 11 | No |
| JO-86 | NP_854067Posi ble secreted protein [Mycobacterium bovis AF2122/97]. | 3 VIARVVGVAACGLSL AVLAAAPT 25 | | VAALLAVLAAAP 12 | No | LAVLAAAP 8 | No |

Fig. 1g-4

| | | | | | | |
|---|---|---|---|---|---|---|
| JO-87 | NP_627802secreted protein [Streptomyces coelicolor A3(2)]. | | 4 VVIAVGVVVLLVLL ALVVVSR 25 | | VVVLLVLLALVVV 13 | | VVVLLVLLALVVV 13 | |
| JO-88 | NP_627802secreted protein [Streptomyces coelicolor A3(2)]. | | 4 VVIAVGVVVLLVLL ALVVVSR 25 | | VVVLLVLLALVVV 13 | | VVIAVVP 7 | |
| JO-89 | NP_627802secreted protein [Streptomyces coelicolor A3(2)]. | | 4 VVIAVGVVVLLVLL ALVVVSR 25 | | VVVLLVLLALVVV 13 | | VLLVLLALV 9 | |
| JO-90 | NP_624483secreted protein [Streptomyces coelicolor A3(2)]. | | 1 MFRHLAAVATALAV VTVTPVEAT 23 | | LAAVAALAVVVP 12 | No | LAAVAALAVV 10 | |

Fig. 1h-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-91 | NP_625203secreted protein [Streptomyces coelicolor A3(2)]. | | 8 EELGLVLVGAVGAAG FFGLMIVIV 30 | 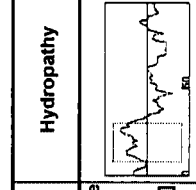 | LGVLVGAVGAA 12 | No | PVLVPAVP 8 | No |
| JO-92 | NP_630960secreted protein [Streptomyces coelicolor A3(2)]. | | 5 RVAISAAMLGALALS ALSATP 25 |  | VAIAAMLGALALALA P 16 | 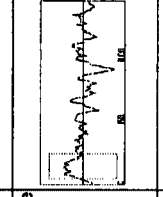 | PALALALA 8 | No |
| JO-93 | NP_630670secreted protein [Streptomyces coelicolor A3(2)]. | | 5 SSFVRVLGAAATAG ALAWAVLAQ 27 | 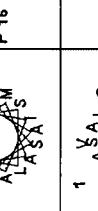 | FVVLGAAAAGALAW AVLA 18 | 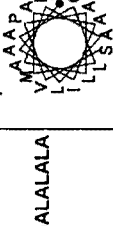 | AAAAPALA 8 | No |

Fig. 1h-2

| | | | | | | |
|---|---|---|---|---|---|---|
| JO-94 | NP_630493secreted protein [Streptomyces coelicolor A3(2)]. | | VRNIVLGVLAAGISATLGWLART 27 | | IVLPVLAAP 9 | No |
| JO-95 | CAC29994putative secreted protein [Mycobacterium leprae]. | | MESLVLLLLFLLIMGGFMFF 20 | | LVLLLLPLLI 10 | |
| JO-96 | NP_624483secreted protein [Streptomyces coelicolor A3(2)]. | | MFRHLAAVATALAVVTVTPVEAT 23 | | LAAVAPALAVV 11 | No |

Fig. 1h-3

| | | | | | | |
|---|---|---|---|---|---|---|
| JO-97 | NP_037375 secretogranin III [Homo sapiens]. | | MGFLGTGTWILVLVL PIQAFPKP 23 | | LGGWILVLVLPIAFPP 16 | | ILVLVLPI 8 | |
| JO-98 | NP_009199 V-set and immunoglobulin domain containing 4 [Homo sapiens]. | | MGILLGLLLLGHLTV DTYGRPIL 23 | | ILLGLLLLGLVGPIL 15 | | ILLPLLLLP 9 | |
| JO-99 | NP_733650 secreted hydrolase [Streptomyces coelicolor A3(2)]. | | MIAGAVVAALGVGA GLWAT 19 | | IAGAVVAALGVGAGL WA 17 | | IAPAVVAALP 10 | No |

Fig. 1h-4

| | | | | | | |
|---|---|---|---|---|---|---|
| JO-100 | NP_057540 transmembrane protein 9 [Homo sapiens]. | MKLLSLVAVVGCLLV PPAEANK 22 | [helical wheel] | MLLLVAVVGCLLVPP AA 16 | [helical wheel] | LLLVAVVPLLVP 12 | No |
| JO-101 | CAI74362 hypothetical protein [Theileria annulata]. | MKLMQLILLLLCIIKT SNGVN 21 | [helical wheel] | MLMLILLLLCIIGV 14 | No | LILLLLPII 9 | No |
| JO-102 | NP_630671 secreted protein [Streptomyces coelicolor A3(2)]. | GGRWFFAVLAASAV LVSGCSGSV 29 | [helical wheel] | FAVLAAAVLVGCGV 14 | No | AVLAAPAVLV 10 | [helical wheel] |
| JO-103 | NP_065695 TMEM9 domain family, member B [Homo sapiens]. | GLLRLGSLLSLSCLA LSVLLLAQ 29 | [helical wheel] | LLLGLLLLCLALVLL A 16 | [helical wheel] | LALPVLLLA 9 | [helical wheel] |

Fig. 1i-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-104 | P06908 Pulmonary surfactant-associated protein A precursor (SP- | | MWLRCLALALTLLM VSGIENNTK 23 | | MWLCLALALLLMVI 14 | | LALALLL 7 | |
| JO-105 | NP_639721 putative secreted protein [Streptomyces coelicolor A3(2)]. | | ASGVAGVCLLGVVA TGAVAAHVA 32 | | AGVAGVCLLGVVAG AVAAVA 20 | | VAVPLLVVA 9 | |
| JO-106 | NP_854954 CONSERVED PROBABLE SECRETED PROTEIN [Mycobacterium | | FAVAVAGVATAAAT TVTLAPAPA 33 | | AVAVAGVAAAAVLA PAPA 18 | | AVAVAPVAAAA 11 | No |

Fig. 1i-2

| | | | | | | | |
|---|---|---|---|---|---|---|---|
| JO-107 | NP_627759 secreted protein [Streptomyces coelicolor A3(2)]. | | 13 AARAVVAAVCAASL AGCAI 31 | | AAAVVAAVCAALAG CAI 17 | | AAAVVAAVPAA 11 | No |
| JO-108 | NP_003842 cellular repressor of E1A-stimulated genes [Homo sapiens]. | | 11 ALLAALLASTLLALL VSPA 29 | | ALLAALLALLALLVP A 16 | | ALLAALLAP 9 | No |
| JO-109 | NP_003842 cellular repressor of E1A-stimulated genes [Homo sapiens]. | | 11 ALLAALLASTLLALL VSPA 29 | | ALLAALLALLALLVP A 16 | | LLALLVP 7 | No |

Fig. 1i-3

| | | | | | | | |
|---|---|---|---|---|---|---|---|
| JO-110 | NP_003842 cellular repressor of E1A-stimulated genes [Homo sapiens]. | 11 ALLAALLASTLLALL VSPA 29 | | ALLAALLALLALLVP A 16 | | ALLAALLALLALLV 14 | No |
| JO-111 | NP_000589 Homo sapiens insulin-like growth factor binding protein 3 (IGFBP3). | 4 ARPTLWAAALTLLVL L 19 | | APLWAAALLLVLL 13 | | AAALPLLVLLP 11 | No |
| JO-112 | CAB59459 putative secreted protein [Streptomyces coelicolor A3(2)]. | 6 ATAAAVTAALATGV ASVAAGRLA 28 | | AAAAVAALAGVAVA AGLA 18 | | AAAVPAALAP 10 | |

Fig. 1i-4

| | | | | | |
|---|---|---|---|---|---|
| JO-113 | NP_628917secreted protein [Streptomyces coelicolor A3(2)]. | 7 ATTALAVAALAAGC A 21 | No | AALAVAALAAGCA 13 | No | AALAVAALAA 10 | No |
| JO-114 | NP_624695secreted protein [Streptomyces coelicolor A3(2)] | 15 AVLAAAVTAGVTAT AVTASPGVAALPAG PA 44 | | AVLAAAVAGVAAVA PGVAALPA 22 | | AVLAAAVP 8 | No |
| JO-115 | NP_624695secreted protein [Streptomyces coelicolor A3(2)] | 15 AVLAAAVTAGVTAT AVTASPGVAALPAG PA 44 | | AVLAAAVAGVAAVA PGVAALPA 22 | | VAALPAPA 8 | No |
| JO-116 | NP_624791secreted protein [Streptomyces coelicolor A3(2)] | 9 AVTGTALALAVSAVL TACGG 28 | | AVGALALAVAVLAC GG 16 | | ALALAVPAVLP 11 | No |

Fig. 1j-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-117 | CAB4579 putative secreted protein [Streptomyces coelicolor A3(2)]. | | 10 CAALLTAAVAVSLGA AGC 27 | | CAALLAAVAVLGAA GC 16 | | AALLPAAVAVP 11 | No |
| JO-118 | NP_627066 secreted protein [Streptomyces coelicolor A3(2)]. | | 13 FAIGTAVVVALAGMN GPWL 31 | No | FAIGAVVVALAGMGP WL 17 | No | AVVVALAP 8 | No |
| JO-119 | NP_630174 secreted substrate-binding protein [Streptomyces coelicolor A3(2)]. | | 16 GAAAVALTAAAALL AGC 32 | | GAAAVALAAAALLA GC 16 | | AAAVALPAAAALLA 1 | No |

Fig. 1j-2

| | | | | | | |
|---|---|---|---|---|---|---|
| JO-120 | P06727 Apolipoprotein A-IV precursor (Apo-AIV) (ApoA-IV). Homo sapiens | 3 LKAVVLTLALVAVAG ARAEVSAD 25 | No | LAVVLLALVAVAGAA VA 17 | (helical wheel) | AVVLPLALVAVAP 13 | (helical wheel) |
| JO-121 | Q62087 Serum paraoxonase/lac tonase 3. Mus musculus | 2 GKLVALTLLGACLAL IGERLLNF 24 | (helical wheel) | GLVALLLGACLALIG LLF 18 | (helical wheel) | LVALPLLP 8 | No |
| JO-122 | NP_627123probable secreted penicillin-binding protein[Streptomyces | 3 STVVVGLLLIVGGFF LGYHLVQI 25 | (helical wheel) | VVVGLLLIVGGFFLG LVI 18 | (helical wheel) | VVVPLLLIVP 10 | (helical wheel) |

Fig. 1j-3

| | | | | | | |
|---|---|---|---|---|---|---|
| JO-123 | CAC30224 putative secreted hydrolase [Mycobacterium leprae]. | 3 VARWLASVVLAVCL AGCVGRQVS 25 | | VAWLAVVLAVCLAG CVGV 18 | | LAVVLAVP 8 |
| JO-124 | O7ZQAM circumsporozoit e protein precursor - Plasmodium cynomolgi | 4 FNLLAVSSILLVDLFR THWGHNV 26 | No | LLAVILLVLFWGV 13 | No | LLAVPILLVP 10 |
| JO-125 | Q15166 Serum paraoxonase/lac tonase 3. Homo sapiens | 4 LVALVLLGVGLSLVG EMFLAFR 25 | | LVALVLLGVGLLVMF LA 17 | | LVALVLLP 8 |

Fig. 1j-4

| | | | | | | |
|---|---|---|---|---|---|---|
| JO-126 | NP_060220 all-trans-13,14-dihydroretinol saturase [Homo sapiens]. | PLVLLLAVLLLAVLC KVYLGLFS 26 | | PLVLLLAVLLLAVLC VL 17 | | LVLLLAVLLLAVLP 14 | No |
| JO-127 | AL627273 Salmonella enterica serovar Typhi (Salmonella typhi) strain | TLMLLAMVVALVILP FFINHGGE 26 | | LMLLAMVVALVILPF FIGG 19 | | LLAPVVALVILP 12 | No |
| JO-128 | NP_625987 secreted protein [Streptomyces coelicolor A3(2)] | TRGVLAVLAVCVLLL TGSAGCG 25 | | GVLAVLAVCVLLLGA GCG 18 | | VLAVLAVPVLLLP 13 | No |
| JO-129 | CAB45474 putative secreted protein [Streptomyces coelicolor A3(2)] | VVIAVVGVVVLLVLL ALVVVSR 25 | | VVIAVVGVVVLLVLL ALVVV 20 | | VVIAVVPVVV 10 | |

Fig. 1k-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-130 | CAB45474 putative secreted protein [Streptomyces coelicolor A3(2)]. | | 4 VVIAVVGVVVLLVLL ALVVVSR 25 | (helical wheel) | VVIAVVGVVVLLVLL ALVVV 20 | (helical wheel) | LLVLLALVVVP 11 | (helical wheel) |
| JO-131 | CAB36605 putative secreted protein [Streptomyces coelicolor A3(2)]. | | 15 VLLRRALPVCVAAG VASIVVFG 36 | (helical wheel) | VLLALPVCVAAGVAI VVFG 19 | (helical wheel) | VLLALPVVAAP 11 | No |
| JO-132 | NP_628377NLP/ P60-family secreted protein [Streptomyces coelicolor A3(2)]. | | 7 VLTTTAVTVVCAITVL AAPG 26 | (helical wheel) | VLAVVVAIVLAAP 13 | No | AVVVPAIVLAAP 12 | No |

Fig. 1k-2

| | | | | | |
|---|---|---|---|---|---|
| JO-133 | CAB59594 putative secreted protein [Streptomyces coelicolor A3(2)]. | PRKPVLAGIGATAVL VTAAALVPG 32 | [helical wheel] | PPVLAGIGAAVLVAA ALVPG 20 | AVLVPAAALVP 11 | No |
| JO-134 | NP_624974 secreted protein [Streptomyces coelicolor A3(2)] | VVAALTLSVLGATGA 22 | No | VVAALLVLGAGA 12 | No | VVAALPLVLP 10 | No |
| JO-135 | NP_733682 secreted ATP/GTP binding protein [Streptomyces coelicolor A3(2)] | WGPAVVMTTAFALA VGSQGAAVALPGAP AKA 39 | [helical wheel] | AFALAVGGAAVALP GAPAA 19 | No | AAVALPAAAP 10 | No |

Fig. 1k-3

| | | | | | | |
|---|---|---|---|---|---|---|
| JO-136 | P27169 Serum paraoxonase/aryl esterase 1 (PON 1) (Serum aryldialkylphosphatase 1) (A-hatase 1) | [plot] | MAKLIALTLLGMGLALF 17 | [helix] | ALIALLLGMGLALF 14 | [helix] | LIALPLLP 8 | No |
| JO-137 | P52430 Serum paraoxonase/aryl esterase 1 (PON 1) (Serum aryldialkylphosphatase 1) (A-hatase 1) | [plot] | MAKLLALTLVGLVLALYK 18 | [helix] | MALLALLVGLVLAL 14 | [helix] | LLALPLVLVLALP 13 | [helix] |
| JO-138 | NP_626569 secreted protein [Streptomyces coelicolor A3(2)] | [plot] | IVPLLLAAFLLIGTAGQAQ 24 | [helix] | IVPLLLAAFLLIGAGA 16 | [helix] | IVPLLLAAP 9 | No |

Fig. 1k-4

| | | | | | |
|---|---|---|---|---|---|
| JO-139 | NP_940995 C1q and tumor necrosis factor related protein 1 isoform 1 [Homo sapiens]. | QGLLLAYCLLLAFAS GLVLSRVP 28 | [helical wheel] | GLLLACLLLAFAGLV LVP 18 | [helical wheel] | LLLAPLLLAP 10 | No |
| JO-140 | NP_626174 large secreted protein [Streptomyces coelicolor A3(2)] | SARLAALTVAAVCSA ASTVVLTT 28 | [helical wheel] | ALAALVAAVCAAVVL 15 | [helical wheel] | LAALPVAAVP 10 | No |
| JO-141 | CAB83860 putative protein-export integral membrane protein [Neisseria] | TLIWIVNIISALAVIVLV LLQH 27 | [helical wheel] | LIWIVIIALAVIVLVLL 17 | [helical wheel] | ALAVIVLVLL 10 | [helical wheel] |
| JO-142 | NP_001009551 cornichon-like isoform 2 [Homo sapiens]. | AFCYMLALLLTAALI FFAIWHII 29 | [helical wheel] | AFCMLALLLAALIFF AIWII 20 | [helical wheel] | LALLLPAALI 10 | [helical wheel] |

Fig. 71-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-143 | NP_626808 secreted protein [Streptomyces coelicolor A3(2)] | 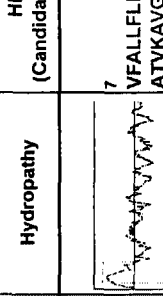 | VFALLFLLAVVLGVY ATVKAVGA 29 |  | VFALLFLLAVVLGVA VAVGA 20 | 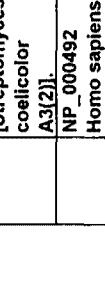 | ALLPLLAVVLP 11 |  |
| JO-144 | NP_639798 putative secreted protein [Streptomyces coelicolor A3(2)]. |  | QALMAIAVSVLAAGV TTLGV 28 | 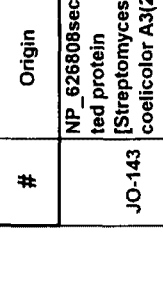 | ALMAIAVVLAAGVLG V 16 | 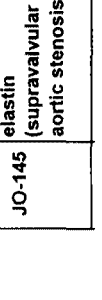 | AIAVPVLAAP 10 | No |
| JO-145 | NP_000492 Homo sapiens elastin (supravalvular aortic stenosis, |  | AAAPRPGVLLLLL 18 | No | AAAPPGVLLLLL 12 | No | AAAPVLLLLL 10 |  |

Fig. 11-2

| | | | | | | | |
|---|---|---|---|---|---|---|---|
| JO-146 | NP_630680 secreted sugar binding protein [Streptomyces coelicolor A3(2)]. | | AAAVGAVTMSLALA ATACGGG 26 | | AAAVGAVMLALAAA CGGG 18 | | AAAVAVLALAP 11 | No |
| JO-147 | CAB56129 putative secreted protein [Streptomyces coelicolor A3(2)]. | | AALAALVVAAGSLVT AGAA 28 | | AALAALVVAAGLVA GAA 17 | | AALAALVVAAP 11 | No |
| JO-148 | NP_625109 secreted solute-binding lipoprotein [Streptomyces coelicolor | | AALAAVTSLALAATA CGG 28 | | AALAAVLALAAACG G 15 | No | AALAAVPLALAP 12 | No |

Fig. 11-3

| | | | | | | |
|---|---|---|---|---|---|---|
| JO-149 | NP_733579 secreted sugar-binding protein [Streptomyces coelicolor A3(2)] | | AALAVAASASLALLA TACTG | | AALAVAAALALLAA CG 16 | | ALAVAAPALALLP 13 | No |
| JO-150 | NP_630126 secreted chitinase (secreted protein) [Streptomyces] | | 9 AALTAAATTVAAVGL AL 25 | | AALAAAVAAVGLAL 14 | No | AALPAAAP 8 | No |
| JO-151 | NP_630126 secreted chitinase (secreted protein) [Streptomyces] | | 9 AALTAAATTVAAVGL AL 25 | | AALAAAVAAVGLAL 14 | No | AAAPVAAVP 9 | No |

Fig. 11-4

| | | | | | | |
|---|---|---|---|---|---|---|
| JO-152 | NP_872425 secretory protein LOC348174 [Homo sapiens]. | | 12 HLAVLLALLGTAW AEVWPPQLQ 34 | No | 12 HLAVLLALLGAWAV WPPL 18 | | LLAVLLALLP 10 | No |
| JO-153 | NP_630107 secreted protein [Streptomyces coelicolor A3(2)]. | | 12 HVRSVLALLVAVVGL LCVFAHAE 34 | | VVLALLVAVVGLLCV FAA 18 | | VLALLVAVVP 10 | |
| JO-154 | NP_733688 peptide-binding transport protein [Streptomyces coelicolor A3(2)]. | | 13 ALVVGACAAVGVLL SGCTGGVS 34 | | ALVVGACAAVGVLL GCGGV 19 | | ALVVPAAVP 9 | No |
| JO-155 | NP_629904 secreted protein [Streptomyces coelicolor A3(2)]. | | 13 AVQGTVAGAVVLGL LLWWLLPLG 35 | | AVGVAGAVVLGLLL WWLLPL 20 | | AVVLPLLLP 9 | |

Fig. 1m-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-156 | YP_177852 MCE-FAMILY PROTEIN MCE3A [Mycobacterium tuberculosis |  | 13 AWWTLILFAVIGVAV LVTAVSFT 35 | 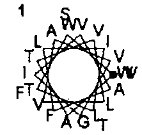  | AWWLILFAVIGVAVL VAVF 19 | 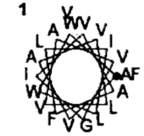  | AVIPVAVLVP 10 | 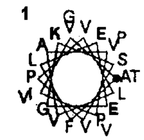  |
| JO-157 | CAA19627putati ve secreted solute binding protein [Streptomyces coelicolor |  | 9 GMLFGAAAVSAGAV LAGC 26 | 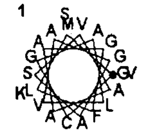  | GMLFGAAAVAGAVL AG 16 | 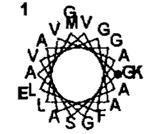  | AAAVPAAVLAP 11 | No |
| JO-158 | NP_639884putat ive large secreted protein [Streptomyces coelicolor A3(2)] |  | 10 GVAVTVVSYLAISLL SEPVAAATGLAL 36 | 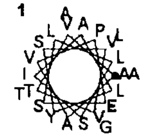  | GVAVVVLAILLPVAA AGLAL 20 | 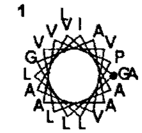  | VAVPVVLAILP 11 |  |

Fig. 1m-2

| | | | | | | |
|---|---|---|---|---|---|---|
| JO-159 | P24327 Foldase protein prsA precursor. | [plot] | IAIAAITATSILAL 17 | No | IAIAAIAILAL 11 | No | IAIAAIPAILAL 12 | [helix wheel] |
| JO-160 | CAB84808 putative membrane lipoprotein [Neisseria meningitidis] | [plot] | IIASALIATFALAAC 18 | No | IIAALIAFALAAC 13 | No | ALIAPALAAP 10 | No |
| JO-161 | NP_639883 putative large secreted protein [Streptomyces coelicolor A3(2)]. | [plot] | ILRAGPAAIALVAMA LTQVELAPHAVAAA 39 | [helix wheel] | PAAIALVAMALVLAP AVAAA 20 | [helix wheel] | AAIALVAPAL 10 | No |

Fig. 1m-3

| | | | | | | |
|---|---|---|---|---|---|---|
| JO-162 | NP_639883putative large secreted protein [Streptomyces coelicolor A3(2)]. | | ILRAGPAAIALVAMA LTQVELAPHAVAAA 39 | 11 | PAAIALVAMALVLAP AVAAA 20 | | LAPAVAAAP 9 | No |
| JO-163 | NP_627362secreted protein [Streptomyces coelicolor A3(2)]. | | NAQVAIIVSAVVAIALI IGGGVW 37 | 15 | AVAIIVAVVAIALIIGG GVW 20 | | VAIIVPAVVAIALII 15 | |
| JO-164 | NP_627362secreted protein [Streptomyces coelicolor A3(2)]. | | NAQVAIIVSAVVAIALI IGGGVW 37 | 15 | AVAIIVAVVAIALIIGG GVW 20 | | AVVAIALII 9 | |

Fig. 1m-4

| | | | | | | |
|---|---|---|---|---|---|---|
| JO-165 | NP_624625secreted protein [Streptomyces coelicolor A3(2)] | | LAAVTATAAAGAVAALGLAASPAAAAP 40 | | LAAVAAAAGAVAALGLAAPAAAAP 24 | | LAAVPAAAP 9 | No |
| JO-166 | NP_624625secreted protein [Streptomyces coelicolor A3(2)] | | LAAVTATAAAGAVAALGLAASPAAAAP 40 | | LAAVAAAAGAVAALGLAAPAAAAP 24 | | AVAALPLAAP 10 | No |
| JO-167 | NP_624625secreted protein [Streptomyces coelicolor A3(2)] | | LAAVTATAAAGAVAALGLAASPAAAAP 40 | | LAAVAAAAGAVAALGLAAPAAAAP 24 | | LAAPAAAAP 9 | No |
| JO-168 | NP_626936secreted protein [Streptomyces coelicolor A3(2)] | | LAAVTGVAAAGVAATPAAAARAVPVPVPL 39 | | LAAVGVAAAVGVAAPAAAAVPVPVPL 28 | | LAAVVPVAAAVP 12 | No |

Fig. 1n-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-169 | NP_626936 secreted protein [Streptomyces coelicolor A3(2)] | | LAAVVTGVAAAVGV AATPAAAARAVPVP VPL 39 | | LAAVVGVAAAVGVA APAAAAAVPVPVPL 28 | | VAAPAAAAP 9 | No |
| JO-170 | NP_626936 secreted protein [Streptomyces coelicolor A3(2)] | | LAAVVTGVAAAVGV AATPAAAARAVPVP VPL 39 | | LAAVVGVAAAVGVA APAAAAAVPVPVPL 28 | | AVPVPVPL 8 | No |
| JO-171 | NP_085072 matrilin 2 isoform b precursor [Homo sapiens] | | LAGCFLLILGQIVLLP A 21 | | LAGCFLLILGIVLLPA 16 | | LLILPIVLLP 10 | |

Fig. 1n-2

| | | | | | | |
|---|---|---|---|---|---|---|
| JO-172 | CAB94057 putative secreted protein [Streptomyces coelicolor A3(2)]. | [plot] | LGAGALALGGALAIA PFAAGPAEAV 44 20 | [helical wheel] | ALAIAPFAAGPAAV 14 | No | ALALPALAIAP 11 | No |
| JO-173 | NP_624384 secreted protein [Streptomyces coelicolor A3(2)] | [plot] | LGLSAVMISILAVTGC GG 21 4 | [helical wheel] | LGLAVMIILAVGCGG | No | AVIPILAVP 9 | [helical wheel] |
| JO-174 | NP_733505 large, multifunctional secreted protein [Streptomyces coelicolor A3(2)]. | [plot] | LILLLTSAVALGGAW AAPASSAAPA 37 13 | [helical wheel] | LILLLAVALGGAWAA PAAAPA 21 | [helical wheel] | LILLLPAVALP 11 | [helical wheel] |

Fig. 1n-3

| | | | | | | |
|---|---|---|---|---|---|---|
| JO-175 | CAB45630 putative secreted protein [Streptomyces coelicolor A3(2)] | 6 LRLVCTAALTAGIVL APVPAAA 27 | | LLVCAALAGIVLAPV PAAA 19 | | IVLAPVPAAA 10 | No |
| JO-176 | NP_627887 secreted protein [Streptomyces coelicolor A3(2)]. | 6 LPVVVGAGPVGLA AAA 22 | | LPVVVGAGPVLAA AA 16 | | VVVVPVLAAAA 11 | No |
| JO-177 | P06832 Bacillolysin precursor | 7 LSVAVAASFMSLTI 20 | No | LVAVAAMLI 9 | | LVAVAAP 7 | No |

Fig. 1n-4

| | | | | | |
|---|---|---|---|---|---|
| JO-178 | NP_625998 secreted hydrolase [Streptomyces coelicolor A3(2)]. | 13 LVLAAGAALTGAATA 27 | No | LVLAAGAALGAAA 13 | No | LVLAAPAAALP 10 | No |
| JO-179 | NP_625057 secreted protein [Streptomyces coelicolor A3(2)] | 10 LVLSVTLIAMAAASV WAVGGSV 31 | (helical wheel) | LVLVLIAMAAAVWAV GGV 18 | (helical wheel) | LIAPAAAVP 9 | No |
| JO-180 | NP_443750 ADP-ribosyltransferase 5 precursor [Homo sapiens]. | 1 MALAALMIALGSLGL 15 | No | MALAALMIALGLGL | No | ALAALPIALP 10 | No |
| JO-181 | CAB84257 putative secreted protein [Neisseria meningitidis Z2491]. | 4 MFLSAVLLLSAAAQT VWADTVF 25 | No | MFLAVLLLAAAVWA VF 16 | (helical wheel) | AVLLLPAAA 9 | No |

Fig. 10-1

| # | Origin | Hydropathy | HRSS (Candidate Domain) | Helix | Preliminarily modified Sequences | Helix | finally modified Sequences | Helix |
|---|---|---|---|---|---|---|---|---|
| JO-182 | P00634 Alkaline phosphatase precursor (APase). | | IALALLPLLFTPVTK 20 | No | IALALLPLLFPV 12 | No | IALALLPLL 9 | (helix wheel) |
| JO-183 | NP_000933 peptidylprolyl isomerase B precursor [Homo sapiens]. | | MKVLLAAALIAGSVF FLLLPG 29 | (helix wheel) | MVLLAAALIAGVFFL LLPG 19 | (helix wheel) | VLLAAALIAP 10 | (helix wheel) |
| JO-184 | CAB71258 putative secreted protein. [Streptomyces coelicolor A3(2)]. | | MTAPAVLTPPVVVIG AGPIGLAAAA 25 | (helix wheel) | MAPAVLPPVVIGAG PIGLAAAA 23 | (helix wheel) | APAVLPPVVVI 11 | No |

Fig. 1o-2

| | | | | | | |
|---|---|---|---|---|---|---|
| JO-185 | CAC31847possible secreted protein [Mycobacterium leprae]. | | 13 MVVGLLVAALTTITP TAVA 31 | | VVGLLVAAL 9 | No |
| JO-186 | NP_626948secreted protein [Streptomyces coelicolor A3(2)]. | | 14 PAHAAAAIAAAAFL AAGPGVAVGEPAAP 42 | | AAIAAAAPLAA 11 | |
| JO-187 | NP_059120 cat eye syndrome critical region protein 1 isoform a precursor | | 10 PALCFLLLAVAMSFF GSAL 28 | | LLLAVAP 7 | No |

Fig. 1o-3

| | | | | | | | |
|---|---|---|---|---|---|---|---|
| JO-188 | NP_006519 tissue factor pathway inhibitor 2 [Homo sapiens]. | (plot) | PARPLGLSILLLFLTE AAAL 21 | (helix) | PAPLGLILLLFLAAL 15 | (helix) | LILLLPLAAL 10 | (helix) |
| JO-189 | P97299 Secreted frizzled-related protein 2 precursor (sFRP-2) (Secreted | (plot) | PASILLLLVLASHCCL GSA 22 | (helix) | PALLLLVLACCLGA 14 | No | ALLLLVLA 8 | (helix) |
| JO-190 | NP_071447 tubulointerstitial nephritis antigen-like 1 | (plot) | PLGLLLLLPLAGHLA L 20 | (helix) | PLLLLLLPLAGLAL 14 | No | LLLLLLPLA 9 | No |

Fig. 1o-4

| | | | | | | |
|---|---|---|---|---|---|---|
| JO-190 | NP_071447 tubulointerstitial nephritis antigen-like 1 | [plot] | PLGLLLLLPLAGHLA L 20 | [helix wheel] | PLLLLLLPLAGLAL 14 | LLLLLLPLA 9 | No |
| JO-191 | NP_056322 epidermal growth factor-like protein 6 precursor [Homo sapiens]. | [plot] | PLPWSLALPLLLSW VAGG 19 | No | PLPWLALPLLLWVA GG 16 | [helix wheel] | LALPLLLP 8 | No |
| JO-192 | NP_628035 secreted penicillin-binding protein [Streptomyces coelicolor A3(2)]. | [plot] | PLRRIALFCGLLVLT LLI 21 | [helix wheel] | PLIALFCGLLVLLI 15 | [helix wheel] | LLVLPLLI 8 | [helix wheel] |
| JO-193 | NP_683880 cathepsin H isoform b precursor [Homo sapiens]. | [plot] | WATLPLLCAAELCV 15 | [helix wheel] | WALPLLCAALCV 12 | [helix wheel] | LPLLPAALV 9 | No |

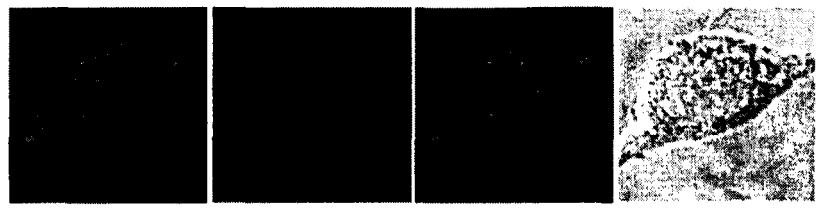

| ID | Origin | Protein | MTD sequence | A/a # | Induction | Purification | Cell permeability |
|---|---|---|---|---|---|---|---|
| JO-192 | *Streptomyces coelicolor* | NP_628035 secreted penicillin-binding protein | LLVLPLLI | 8 | | | ND |
| JO-193 | *Homo sapiens* | NP_683880 cathepsin H isoform b precursor | LPLLPAALV | 9 | | | ND |

* ND: Recombinant His-MTD-EGFP proteins of novel MTDs could not be prepared overall due to failure either on construction of expression vector, inducible expression, purification or preparation in soluble form.

Fig. 10i

|              | Liver | Kidney | Spleen | Lung | Heart | Brain |
|--------------|-------|--------|--------|------|-------|-------|
| FITC only    |       |        |        |      |       |       |
| Negative control |   |        |        |      |       |       |
| Positive control |   |        |        |      |       |       |
| JO-01 (1.1)  |       |        |        |      |       |       |
| JO-08 (0.5)  |       |        |        |      |       |       |

Fig. 12a

|   | Liver | Kidney | Spleen | Lung | Heart | Brain |
|---|---|---|---|---|---|---|
| JO-09 (0.5) | | | | | | |
| JO-10 (0.8) | | | | | | |
| JO-13 (0.9) | | | | | | |
| JO-17 (0.2) | | | | | | |
| JO-18 (0.4) | | | | | | |

Fig. 12b

|  | Liver | Kidney | Spleen | Lung | Heart | Brain |
|---|---|---|---|---|---|---|
| JO-20 (0.7) | | | | | | |
| JO-21 (0.4) | | | | | | |
| JO-26 (0.6) | | | | | | |
| JO-31 (0) | | | | | | |
| JO-36 (0.7) | | | | | | |

Fig. 12c

| | Liver | Kidney | Spleen | Lung | Heart | Brain |
|---|---|---|---|---|---|---|
| JO-39 (0.6) | | | | | | |
| JO-41 (0.4) | | | | | | |
| JO-49 (0.3) | | | | | | |
| JO-52 (1.6) | | | | | | |
| JO-56 (1.4) | | | | | | |

Fig. 12d

|          | Liver | Kidney | Spleen | Lung | Heart | Brain |
|----------|-------|--------|--------|------|-------|-------|
| JO-57 (1.8) |   |   |   |   |   |   |
| JO-58 (2.0) |   |   |   |   |   |   |
| JO-66 (1.3) |   |   |   |   |   |   |
| JO-68 (2.0) |   |   |   |   |   |   |
| JO-73 (2.7) |   |   |   |   |   |   |

Fig. 12e

|  | Liver | Kidney | Spleen | Lung | Heart | Brain |
|---|---|---|---|---|---|---|
| JO-77 (4) | | | | | | |
| JO-78 (5) | | | | | | |
| JO-86 (3.7) | | | | | | |
| JO-88 (0.3) | | | | | | |
| JO-101 (0.6) | | | | | | |

Fig. 12f

|  | Liver | Kidney | Spleen | Lung | Heart | Brain |
|---|---|---|---|---|---|---|
| JO-103 (0.8) | | | | | | |
| JO-108 (1.1) | | | | | | |
| JO-132 (1.3) | | | | | | |
| JO-133 (1.5) | | | | | | |
| JO-134 (1.5) | | | | | | |

Fig. 12g

|  | Liver | Kidney | Spleen | Lung | Heart | Brain |
|---|---|---|---|---|---|---|
| JO-162 (2.5) | | | | | | |
| JO-178 (4.1) | | | | | | |
| JO-181 (3.5) | | | | | | |
| JO-182 (4.1) | | | | | | |
| JO-183 (3.7) | | | | | | |
| JO-187 (3.2) | | | | | | |

| ID | Origin | Protein | MTD sequence | A/a # | Induction | Purification | Cell permeability |
|---|---|---|---|---|---|---|---|
| JO-01 | Streptomyces coelicolor | CAC04038 putative NLP/P60-family secreted protein | AVVVCAIVLAAP | 12 | + + + + | + + + + | 1.1 |
| JO-02 | Homo sapiens | NP_057021 phosphatidyl inositol glycan, class T precursor | PLALLVLLLLGP | 12 | | | ND |
| JO-03 | Homo sapiens | NP_072171 chorionic somatomammotropin hormone 2 isoform 3 | LLLAFALLCLP | 11 | - | - | ND |
| JO-04 | Homo sapiens | NP_932156 nudix-type motif 9 isoform a | LLGALAAVLLALA | 13 | | | ND |
| JO-05 | Homo sapiens | NP_057327 NAD(P)H quinone oxidoreductase type 3, polypeptide A2 | PVLLALGVGLAVLLGLAV | 17 | | | ND |
| JO-06 | Streptomyces coelicolor | CAD55360 putative secreted protein | AAAAVLLAA | 9 | - | - | ND |
| JO-07 | Streptomyces coelicolor | NP_629514 secreted protein | IVVAVVVI | 8 | - | - | ND |
| JO-08 | Streptomyces coelicolor | CAB57190 putative secreted chitin binding protein | AVLAPVVAV | 9 | + + + + | + + + + | 0.5 |
| JO-09 | Streptomyces coelicolor | CAB51015 putative secreted protein | LAVCGLPVVALLA | 13 | + + + + | + + + + | 0.5 |
| JO-10 | Streptomyces coelicolor | NP_625021 glycosyl hydrolase (secreted protein) | LGGAVVAAPVAAAVAP | 16 | + + + + | + + + + | 0.8 |
| JO-11 | Streptomyces coelicolor | NP_630686 secreted protein | LLLVLAVLLAVLP | 13 | | | ND |
| JO-12 | Homo sapiens | NP_057329 dehydrogenase/reductase (SDR family) member 8 | LLLLLLLPLLIV | 12 | - | - | ND |
| JO-13 | Streptomyces coelicolor | NP_639877 putative secreted protein | LAAAALAVLPL | 11 | + + + + | + + + + | 0.9 |
| JO-14 | Homo sapiens | NP_099201 protease inhibitor 16 precursor | FLMLLLPLLLLLVA | 14 | - | - | ND |
| JO-15 | Streptomyces coelicolor | NP_639871 putative secreted protein | AAAAAALGLAAAVPA | 15 | - | - | ND |
| JO-16 | Neisseria meningitidis | CAB85250 putative secreted protein | LLLAALLLIAFAAV | 14 | - | - | ND |
| JO-17 | Streptomyces coelicolor | NP_626397 small secreted hydrophilic protein | ALAAVVLIPLGLAA | 14 | + + + + | + + + + | 0.2 |
| JO-18 | Streptomyces coelicolor | CAB57190 putative secreted chitin binding protein | AALIGAVLAPVVAV | 14 | + + + + | + + + + | 0.4 |
| JO-19 | Streptomyces coelicolor | NP_626007 secreted cellulose-binding protein | AAGIAVAIAAIVPLA | 15 | - | - | ND |

Fig. 13b

| ID | Origin | Protein | MTD sequence | A/a # | Induction | Purification | Cell permeability |
|---|---|---|---|---|---|---|---|
| JO-20 | Streptomyces coelicolor | NP_625632 secreted protein | IAVAIAAIVPLA | 12 | ++++ | ++++ | 0.7 |
| JO-21 | Mycobacterium leprae | CAC31796 putative secreted protein | VAMAAAAVLAAPALA | 15 | ++++ | ++++ | 0.4 |
| JO-22 | Streptomyces coelicolor | CAB38593 putative secreted protein | AALALGVAAAPAAALA | 16 | - |  | ND |
| JO-23 | Streptomyces coelicolor | NP_630266 secreted Protein | LAVLVLLVLLP | 11 | - |  | ND |
| JO-24 | Streptomyces coelicolor | NP_630106 secreted Protein | VVAVLAAVL | 9 | - |  | ND |
| JO-25 | Streptomyces coelicolor | NC_003888 secreted Protein | AALLLPLLLLLP | 12 |  |  | ND |
| JO-26 | Streptomyces coelicolor | NP_627363 secreted Protein | PAAVAALLVI | 10 | ++++ | ++++ | 0.6 |
| JO-27 | Streptomyces coelicolor | NP_631286 secreted Protein | LLIAALLP | 8 | - |  | ND |
| JO-28 | Streptomyces coelicolor | NP_630325 secreted Protein | AAVVLLPLAAAP | 12 | - | ++ | 0.1 |
| JO-29 | Streptomyces coelicolor | NP_631283 secreted Protein | AAAAAALLVP | 10 | - |  | ND |
| JO-30 | Streptomyces coelicolor | CAB51015 Putative secreted Protein | LPVVALLA | 8 | ++++ | ++ | ND |
| JO-31 | Streptomyces coelicolor | NP_629515 chitinase C (secreted Protein) | AAALAAPLALP | 11 | - | ++++ | ND |
| JO-32 | Homo sapiens | NP_940995 C1q and tumor necrosis factor related Protein1 isoform1 | LLLALLLAA | 9 | - |  | ND |
| JO-33 | Mycobacterium bovis | NP_851150 POSSIBLE CONSERVED SECRETED PROTEIN | AVAVVALL | 8 | - |  | ND |
| JO-34 | Streptomyces coelicolor | NP_630361 Probable secreted Protein | LLLIVLLIVP | 11 | - | - | ND |
| JO-35 | Bacillus subtilis | P39790 Extracellular metalloProtease Precursor | LALAAAVVP | 9 | ++++ | ++++ | 0.5 |
| JO-36 | Streptomyces coelicolor | CAA19252 Putative liPoProtein | PAALALLLVA | 10 | ++++ | ++++ | 0.7 |
| JO-37 | Streptomyces coelicolor | NP_625685 large secreted Protein | IVALLLVPIAVLAIAAVL | 17 | - | - | ND |
| JO-38 | Streptomyces coelicolor | NP_625685 large secreted Protein | IVALLLVP | 8 | ++++ | ++++ | 0.2 |
| JO-39 | Streptomyces coelicolor | NP_625685 large secreted Protein | PLVLAIAAVL | 10 | ++++ | ++++ | 0.6 |

Fig. 13c

| ID | Origin | Protein | MTD sequence | A/a # | Induction | Purification | Cell permeability |
|---|---|---|---|---|---|---|---|
| JO-40 | Homo sapiens | NP_808800 golgi PhosPhoProtein 2 | PLVLAALVA | 9 | + + + + | + + + + | 0.2 |
| JO-41 | Streptomyces coelicolor | NP_628993 secreted Protein | AAALLAVA | 8 | + + + + | + + + + | 0.4 |
| JO-42 | Homo sapiens | NP_004853 thymic dendritic cell-derived factor 1 | PLLLLALA | 8 | | | ND |
| JO-43 | Streptomyces coelicolor | NP_631398 secreted Protein | ALALVVA | 7 | - | - | ND |
| JO-44 | Streptomyces coelicolor | NP_627673 Penicillin-binding Protein (secreted Protein) | VAAVVVAA | 8 | - | - | ND |
| JO-45 | Homo sapiens | NP_056220 sulfatase-modifying factor 2 | PLLPLLLV | 9 | - | - | ND |
| JO-46 | Mycobacterium bovis | NP_854998 Conserved hypothetical secreted protein | VVLVVVLPLAVLA | 13 | - | - | ND |
| JO-47 | Streptomyces coelicolor | NP_627512 Secreted Protein | AAAVPVLVAA | 10 | - | - | ND |
| JO-48 | Homo sapience | NP_110418 phospholipase A2, group XIIA | PALLLLLLAAV | 12 | + + | + + | 1.8 |
| JO-49 | Homo sapience | NP_003245 tissue inhibitor of metalloproteinase 1 precursor | PLALLLLLAP | 12 | + + + + | + + + + | 0.3 |
| JO-50 | Homo sapience | NP_002978 small inducible cytokine A17 precursor | PLLALVLLLALA | 12 | - | - | ND |
| JO-51 | Mus musculus | NP_0010121495 stromal cell derived factor 1 isoform gamma precursor | VVAVLALVLAAL | 12 | - | - | ND |
| JO-52 | Homo sapience | NP_775623 ficolin 3 isoform 2 precursor | PLLLLLPAL | 9 | + + + + | + + + + | 1.6 |
| JO-53 | Streptomyces coelicolor | NP_624482 secreted protein | LAAVAALAVVVT | 12 | + + | + + | 1.9 |
| JO-54 | Homo sapience | NP_997465 HERV-FRD provirus ancestral Env polyprotein | LLLLVLILPLAA | 12 | + + | + + | 2.5 |
| JO-55 | Mycobacterium bovis | NP_854234 posible conserved secreted protein | LAVVVVAAV | 9 | - | - | ND |
| JO-56 | Homo sapience | P23284 Peptidyl-prolyl cis-trans isomerase B precursor (PPIase) (Rotamase) (Cyclophilin B) | VLLAAALIA | 9 | + + + + | + + + + | 1.4 |
| JO-57 | Salmonella enterica | CAD05047 hypothetical secreted protein | LIALLAAPLA | 10 | + + + + | + + + + | 1.8 |
| JO-58 | Homo sapience | P05067 Amyloid beta A4 protein precursor (APP) (ABPP) (Alzheimer disease amyloid protein) | LALLLLAA | 8 | + + + + | + + + + | 2.0 |

Fig. 13d

| ID | Origin | Protein | MTD sequence | A/a # | Induction | Purification | Cell permeability |
|---|---|---|---|---|---|---|---|
| JO-59 | Homo sapience | NP_004878 small inducible cytokine B14 precursor | LLAAALLLLLA | 12 | - | - | ND |
| JO-60 | Streptomyces coelicolor | NP_626589 secreted protein | VHALIVIVA | 10 | + + | + + | 3.1 |
| JO-61 | Streptomyces coelicolor | NP_626589 secreted protein | VVIAVAAVLAL | 11 | - | - | ND |
| JO-62 | Mycobacterium bovis | NP_856518 SOLUBLE SECRETED ANTIGEN MPB73 | VAVAIAVVL | 9 | - | + + | 2.5 |
| JO-63 | Streptomyces coelicolor | NP_629854 secreted protein | PLIVVVAAAVVAV | 13 | - | + + | 2.4 |
| JO-64 | Escherichia coli | AAB59058 lambda receptor protein | PLAVAVAAVAA | 11 | - | + + | 0.9 |
| JO-65 | Streptomyces avermitilis | NP_825185 NLPF00-family secreted protein | AAIALVAVVL | 10 | | - | ND |
| JO-66 | Streptomyces coelicolor | NP_626568 secreted protein | AAALAAIAVI | 10 | + + + + | + + + + | 1.3 |
| JO-67 | Streptomyces coelicolor | NP_626568 secreted protein | AAAPAVAA | 8 | + + + + | + + + + | 0.1 |
| JO-68 | Streptomyces coelicolor | NP_625639 secreted protein | LLLAALP | 7 | + + + + | + + + + | 2.0 |
| JO-69 | Mycobacterium leprae | CAC32055 putative secreted protein | ALLAVVAA | 8 | + + | + + + + | 1.6 |
| JO-70 | Streptomyces coelicolor | NP_620054 secreted protein | AVVVVLPILL | 10 | | - | ND |
| JO-71 | Mus musculus | P97300 Neuroplastin precursor (Stromal cell-derived receptor 1) (SDR-1) | ALALLLLAP | 9 | + + | + + + + | 2.4 |
| JO-72 | Streptomyces coelicolor | AAA41949 Rat parotid gland acidic proline-rich protein mRNA, complete CDS | LAVLLAAMLAL | 11 | - | - | ND |
| JO-73 | Drosophila melanogaster | AAA17857 Drosophila melanogaster spatzle (spz) gene | PVLLLLA | 7 | + + + + | + + + + | 2.7 |
| JO-74 | Streptomyces coelicolor | NP_627867 conserved secreted protein | ALAVVAAP | 8 | + + | + + + + | 1.5 |
| JO-75 | Streptomyces coelicolor | NP_631283 secreted protein | VIVALLAV | 8 | | - | + + | 4.2 |
| JO-76 | Homo sapience | NP_003281 endometrial bleeding associated factor preproprotein | ALVLPLAP | 8 | + + + + | + + + + | 2.2 |
| JO-77 | Streptomyces coelicolor | CAB76313 putative secreted protein | AVALILAV | 9 | + + + + | + + + + | 4.0 |

Fig. 13e

| ID | Origin | Protein | MTD sequence | A/a # | Induction | Purification | Cell permeability |
|---|---|---|---|---|---|---|---|
| JO-78 | Xenopus laevis | P07198 Xenopsin precursor | VLLAVIP | 7 | + + + + | + + + + | 5.0 |
| JO-79 | Xenopus laevis | NP_631293 secreted protein | LIVAAVVVVAVLI | 13 | - | - | ND |
| JO-80 | Streptomyces coelicolor | NP_626373 secreted protein | AVVVAAP | 7 | - | + + | 0.2 |
| JO-81 | Streptomyces coelicolor | NP_624952 secreted cellulose-binding protein | LAAVLLLIP | 9 | + + + + | + + + + | 0.8 |
| JO-82 | Streptomyces coelicolor | NP_009104 protease, serine, 23 precursor | LLLLLAVVP | 10 | - | - | ND |
| JO-83 | Homo sapience | AAK63068 phytotoxic protein PcF precursor | AVALVAVVAVA | 11 | - | | ND |
| JO-84 | Streptomyces coelicolor | NC_003903 plasmid SCP1, complete sequence | LVAALLAVL | 9 | + + + + | + + + + | 1.9 |
| JO-85 | Streptomyces coelicolor | NP_629842 peptide transport system secreted peptide binding protein | LLAAAAALLLA | 11 | + + + + | + + + + | 1.8 |
| JO-86 | Mycobacterium bovis | NP_854367 Possible secreted protein | LAVLAAAP | 8 | + + + + | + + + + | 3.7 |
| JO-87 | Mycobacterium bovis | NP_627802 secreted protein | VVVLLVLLALVVV | 13 | | | ND |
| JO-88 | Streptomyces coelicolor | NP_627802 secreted protein | VVIAVVP | 7 | - | + + | 0.3 |
| JO-89 | Streptomyces coelicolor | NP_627802 secreted protein | VLLVLLALV | 9 | - | + + | 0.7 |
| JO-90 | Streptomyces coelicolor | NP_624183 secreted protein | LAAVAALAVV | 10 | + + | - | ND |
| JO-91 | Streptomyces coelicolor | NP_625203 secreted protein | PVLVPAVP | 8 | + + + + | + + + + | 0.1 |
| JO-92 | Streptomyces coelicolor | NP_630960 secreted protein | PALALALA | 8 | + + + + | + + + + | 0.1 |
| JO-93 | Streptomyces coelicolor | NP_630670 secreted protein | AAAAPALA | 8 | - | - | ND |
| JO-94 | Streptomyces coelicolor | NP_630493 secreted protein | IVLPVLAAP | 9 | + + + + | + + + + | 0.2 |
| JO-95 | Mycobacterium leprae | CAC29994 putative secreted protein | LVLLLLPLLI | 10 | + + | + + | 1.6 |
| JO-96 | Streptomyces coelicolor | NP_624183 secreted protein | LAAVAPALAVV | 11 | + + + + | + + + + | 0.6 |

Fig. 13f

| ID | Origin | Protein | MTD sequence | A/a # | Induction | Purification | Cell permeability |
|---|---|---|---|---|---|---|---|
| JO-97 | Homo sapiens | NP_037375 secretogranin III | LVLVLPI | 8 | + + | + + | 0.2 |
| JO-98 | Homo sapiens | NP_003199 V-set and immunoglobulin domain containing 4 | LLPLLLLP | 9 | + + + + | + + + + | 0.4 |
| JO-99 | Streptomyces coelicolor | NP_733050 secreted hydrolase | IAPAVVAALP | 10 | + + | - | ND |
| JO-100 | Homo sapiens | NP_057540 transmembrane protein 9 | LLLVAVVPLLAP | 12 | - | - | ND |
| JO-101 | Theileria annulata | CAI74362 hypothetical protein | LILLLLPH | 9 | + + + + | + + | 0.6 |
| JO-102 | Streptomyces coelicolor | NP_630071 secreted protein | AVLAAPAVLV | 10 | + + + + | + + + + | 0.1 |
| JO-103 | Homo sapiens | NP_055695 TMEM9 domain family, member B | LALPVLLLA | 9 | + + + + | + + + + | 0.8 |
| JO-104 | Canis lupus familiaris | I56968 Pulmonary surfactant-associated protein A precursor (SP-A) (PSP-A) (PSAP) | LALALLL | 7 | + + + + | + + + + | 0.3 |
| JO-105 | Streptomyces coelicolor | NP_629721 putative secreted protein | VAVPLLVVA | 9 | + + | + + + + | 0.4 |
| JO-106 | Mycobacterium bovis | NP_854954 CONSERVED PROBABLE SECRETED PROTEIN | AVAVAPVAAA | 11 | + + + + | + + + + | 0.2 |
| JO-107 | Streptomyces coelicolor | NP_627759 secreted protein | AAAVVAAVPAA | 11 | + + | + + + + | 0.1 |
| JO-108 | Homo sapiens | NP_003842 cellular repressor of E1A-stimulated genes | ALLAALLAP | 9 | + + + + | + + + + | 1.1 |
| JO-109 | Homo sapiens | NP_003842 cellular repressor of E1A-stimulated genes | LLALLVP | 7 | - | - | ND |
| JO-110 | Homo sapiens | NP_003842 cellular repressor of E1A-stimulated genes | ALLAALLALLALLV | 14 | - | - | ND |
| JO-111 | Homo sapiens | NP_000589 insulin-like growth factor binding protein 3 (IGFBP3) | AAMLPLLVLLP | 11 | - | - | ND |
| JO-112 | Streptomyces coelicolor | CAB59459 putative secreted protein | AAAVPAALAP | 10 | - | - | ND |
| JO-113 | Streptomyces coelicolor | NP_628047 secreted protein | AALAVAALAA | 10 | + + + + | + + + + | 0.3 |
| JO-114 | Streptomyces coelicolor | NP_624605 secreted protein | AVLAAAVP | 8 | + + + + | + + + + | 0.3 |
| JO-115 | Streptomyces coelicolor | NP_624605 secreted protein | VAALPAPA | 8 | + + + + | + + + + | 0.2 |

Fig. 13g

| ID | Origin | Protein | MTD sequence | A/a # | Induction | Purification | Cell permeability |
|---|---|---|---|---|---|---|---|
| JO-116 | Streptomyces coelicolor | NP_624791 secreted protein | ALALAVLAVLP | 11 | ++++ | ++++ | 0.4 |
| JO-117 | Streptomyces coelicolor | CAB45579 putative secreted protein | AALLPAAVAVP | 11 | ++++ | ++++ | 0.1 |
| JO-118 | Streptomyces coelicolor | NP_627060 secreted protein | AVVVALAP | 8 | - | - | 4.0 |
| JO-119 | Streptomyces coelicolor | NP_630174 secreted substrate-binding protein | AAAVALPAAAALLA | 14 | ++++ | ++++ | 0.5 |
| JO-120 | Homo sapiens | P06727 Apolipoprotein A-IV precursor (Apo-AIV) (ApoA-IV) | AVVLPLALVAVAP | 13 | ++ | ++ | 0.5 |
| JO-121 | Mus musculus | Q62087 Serum paraoxonase/lactonase 3 | LVALPLLP | 8 | - | - | ND |
| JO-122 | Streptomyces coelicolor | NP_627123 probable secreted penicillin-binding protein | VVVPLLLVP | 10 | - | ++ | 0.5 |
| JO-123 | Mycobacterium leprae | CAC30224 putative secreted hydrolase | LAVVLAVP | 8 | ++ | ++ | 1.9 |
| JO-124 | Plasmodium cynomolgi | O77QAM circumsporozoite protein precursor | LLAVPLLAP | 10 | ++++ | ++++ | 1.8 |
| JO-125 | Homo sapiens | Q15166 Serum paraoxonase/lactonase 3 | LVALVLLP | 8 | - | - | ND |
| JO-126 | Homo sapiens | NP_060220 all-trans-13,14-dihydroretinol saturase | LVLLLAVLLAVLP | 14 | - | - | ND |
| JO-127 | Salmonella typhi | AL627273 Salmonella enterica serovar Typhi (Salmonella typhi) strain CT18 | LLAPVVALVILP | 12 | ++ | - | 1.4 |
| JO-128 | Streptomyces coelicolor | NP_625987 secreted protein | VLAVLAVPVLLLP | 13 | ++ | - | ND |
| JO-129 | Streptomyces coelicolor | CAB45474 putative secreted protein | VVLAVVPVVV | 10 | - | - | ND |
| JO-130 | Streptomyces coelicolor | CAB45474 putative secreted protein | LLVLLALVVVP | 11 | - | - | ND |
| JO-131 | Streptomyces coelicolor | CAB36605 putative secreted protein | VLLALPVVAAP | 11 | ++ | ++ | 1.2 |
| JO-132 | Streptomyces coelicolor | NP_628377 NLP/P60-family secreted protein | AVVVPAIVLAAP | 12 | ++ | ++ | 1.3 |
| JO-133 | Streptomyces coelicolor | CAB59594 putative secreted protein | AVLVPAAAIAVP | 11 | ++++ | ++++ | 1.5 |
| JO-134 | Streptomyces coelicolor | NP_624974 secreted protein | VVAALPLVLP | 10 | ++ | ++ | 1.5 |

Fig. 13h

| ID | Origin | Protein | MTD sequence | A/a # | Induction | Purification | Cell permeability |
|---|---|---|---|---|---|---|---|
| JO-135 | Streptomyces coelicolor | NP_733082 secreted ATP/GTP binding protein | AAVALPAAAP | 10 | ++++ | +++- | 3.5 |
| JO-136 | Homo sapiens | P27169 Serum paraoxonase/arylesterase 1 (PON 1) (Serum aryldialkylphosphatase 1) (A-esterase 1) | LIALPLLP | 8 | ++++ | +++ | 3.5 |
| JO-137 | Homo sapiens | P52430 Serum paraoxonase/arylesterase 1 (PON 1) (Serum aryldialkylphosphatase 1) (A-esterase 1) | LLALPLVLVLALP | 13 | | | ND |
| JO-138 | Streptomyces coelicolor | NP_626568 secreted protein | IVPLLLAAP | 9 | ++++ | ++++ | 0.7 |
| JO-139 | Homo sapiens | NP_940995 C1q and tumor necrosis factor related protein 1 isoform 1 | LLLAPLLLAP | 10 | - | - | ND |
| JO-140 | Streptomyces coelicolor | NP_626174 large secreted protein | LAALPVAAVP | 10 | ++++ | ++++ | 0.5 |
| JO-141 | Neisseria meningitidis | CAB83860 putative protein-export integral membrane protein | ALAVIVLVLL | 10 | - | - | ND |
| JO-142 | Homo sapiens | NP_001009551 cornichon-like isoform 2 | LALLLPAALI | 10 | - | - | ND |
| JO-143 | Streptomyces coelicolor | NP_626803 secreted protein | ALLPLLAVVLP | 11 | ++ | ++ | 1.5 |
| JO-144 | Streptomyces coelicolor | NP_639798 putative secreted protein | AIAVPVLAAP | 10 | - | - | ND |
| JO-145 | Homo sapiens | NP_000492 elastin(supravalvular aortic stenosis) | AAAPVLLLLL | 10 | ++++ | ++++ | 1.3 |
| JO-146 | Streptomyces coelicolor | NP_630680 secreted sugar binding protein | AAAVAVLALAP | 11 | ++++ | ++++ | 0.4 |
| JO-147 | Streptomyces coelicolor | CAB56129 putative secreted protein | AALAALVVAAP | 11 | ++ | ++ | 0.7 |
| JO-148 | Streptomyces coelicolor | NP_625109 secreted solute-binding lipoprotein | AALAAVPLALAP | 12 | ++++ | ++++ | 2.0 |
| JO-149 | Streptomyces coelicolor | NP_733579 secreted sugar binding protein | ALAVAAPALALLP | 13 | - | - | ND |
| JO-150 | Streptomyces coelicolor | NP_630126 secreted chitinase (secreted protein) | AALPAAAP | 8 | - | - | ND |
| JO-151 | Streptomyces coelicolor | NP_630126 secreted chitinase (secreted protein) | AAAPVAAVP | 9 | ++++ | ++++ | 2.5 |
| JO-152 | Homo sapiens | NP_872425 secretory protein LOC348174 | LLAVLLALLP | 10 | - | - | ND |

Fig. 13i

| ID | Origin | Protein | MTD sequence | A/a # | Induction | Purification | Cell permeability |
|---|---|---|---|---|---|---|---|
| JO-153 | Streptomyces coelicolor | NP_630107 secreted protein | VLALLVAVVP | 10 | - | - | ND |
| JO-154 | Streptomyces coelicolor | NP_733688 peptide-binding transport protein | ALVVIAAVP | 9 | + + | + + | 2.3 |
| JO-155 | Streptomyces coelicolor | NP_629004 secreted protein | AVVLPLLLP | 9 | + + | + + | 0.6 |
| JO-156 | Mycobacterium tuberculosis | YP_177852 MCE-FAMILY PROTEIN MCE2A | AVIPVAVLVP | 10 | - | - | ND |
| JO-157 | Streptomyces coelicolor | CAA19627 putative secreted solute binding protein | AAAVPAAVLAP | 11 | - | - | ND |
| JO-158 | Streptomyces coelicolor | NP_639884 putative large secreted protein | VAVPVVLALP | 11 | - | + + | 0.3 |
| JO-159 | Bacillus subtilis | P24327 Foldase protein prsA precursor | IAIAAIPAILAL | 12 | + + + + | + + + + | 2.6 |
| JO-160 | Neisseria meningitidis | CAB84898 putative membrane lipoprotein | ALIAPALAAP | 10 | - | - | ND |
| JO-161 | Streptomyces coelicolor | NP_639882 putative large secreted protein | AAIALVAPAL | 10 | + + + + | + + + + | 0.5 |
| JO-162 | Streptomyces coelicolor | NP_639883 putative large secreted protein | LAPAVAAAP | 9 | + + + + | + + + + | 2.5 |
| JO-163 | Streptomyces coelicolor | NP_627362 secreted protein | VAIVPAVVALALII | 13 | - | - | ND |
| JO-164 | Streptomyces coelicolor | NP_627362 secreted protein | AVVAIALII | 9 | - | - | ND |
| JO-165 | Streptomyces coelicolor | NP_624625 secreted protein | LAAVPAAAP | 9 | - | - | ND |
| JO-166 | Streptomyces coelicolor | NP_624625 secreted protein | AVAALPLAAP | 10 | - | - | ND |
| JO-167 | Streptomyces coelicolor | NP_624625 secreted protein | LAAPAAAAP | 9 | - | - | ND |
| JO-168 | Streptomyces coelicolor | NP_626939 secreted protein | LAAVVPVAAAVP | 12 | + + | + + | 3.8 |
| JO-169 | Streptomyces coelicolor | NP_626936 secreted protein | VAAPAAAAP | 9 | + + + + | + + + + | 0.4 |
| JO-170 | Streptomyces coelicolor | NP_626936 secreted protein | AVPVPVLL | 8 | + + + + | + + + + | 0.8 |
| JO-171 | Homo sapiens | NP_085072 matrilin 2 isoform b precursor | LLILIVLLP | 10 | + + | - | 1.9 |
| JO-172 | Streptomyces coelicolor | CAB34957 putative secreted protein | ALALPALAIAP | 11 | + + + + | + + + + | 3.1 |

Fig. 13j

| ID | Origin | Protein | MTD sequence | A/a # | Induction | Purification | Cell permeability |
|---|---|---|---|---|---|---|---|
| JO-173 | Streptomyces coelicolor | NP_624381 secreted protein | AVIPILAVP | 9 | ++++ | ++++ | 2.3 |
| JO-174 | Streptomyces coelicolor | NP_733505 large multifunctional secreted protein | LILLLPAVALP | 11 | ++ | ++ | 3.6 |
| JO-175 | Streptomyces coelicolor | CAB45630 putative secreted protein | IVLAPVPAAA | 10 | - | - | ND |
| JO-176 | Streptomyces coelicolor | NP_627887 secreted protein | VVVVTVLAAA | 11 | - | - | 3.6 |
| JO-177 | Bacillolysin | P06832 Bacillolysin precursor | LVAVAAP | 7 | - | - | 3.5 |
| JO-178 | Streptomyces coelicolor | NP_625008 secreted hydrolase | LVLAAPAALP | 10 | ++ | +++ | 4.1 |
| JO-179 | Streptomyces coelicolor | NP_625057 secreted protein | LIAPAAAVP | 9 | - | - | ND |
| JO-180 | Homo sapiens | NP_443760 ADP-ribosyltransferase 5 precursor | ALAALPIALP | 10 | - | - | ND |
| JO-181 | Neisseria meningitidis | CAB84257 putative secreted protein | AVLLLPAAA | 9 | ++++ | ++++ | 3.5 |
| JO-182 | Escherichia coli | P06654 Alkaline phosphatase precursor (APase) | IALALLPLL | 9 | ++++ | ++++ | 4.1 |
| JO-183 | Homo sapiens | NP000925 peptidylprolyl isomerase B precursor | VLLAAALIAP | 10 | ++++ | ++++ | 3.7 |
| JO-184 | Streptomyces coelicolor | CAB71258 putative secreted protein | APAVLPPVVVI | 11 | - | - | ND |
| JO-185 | Mycobacterium leprae | CAC31847 possible secreted protein | VVGLLVAAL | 9 | - | - | ND |
| JO-186 | Streptomyces coelicolor | NP_626048 secreted protein | AAIAAAAPLAA | 11 | - | - | ND |
| JO-187 | Homo sapiens | NP_059120 cat eye syndrome critical region protein 1 isoform a precursor | LLLAVAP | 7 | ++ | ++ | 3.2 |
| JO-188 | Homo sapiens | NP_006519 tissue factor pathway inhibitor 2 | LILLLPLAAL | 10 | - | - | ND |
| JO-189 | Mus musculus | P97299 Secreted frizzled-related protein 2 precursor (tsFRP-2) (Secreted apoptosis-related protein 1) | ALLLLVLA | 8 | - | - | 4.7 |
| JO-190 | Homo sapiens | NP_071417 tubulointerstitial nephritis antigen-like 1 | LLLLLLPLA | 9 | - | - | ND |
| JO-191 | Homo sapiens | NP_056322 epidermal growth factor-like protein 6 precursor | LALPLLLP | 8 | - | - | ND |

| ID | Origin | Protein | MTD sequence | A/a # | Induction | Purification | Cell permeability |
|---|---|---|---|---|---|---|---|
| JO-192 | *Streptomyces coelicolor* | NP_628035 secreted penicillin-binding protein | LLVLPLLI | 8 | - | - | ND |
| JO-193 | *Homo sapiens* | NP_682880 cathepsin H isoform b precursor | LPLLPAALV | 9 | - | - | ND |

* ND: Recombinant His-MTD-EGFP proteins of novel MTDs could not be prepared overall due to failure either on construction of expression vector, inducible expression, purification or preparation in soluble form.

Fig. 13k

SEQUENCE LISTING

```
<160> NUMBER OF SEQ ID NOS: 996

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Val Val Val Cys Ala Ile Val Leu Ala Ala Pro
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Leu Ala Leu Leu Val Leu Leu Leu Leu Gly Pro
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

```
Leu Leu Leu Ala Phe Ala Leu Leu Cys Leu Pro
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Leu Gly Ala Leu Ala Ala Val Leu Leu Ala Leu Ala
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Val Leu Leu Ala Leu Gly Val Gly Leu Val Leu Leu Gly Leu Ala
1               5                   10                  15

Val

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ala Ala Ala Val Leu Leu Ala Ala
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Val Val Ala Val Val Val Ile
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Val Leu Ala Pro Val Val Ala Val
1               5

<210> SEQ ID NO 9
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 9

Leu Ala Val Cys Gly Leu Pro Val Val Ala Leu Leu Ala
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Gly Gly Ala Val Val Ala Ala Pro Val Ala Ala Val Ala Pro
1               5                   10                  15

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Leu Leu Val Leu Ala Val Leu Leu Ala Val Leu Pro
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Leu Ile Leu Leu Leu Leu Pro Leu Leu Ile Val
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Ala Ala Ala Ala Leu Ala Val Leu Pro Leu
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Leu Met Leu Leu Leu Pro Leu Leu Leu Leu Val Ala
1               5                   10
```

```
<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ala Ala Ala Ala Leu Gly Leu Ala Ala Ala Val Pro Ala
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Leu Leu Ala Ala Leu Leu Leu Ile Ala Phe Ala Ala Val
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Leu Ala Ala Val Val Leu Ile Pro Leu Gly Ile Ala Ala
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Ala Leu Ile Gly Ala Val Leu Ala Pro Val Val Ala Val
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Gly Ile Ala Val Ala Ile Ala Ala Ile Val Pro Leu Ala
1               5                   10                  15

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

Ile Ala Val Ala Ile Ala Ala Ile Val Pro Leu Ala
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Ala Met Ala Ala Ala Ala Val Leu Ala Ala Pro Ala Leu Ala
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Leu Ala Leu Gly Val Ala Ala Pro Ala Ala Ala Pro Ala
1               5                   10                  15

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Ala Val Leu Val Leu Leu Val Leu Leu Pro
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Val Ala Val Leu Ala Pro Val Leu
1               5

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ala Leu Leu Leu Pro Leu Leu Leu Leu Leu Pro
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Pro Ala Ala Val Ala Ala Leu Leu Val Ile
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Leu Ile Ala Ala Leu Leu Pro
1               5

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ala Val Val Leu Leu Pro Leu Ala Ala Ala Pro
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ala Ala Ala Ala Ala Leu Leu Val Pro
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Pro Val Val Ala Leu Leu Ala
1               5

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ala Ala Leu Ala Ala Pro Leu Ala Leu Pro
1               5                   10

<210> SEQ ID NO 32
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Leu Leu Ala Leu Leu Ala Ala
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Val Ala Val Val Ala Leu Leu
1               5

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Leu Leu Ile Ile Val Leu Leu Ile Val Pro
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Ala Leu Ala Ala Ala Val Val Pro
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Pro Ala Ala Leu Ala Leu Leu Leu Val Ala
1               5                   10

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ile Val Ala Leu Leu Leu Val Pro Leu Val Leu Ala Ile Ala Ala Val
1               5                   10                  15
```

Leu

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Val Ala Leu Leu Leu Val Pro
1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Pro Leu Val Leu Ala Ile Ala Ala Val Leu
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Leu Val Leu Ala Ala Leu Val Ala
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Ala Ala Leu Leu Ala Val Ala
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Pro Leu Leu Leu Leu Ala Leu Ala
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Ala Leu Ala Leu Val Val Ala
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Val Ala Ala Val Val Val Ala Ala
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Leu Leu Pro Leu Leu Leu Leu Val
1               5

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Val Leu Val Val Val Leu Pro Leu Ala Val Leu Ala
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Ala Ala Val Pro Val Leu Val Ala Ala
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Ala Leu Leu Leu Leu Leu Leu Ala Ala Val Val
1               5                   10

<210> SEQ ID NO 49
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Pro Leu Ala Ile Leu Leu Leu Leu Ile Ala Pro
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Leu Leu Ala Leu Val Leu Leu Leu Ala Leu Ile Ala
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Val Ala Val Leu Ala Leu Val Leu Ala Ala Leu
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Leu Leu Leu Leu Leu Pro Ala Leu
1               5

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Ala Ala Val Ala Ala Leu Ala Val Val Val Pro
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Leu Leu Leu Val Leu Ile Leu Pro Leu Ala Ala
1               5                   10
```

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Ala Val Val Val Val Ala Ala Val
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Val Leu Leu Ala Ala Ala Leu Ile Ala
1               5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Ile Ala Leu Leu Ala Ala Pro Leu Ala
1               5                   10

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Ala Leu Leu Leu Leu Ala Ala
1               5

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Leu Ala Ala Ala Leu Leu Leu Leu Leu Leu Ala
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 60

Val Ile Ile Ala Leu Ile Val Ile Val Ala
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Val Val Leu Val Val Ala Ala Val Leu Ala Leu
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Val Ala Val Ala Ile Ala Val Val Leu
1               5

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Pro Leu Ile Val Val Val Ala Ala Ala Val Val Ala Val
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Pro Leu Ala Val Ala Val Ala Ala Val Ala Ala
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Ile Ala Leu Val Ala Val Val Leu
1               5                   10

<210> SEQ ID NO 66
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 66

Ala Ala Ala Leu Ala Ala Ile Ala Val Ile
1               5                   10

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Ala Ala Pro Ala Val Ala Ala
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Leu Leu Ala Ala Leu Pro
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Leu Leu Ala Val Val Ala Ala
1               5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Val Val Val Val Leu Pro Ile Leu Leu
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Leu Ala Leu Leu Leu Leu Val Pro
1               5
```

```
<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Val Val Leu Leu Ala Ala Leu Leu Val Leu
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Val Leu Leu Leu Leu Ala
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Leu Ala Val Val Ala Ala Pro
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Val Ile Val Ala Leu Leu Ala Val
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Leu Val Leu Pro Leu Ala Pro
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77
```

```
Ala Val Ala Leu Leu Ile Leu Ala Val
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Val Leu Leu Ala Val Ile Pro
1               5

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Ile Val Ala Ala Val Val Val Val Ala Val Leu Ile
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Val Val Val Ala Ala Pro
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Ala Ala Val Leu Leu Leu Ile Pro
1               5

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Leu Leu Leu Leu Leu Ala Val Val Pro
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 83

Ala Val Ala Leu Val Ala Val Val Ala Val Ala
1               5                   10

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Val Ala Ala Leu Leu Ala Val Leu
1               5

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Leu Ala Ala Ala Ala Ala Leu Leu Leu Ala
1               5                   10

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Ala Val Leu Ala Ala Ala Pro
1               5

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Val Val Leu Leu Val Leu Leu Ala Leu Val Val Val
1               5                   10

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Val Val Ile Ala Val Val Pro
1               5

<210> SEQ ID NO 89
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Leu Leu Val Leu Leu Ala Leu Val
1               5

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu Ala Ala Val Ala Ala Leu Ala Val Val
1               5                   10

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Pro Val Leu Val Pro Ala Val Pro
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Pro Ala Leu Ala Leu Ala Leu Ala
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Ala Ala Ala Pro Ala Leu Ala
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ile Val Leu Pro Val Leu Ala Ala Pro
1               5
```

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Val Leu Leu Leu Leu Pro Leu Leu Ile
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Ala Ala Val Ala Pro Ala Leu Ala Val Val
1               5                   10

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ile Leu Val Leu Val Leu Pro Ile
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ile Leu Leu Pro Leu Leu Leu Leu Pro
1               5

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Ala Pro Ala Val Val Ala Ala Leu Pro
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 100

Leu Leu Leu Val Ala Val Val Pro Leu Val Pro
1               5                   10

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Ile Leu Leu Leu Leu Pro Ile Ile
1               5

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Val Leu Ala Ala Pro Ala Val Leu Val
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Ala Leu Pro Val Leu Leu Leu Ala
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu Ala Leu Ala Leu Leu Leu
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Val Ala Val Pro Leu Leu Val Val Ala
1               5

<210> SEQ ID NO 106
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 106

Ala Val Ala Val Ala Pro Val Ala Ala Ala
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Ala Ala Val Val Ala Ala Val Pro Ala Ala
1               5                   10

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ala Leu Leu Ala Ala Leu Leu Ala Pro
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Leu Leu Ala Leu Leu Val Pro
1               5

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Leu Leu Ala Ala Leu Leu Ala Leu Leu Ala Leu Leu Val
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Ala Ala Leu Pro Leu Leu Val Leu Leu Pro
1               5                   10
```

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ala Ala Ala Val Pro Ala Ala Leu Ala Pro
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Ala Leu Ala Val Ala Ala Leu Ala Ala
1               5                   10

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ala Val Leu Ala Ala Ala Val Pro
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Val Ala Ala Leu Pro Ala Pro Ala
1               5

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Leu Ala Leu Ala Val Pro Ala Val Leu Pro
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Ala Ala Leu Leu Pro Ala Ala Val Ala Val Pro
1               5                   10

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Val Val Val Ala Leu Ala Pro
1               5

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Ala Ala Val Ala Leu Pro Ala Ala Ala Ala Leu Leu Ala
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Val Val Leu Pro Leu Ala Leu Val Ala Val Ala Pro
1               5                   10

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Leu Val Ala Leu Pro Leu Leu Pro
1               5

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Val Val Val Pro Leu Leu Leu Ile Val Pro
1               5                   10

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                             -continued peptide

<400> SEQUENCE: 123

Leu Ala Val Val Leu Ala Val Pro
1               5

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Leu Leu Ala Val Pro Ile Leu Leu Val Pro
1               5                   10

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Leu Val Ala Leu Val Leu Leu Pro
1               5

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Leu Val Leu Leu Leu Ala Val Leu Leu Ala Val Leu Pro
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Leu Leu Ala Pro Val Val Ala Leu Val Ile Leu Pro
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Val Leu Ala Val Leu Ala Val Pro Val Leu Leu Pro
1               5                   10

<210> SEQ ID NO 129
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Val Val Ile Ala Val Val Pro Val Val Val
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Leu Leu Val Leu Leu Ala Leu Val Val Pro
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Val Leu Leu Ala Leu Pro Val Val Ala Ala Pro
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Val Val Val Pro Ala Ile Val Leu Ala Ala Pro
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Val Leu Val Pro Ala Ala Ala Leu Val Pro
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Val Val Ala Ala Leu Pro Leu Val Leu Pro
1               5                   10
```

```
<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Ala Val Ala Leu Pro Ala Ala Ala Pro
1               5                   10

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Leu Ile Ala Leu Pro Leu Leu Pro
1               5

<210> SEQ ID NO 137
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Leu Leu Ala Leu Pro Leu Val Leu Val Leu Ala Leu Pro
1               5                   10

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ile Val Pro Leu Leu Leu Ala Ala Pro
1               5

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Leu Leu Leu Ala Pro Leu Leu Leu Ala Pro
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 140

Leu Ala Ala Leu Pro Val Ala Ala Val Pro
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Leu Ala Val Ile Val Leu Val Leu Leu
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Leu Ala Leu Leu Leu Pro Ala Ala Leu Ile
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Leu Leu Pro Leu Leu Ala Val Val Leu Pro
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Ile Ala Val Pro Val Leu Ala Ala Pro
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Ala Ala Pro Val Leu Leu Leu Leu Leu
1               5                   10

<210> SEQ ID NO 146
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 146

Ala Ala Ala Val Ala Val Leu Ala Leu Ala Pro
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Ala Leu Ala Ala Leu Val Val Ala Ala Pro
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Ala Leu Ala Ala Val Pro Leu Ala Leu Ala Pro
1               5                   10

<210> SEQ ID NO 149
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ala Leu Ala Val Ala Ala Pro Ala Leu Ala Leu Leu Pro
1               5                   10

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Ala Leu Pro Ala Ala Ala Pro
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Ala Ala Pro Val Ala Ala Val Pro
1               5
```

```
<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Leu Leu Ala Val Leu Leu Ala Leu Leu Pro
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Val Leu Ala Leu Leu Val Ala Val Val Pro
1               5                   10

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Leu Val Val Pro Ala Ala Val Pro
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Val Val Leu Pro Leu Leu Leu Pro
1               5

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Val Ile Pro Val Ala Val Leu Val Pro
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157
```

```
Ala Ala Ala Val Pro Ala Ala Val Leu Ala Pro
1               5                   10
```

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

```
Val Ala Val Pro Val Val Leu Ala Ile Leu Pro
1               5                   10
```

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

```
Ile Ala Ile Ala Ala Ile Pro Ala Ile Leu Ala Leu
1               5                   10
```

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

```
Ala Leu Ile Ala Pro Ala Leu Ala Ala Pro
1               5                   10
```

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

```
Ala Ala Ile Ala Leu Val Ala Pro Ala Leu
1               5                   10
```

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

```
Leu Ala Pro Ala Val Ala Ala Ala Pro
1               5
```

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Val Ala Ile Ile Val Pro Ala Val Ala Ile Ala Leu Ile Ile
1               5                   10                  15

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ala Val Val Ala Ile Ala Leu Ile Ile
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Leu Ala Ala Val Pro Ala Ala Ala Pro
1               5

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Val Ala Ala Leu Pro Leu Ala Ala Pro
1               5                   10

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Leu Ala Ala Pro Ala Ala Ala Ala Pro
1               5

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Leu Ala Ala Val Val Pro Val Ala Ala Ala Val Pro
1               5                   10

<210> SEQ ID NO 169
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Val Ala Ala Pro Ala Ala Ala Pro
1               5

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Val Pro Val Pro Val Pro Leu
1               5

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Leu Leu Ile Leu Pro Ile Val Leu Leu Pro
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Leu Ala Leu Pro Ala Leu Ala Ile Ala Pro
1               5                   10

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Val Ile Pro Ile Leu Ala Val Pro
1               5

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Leu Ile Leu Leu Leu Pro Ala Val Ala Leu Pro
1               5                   10
```

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ile Val Leu Ala Pro Val Pro Ala Ala Ala
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Val Val Val Val Pro Val Leu Ala Ala Ala
1               5                   10

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Leu Val Ala Val Ala Ala Pro
1               5

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Leu Val Leu Ala Ala Pro Ala Ala Leu Pro
1               5                   10

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Leu Ile Ala Pro Ala Ala Ala Val Pro
1               5

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
-continued

<400> SEQUENCE: 180

Ala Leu Ala Ala Leu Pro Ile Ala Leu Pro
1               5                   10

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Val Leu Leu Leu Pro Ala Ala Ala
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ile Ala Leu Ala Leu Leu Pro Leu Leu
1               5

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Val Leu Leu Ala Ala Ala Leu Ile Ala Pro
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Pro Ala Val Leu Pro Pro Val Val Val Ile
1               5                   10

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Val Val Gly Leu Leu Val Ala Ala Leu
1               5

<210> SEQ ID NO 186
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 186

Ala Ala Ile Ala Ala Ala Ala Pro Leu Ala Ala
1               5                   10

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Leu Leu Leu Ala Val Ala Pro
1               5

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Leu Ile Leu Leu Leu Pro Leu Ala Ala Leu
1               5                   10

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ala Leu Leu Leu Leu Val Leu Ala
1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Leu Leu Leu Leu Leu Leu Pro Leu Ala
1               5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Leu Ala Leu Pro Leu Leu Leu Pro
1               5
```

```
<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Leu Leu Val Leu Pro Leu Leu Ile
1               5

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Leu Pro Leu Leu Pro Ala Ala Leu Val
1               5

<210> SEQ ID NO 194
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gcggtggtgg tgtgcgcgat tgtgctggcg gcgccg                                36

<210> SEQ ID NO 195
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ccgctggcgc tgctggtgct gctgctgctg ggcccg                                36

<210> SEQ ID NO 196
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ctgctgctgg cgtttgcgct gctgtgcctg ccg                                   33

<210> SEQ ID NO 197
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ctgctgggcg cactggcggc ggtgctgctg gcgctggcg                             39
```

<210> SEQ ID NO 198
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ccggtgctgc tggcgctggg cgtgggcctg gtgctgctgg cctggcggt g            51

<210> SEQ ID NO 199
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gcggcggcgg cggtgctgct ggcggcg                                      27

<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
attgtggtgg cggtggtggt gatt                                         24

<210> SEQ ID NO 201
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gcggtgctgg cgccggtggt ggcggtg                                      27

<210> SEQ ID NO 202
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ctggcggtgt gcggcctgcc ggtggtggcg ctgctggcg                         39

<210> SEQ ID NO 203
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ctgggcggcg cggtggtggc ggcgccggtg gcggcggcgg tggcgccg               48

<210> SEQ ID NO 204
<211> LENGTH: 39

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ctgctgctgg tgctggcggt gctgctggcg gtgctgccg                         39

<210> SEQ ID NO 205
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ctgctgattc tgctgctgct gccgctgctg attgtg                            36

<210> SEQ ID NO 206
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ctggcggcgg cggcgctggc ggtgctgccg ctg                               33

<210> SEQ ID NO 207
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tttctgatgc tgctgctgcc gctgctgctg ctgctggtgg cg                     42

<210> SEQ ID NO 208
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gcggcggcgg cggcggcgct gggcctggcg gcggcggtgc cggcg                  45

<210> SEQ ID NO 209
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ctgctgctgg cggcgctgct gctgattgcg tttgcggcgg tg                     42

<210> SEQ ID NO 210
<211> LENGTH: 42
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 210
gcgctggcgg cggtggtgct gattccgctg ggcattgcgg cg                               42

<210> SEQ ID NO 211
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 211
gcggcgctga ttggcgcggt gctggcgccg gtggtggcgg tg                               42

<210> SEQ ID NO 212
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 212
gcggcgggca ttgcggtggc gattgcggcg attgtgccgc tggcg                            45

<210> SEQ ID NO 213
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 213
attgcggtgg cgattgcggc gattgtgccg ctggcg                                      36

<210> SEQ ID NO 214
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 214
gtggcgatgg cggcggcggc ggtgctggcg gcgccggcgc tggcg                            45

<210> SEQ ID NO 215
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 215
gcggcgctgg cgctgggcgt ggcggcggcg ccggcggcgg cgccggcg                         48

<210> SEQ ID NO 216
<211> LENGTH: 33
<212> TYPE: DNA
<213> ORGANISM: Artificial Sequence
<220> FEATURE:
<223> OTHER INFORMATION: Description of Artificial Sequence: Synthetic

```
                              oligonucleotide

<400> SEQUENCE: 216
ctggcggtgc tggtgctgct ggtgctgctg ccg                               33

<210> SEQ ID NO 217
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gtggtggcgg tgctggcgcc ggtgctg                                     27

<210> SEQ ID NO 218
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
gcggcgctgc tgctgccgct gctgctgctg ctgccg                           36

<210> SEQ ID NO 219
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ccggcggcgg tggcggcgct gctggtgatt                                  30

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ctgctgattg cggcgctgct gccg                                        24

<210> SEQ ID NO 221
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gcggcggtgg tgctgctgcc gctggcggcg gcgccg                           36

<210> SEQ ID NO 222
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 222
gcggcggcgg cggcggcgct gctggtgccg                                      30

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ctgccggtgg tggcgctgct ggcg                                            24

<210> SEQ ID NO 224
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gcggcggcgc tggcggcgcc gctggcgctg ccg                                  33

<210> SEQ ID NO 225
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ctgctgctgg cgctgctgct ggcggcg                                         27

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gcggtggcgg tggtggcgct gctg                                            24

<210> SEQ ID NO 227
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ctgctgctga ttattgtgct gctgattgtg ccg                                  33

<210> SEQ ID NO 228
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228

-continued ctggcgctgg cggcggcggt ggtgccg         27

<210> SEQ ID NO 229
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ccggcggcgc tggcgctgct gctggtggcg         30

<210> SEQ ID NO 230
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
attgtggcgc tgctgctggt gccgctggtg ctggcgattg cggcggtgct g         51

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
attgtggcgc tgctgctggt gccg         24

<210> SEQ ID NO 232
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ccgctggtgc tggcgattgc ggcggtgctg         30

<210> SEQ ID NO 233
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ccgctggtgc tggcggcgct ggtggcg         27

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
gcggcggcgc tgctggcggt ggcg         24

```
<210> SEQ ID NO 235
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ccgctgctgc tgctggcgct ggcg                                          24

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
gcgctggcgc tggtggtggc g                                             21

<210> SEQ ID NO 237
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gtggcggcgg tggtggtggc ggcg                                          24

<210> SEQ ID NO 238
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ccgctgctgc cgctgctgct gctggtg                                       27

<210> SEQ ID NO 239
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
gtggtgctgg tggtggtgct gccgctggcg gtgctggcg                          39

<210> SEQ ID NO 240
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
gcggcggcgg tgccggtgct ggtggcggcg                                    30

<210> SEQ ID NO 241
```

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ccggcgctgc tgctgctgct gctggcggcg gtggtg                                  36

<210> SEQ ID NO 242
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ccgctggcga ttctgctgct gctgctgatt gcgccg                                  36

<210> SEQ ID NO 243
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ccgctgctgg cgctggtgct gctgctggcg ctgattgcg                               39

<210> SEQ ID NO 244
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gtggtggcgg tgctggcgct ggtgctggcg gcgctg                                  36

<210> SEQ ID NO 245
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ccgctgctgc tgctgctgcc ggcgctg                                            27

<210> SEQ ID NO 246
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ctggcggcgg tggcggcgct ggcggtggtg gtgccg                                  36

<210> SEQ ID NO 247
<211> LENGTH: 36
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 247
ctgctgctgc tggtgctgat tctgccgctg gcggcg                                36

<210> SEQ ID NO 248
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ctggcggtgg tggtggtggc ggcggtg                                          27

<210> SEQ ID NO 249
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gtgctgctgg cggcggcgct gattgcg                                          27

<210> SEQ ID NO 250
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ctgattgcgc tgctggcggc gccgctggcg                                       30

<210> SEQ ID NO 251
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ctggcgctgc tgctgctggc ggcg                                             24

<210> SEQ ID NO 252
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
ctgctggcgg cggcgctgct gctgctgctg ctggcg                                36

<210> SEQ ID NO 253
<211> LENGTH: 30
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 253
gtgattattg cgctgattgt gattgtggcg                                        30

<210> SEQ ID NO 254
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gtggtgctgg tggtggcggc ggtgctggcg ctg                                    33

<210> SEQ ID NO 255
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonuceotide

<400> SEQUENCE: 255
gtggcggtgg cgattgcggt ggtgctg                                           27

<210> SEQ ID NO 256
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
ccgctgattg tggtggtggc ggcggcggtg gtggcggtg                              39

<210> SEQ ID NO 257
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
ccgctggcgg tggcggtggc ggcggtggcg gcg                                    33

<210> SEQ ID NO 258
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gcggcgattg cgctggtggc ggtggtgctg                                        30

<210> SEQ ID NO 259
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gcggcggcgc tggcggcgat tgcggtgatt                    30

<210> SEQ ID NO 260
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gcggcggcgc cggcggtggc ggcg                          24

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ctgctgctgg cggcgctgcc g                             21

<210> SEQ ID NO 262
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gcgctgctgg cggtggtggc ggcg                          24

<210> SEQ ID NO 263
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
gcggtggtgg tggtgctgcc gattctgctg                    30

<210> SEQ ID NO 264
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gcgctggcgc tgctgctgct ggtgccg                       27

<210> SEQ ID NO 265
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265

```
ctggtggtgc tgctggcggc gctgctggtg ctg                          33
```

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 266

```
ccggtgctgc tgctgctggc g                                       21
```

<210> SEQ ID NO 267
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 267

```
gcgctggcgg tggtggcggc gccg                                    24
```

<210> SEQ ID NO 268
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 268

```
gtgattgtgg cgctgctggc ggtg                                    24
```

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 269

```
gcgctggtgc tgccgctggc gccg                                    24
```

<210> SEQ ID NO 270
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 270

```
gcggtggcgc tgctgattct ggcggtg                                 27
```

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 271

```
gtgctgctgg cggtgattcc g                                       21
```

<210> SEQ ID NO 272
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ctgattgtgg cggcggtggt ggtggtggcg gtgctgatt                                39

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gcggtggtgg tggcggcgcc g                                                   21

<210> SEQ ID NO 274
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ctggcggcgg tgctgctgct gattccg                                             27

<210> SEQ ID NO 275
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ctgctgctgc tgctgctggc ggtggtgccg                                          30

<210> SEQ ID NO 276
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gcggtggcgc tggtggcggt ggtggcggtg gcg                                      33

<210> SEQ ID NO 277
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ctggtggcgg cgctgctggc ggtgctg                                             27

<210> SEQ ID NO 278
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 278
ctgctggcgg cggcggcggc gctgctgctg gcg                33

<210> SEQ ID NO 279
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 279
ctggcggtgc tggcggcggc gccg                24

<210> SEQ ID NO 280
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 280
gtggtggtgc tgctggtgct gctggcgctg gtggtggtg                39

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 281
gtggtgattg cggtggtgcc g                21

<210> SEQ ID NO 282
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 282
gtgctgctgg tgctgctggc gctggtg                27

<210> SEQ ID NO 283
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 283
gtgctgctgg tgctgctggc gctggtg                27

<210> SEQ ID NO 284
<211> LENGTH: 24

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ccggtgctgg tgccggcggt gccg                                              24

<210> SEQ ID NO 285
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
ccggcgctgg cgctggcgct ggcg                                              24

<210> SEQ ID NO 286
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
gcggcggcgg cgccggcgct ggcg                                              24

<210> SEQ ID NO 287
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
attgtgctgc cggtgctggc ggcgccg                                           27

<210> SEQ ID NO 288
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
ctggtgctgc tgctgctgcc gctgctgatt                                        30

<210> SEQ ID NO 289
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ctggcggcgg tggcgccggc gctggcggtg gtg                                    33

<210> SEQ ID NO 290
<211> LENGTH: 24
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 290
attctggtgc tggtgctgcc gatt                                          24

<210> SEQ ID NO 291
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
attctgctgc cgctgctgct gctgccg                                       27

<210> SEQ ID NO 292
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
attgcgccgg cggtggtggc ggcgctgccg                                    30

<210> SEQ ID NO 293
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ctgctgctgg tggcggtggt gccgctgctg gtgccg                             36

<210> SEQ ID NO 294
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
ctgattctgc tgctgctgcc gattatt                                       27

<210> SEQ ID NO 295
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
gcggtgctgg cggcgccggc ggtgctggtg                                    30

<210> SEQ ID NO 296
<211> LENGTH: 27
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 296
ctggcgctgc cggtgctgct gctggcg                                        27

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
ctggcgctgg cgctgctgct g                                              21

<210> SEQ ID NO 298
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gtggcggtgc cgctgctggt ggtggcg                                        27

<210> SEQ ID NO 299
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
gcggtggcgg tggcgccggt ggcggcggcg gcg                                 33

<210> SEQ ID NO 300
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
gcggcggcgg tggtggcggc ggtgccggcg gcg                                 33

<210> SEQ ID NO 301
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
gcgctgctgg cggcgctgct ggcgccg                                        27

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 302
ctgctggcgc tgctggtgcc g                                              21

<210> SEQ ID NO 303
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
gcgctgctgg cggcgctgct ggcgctgctg gcgctgctgg tg                        42

<210> SEQ ID NO 304
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
gcggcggcgc tgccgctgct ggtgctgctg ccg                                  33

<210> SEQ ID NO 305
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
gcggcggcgg tgccggcggc gctggcgccg                                      30

<210> SEQ ID NO 306
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
gcggcgctgg cggtggcggc gctggcggcg                                      30

<210> SEQ ID NO 307
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
gcggtgctgg cggcggcggt gccg                                            24

<210> SEQ ID NO 308
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
```

```
gtggcggcgc tgccggcgcc ggcg                                          24
```

<210> SEQ ID NO 309
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309

```
gcgctggcgc tggcggtgcc ggcggtgctg ccg                                 33
```

<210> SEQ ID NO 310
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310

```
gcggcgctgc tgccggcggc ggtggcggtg ccg                                 33
```

<210> SEQ ID NO 311
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311

```
gcggtggtgg tggcgctggc gccg                                          24
```

<210> SEQ ID NO 312
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312

```
gcggcggcgg tggcgctgcc ggcggcggcg gcgctgctgg cg                       42
```

<210> SEQ ID NO 313
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313

```
gcggtggtgc tgccgctggc gctggtggcg gtggcgccg                           39
```

<210> SEQ ID NO 314
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314

```
ctggtggcgc tgccgctgct gccg                                          24
```

```
<210> SEQ ID NO 315
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gtggtggtgc cgctgctgct gattgtgccg                                    30

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
ctggcggtgg tgctggcggt gccg                                          24

<210> SEQ ID NO 317
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
ctgctggcgg tgccgattct gctggtgccg                                    30

<210> SEQ ID NO 318
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
ctggtggcgc tggtgctgct gccg                                          24

<210> SEQ ID NO 319
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
ctggtgctgc tgctggcggt gctgctgctg gcggtgctgc cg                      42

<210> SEQ ID NO 320
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
ctgctggcgc cggtggtggc gctggtgatt ctgccg                             36

<210> SEQ ID NO 321
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
gtgctggcgg tgctggcggt gccggtgctg ctgctgccg                           39

<210> SEQ ID NO 322
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gtggtgattg cggtggtgcc ggtggtggtg                                     30

<210> SEQ ID NO 323
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
ctgctggtgc tgctggcgct ggtggtggtg ccg                                 33

<210> SEQ ID NO 324
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
gtgctgctgg cgctgccggt ggtggcggcg ccg                                 33

<210> SEQ ID NO 325
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gcggtggtgg tgccggcgat tgtgctggcg gcgccg                              36

<210> SEQ ID NO 326
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
gcggtgctgg tgccggcggc ggcgctggtg ccg                                 33

<210> SEQ ID NO 327
<211> LENGTH: 30
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 327
gtggtggcgg cgctgccgct ggtgctgccg                               30

<210> SEQ ID NO 328
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gcggcggtgg cgctgccggc ggcggcgccg                               30

<210> SEQ ID NO 329
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
ctgattgcgc tgccgctgct gccg                                     24

<210> SEQ ID NO 330
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
ctgctggcgc tgccgctggt gctggtgctg gcgctgccg                     39

<210> SEQ ID NO 331
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
attgtgccgc tgctgctggc ggcgccg                                  27

<210> SEQ ID NO 332
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
ctgctgctgg cgccgctgct gctggcgccg                               30

<210> SEQ ID NO 333
<211> LENGTH: 30
<212> TYPE: DNA
<213> ORGANISM: Artificial Sequence
<220> FEATURE:

-continued

<223> OTHER INFORMATION: Description of Artificial Sequence: Synthetic
     oligonucleotide

<400> SEQUENCE: 333
ctggcggcgc tgccggtggc ggcggtgccg                                    30

<210> SEQ ID NO 334
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 334
gcgctggcgg tgattgtgct ggtgctgctg                                    30

<210> SEQ ID NO 335
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 335
ctggcgctgc tgctgccggc ggcgctgatt                                    30

<210> SEQ ID NO 336
<211> LENGTH: 33
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 336
gcgctgctgc cgctgctggc ggtggtgctg ccg                                33

<210> SEQ ID NO 337
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 337
gcgattgcgg tgccggtgct ggcggcgccg                                    30

<210> SEQ ID NO 338
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 338
gcggcggcgc cggtgctgct gctgctgctg                                    30

<210> SEQ ID NO 339
<211> LENGTH: 33
<212> TYPE: DNA
<213> ORGANISM: Artificial Sequence
<220> FEATURE:
<223> OTHER INFORMATION: Description of Artificial Sequence: Synthetic
     oligonucleotide

```
<400> SEQUENCE: 339
gcggcggcgg tggcggtgct ggcgctggcg ccg                                33

<210> SEQ ID NO 340
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
gcggcgctgg cggcgctggt ggtggcggcg ccg                                33

<210> SEQ ID NO 341
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gcggcgctgg cggcggtgcc gctggcgctg gcgccg                             36

<210> SEQ ID NO 342
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gcgctggcgg tggcggcgcc ggcgctggcg ctgctgccg                          39

<210> SEQ ID NO 343
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
gcggcgctgc cggcggcggc gccg                                          24

<210> SEQ ID NO 344
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gcggcggcgc cggtggcggc ggtgccg                                       27

<210> SEQ ID NO 345
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
```
ctgctggcgg tgctgctggc gctgctgccg                                    30

<210> SEQ ID NO 346
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
gtgctggcgc tgctggtggc ggtggtgccg                                    30

<210> SEQ ID NO 347
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
gcgctggtgg tgccggcggc ggtgccg                                       27

<210> SEQ ID NO 348
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
gcggtggtgc tgccgctgct gctgccg                                       27

<210> SEQ ID NO 349
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
gcggtgattc cggtggcggt gctggtgccg                                    30

<210> SEQ ID NO 350
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
gcggcggcgg tgccggcggc ggtgctggcg ccg                                33

<210> SEQ ID NO 351
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
gtggcggtgc cggtggtgct ggcgattctg ccg                                33

-continued

```
<210> SEQ ID NO 352
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
attgcgattg cggcgattcc ggcgattctg gcgctg                                  36

<210> SEQ ID NO 353
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
gcgctgattg cgccggcgct ggcggcgccg                                         30

<210> SEQ ID NO 354
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
gcggcgattg cgctggtggc gccggcgctg                                         30

<210> SEQ ID NO 355
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
ctggcgccgg cggtggcggc ggcgccg                                            27

<210> SEQ ID NO 356
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
gtggcgatta ttgtgccggc ggtggtggcg attgcgctga ttatt                        45

<210> SEQ ID NO 357
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
gcggtggtgg cgattgcgct gattatt                                            27
```

-continued

<210> SEQ ID NO 358
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
ctggcggcgg tgccggcggc ggcgccg                                        27

<210> SEQ ID NO 359
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
gcggtggcgg cgctgccgct ggcggcgccg                                     30

<210> SEQ ID NO 360
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
ctggcggcgc cggcggcggc ggcgccg                                        27

<210> SEQ ID NO 361
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
ctggcggcgg tggtgccggt ggcggcggcg gtgccg                              36

<210> SEQ ID NO 362
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
gtggcggcgc cggcggcggc ggcgccg                                        27

<210> SEQ ID NO 363
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
gcggtgccgg tgccggtgcc gctg                                           24

<210> SEQ ID NO 364
<211> LENGTH: 30

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
ctgctgattc tgccgattgt gctgctgccg                                         30

<210> SEQ ID NO 365
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
gcgctggcgc tgccggcgct ggcgattgcg ccg                                     33

<210> SEQ ID NO 366
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
gcggtgattc cgattctggc ggtgccg                                            27

<210> SEQ ID NO 367
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
ctgattctgc tgctgccggc ggtggcgctg ccg                                     33

<210> SEQ ID NO 368
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
attgtgctgg cgccggtgcc ggcggcggcg                                         30

<210> SEQ ID NO 369
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
gtggtggtgg tgccggtgct ggcggcggcg gcg                                     33

<210> SEQ ID NO 370
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 370
ctggtggcgg tggcggcgcc g                                           21

<210> SEQ ID NO 371
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
ctggtgctgg cggcgccggc ggcgctgccg                                  30

<210> SEQ ID NO 372
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
ctgattgcgc cggcggcggc ggtgccg                                     27

<210> SEQ ID NO 373
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
gcgctggcgg cgctgccgat tgcgctgccg                                  30

<210> SEQ ID NO 374
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gcggtgctgc tgctgccggc ggcggcg                                     27

<210> SEQ ID NO 375
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
attgcgctgg cgctgctgcc gctgctg                                     27

<210> SEQ ID NO 376
<211> LENGTH: 30
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 376
gtgctgctgg cggcggcgct gattgcgccg                                             30

<210> SEQ ID NO 377
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
gcgccggcgg tgctgccgcc ggtggtggtg att                                         33

<210> SEQ ID NO 378
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
gtggtgggcc tgctggtggc ggcgctg                                                27

<210> SEQ ID NO 379
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
gcggcgattg cggcggcggc gccgctggcg gcg                                         33

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
ctgctgctgg cggtggcgcc g                                                      21

<210> SEQ ID NO 381
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
ctgattctgc tgctgccgct ggcggcgctg                                             30

<210> SEQ ID NO 382
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 382
gcgctgctgc tgctggtgct ggcg                                    24

<210> SEQ ID NO 383
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
ctgctgctgc tgctgctgcc gctggcg                                 27

<210> SEQ ID NO 384
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
ctggcgctgc cgctgctgct gccg                                    24

<210> SEQ ID NO 385
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
ctgctggtgc tgccgctgct gatt                                    24

<210> SEQ ID NO 386
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
ctgccgctgc tgccggcggc gctggtg                                 27

<210> SEQ ID NO 387
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ser Ala Asn Val Glu Pro Leu Glu Arg Leu
1               5                   10

<210> SEQ ID NO 388
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
```
tcagcgaatg tcgaccccct agaccgacta                                                    30

<210> SEQ ID NO 389
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Ala Ala Val Leu Leu Pro Val Leu Leu Ala Ala Pro
1               5                   10

<210> SEQ ID NO 390
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
gccgcggtac tgctcccggt cctgctggcc gcgccc                                             36

<210> SEQ ID NO 391
<211> LENGTH: 265
<212> TYPE: PRT
<213> ORGANISM: Homo sapiens

<400> SEQUENCE: 391

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

```
Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Ala Val Asp Gly Thr
            245                 250                 255

Ala Gly Pro Gly Ser Thr Gly Ser Arg
        260                 265

<210> SEQ ID NO 392
<211> LENGTH: 798
<212> TYPE: DNA
<213> ORGANISM: Homo sapiens

<400> SEQUENCE: 392
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtcc    720
ggactcagat ctcgagctca agcttcgaat tctgcagtcg acggtaccgc gggcccggga    780
tccaccggat ctagataa                                                  798

<210> SEQ ID NO 393
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
ccgcatatgg cggtggtggt gtgcgcgatt gtgctggcgg cgccggtgag caagggcgag     60
gagctg                                                               66

<210> SEQ ID NO 394
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
ccgcatatgc cgctggcgct gctggtgctg ctgctgctgg gcccggtgag caagggcgag     60
gagctg                                                               66

<210> SEQ ID NO 395
<211> LENGTH: 63
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 395
ccgcatatgc tgctgctggc gtttgcgctg ctgtgcctgc cggtgagcaa gggcgaggag    60
ctg                                                                 63

<210> SEQ ID NO 396
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
ccgcatatgc tgctgggcgc actggcggcg gtgctgctgg cgctggcggt gagcaagggc    60
gaggagctg                                                           69

<210> SEQ ID NO 397
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
ccgcatatgc cggtgctgct ggcgctgggc gtgggcctgg tgctgctggg cctggcggtg    60
gtgagcaagg gcgaggagct g                                             81

<210> SEQ ID NO 398
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
ccgcatatgg cggcggcggc ggtgctgctg gcggcggtga gcaagggcga ggagctg      57

<210> SEQ ID NO 399
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
ccgcatatga ttgtggtggc ggtggtggtg attgtgagca agggcgagga gctg         54

<210> SEQ ID NO 400
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
ccgcatatgg cggtgctggc gccggtggtg gcggtggtga gcaagggcga ggagctg      57
```

```
<210> SEQ ID NO 401
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
ccgcatatgc tggcggtgtg cggcctgccg gtggtggcgc tgctggcggt gagcaagggc      60
gaggagctg                                                             69

<210> SEQ ID NO 402
<211> LENGTH: 77
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
ccgcatatgc tgggcggcgc ggtggtggcg gcgccggtgg cgcggcggtg gcgccggtga      60
gcaagggcga ggagctg                                                    77

<210> SEQ ID NO 403
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
ccgcatatgc tgctgctggt gctggcggtg ctgctggcgg tgctgccggt gagcaagggc      60
gaggagctg                                                             69

<210> SEQ ID NO 404
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
ccgcatatgc tgctgattct gctgctgctg ccgctgctga ttgtggtgag caagggcgag      60
gagctg                                                                66

<210> SEQ ID NO 405
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
ccgcatatgc tggcggcggc ggcgctggcg gtgctgccgc tggtgagcaa gggcgaggag      60
ctg                                                                   63

<210> SEQ ID NO 406
<211> LENGTH: 72
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 406
ccgcatatgt ttctgatgct gctgctgccg ctgctgctgc tgctggtggc ggtgagcaag    60
ggcgaggagc tg                                                       72

<210> SEQ ID NO 407
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407
ccgcatatgg cggcggcggc ggcggcgctg ggtctggcgg cggcggtgcc ggcggtgagc    60
aagggcgagg agctg                                                    75

<210> SEQ ID NO 408
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
ccgcatatgc tgctgctggc ggcgctgctg ctgattgcgt ttgcggcggt ggtgagcaag    60
ggcgaggagc tg                                                       72

<210> SEQ ID NO 409
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
ccgcatatgg cgctggcggc ggtggtgctg attccgctgg gcattgcggc ggtgagcaag    60
ggcgaggagc tg                                                       72

<210> SEQ ID NO 410
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
ccgcatatgg cggcgctgat tggcgcggtg ctggcgccgg tggtggcggt ggtgagcaag    60
ggcgaggagc tg                                                       72

<210> SEQ ID NO 411
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411

```
ccgcatatgg cggcggcggt ggcggtggcg ggcctggcgc cgctggcgct ggtgagcaag    60
ggcgaggagc tg                                                        72

<210> SEQ ID NO 412
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
ccgcatatga ttgcggtggc gattgcggcg attgtgccgc tggcggtgag caagggcgag    60
gagctg                                                               66

<210> SEQ ID NO 413
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
ccgcatatgg cggcggcggc ggtgctggcg gcgccggcgc tggcggtgag caagggcgag    60
gagctg                                                               66

<210> SEQ ID NO 414
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
ccgcatatgg cggcgctggc gctgggcgtg gcggcggcgc cggcggcggc gccggcggtg    60
agcaagggcg aggagctg                                                  78

<210> SEQ ID NO 415
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
ccgcatatgc tggcggtgct ggtgctgctg gtgctgctgc cggtgagcaa gggcgaggag    60
ctg                                                                  63

<210> SEQ ID NO 416
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
ccgcatatgg tggtggcggt gctggcgccg gtgctggtga gcaagggcga ggagctg       57

<210> SEQ ID NO 417
<211> LENGTH: 66
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
ccgcatatgg cggcgctgct gctgccgctg ctgctgctgc tgccggtgag caagggcgag      60
gagctg                                                                66

<210> SEQ ID NO 418
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
ccgcatatgc cggcggcggt ggcggcgctg ctggtgattg tgagcaaggg cgaggagctg      60

<210> SEQ ID NO 419
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
ccgcatatgc tgctgattgc ggcgctgctg ccggtgagca agggcgagga gctg            54

<210> SEQ ID NO 420
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
ccgcatatgg cggcggtggt gctgctgccg ctggcggcgg cgccggtgag caagggcgag      60
gagctg                                                                66

<210> SEQ ID NO 421
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
ccgcatatgg cggcggcggc ggcggcgctg ctggtgccgg tgagcaaggg cgaggagctg      60

<210> SEQ ID NO 422
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
ccgcatatgc tgccggtggt ggcgctgctg gcggtgagca agggcgagga gctg            54
```

```
<210> SEQ ID NO 423
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
ccgcatatgg cggcggcgct ggcggcgccg ctggcgctgc cggtgagcaa gggcgaggag    60
ctg                                                                 63

<210> SEQ ID NO 424
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
ccgcatatgc tgctgctggc gctgctgctg gcggcggtga gcaagggcga ggagctg       57

<210> SEQ ID NO 425
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
ccgcatatgg cggtggcggt ggtggcgctg ctggtgagca agggcgagga gctg          54

<210> SEQ ID NO 426
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
ccgcatatgc tgctgctgat tattgtgctg ctgattgtgc cggtgagcaa gggcgaggag    60
ctg                                                                 63

<210> SEQ ID NO 427
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 427
ccgcatatgc tggcgctggc ggcggcggtg gtgccggtga gcaagggcga ggagctg       57

<210> SEQ ID NO 428
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 428
ccgcatatgc cggcggcgct ggcgctgctg ctggtggcgg tgagcaaggg cgaggagctg    60
```

<210> SEQ ID NO 429
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
ccgcatatga ttgtggcgct gctgctggtg ccgctggtgc tggcgattgc ggcggtgctg      60
gtgagcaagg gcgaggagct g                                               81

<210> SEQ ID NO 430
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
ccgcatatga ttgtggcgct gctgctggtg ccggtgagca agggcgagga gctg            54

<210> SEQ ID NO 431
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 431
ccgcatatgc cgctggtgct ggcgattgcg gcggtgctgg tgagcaaggg cgaggagctg      60

<210> SEQ ID NO 432
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
ccgcatatgc cgctggtgct ggcggcgctg gtggcggtga gcaagggcga ggagctg         57

<210> SEQ ID NO 433
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
ccgcatatgg cggcggcgct gctggcggtg gcggtgagca agggcgagga gctg            54

<210> SEQ ID NO 434
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
ccgcatatgc cgctgctgct gctggcgctg gcggtgagca agggcgagga gctg            54

<210> SEQ ID NO 435
<211> LENGTH: 51
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 435
ccgcatatgg cgctggcgct ggtggtggcg gtgagcaagg gcgaggagct g     51

<210> SEQ ID NO 436
<211> LENGTH: 54
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 436
ccgcatatgg tggcggcggt ggtggtggcg gcggtgagca agggcgagga gctg     54

<210> SEQ ID NO 437
<211> LENGTH: 57
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 437
ccgcatatgc cgctgctgcc gctgctgctg ctggtggtga gcaagggcga ggagctg     57

<210> SEQ ID NO 438
<211> LENGTH: 69
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 438
ccgcatatgg tggtgctggt ggtggtgctg ccgctggcgg tgctggcggt gagcaagggc     60
gaggagctg                                                             69

<210> SEQ ID NO 439
<211> LENGTH: 60
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 439
ccgcatatgg cggcggcggt gccggtgctg gtggcggcgg tgagcaaggg cgaggagctg     60

<210> SEQ ID NO 440
<211> LENGTH: 66
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 440
ccgcatatgc cggcgctgct gctgctgctg ctggcggcgg tggtggtgag caagggcgag     60

```
<210> SEQ ID NO 441
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
ccgcatatgc cgctggcgat tctgctgctg ctgctgattg cgccggtgag caagggcgag    60
gagctg                                                              66

<210> SEQ ID NO 442
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
ccgcatatgc cgctgctggc gctggtgctg ctgctggcgc tgattgcggt gagcaagggc    60
gaggagctg                                                           69

<210> SEQ ID NO 443
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 443
ccgcatatgg tggtggcggt gctggcgctg gtgctggcgg cgctggtgag caagggcgag    60
gagctg                                                              66

<210> SEQ ID NO 444
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444
ccgcatatgc cgctgctgct gctgctgccg gcgctggtga gcaagggcga ggagctg       57

<210> SEQ ID NO 445
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
ccgcatatgc tggcggcggt ggcggcgctg gcggtggtgg tgccggtgag caagggcgag    60
gagctg                                                              66

<210> SEQ ID NO 446
<211> LENGTH: 66
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 446
ccgcatatgc tgctgctgct ggtgctgatt ctgccgctgg cggcggtgag caagggcgag      60
gagctg                                                                 66

<210> SEQ ID NO 447
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
ccgcatatgc tggcggtggt ggtggtggcg gcggtggtga gcaagggcga ggagctg         57

<210> SEQ ID NO 448
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
ccgcatatgg tgctgctggc ggcggcgctg attgcggtga gcaagggcga ggagctg         57

<210> SEQ ID NO 449
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
ccgcatatgc tgattgcgct gctggcggcg ccgctggcgg tgagcaaggg cgaggagctg      60

<210> SEQ ID NO 450
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 450
ccgcatatgc tggcgctgct gctgctggcg gcggtgagca agggcgagga gctg            54

<210> SEQ ID NO 451
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
ccgcatatgc tgctggcggc ggcgctgctg ctgctgctgc tggcggtgag caagggcgag      60
gagctg                                                                 66

<210> SEQ ID NO 452

```
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452
ccgcatatgg tgattattgc gctgattgtg attgtggcgg tgagcaaggg cgaggagctg      60

<210> SEQ ID NO 453
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
ccgcatatgg tggtgctggt ggtggcggcg gtgctggcgc tggtgagcaa gggcgaggag      60
ctg                                                                   63

<210> SEQ ID NO 454
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
ccgcatatgg tggcggtggc gattgcggtg gtgctggtga gcaagggcga ggagctg         57

<210> SEQ ID NO 455
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455
ccgcatatgc cgctgattgt ggtggtggcg gcggcggtgg tggcggtggt gagcaagggc      60
gaggagctg                                                             69

<210> SEQ ID NO 456
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
ccgcatatgc cgctggcggt ggcggtggcg gcggtggcgg cggtgagcaa gggcgaggag      60
ctg                                                                   63

<210> SEQ ID NO 457
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
```

-continued ccgcatatgg cggcgattgc gctggtggcg gtggtgctgg tgagcaaggg cgaggagctg        60

<210> SEQ ID NO 458
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
ccgcatatgg cggcggcgct ggcggcgatt gcggtgattg tgagcaaggg cgaggagctg        60

<210> SEQ ID NO 459
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
ccgcatatgg cggcggcgcc ggcggtggcg gcggtgagca agggcgagga gctg              54

<210> SEQ ID NO 460
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
ccgcatatgc tgctgctggc ggcgctgccg gtgagcaagg gcgaggagct g                 51

<210> SEQ ID NO 461
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
ccgcatatgg cgctgctggc ggtggtggcg gcggtgagca agggcgagga gctg              54

<210> SEQ ID NO 462
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
ccgcatatgg cggtggtggt ggtgctgccg attctgctgg tgagcaaggg cgaggagctg        60

<210> SEQ ID NO 463
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
ccgcatatgg cgctggcgct gctgctgctg gtgccggtga gcaagggcga ggagctg           57

<210> SEQ ID NO 464
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
ccgcatatgc tggtggtgct gctggcggcg ctgctggtgc tggtgagcaa gggcgaggag    60
ctg                                                                  63

<210> SEQ ID NO 465
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
ccgcatatgc cggtgctgct gctgctggcg ccggtgagca agggcgagga gctg          54

<210> SEQ ID NO 466
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
ccgcatatgg cgctggcggt ggtggcggcg ccggtgagca agggcgagga gctg          54

<210> SEQ ID NO 467
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 467
ccgcatatgg tgattgtggc gctgctggcg gtggtgagca agggcgagga gctg          54

<210> SEQ ID NO 468
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 468
ccgcatatgg cgctggtgct gccgctggcg ccggtgagca agggcgagga gctg          54

<210> SEQ ID NO 469
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 469
ccgcatatgg cggtggcgct gctgattctg gcggtggtga gcaagggcga ggagctg       57

```
<210> SEQ ID NO 470
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 470
ccgcatatgg tgctgctggc ggtgattccg gtgagcaagg gcgaggagct g            51

<210> SEQ ID NO 471
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 471
ccgcatatgc tgattgtggc ggcggtggtg gtggtggcgg tgctgattgt gagcaagggc   60
gaggagctg                                                          69

<210> SEQ ID NO 472
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 472
ccgcatatgg cggtggtggt ggcggcgccg gtgagcaagg gcgaggagct g            51

<210> SEQ ID NO 473
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 473
ccgcatatgc tggcggcggt gctgctgctg attccggtga gcaagggcga ggagctg      57

<210> SEQ ID NO 474
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 474
ccgcatatgc tgctgctgct gctgctggcg gtggtgccgg tgagcaaggg cgaggagctg   60

<210> SEQ ID NO 475
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 475
ccgcatatgg cggtggcgct ggtggcggtg gtggcggtgg cggtgagcaa gggcgaggag   60
```

```
ctg                                                                63
```

<210> SEQ ID NO 476
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 476

```
ccgcatatgc tggtggcggc gctgctggcg gtgctggtga gcaagggcga ggagctg    57
```

<210> SEQ ID NO 477
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 477

```
ccgcatatgc tgctggcggc ggcggcggcg ctgctgctgg cggtgagcaa gggcgaggag    60
ctg                                                                  63
```

<210> SEQ ID NO 478
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 478

```
ccgcatatgc tggcggtgct ggcggcggcg ccggtgagca agggcgagga gctg    54
```

<210> SEQ ID NO 479
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 479

```
ccgcatatgg tggtggtgct gctggtgctg ctggcgctgg tggtggtggt gagcaagggc    60
gaggagctg                                                            69
```

<210> SEQ ID NO 480
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 480

```
ccgcatatgg tggtgattgc ggtggtgccg gtgagcaagg gcgaggagct g              51
```

<210> SEQ ID NO 481
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 481
ccgcatatgg tgctgctggt gctgctggcg ctggtggtga gcaagggcga ggagctg      57

<210> SEQ ID NO 482
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 482
ccgcatatgg tgctgctggt gctgctggcg ctggtggtga gcaagggcga ggagctg      57

<210> SEQ ID NO 483
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 483
ccgcatatgc cggtgctggt gccggcggtg ccggtgagca agggcgagga gctg         54

<210> SEQ ID NO 484
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 484
ccgcatatgc cggcgctggc gctggcgctg gcggtgagca agggcgagga gctg         54

<210> SEQ ID NO 485
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 485
ccgcatatgg cggcggcggc gccggcgctg gcggtgagca agggcgagga gctg         54

<210> SEQ ID NO 486
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 486
ccgcatatga ttgtgctgcc ggtgctggcg gcgccggtga gcaagggcga ggagctg      57

<210> SEQ ID NO 487
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487
```

```
ccgcatatgc tggtgctgct gctgctgccg ctgctgattg tgagcaaggg cgaggagctg    60
```

<210> SEQ ID NO 488
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488

```
ccgcatatgc tggcggcggt ggcgccggcg ctggcggtgg tggtgagcaa gggcgaggag    60
ctg                                                                  63
```

<210> SEQ ID NO 489
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489

```
ccgcatatga ttctggtgct ggtgctgccg attgtgagca agggcgagga gctg          54
```

<210> SEQ ID NO 490
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490

```
ccgcatatga ttctgctgcc gctgctgctg ctgccggtga gcaagggcga ggagctg       57
```

<210> SEQ ID NO 491
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 491

```
ccgcatatga ttgcgccggc ggtggtggcg gcgctgccgg tgagcaaggg cgaggagctg    60
```

<210> SEQ ID NO 492
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 492

```
ccgcatatgc tgctgctggt ggcggtggtg ccgctgctgg tgccggtgag caagggcgag    60
gagctg                                                               66
```

<210> SEQ ID NO 493
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 493
ccgcatatgc tgattctgct gctgctgccg attattgtga gcaagggcga ggagctg        57

<210> SEQ ID NO 494
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 494
ccgcatatgg cggtgctggc ggcgccggcg gtgctggtgg tgagcaaggg cgaggagctg     60

<210> SEQ ID NO 495
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
ccgcatatgc tggcgctgcc ggtgctgctg ctggcggtga gcaagggcga ggagctg        57

<210> SEQ ID NO 496
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 496
ccgcatatgc tggcgctggc gctgctgctg gtgagcaagg gcgaggagct g              51

<210> SEQ ID NO 497
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 497
ccgcatatgg tggcggtgcc gctgctggtg gtggcggtga gcaagggcga ggagctg        57

<210> SEQ ID NO 498
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 498
ccgcatatgg cggtggcggt ggcgccggtg gcggcggcgg cggtgagcaa gggcgaggag     60
ctg                                                                   63

<210> SEQ ID NO 499
<211> LENGTH: 62
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 499
cccatatggc ggcggcggtg gtggcggcgg tgccggcggc ggtgagcaag ggcgaggagc    60
tg                                                                  62

<210> SEQ ID NO 500
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 500
cccatatggc gctgctggcg gcgctgctgg cgccggtgag caagggcgag gagctg        56

<210> SEQ ID NO 501
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 501
cccattgcgc tggcgctgct ggtgccggtg agcaagggcg aggagctg                 48

<210> SEQ ID NO 502
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 502
ccgcatatgg cgctgctggc ggcgctgctg gcgctgctgg cgctgctggt ggtgagcaag    60
ggcgaggagc tg                                                       72

<210> SEQ ID NO 503
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 503
ccgcatatgg cggcggcgct gccgctgctg gtgctgctgc cggtgagcaa gggcgaggag    60
ctg                                                                 63

<210> SEQ ID NO 504
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 504
cccatatggc ggcggcggtg ccggcggcgc tggcgccggt gagcaagggc gaggagctg     59

<210> SEQ ID NO 505
<211> LENGTH: 58
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 505
cccattggcg gcgctggcgg tggcggcgct ggcggcggtg agcaagggcg aggagctg        58

<210> SEQ ID NO 506
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 506
cccattggcg gtgctggcgg cggcggtgcc ggtgagcaag ggcgaggagc tg              52

<210> SEQ ID NO 507
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 507
ccgcatatgg tggcggcgct gccggcgccg gcggtgagca agggcgagga gctg            54

<210> SEQ ID NO 508
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 508
ccgcatatgg cgctggcgct ggcggtgccg gcggtgctgc cggtgagcaa gggcgaggag      60
ctg                                                                   63

<210> SEQ ID NO 509
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 509
ccgcatatgg cggcgctgct gccggcggcg gtggcggtgc cggtgagcaa gggcgaggag      60
ctg                                                                   63

<210> SEQ ID NO 510
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 510
ccgcatatgg cggtggtggt ggcgctggcg ccggtgagca agggcgagga gctg            54

<210> SEQ ID NO 511
<211> LENGTH: 72
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 511
ccgcatatgg cggcggcggt ggcgctgccg gcggcggcgg cgctgctggc ggtgagcaag    60
ggcgaggagc tg                                                        72

<210> SEQ ID NO 512
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 512
ccgcatatgg cggtggtgct gccgctggcg ctggtggcgg tggcgccggt gagcaagggc    60
gaggagctg                                                            69

<210> SEQ ID NO 513
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 513
ccgcatatgc tggtggcgct gccgctgctg ccggtgagca agggcgagga gctg          54

<210> SEQ ID NO 514
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 514
ccgcatatgg tggtggtgcc gctgctgctg attgtgccgg tgagcaaggg cgaggagctg    60

<210> SEQ ID NO 515
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 515
ccgcatatgc tggcggtggt gctggcggtg ccggtgagca agggcgagga gctg          54

<210> SEQ ID NO 516
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 516
ccgcatatgc tgctggcggt gccgattctg ctggtgccgg tgagcaaggg cgaggagctg    60

```
<210> SEQ ID NO 517
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 517
ccgcatatgc tggtggcgct ggtgctgctg ccggtgagca agggcgagga gctg        54

<210> SEQ ID NO 518
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 518
ccgcatatgc tggtgctgct gctggcggtg ctgctgctgg cggtgctgcc ggtgagcaag    60
ggcgaggagc tg                                                        72

<210> SEQ ID NO 519
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 519
ccgcatatgc tgctggcgcc ggtggtggcg ctggtgattc tgccggtgag caagggcgag    60
gagctg                                                               66

<210> SEQ ID NO 520
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 520
ccgcatatgg tgctggcggt gctggcggtg ccggtgctgc tgctgccggt gagcaagggc    60
gaggagctg                                                            69

<210> SEQ ID NO 521
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 521
ccgcatatgg tggtgattgc ggtggtgccg gtggtggtgg tgagcaaggg cgaggagctg    60

<210> SEQ ID NO 522
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 522
```
ccgcatatgc tgctggtgct gctggcgctg gtggtggtgc cggtgagcaa gggcgaggag    60
ctg                                                                  63

<210> SEQ ID NO 523
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 523
ccgcatatgg tgctgctggc gctgccggtg gtggcggcgc cggtgagcaa gggcgaggag    60
ctg                                                                  63

<210> SEQ ID NO 524
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 524
ccgcatatgg cggtggtggt gccggcgatt gtgctggcgg cgccggtgag caagggcgag    60
gagctg                                                               66

<210> SEQ ID NO 525
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 525
ccgcatatgg cggtgctggt gccggcggcg gcgctggtgc cggtgagcaa gggcgaggag    60
ctg                                                                  63

<210> SEQ ID NO 526
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 526
ccgcatatgg tggtggcggc gctgccgctg gtgctgccgg tgagcaaggg cgaggagctg    60

<210> SEQ ID NO 527
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 527
ccgcatatgg cggcggtggc gctgccggcg gcggcgccgg tgagcaaggg cgaggagctg    60

<210> SEQ ID NO 528
<211> LENGTH: 54
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 528
ccgcatatgc tgattgcgct gccgctgctg ccggtgagca agggcgagga gctg         54

<210> SEQ ID NO 529
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 529
ccgcatatgc tgctggcgct gccgctggtg ctggtgctgg cgctgccggt gagcaagggc    60
gaggagctg                                                           69

<210> SEQ ID NO 530
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 530
ccgcatatga ttgtgccgct gctgctggcg gcgccggtga gcaagggcga ggagctg       57

<210> SEQ ID NO 531
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 531
ccgcatatgc tgctgctggc gccgctgctg ctggcgccgg tgagcaaggg cgaggagctg    60

<210> SEQ ID NO 532
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 532
ccgcatatgc tggcggcgct gccggtggcg gcggtgccgg tgagcaaggg cgaggagctg    60

<210> SEQ ID NO 533
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 533
ccgcatatgg cgctggcggt gattgtgctg gtgctgctgg tgagcaaggg cgaggagctg    60

<210> SEQ ID NO 534
<211> LENGTH: 63
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 534
ccgcatatgc tggcgctgct gctgccggcg gcgctgattc cggtgagcaa gggcgaggag    60
ctg                                                                 63

<210> SEQ ID NO 535
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 535
ccgcatatgg cgctgctgcc gctgctggcg gtggtgctgc cgccggtgag caagggcgag    60
gagctg                                                              66

<210> SEQ ID NO 536
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 536
ccgcatatgg cgattgcggt gccggtgctg gcggcgccgg tgagcaaggg cgaggagctg    60

<210> SEQ ID NO 537
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 537
ccgcatatgg cggcggcgcc ggtgctgctg ctgctgctgc cggtgagcaa gggcgaggag    60
ctg                                                                 63

<210> SEQ ID NO 538
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 538
ccgcatatgg cggcggcgcc ggtgctgctg ctgctgctgc cggtgagcaa gggcgaggag    60
ctg                                                                 63

<210> SEQ ID NO 539
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 539

```
ccgcatatgg cggcgctggc ggcgctggtg gtggcggcgc cgccggtgag caagggcgag    60
gagctg                                                               66
```

<210> SEQ ID NO 540
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 540

```
ccgcatatgg cggcgctggc ggcggtgccg ctggcgctgg cgccggtgag caagggcgag    60
gagctg                                                               66
```

<210> SEQ ID NO 541
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 541

```
ccgcatatgg cgctggcggt ggcggcgccg gcgctggcgc tgctgccgcc ggtgagcaag    60
ggcgaggagc tg                                                        72
```

<210> SEQ ID NO 542
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 542

```
ccgcatatgc tggtggcgct ggtgctgctg ccggtgagca agggcgagga gctg           54
```

<210> SEQ ID NO 543
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 543

```
ccgcatatgc tggtgctgct gctggcggtg ctgctgctgg cggtgctgcc ggtgagcaag    60
ggcgaggagc tg                                                        72
```

<210> SEQ ID NO 544
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 544

```
ccgcatatgc tgctggcgcc ggtggtggcg ctggtgattc tgccggtgag caagggcgag    60
gagctg                                                               66
```

<210> SEQ ID NO 545
<211> LENGTH: 69

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 545
ccgcatatgg tgctggcggt gctggcggtg ccggtgctgc tgctgccggt gagcaagggc      60
gaggagctg                                                             69

<210> SEQ ID NO 546
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 546
ccgcatatgg tggtgattgc ggtggtgccg gtggtggtgg tgagcaaggg cgaggagctg     60

<210> SEQ ID NO 547
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 547
ccgcatatgc tgctggtgct gctggcgctg gtggtggtgc cggtgagcaa gggcgaggag     60
ctg                                                                  63

<210> SEQ ID NO 548
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 548
ccgcatatgg tgctgctggc gctgccggtg gtggcggcgc cggtgagcaa gggcgaggag     60
ctg                                                                  63

<210> SEQ ID NO 549
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 549
ccgcatatgg cggtggtggt gccggcgatt gtgctggcgg cgccggtgag caagggcgag     60
gagctg                                                               66

<210> SEQ ID NO 550
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 550
```
ccgcatatgg cggtgctggt gccggcggcg gcgctggtgc cggtgagcaa gggcgaggag    60
ctg                                                                 63

<210> SEQ ID NO 551
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 551
ccgcatatgg tggtggcggc gctgccgctg gtgctgccgg tgagcaaggg cgaggagctg    60

<210> SEQ ID NO 552
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 552
ccgcatatgg cggcggtggc gctgccggcg gcggcgccgg tgagcaaggg cgaggagctg    60

<210> SEQ ID NO 553
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 553
ccgcatatgc tgattgcgct gccgctgctg ccggtgagca agggcgagga gctg          54

<210> SEQ ID NO 554
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 554
ccgcatatgc tgctggcgct gccgctggtg ctggtgctgg cgctgccggt gagcaagggc    60
gaggagctg                                                           69

<210> SEQ ID NO 555
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 555
ccgcatatga ttgtgccgct gctgctggcg gcgccggtga gcaagggcga ggagctg       57

<210> SEQ ID NO 556
<211> LENGTH: 60
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 556
ccgcatatgc tgctgctggc gccgctgctg ctggcgccgg tgagcaaggg cgaggagctg    60

<210> SEQ ID NO 557
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 557
ccgcatatgc tggcggcgct gccggtggcg gcggtgccgg tgagcaaggg cgaggagctg    60

<210> SEQ ID NO 558
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 558
ccgcatatgg cgctggcggt gattgtgctg gtgctgctgg tgagcaaggg cgaggagctg    60

<210> SEQ ID NO 559
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 559
ccgcatatgc tggcgctgct gctgccggcg gcgctgattc cggtgagcaa gggcgaggag    60
ctg                                                                  63

<210> SEQ ID NO 560
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 560
ccgcatatgc tggcggcggt ggtgccggtg gcggcggcgg tgccggtgag caagggcgag    60
gagctg                                                               66

<210> SEQ ID NO 561
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 561
ccgcatatgg tggcggcgcc ggcggcggcg gcgccggtga gcaagggcga ggagctg       57

<210> SEQ ID NO 562
<211> LENGTH: 54
<212> TYPE: DNA
<213> ORGANISM: Artificial Sequence
<220> FEATURE:

<223> OTHER INFORMATION: Description of Artificial Sequence: Synthetic
     primer

<400> SEQUENCE: 562
ccgcatatgg cggtgccggt gccggtgccg ctggtgagca agggcgagga gctg      54

<210> SEQ ID NO 563
<211> LENGTH: 60
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 563
ccgcatatgc tgctgattct gccgattgtg ctgctgccgg tgagcaaggg cgaggagctg      60

<210> SEQ ID NO 564
<211> LENGTH: 63
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 564
ccgcatatgg cgctggcgct gccggcgctg gcgattgcgc cggtgagcaa gggcgaggag      60
ctg      63

<210> SEQ ID NO 565
<211> LENGTH: 57
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 565
ccgcatatgg cggtgattcc gattctggcg gtgccggtga gcaagggcga ggagctg      57

<210> SEQ ID NO 566
<211> LENGTH: 63
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 566
ccgcatatgc tgattctgct gctgccggcg gtggcgctgc cggtgagcaa gggcgaggag      60
ctg      63

<210> SEQ ID NO 567
<211> LENGTH: 60
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 567
ccgcatatga ttgtgctggc gccggtgccg gcggcggcgg tgagcaaggg cgaggagctg      60

<210> SEQ ID NO 568
<211> LENGTH: 63
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 568
ccgcatatgg tggtggtggt gccggtgctg gcggcggcgg cggtgagcaa gggcgaggag    60
ctg                                                                 63

<210> SEQ ID NO 569
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 569
ccgcatatgc tggtggcggt ggcggcgccg gtgagcaagg gcgaggagct g             51

<210> SEQ ID NO 570
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 570
ccgcatatgc tggtgctggc ggcgccggcg gcgctgccgg tgagcaaggg cgaggagctg    60

<210> SEQ ID NO 571
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 571
ccgcatatgc tgattgcgcc ggcggcggcg gtgccggtga gcaagggcga ggagctg       57

<210> SEQ ID NO 572
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 572
ccgcatatgg cgctggcggc gctgccgatt gcgctgccgg tgagcaaggg cgaggagctg    60

<210> SEQ ID NO 573
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 573
ccgcatatgg cggtgctgct gctgccggcg gcggcggtga gcaagggcga ggagctg       57

<210> SEQ ID NO 574
<211> LENGTH: 57
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 574
ccgcatatga ttgcgctggc gctgctgccg ctgctggtga gcaagggcga ggagctg      57

<210> SEQ ID NO 575
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 575
ccgcatatgg tgctgctggc ggcggcgctg attgcgccgg tgagcaaggg cgaggagctg   60

<210> SEQ ID NO 576
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 576
ccgcatatgg cgccggcggt gctgccgccg gtggtggtga ttgtgagcaa gggcgaggag   60
ctg                                                                 63

<210> SEQ ID NO 577
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 577
ccgcatatgg tggtgggcct gctggtggcg gcgctggtga gcaagggcga ggagctg      57

<210> SEQ ID NO 578
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 578
ccgcatatgg cggcgattgc ggcggcggcg ccgctggcgg cggtgagcaa gggcgaggag   60
ctg                                                                 63

<210> SEQ ID NO 579
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 579
ccgcatatgc tgctgctggc ggtggcgccg gtgagcaagg gcgaggagct g            51

<210> SEQ ID NO 580
```

```
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 580
ccgcatatgc tgattctgct gctgccgctg gcggcgctgg tgagcaaggg cgaggagctg      60

<210> SEQ ID NO 581
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 581
ccgcatatgg cgctgctgct gctggtgctg gcggtgagca agggcgagga gctg            54

<210> SEQ ID NO 582
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 582
ccgcatatgc tgctgctgct gctgctgccg ctggcggtga gcaagggcga ggagctg         57

<210> SEQ ID NO 583
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 583
ccgcatatgc tggcgctgcc gctgctgctg ccggtgagca agggcgagga gctg            54

<210> SEQ ID NO 584
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 584
ccgcatatgc tgctggtgct gccgctgctg attgtgagca agggcgagga gctg            54

<210> SEQ ID NO 585
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 585
ccgcatatgc tgccgctgct gccggcggcg ctggtggtga gcaagggcga ggagctg         57

<210> SEQ ID NO 586
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 586 ccgggccta ggtggcctag atctatt                                              27

<210> SEQ ID NO 587
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Pro Pro Lys Lys Lys Arg Lys Val
1               5

<210> SEQ ID NO 588
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Met Met Ser Phe Val Ser Leu Leu Leu Val Gly Ile Leu Phe Trp Ala
1               5                   10                  15

Thr Glu Ala Glu Gln Leu Thr Lys Cys Glu Val Phe Gln
            20                  25

<210> SEQ ID NO 589
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Lys Asp Glu Leu
1

<210> SEQ ID NO 590
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 591
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (3)..(7)
<223> OTHER INFORMATION: Any amino acid

<400> SEQUENCE: 591

Arg Leu Xaa Xaa Xaa Xaa Xaa His Leu
1               5

<210> SEQ ID NO 592
<211> LENGTH: 16
<212> TYPE: PRT
<213> ORGANISM: Unknown
<220> FEATURE:
<223> OTHER INFORMATION: Description of Unknown: Penetratin peptide

<400> SEQUENCE: 592

Arg Gln Ile Lys Ile Trp Phe Gln Asn Arg Arg Met Lys Trp Lys Lys
1               5                   10                  15

<210> SEQ ID NO 593
<211> LENGTH: 9
<212> TYPE: PRT
<213> ORGANISM: Human immunodeficiency virus

<400> SEQUENCE: 593

Arg Lys Lys Arg Arg Gln Arg Arg Pro
1               5

<210> SEQ ID NO 594
<211> LENGTH: 26
<212> TYPE: PRT
<213> ORGANISM: Unknown
<220> FEATURE:
<223> OTHER INFORMATION: Description of Unknown: Transportan peptide

<400> SEQUENCE: 594

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 595
<211> LENGTH: 21
<212> TYPE: PRT
<213> ORGANISM: Unknown
<220> FEATURE:
<223> OTHER INFORMATION: Description of Unknown: Buforin II peptide

<400> SEQUENCE: 595

Thr Arg Ser Ser Arg Ala Gly Leu Gln Phe Arg Val Gly Arg Val His
1               5                   10                  15

Arg Leu Leu Arg Lys
            20

<210> SEQ ID NO 596
<211> LENGTH: 18
<212> TYPE: PRT
<213> ORGANISM: Unknown
<220> FEATURE:
<223> OTHER INFORMATION: Description of Unknown: Model amphiphatic
      peptide peptide

<400> SEQUENCE: 596

Lys Leu Ala Leu Lys Ala Ser Leu Lys Ala Leu Lys Ala Ala Leu Lys
1               5                   10                  15

Leu Ala
```

```
<210> SEQ ID NO 597
<211> LENGTH: 16
<212> TYPE: PRT
<213> ORGANISM: Unknown
<220> FEATURE:
<223> OTHER INFORMATION: Description of Unknown: K-FGF peptide

<400> SEQUENCE: 597

Ala Ala Val Ala Leu Leu Pro Ala Val Leu Leu Ala Leu Leu Ala Pro
 1               5                  10                  15

<210> SEQ ID NO 598
<211> LENGTH: 10
<212> TYPE: PRT
<213> ORGANISM: Unknown
<220> FEATURE:
<223> OTHER INFORMATION: Description of Unknown: Ku 70 peptide

<400> SEQUENCE: 598

Val Pro Met Leu Lys Pro Met Leu Lys Glu
 1               5                  10

<210> SEQ ID NO 599
<211> LENGTH: 28
<212> TYPE: PRT
<213> ORGANISM: Unknown
<220> FEATURE:
<223> OTHER INFORMATION: Description of Unknown: Prion peptide

<400> SEQUENCE: 599

Met Ala Asn Leu Gly Tyr Trp Leu Leu Ala Leu Phe Val Thr Met Trp
 1               5                  10                  15

Thr Asp Val Gly Leu Cys Lys Lys Arg Pro Lys Pro
             20                  25

<210> SEQ ID NO 600
<211> LENGTH: 18
<212> TYPE: PRT
<213> ORGANISM: Unknown
<220> FEATURE:
<223> OTHER INFORMATION: Description of Unknown: pVEC peptide

<400> SEQUENCE: 600

Leu Leu Ile Ile Leu Arg Arg Arg Ile Arg Lys Gln Ala His Ala His
 1               5                  10                  15

Ser Lys

<210> SEQ ID NO 601
<211> LENGTH: 21
<212> TYPE: PRT
<213> ORGANISM: Unknown
<220> FEATURE:
<223> OTHER INFORMATION: Description of Unknown: Pep-1 peptide

<400> SEQUENCE: 601

Lys Glu Thr Trp Trp Glu Thr Trp Trp Thr Glu Trp Ser Gln Pro Lys
 1               5                  10                  15

Lys Lys Arg Lys Val
             20

<210> SEQ ID NO 602
<211> LENGTH: 18
<212> TYPE: PRT
<213> ORGANISM: Unknown
<220> FEATURE:
```

<223> OTHER INFORMATION: Description of Unknown: SynB1 peptide

<400> SEQUENCE: 602

Arg Gly Gly Arg Leu Ser Tyr Ser Arg Arg Arg Phe Ser Thr Ser Thr
1               5                   10                  15

Gly Arg

<210> SEQ ID NO 603
<211> LENGTH: 15
<212> TYPE: PRT
<213> ORGANISM: Unknown
<220> FEATURE:
<223> OTHER INFORMATION: Description of Unknown: Pep-7 peptide

<400> SEQUENCE: 603

Ser Asp Leu Trp Glu Met Met Met Val Ser Leu Ala Cys Gln Tyr
1               5                   10                  15

<210> SEQ ID NO 604
<211> LENGTH: 12
<212> TYPE: PRT
<213> ORGANISM: Unknown
<220> FEATURE:
<223> OTHER INFORMATION: Description of Unknown: HN-1 peptide

<400> SEQUENCE: 604

Thr Ser Pro Leu Leu Ile His Asn Gly Gln Lys Leu
1               5                   10

<210> SEQ ID NO 605
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Met Gly Ile Leu Leu Gly Leu Leu Leu Gly His Leu Thr Val Asp
1               5                   10                  15

Thr Tyr Gly Arg Pro Ile Leu
            20

<210> SEQ ID NO 606
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Ile Leu Leu Gly Leu Leu Leu Gly His Leu Thr Val Asp Thr Tyr
1               5                   10                  15

Gly Arg Pro Ile Leu
            20

<210> SEQ ID NO 607
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

-continued

```
Ile Leu Leu Gly Leu Leu Leu Gly Leu Val Gly Pro Ile Leu
1               5                   10                  15

<210> SEQ ID NO 608
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Ile Leu Leu Pro Leu Leu Leu Gly Leu Val Pro Pro Ile Leu
1               5                   10                  15

<210> SEQ ID NO 609
<211> LENGTH: 11
<212> TYPE: PRT
<213> ORGANISM: Human immunodeficiency virus

<400> SEQUENCE: 609

Tyr Gly Arg Lys Lys Arg Arg Gln Arg Arg Arg
1               5                   10

<210> SEQ ID NO 610
<211> LENGTH: 11
<212> TYPE: PRT
<213> ORGANISM: Human immunodeficiency virus

<400> SEQUENCE: 610

Tyr Ala Arg Val Arg Arg Arg Gly Pro Arg Arg
1               5                   10

<210> SEQ ID NO 611
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Val Leu Thr Thr Thr Ala Val Thr Val Val Cys Ala Ile Thr Val Leu
1               5                   10                  15

Ala Ala Pro Gly
            20

<210> SEQ ID NO 612
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Met Ala Ala Ala Met Pro Leu Ala Leu Leu Val Leu Leu Leu Leu Gly
1               5                   10                  15

Pro Gly Gly Trp Cys Leu Ala
            20

<210> SEQ ID NO 613
<211> LENGTH: 23
<212> TYPE: PRT
<213> ORGANISM: Artificial Sequence
<220> FEATURE:
<223> OTHER INFORMATION: Description of Artificial Sequence: Synthetic
```

```
                               peptide

<400> SEQUENCE: 613

Met Ala Ala Gly Ser Arg Thr Ser Leu Leu Ala Phe Ala Leu Leu
1               5                   10                  15

Cys Leu Pro Trp Leu Gln Glu
            20

<210> SEQ ID NO 614
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Leu Leu Gly Lys Ala Leu Ala Ala Val Ser Leu Ser Leu Ala Leu Ala
1               5                   10                  15

Ser Val Thr Ile Arg Ser Ser
            20

<210> SEQ ID NO 615
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Thr Ser Pro Val Leu Leu Ala Ser Leu Gly Val Gly Leu Val Thr Leu
1               5                   10                  15

Leu Gly Leu Ala Val Gly Ser
            20

<210> SEQ ID NO 616
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Trp Ile Ala Gly Ala Ala Ala Ala Val Leu Leu Ala Ala Gly Gly Ile
1               5                   10                  15

Thr Tyr Ala Val Ala Gly Asp
            20

<210> SEQ ID NO 617
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

Leu Ala Leu Thr Val Cys Gly Ile Val Val Ala Val Val Val Ile Gly
1               5                   10                  15

Leu Phe Val Phe Gly Leu
            20

<210> SEQ ID NO 618
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Thr Ala Ala Leu Ile Gly Ala Val Leu Ala Pro Val Val Ala Val Ser
1               5                   10                  15

Leu Pro Ala

<210> SEQ ID NO 619
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Gln Phe Leu Ala Val Cys Gly Leu Pro Val Val Ala Leu Leu Ala Thr
1               5                   10                  15

Ala Leu Phe Ala Pro Leu Pro
            20

<210> SEQ ID NO 620
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Leu Leu Val Ala Leu Gly Gly Ala Val Val Ala Ala Pro Val Ala Ala
1               5                   10                  15

Ala Val Ala Pro His Ala Leu
            20

<210> SEQ ID NO 621
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Arg Leu Leu Leu Val Leu Ala Val Leu Leu Ala Val Leu Thr Pro Thr
1               5                   10                  15

Ala Pro Glu Ala Leu Ala
            20

<210> SEQ ID NO 622
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

Leu Leu Asp Ile Leu Leu Leu Leu Pro Leu Leu Ile Val Cys Ser Leu
1               5                   10                  15

Glu Ser Phe Val Lys Leu Phe
```

<210> SEQ ID NO 623
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 623

Ser Val Leu Arg Gly Leu Ala Ala Ala Leu Ala Val Leu Pro Leu
1               5                   10                  15

Thr Val Ser Thr Pro Ala His
            20

<210> SEQ ID NO 624
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 624

Cys Ser Phe Leu Met Leu Leu Leu Pro Leu Leu Leu Leu Val Ala
1               5                   10                  15

Thr Thr Gly Pro Val Gly
            20

<210> SEQ ID NO 625
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 625

Ala Leu Thr Ala Ser Ala Ala Thr Ala Ala Ala Ala Ala Leu Gly Leu
1               5                   10                  15

Ala Ala Ala Val Pro Ala Gln
            20

<210> SEQ ID NO 626
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 626

Leu Leu Leu Ala Ala Leu Leu Leu Ile Ala Phe Ala Ala Val Lys Leu
1               5                   10                  15

Val Leu Leu Gln Trp
            20

<210> SEQ ID NO 627
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 627

```
Met Ala Ala Leu Ala Ala Val Val Leu Ile Pro Leu Gly Ile Ala Ala
1               5                   10                  15

Thr Ser Phe Ala Leu
            20

<210> SEQ ID NO 628
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Thr Ala Ala Leu Ile Gly Ala Val Leu Ala Pro Val Val Ala Val Ser
1               5                   10                  15

Leu Pro Ala

<210> SEQ ID NO 629
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Ala Ala Ala Val Ala Val Ala Gly Leu Ala Pro Leu Ala Leu
1               5                   10

<210> SEQ ID NO 630
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Gly Ala Ala Gly Ile Ala Val Ala Ile Ala Ala Ile Val Pro Leu Ala
1               5                   10                  15

Asp Pro Ala Pro Ala
            20

<210> SEQ ID NO 631
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Gly Leu Ala Ala Asn Val Ala Met Ala Ala Ala Ala Thr Val Leu Ala
1               5                   10                  15

Ala Pro Ala Leu Ala
            20

<210> SEQ ID NO 632
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 632

Leu Ala Ala Val Gly Ala Ala Leu Ala Leu Gly Val Ala Ala Ala Pro
1               5                   10                  15

Ala Gln Ala Ala Pro Ala
            20

<210> SEQ ID NO 633
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Leu Ala Ser Val Leu Thr Val Leu Leu Thr Val Leu Leu Pro Leu Val
1               5                   10                  15

Pro Ala Trp Pro Ala Ala Gly
            20

<210> SEQ ID NO 634
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Thr Ala Ala Arg Thr Val Val Ala Val Leu Ala Pro Val Leu Phe Ala
1               5                   10                  15

Leu Gln Phe Phe Ala Pro Ser
            20

<210> SEQ ID NO 635
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Ala Ala Pro Ala Ala Leu Leu Leu Pro Leu Leu Leu Leu Leu Pro Leu
1               5                   10                  15

Thr Gly Cys Asp Arg Leu Ala
            20

<210> SEQ ID NO 636
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Ala Leu Ala Val Gly Ala Ala Val Ala Ala Leu Leu Val Ile Gly Gly
1               5                   10                  15

Ser Val Trp Ala Val Thr Ala
            20

<210> SEQ ID NO 637
<211> LENGTH: 23
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 637

Ser Val Arg Ala Tyr Ser Leu Leu Ile Ala Ala Leu Leu Pro Leu Ser
1               5                   10                  15

Ala Cys Gly Ile Pro Glu Thr
            20

<210> SEQ ID NO 638
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Thr Arg Ala Leu Ser Ala Ala Val Val Leu Leu Gly Leu Ala Ala Ala
1               5                   10                  15

Pro Ala Ala Ala Asp Ser Ser
            20

<210> SEQ ID NO 639
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 639

Leu Trp Ala Ala Ala Ala Ala Ala Leu Thr Leu Val Gly Ala Ala Pro
1               5                   10                  15

Ala Ala Ala Gln Ala Ala Pro
            20

<210> SEQ ID NO 640
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 640

Gln Phe Leu Ala Val Cys Gly Leu Pro Val Val Ala Leu Leu Ala Thr
1               5                   10                  15

Ala Leu Phe Ala Pro Leu Pro
            20

<210> SEQ ID NO 641
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 641

Ala Ala Ala Leu Ala Ala Thr Leu Ala Leu Pro Leu Ala Gly Leu Val
1               5                   10                  15

Gly Leu Ala
```

```
<210> SEQ ID NO 642
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

Gln Gly Leu Leu Leu Ala Tyr Cys Leu Leu Leu Ala Phe Ala Ser Gly
1               5                   10                  15

Leu Val Leu Ser Arg Val Pro
            20

<210> SEQ ID NO 643
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Met Lys Ala Leu Val Ala Val Ser Ala Val Ala Val Val Ala Leu Leu
1               5                   10                  15

Gly Val Ser Ser Ala Gln
            20

<210> SEQ ID NO 644
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 644

Leu Thr Leu Leu Ile Ile Val Leu Leu Ile Gly Val Pro Ala Gly Tyr
1               5                   10                  15

Leu Val Ile Ser Ala Asn Gln
            20

<210> SEQ ID NO 645
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Phe Ala Tyr Leu Thr Val Leu Cys Leu Ala Leu Ala Ala Ala Val Ser
1               5                   10                  15

Phe Gly Val Pro Ala Lys
            20

<210> SEQ ID NO 646
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Ala Ala Pro Arg Ser Val Pro Pro Ala Arg Ala Leu Ala Gly Leu Leu
```

-continued

```
                1               5                   10                  15
Leu Val Thr Ala Leu Ala Leu
            20

<210> SEQ ID NO 647
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Ile Val Ala Leu Leu Leu Val Pro Leu Val Ser Leu Thr Ala Ile Trp
1               5                   10                  15

Ala Phe Ala Thr Val Leu Thr
            20

<210> SEQ ID NO 648
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Ile Val Ala Leu Leu Leu Val Pro Leu Val Ser Leu Thr Ala Ile Trp
1               5                   10                  15

Ala Phe Ala Thr Val Leu Thr
            20

<210> SEQ ID NO 649
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649

Ile Val Ala Leu Leu Leu Val Pro Leu Val Ser Leu Thr Ala Ile Trp
1               5                   10                  15

Ala Phe Ala Thr Val Leu Thr
            20

<210> SEQ ID NO 650
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Lys Ser Pro Pro Leu Val Leu Ala Ala Leu Val Ala Cys Ile Ile Val
1               5                   10                  15

Leu Gly Phe Asn Tyr Trp Ile
            20

<210> SEQ ID NO 651
<211> LENGTH: 23
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 651

Leu Ala Leu Gly Thr Ala Val Leu Ser Ala Ala Leu Leu Ala Val
1               5                   10                  15

Ala Met Pro Gln Glu Ala Gln
            20

<210> SEQ ID NO 652
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Gln Leu Gly Leu Pro Pro Leu Leu Leu Thr Met Ala Leu Ala Gly
1               5                   10                  15

Gly Ser Gly Thr Ala Ser Ala
            20

<210> SEQ ID NO 653
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Leu Thr Val Pro Leu Gly Ala Leu Ala Leu Val Val Ala Phe Pro Ala
1               5                   10                  15

Thr Ala

<210> SEQ ID NO 654
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Lys Pro Ala Val Ile Gly Ser Val Ala Ala Val Val Ala Gly Ala
1               5                   10                  15

Gly Phe Gly Ala Tyr Ala Met
            20

<210> SEQ ID NO 655
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Ala Arg His Gly Leu Pro Leu Leu Pro Leu Leu Ser Leu Leu Val Gly
1               5                   10                  15

Ala Trp Leu Lys Leu Gly
            20

<210> SEQ ID NO 656
<211> LENGTH: 23

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Pro Met Ile Gly Met Val Val Leu Val Val Val Leu Gly Leu Ala Val
1               5                   10                  15

Leu Ala Leu Ser Tyr Arg Leu
            20

<210> SEQ ID NO 657
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Val Leu Val Gly Ala Ala Ala Val Pro Val Met Leu Val Ala Ala Gly
1               5                   10                  15

Cys

<210> SEQ ID NO 658
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

Met Ala Leu Leu Ser Arg Pro Ala Leu Thr Leu Leu Leu Leu Leu Met
1               5                   10                  15

Ala Ala Val Val Arg Cys Gln
            20

<210> SEQ ID NO 659
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Met Ala Pro Phe Glu Pro Leu Ala Ser Gly Ile Leu Leu Leu Leu Trp
1               5                   10                  15

Leu Ile Ala Pro Ser Arg Ala
            20

<210> SEQ ID NO 660
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Met Ala Pro Leu Lys Met Leu Ala Leu Val Thr Leu Leu Leu Gly Ala
1               5                   10                  15

Ser Leu Gln His Ile His Ala
            20
```

-continued

<210> SEQ ID NO 661
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Met Asp Ala Lys Val Val Ala Val Leu Ala Leu Val Leu Ala Ala Leu
1               5                   10                  15

Cys Ile Ser Asp Gly Lys
            20

<210> SEQ ID NO 662
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Met Asp Leu Leu Trp Ile Leu Pro Ser Leu Trp Leu Leu Leu Leu Gly
1               5                   10                  15

Gly Pro Ala Cys Leu Lys
            20

<210> SEQ ID NO 663
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Met Phe Arg His Leu Ala Ala Val Ala Thr Ala Leu Ala Val Val Thr
1               5                   10                  15

Val Thr Pro Val Glu Ala Thr
            20

<210> SEQ ID NO 664
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Met Gly Leu Leu Leu Leu Val Leu Ile Leu Thr Pro Ser Leu Ala Ala
1               5                   10                  15

Tyr

<210> SEQ ID NO 665
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Met Lys Gly Thr Lys Leu Ala Val Val Val Gly Met Thr Val Ala Ala

```
                1               5                   10                  15

Val Ser Leu Ala Ala Pro
                20

<210> SEQ ID NO 666
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Met Lys Val Leu Leu Ala Ala Ala Leu Ile Ala Gly Ser Val Phe Phe
1               5                   10                  15

Leu Leu Leu Pro Gly Pro
                20

<210> SEQ ID NO 667
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Met Leu Lys Val Thr Thr Leu Ile Ala Ser Leu Leu Ala Ala Pro Leu
1               5                   10                  15

Ala Phe Ser Ala Ser Ala Gln
                20

<210> SEQ ID NO 668
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Met Leu Pro Gly Leu Ala Leu Leu Leu Ala Ala Trp Thr Ala Arg
1               5                   10                  15

Ala Leu Glu Val Pro Thr Asp
                20

<210> SEQ ID NO 669
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

Pro Val Ser Met Arg Leu Leu Ala Ala Ala Leu Leu Leu Leu Leu
1               5                   10                  15

Ala Leu Tyr Thr Ala Arg
                20

<210> SEQ ID NO 670
<211> LENGTH: 22
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 670

Val Ile Ile Ala Leu Ile Val Ile Val Ala Val Val Leu Val Val Ala
1               5                   10                  15

Ala Val Leu Ala Leu Arg
            20

<210> SEQ ID NO 671
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Val Ile Ile Ala Leu Ile Val Ile Val Ala Val Val Leu Val Val Ala
1               5                   10                  15

Ala Val Leu Ala Leu Arg
            20

<210> SEQ ID NO 672
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Val Ser Pro Ile Lys Ala Phe Ala Asp Gly Ile Val Ala Val Ala Ile
1               5                   10                  15

Ala Val Val Leu Met Phe Gly
            20

<210> SEQ ID NO 673
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Pro Leu Ile Val Val Ala Ala Ala Val Val Ala Val Gly Ala Gly
1               5                   10                  15

Leu Ala Val Trp Ala Thr Ala
            20

<210> SEQ ID NO 674
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Lys Leu Pro Leu Ala Val Ala Val Ala Ala Gly Val Met Ser Ala Gln
1               5                   10                  15

Ala Met Ala Val Asp Phe
            20

<210> SEQ ID NO 675

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Leu Thr Met Ala Ala Ile Ala Leu Val Cys Ala Val Thr Val Leu Gly
1               5                   10                  15

Ala Pro Gly Ala Ala His Ala
            20

<210> SEQ ID NO 676
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Ala Ala Ala Leu Ala Ala Ile Ala Val Ile Gly Ala Ala Thr Ala Pro
1               5                   10                  15

Ala Val Ala Ala
            20

<210> SEQ ID NO 677
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677

Ala Ala Ala Leu Ala Ala Ile Ala Val Ile Gly Ala Ala Thr Ala Pro
1               5                   10                  15

Ala Val Ala Ala
            20

<210> SEQ ID NO 678
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

Gly Ala Gly Ala Leu Leu Ala Ser Leu Leu Ala Ala Leu Pro Phe
1               5                   10                  15

Thr Ala Glu Ala Ala Glu Ser
            20

<210> SEQ ID NO 679
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

Ala Leu Leu Ser Ala Val Val Cys Ala Ala Trp Ala Thr Leu Ile Leu
1               5                   10                  15
```

```
Ala Pro Ile Gly Ala Ala Ala
            20

<210> SEQ ID NO 680
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 680

Ala Val Val Gly Val Val Phe Leu Ser Pro Ile Leu Leu Ala Gly Ala
1               5                   10                  15

Gly Met Val Leu Val Ser Ser
            20

<210> SEQ ID NO 681
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

Leu Pro Gly Ala Leu Ala Leu Ser Leu Leu Val Ser Gly Ser Leu
1               5                   10                  15

Leu Pro Gly Pro Gly Ala
            20

<210> SEQ ID NO 682
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 682

Met Leu Val Val Leu Leu Thr Ala Ala Leu Leu Val Leu Ser Ser Ala
1               5                   10                  15

His Gly Ser Asp Glu Glu Val
            20

<210> SEQ ID NO 683
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 683

Met Met Thr Pro Met Trp Ile Ser Leu Phe Lys Val Leu Leu Leu Leu
1               5                   10                  15

Phe Ala Phe Phe Ala Thr
            20

<210> SEQ ID NO 684
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 684

Ala Val Ser Ala Leu Ala Gly Leu Val Leu Ala Gly Ser Ala Leu Ala
1               5                   10                  15

Val Val Asn Ala Ala Pro Ala
            20

<210> SEQ ID NO 685
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

Phe Leu Ile Ala Gly Val Ile Val Ala Leu Leu Ala Val Phe Thr Val
1               5                   10                  15

Val Arg Ala Val Arg Ile Val
            20

<210> SEQ ID NO 686
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 686

Met Trp Pro Leu Trp Leu Cys Trp Ala Leu Trp Val Leu Pro Leu Ala
1               5                   10                  15

Gly Pro Gly Ala Ala Leu Thr
            20

<210> SEQ ID NO 687
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 687

Met Val Leu Cys Ala Val Ala Leu Leu Ile Leu Ala Val Ser Leu Val
1               5                   10                  15

Gly Gly Asn Asp
            20

<210> SEQ ID NO 688
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 688

Met Tyr Lys Gly Ile Phe Leu Cys Val Leu Leu Ala Val Ile Cys Ala
1               5                   10                  15

Asn Ser Leu Ala Thr Pro Ser
            20

<210> SEQ ID NO 689
<211> LENGTH: 23
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 689

Ser Gly Ala Leu Ala Val Trp Leu Ile Val Ala Ala Val Val Val Val
1               5                   10                  15

Ala Val Leu Ile Gly Ala Phe
            20

<210> SEQ ID NO 690
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 690

Val Tyr Gly Val Ala Ser Ala Val Val Val Ala Ala Thr Thr Gly Thr
1               5                   10                  15

Leu Ala Leu Ala Ser Pro Gly
            20

<210> SEQ ID NO 691
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 691

Ala Thr Thr Leu Val Leu Ser Thr Leu Ala Ala Val Leu Leu Thr Leu
1               5                   10                  15

Ile Pro Trp Ser Gly Thr Ala
            20

<210> SEQ ID NO 692
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 692

Ala Gly Ile Pro Gly Leu Leu Phe Leu Leu Phe Phe Leu Leu Cys Ala
1               5                   10                  15

Val Gly Gln Val Ser Pro Tyr
            20

<210> SEQ ID NO 693
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 693

Asn Phe Lys Thr Cys Pro Ala Val Ala Leu Val Ala Val Val Ala Thr
1               5                   10                  15

Val Ala Thr Ala Glu Asp Pro
            20
```

<210> SEQ ID NO 694
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 694

Val Thr Ser Val Leu Arg Gly Leu Val Ala Ala Leu Leu Ala Val Leu
1               5                   10                  15

Ser Ile Thr Ala Ser Thr Pro
            20

<210> SEQ ID NO 695
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 695

Arg Leu Leu Ala Ala Ala Gly Ala Gly Ala Leu Leu Leu Ala Ser Gly
1               5                   10                  15

Ala Val Ala Pro Ser Val Ala
            20

<210> SEQ ID NO 696
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 696

Val Ile Ala Arg Val Val Gly Val Ala Ala Cys Gly Leu Ser Leu Ala
1               5                   10                  15

Val Leu Ala Ala Ala Pro Thr
            20

<210> SEQ ID NO 697
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 697

Val Val Ile Ala Val Val Gly Val Val Leu Leu Val Leu Leu Ala
1               5                   10                  15

Leu Val Val Val Ser Arg
            20

<210> SEQ ID NO 698
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 698

-continued

Val Val Ile Ala Val Val Gly Val Val Leu Leu Val Leu Leu Ala
1               5                   10                  15

Leu Val Val Val Ser Arg
            20

<210> SEQ ID NO 699
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 699

Val Val Ile Ala Val Val Gly Val Val Leu Leu Val Leu Leu Ala
1               5                   10                  15

Leu Val Val Val Ser Arg
            20

<210> SEQ ID NO 700
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 700

Met Phe Arg His Leu Ala Ala Val Ala Thr Ala Leu Ala Val Val Thr
1               5                   10                  15

Val Thr Pro Val Glu Ala Thr
            20

<210> SEQ ID NO 701
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 701

Glu Glu Leu Gly Val Leu Val Gly Ala Val Gly Ala Ala Gly Phe Phe
1               5                   10                  15

Gly Leu Met Ile Val Ile Val
            20

<210> SEQ ID NO 702
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 702

Arg Val Ala Ile Ser Ala Ala Met Leu Gly Ala Leu Ala Leu Ser Ala
1               5                   10                  15

Leu Ser Ala Thr Pro
            20

<210> SEQ ID NO 703
<211> LENGTH: 23
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 703

Ser Ser Phe Val Arg Val Leu Gly Ala Ala Thr Ala Gly Ala Leu
1               5                   10                  15

Ala Trp Ala Val Leu Ala Gln
            20

<210> SEQ ID NO 704
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 704

Val Arg Asn Ile Val Leu Gly Val Leu Ala Ala Gly Ile Ser Ala Thr
1               5                   10                  15

Leu Gly Trp Leu Ala Arg Thr
            20

<210> SEQ ID NO 705
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 705

Met Glu Ser Leu Val Leu Leu Leu Phe Leu Leu Ile Met Gly Gly
1               5                   10                  15

Phe Met Phe Phe
            20

<210> SEQ ID NO 706
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 706

Met Phe Arg His Leu Ala Ala Val Ala Thr Ala Leu Ala Val Val Thr
1               5                   10                  15

Val Thr Pro Val Glu Ala Thr
            20

<210> SEQ ID NO 707
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 707

Met Gly Phe Leu Gly Thr Gly Thr Trp Ile Leu Val Leu Val Leu Pro
1               5                   10                  15

Ile Gln Ala Phe Pro Lys Pro
            20
```

```
<210> SEQ ID NO 708
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 708

Met Gly Ile Leu Leu Gly Leu Leu Leu Gly His Leu Thr Val Asp
1               5                   10                  15

Thr Tyr Gly Arg Pro Ile Leu
            20

<210> SEQ ID NO 709
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 709

Met Ile Ala Gly Ala Val Val Ala Ala Leu Gly Val Gly Ala Gly Leu
1               5                   10                  15

Trp Ala Thr

<210> SEQ ID NO 710
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

Met Lys Leu Leu Ser Leu Val Ala Val Val Gly Cys Leu Leu Val Pro
1               5                   10                  15

Pro Ala Glu Ala Asn Lys
            20

<210> SEQ ID NO 711
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

Met Lys Leu Met Gln Leu Ile Leu Leu Leu Cys Ile Ile Lys Thr
1               5                   10                  15

Ser Asn Gly Val Asn
            20

<210> SEQ ID NO 712
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 712

Gly Gly Arg Trp Phe Phe Ala Val Leu Ala Ala Ser Ala Val Leu Val
1               5                   10                  15
```

Ser Gly Cys Ser Gly Ser Val
            20

<210> SEQ ID NO 713
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 713

Gly Leu Leu Arg Leu Gly Ser Leu Leu Ser Leu Ser Cys Leu Ala Leu
1               5                   10                  15

Ser Val Leu Leu Leu Ala Gln
            20

<210> SEQ ID NO 714
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 714

Met Trp Leu Arg Cys Leu Ala Leu Ala Leu Thr Leu Leu Met Val Ser
1               5                   10                  15

Gly Ile Glu Asn Asn Thr Lys
            20

<210> SEQ ID NO 715
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 715

Ala Ser Gly Val Ala Gly Val Cys Leu Leu Gly Val Val Ala Thr Gly
1               5                   10                  15

Ala Val Ala Ala His Val Ala
            20

<210> SEQ ID NO 716
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 716

Phe Ala Val Ala Val Ala Gly Val Ala Thr Ala Ala Thr Thr Val
1               5                   10                  15

Thr Leu Ala Pro Ala Pro Ala
            20

<210> SEQ ID NO 717
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 717

Ala Ala Arg Ala Val Val Ala Ala Val Cys Ala Ala Ser Leu Ala Gly
1               5                   10                  15

Cys Ala Ile

<210> SEQ ID NO 718
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 718

Ala Leu Leu Ala Ala Leu Leu Ala Ser Thr Leu Leu Ala Leu Leu Val
1               5                   10                  15

Ser Pro Ala

<210> SEQ ID NO 719
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 719

Ala Leu Leu Ala Ala Leu Leu Ala Ser Thr Leu Leu Ala Leu Leu Val
1               5                   10                  15

Ser Pro Ala

<210> SEQ ID NO 720
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 720

Ala Leu Leu Ala Ala Leu Leu Ala Ser Thr Leu Leu Ala Leu Leu Val
1               5                   10                  15

Ser Pro Ala

<210> SEQ ID NO 721
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 721

Ala Arg Pro Thr Leu Trp Ala Ala Ala Leu Thr Leu Leu Val Leu Leu
1               5                   10                  15

<210> SEQ ID NO 722
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 722
```

```
Ala Thr Ala Ala Ala Val Thr Ala Ala Leu Ala Thr Gly Val Ala Ser
1               5                   10                  15

Val Ala Ala Gly Arg Leu Ala
            20
```

<210> SEQ ID NO 723
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 723

```
Ala Thr Thr Ala Leu Ala Val Ala Ala Leu Ala Ala Gly Cys Ala
1               5                   10                  15
```

<210> SEQ ID NO 724
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 724

```
Ala Val Leu Ala Ala Ala Val Thr Ala Gly Val Thr Ala Thr Ala Val
1               5                   10                  15

Thr Ala Ser Pro Gly Val Ala Ala Leu Pro Ala Gly Pro Ala
            20                  25                  30
```

<210> SEQ ID NO 725
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 725

```
Ala Val Leu Ala Ala Ala Val Thr Ala Gly Val Thr Ala Thr Ala Val
1               5                   10                  15

Thr Ala Ser Pro Gly Val Ala Ala Leu Pro Ala Gly Pro Ala
            20                  25                  30
```

<210> SEQ ID NO 726
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 726

```
Ala Val Thr Gly Thr Ala Leu Ala Leu Ala Val Ser Ala Val Leu Thr
1               5                   10                  15

Ala Cys Gly Gly
            20
```

<210> SEQ ID NO 727
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 727

Cys Ala Ala Leu Leu Thr Ala Ala Val Ala Val Ser Leu Gly Ala Ala
1               5                   10                  15

Gly Cys

<210> SEQ ID NO 728
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 728

Phe Ala Ile Gly Thr Ala Val Val Val Ala Leu Ala Gly Met Asn Gly
1               5                   10                  15

Pro Trp Leu

<210> SEQ ID NO 729
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 729

Gly Ala Ala Ala Val Ala Leu Thr Ala Ala Ala Ala Leu Leu Ala Gly
1               5                   10                  15

Cys

<210> SEQ ID NO 730
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 730

Leu Lys Ala Val Val Leu Thr Leu Ala Leu Val Ala Val Ala Gly Ala
1               5                   10                  15

Arg Ala Glu Val Ser Ala Asp
            20

<210> SEQ ID NO 731
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 731

Gly Lys Leu Val Ala Leu Thr Leu Leu Gly Ala Cys Leu Ala Leu Ile
1               5                   10                  15

Gly Glu Arg Leu Leu Asn Phe
            20

<210> SEQ ID NO 732
<211> LENGTH: 23
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 732

Ser Thr Val Val Val Gly Leu Leu Leu Ile Val Gly Gly Phe Phe Leu
1               5                   10                  15

Gly Tyr His Leu Val Gln Ile
            20

<210> SEQ ID NO 733
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 733

Val Ala Arg Trp Leu Ala Ser Val Val Leu Ala Val Cys Leu Ala Gly
1               5                   10                  15

Cys Val Gly Arg Gln Val Ser
            20

<210> SEQ ID NO 734
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Phe Asn Leu Leu Ala Val Ser Ser Ile Leu Leu Val Asp Leu Phe Arg
1               5                   10                  15

Thr His Trp Gly His Asn Val
            20

<210> SEQ ID NO 735
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 735

Leu Val Ala Leu Val Leu Leu Gly Val Gly Leu Ser Leu Val Gly Glu
1               5                   10                  15

Met Phe Leu Ala Phe Arg
            20

<210> SEQ ID NO 736
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 736

Pro Leu Val Leu Leu Leu Ala Val Leu Leu Leu Ala Val Leu Cys Lys
1               5                   10                  15

Val Tyr Leu Gly Leu Phe Ser
            20

<210> SEQ ID NO 737

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 737

Thr Leu Met Leu Leu Ala Met Val Val Ala Leu Val Ile Leu Pro Phe
1               5                   10                  15

Phe Ile Asn His Gly Gly Glu
            20

<210> SEQ ID NO 738
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 738

Thr Arg Gly Val Leu Ala Val Leu Ala Val Cys Val Leu Leu Leu Thr
1               5                   10                  15

Gly Ser Ala Gly Cys Gly
            20

<210> SEQ ID NO 739
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 739

Val Val Ile Ala Val Val Gly Val Val Val Leu Leu Val Leu Leu Ala
1               5                   10                  15

Leu Val Val Val Ser Arg
            20

<210> SEQ ID NO 740
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 740

Val Val Ile Ala Val Val Gly Val Val Val Leu Leu Val Leu Leu Ala
1               5                   10                  15

Leu Val Val Val Ser Arg
            20

<210> SEQ ID NO 741
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 741

Val Leu Leu Arg Arg Ala Leu Pro Val Cys Val Ala Ala Gly Val Ala
1               5                   10                  15
```

```
Ser Ile Val Val Phe Gly
            20

<210> SEQ ID NO 742
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742

Val Leu Thr Thr Thr Ala Val Thr Val Val Cys Ala Ile Thr Val Leu
1               5                   10                  15

Ala Ala Pro Gly
            20

<210> SEQ ID NO 743
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 743

Pro Arg Lys Pro Val Leu Ala Gly Ile Gly Ala Thr Ala Val Leu Val
1               5                   10                  15

Thr Ala Ala Ala Leu Val Pro Gly
            20

<210> SEQ ID NO 744
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 744

Val Val Ala Ala Leu Thr Leu Ser Val Leu Gly Ala Thr Gly Ala
1               5                   10                  15

<210> SEQ ID NO 745
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 745

Trp Gly Pro Ala Val Val Met Thr Thr Ala Phe Ala Leu Ala Val Gly
1               5                   10                  15

Ser Gln Gly Ala Ala Val Ala Leu Pro Gly Ala Pro Ala Lys Ala
            20                  25                  30

<210> SEQ ID NO 746
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 746

Met Ala Lys Leu Ile Ala Leu Thr Leu Leu Gly Met Gly Leu Ala Leu
```

```
                1               5                  10                  15

Phe

<210> SEQ ID NO 747
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747

Met Ala Lys Leu Leu Ala Leu Thr Leu Val Gly Leu Val Leu Ala Leu
1               5                  10                  15

Tyr Lys

<210> SEQ ID NO 748
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 748

Ile Val Pro Leu Leu Leu Ala Ala Phe Leu Leu Ile Gly Thr Ala Gly
1               5                  10                  15

Gln Ala Gln

<210> SEQ ID NO 749
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 749

Gln Gly Leu Leu Leu Ala Tyr Cys Leu Leu Leu Ala Phe Ala Ser Gly
1               5                  10                  15

Leu Val Leu Ser Arg Val Pro
            20

<210> SEQ ID NO 750
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 750

Ser Ala Arg Leu Ala Ala Leu Thr Val Ala Ala Val Cys Ser Ala Ala
1               5                  10                  15

Ser Thr Val Val Leu Thr Thr
            20

<210> SEQ ID NO 751
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 751
```

-continued

```
Thr Leu Ile Trp Ile Val Asn Ile Ile Ser Ala Leu Ala Val Ile Val
1               5                   10                  15

Leu Val Leu Leu Gln His
            20

<210> SEQ ID NO 752
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Ala Phe Cys Tyr Met Leu Ala Leu Leu Leu Thr Ala Ala Leu Ile Phe
1               5                   10                  15

Phe Ala Ile Trp His Ile Ile
            20

<210> SEQ ID NO 753
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 753

Val Phe Ala Leu Leu Phe Leu Leu Ala Val Val Leu Gly Val Tyr Ala
1               5                   10                  15

Thr Val Lys Ala Val Gly Ala
            20

<210> SEQ ID NO 754
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 754

Gln Ala Leu Met Ala Ile Ala Val Ser Val Leu Ala Ala Gly Val Thr
1               5                   10                  15

Thr Leu Gly Val
            20

<210> SEQ ID NO 755
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Ala Ala Ala Pro Arg Pro Gly Val Leu Leu Leu Leu Leu
1               5                   10

<210> SEQ ID NO 756
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 756

Ala Ala Ala Val Gly Ala Val Thr Met Ser Leu Ala Leu Ala Ala Thr
1               5                   10                  15

Ala Cys Gly Gly Gly
            20

<210> SEQ ID NO 757
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

Ala Ala Leu Ala Ala Leu Val Val Ala Ala Gly Ser Leu Val Thr Ala
1               5                   10                  15

Gly Ala Ala

<210> SEQ ID NO 758
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 758

Ala Ala Leu Ala Ala Val Thr Ser Leu Ala Leu Ala Ala Thr Ala Cys
1               5                   10                  15

Gly Gly

<210> SEQ ID NO 759
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 759

Ala Ala Leu Ala Val Ala Ala Ser Ala Ser Leu Ala Leu Leu Ala Thr
1               5                   10                  15

Ala Cys Thr Gly
            20

<210> SEQ ID NO 760
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 760

Ala Ala Leu Thr Ala Ala Ala Thr Thr Val Ala Ala Val Gly Leu Ala
1               5                   10                  15

Leu

<210> SEQ ID NO 761
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 761

Ala Ala Leu Thr Ala Ala Ala Thr Thr Val Ala Ala Val Gly Leu Ala
1               5                   10                  15

Leu

<210> SEQ ID NO 762
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 762

His Leu Leu Ala Val Leu Leu Ala Leu Leu Gly Thr Ala Trp Ala Glu
1               5                   10                  15

Val Trp Pro Pro Gln Leu Gln
            20

<210> SEQ ID NO 763
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 763

His Val Arg Ser Val Leu Ala Leu Leu Val Ala Val Val Gly Leu Leu
1               5                   10                  15

Cys Val Phe Ala His Ala Glu
            20

<210> SEQ ID NO 764
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 764

Ala Leu Val Val Gly Ala Cys Ala Ala Val Gly Val Leu Leu Ser Gly
1               5                   10                  15

Cys Thr Gly Gly Val Ser
            20

<210> SEQ ID NO 765
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 765

Ala Val Gln Gly Thr Val Ala Gly Ala Val Val Leu Gly Leu Leu Leu
1               5                   10                  15

Trp Trp Leu Leu Pro Leu Gly
            20

<210> SEQ ID NO 766
```

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 766

Ala Trp Trp Thr Leu Ile Leu Phe Ala Val Ile Gly Val Ala Val Leu
1               5                   10                  15

Val Thr Ala Val Ser Phe Thr
            20

<210> SEQ ID NO 767
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 767

Gly Met Leu Phe Gly Ala Ala Val Ser Ala Gly Ala Val Leu Ala
1               5                   10                  15

Gly Cys

<210> SEQ ID NO 768
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 768

Gly Val Ala Val Thr Val Val Ser Tyr Leu Ala Ile Ser Leu Leu Ser
1               5                   10                  15

Glu Pro Val Ala Ala Ala Thr Gly Leu Ala Leu
            20                  25

<210> SEQ ID NO 769
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 769

Ile Ala Ile Ala Ala Ile Thr Ala Thr Ser Ile Leu Ala Leu
1               5                   10

<210> SEQ ID NO 770
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 770

Ile Ile Ala Ser Ala Leu Ile Ala Thr Phe Ala Leu Ala Ala Cys
1               5                   10                  15

<210> SEQ ID NO 771
<211> LENGTH: 29
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 771

Ile Leu Arg Ala Gly Pro Ala Ala Ile Ala Leu Val Ala Met Ala Leu
1               5                   10                  15

Thr Gln Val Glu Leu Ala Pro His Ala Val Ala Ala Ala
            20                  25

<210> SEQ ID NO 772
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 772

Ile Leu Arg Ala Gly Pro Ala Ala Ile Ala Leu Val Ala Met Ala Leu
1               5                   10                  15

Thr Gln Val Glu Leu Ala Pro His Ala Val Ala Ala Ala
            20                  25

<210> SEQ ID NO 773
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 773

Asn Ala Gln Val Ala Ile Ile Val Ser Ala Val Val Ala Ile Ala Leu
1               5                   10                  15

Ile Ile Gly Gly Gly Val Trp
            20

<210> SEQ ID NO 774
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 774

Asn Ala Gln Val Ala Ile Ile Val Ser Ala Val Val Ala Ile Ala Leu
1               5                   10                  15

Ile Ile Gly Gly Gly Val Trp
            20

<210> SEQ ID NO 775
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 775

Leu Ala Ala Val Thr Ala Thr Ala Ala Ala Gly Ala Val Ala Ala Leu
1               5                   10                  15

Gly Leu Ala Ala Ser Pro Ala Ala Ala Ala Pro
            20                  25
```

<210> SEQ ID NO 776
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 776

Leu Ala Ala Val Thr Ala Thr Ala Ala Ala Gly Ala Val Ala Ala Leu
1               5                   10                  15

Gly Leu Ala Ala Ser Pro Ala Ala Ala Ala Pro
            20                  25

<210> SEQ ID NO 777
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 777

Leu Ala Ala Val Thr Ala Thr Ala Ala Ala Gly Ala Val Ala Ala Leu
1               5                   10                  15

Gly Leu Ala Ala Ser Pro Ala Ala Ala Ala Pro
            20                  25

<210> SEQ ID NO 778
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 778

Leu Ala Ala Val Val Thr Gly Val Ala Ala Ala Val Gly Val Ala Ala
1               5                   10                  15

Thr Pro Ala Ala Ala Ala Arg Ala Val Pro Val Pro Val Pro Leu
            20                  25                  30

<210> SEQ ID NO 779
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 779

Leu Ala Ala Val Val Thr Gly Val Ala Ala Ala Val Gly Val Ala Ala
1               5                   10                  15

Thr Pro Ala Ala Ala Ala Arg Ala Val Pro Val Pro Val Pro Leu
            20                  25                  30

<210> SEQ ID NO 780
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 780

-continued

Leu Ala Ala Val Val Thr Gly Val Ala Ala Val Gly Val Ala Ala
1               5                   10                  15

Thr Pro Ala Ala Ala Arg Ala Val Pro Val Pro Val Pro Leu
            20                  25                  30

<210> SEQ ID NO 781
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 781

Leu Ala Gly Cys Phe Leu Leu Ile Leu Gly Gln Ile Val Leu Leu Pro
1               5                   10                  15

Ala

<210> SEQ ID NO 782
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 782

Leu Gly Ala Gly Ala Leu Ala Leu Gly Gly Ala Leu Ala Ile Ala Pro
1               5                   10                  15

Phe Ala Ala Gly Pro Ala Glu Ala Val
            20                  25

<210> SEQ ID NO 783
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 783

Leu Gly Leu Ser Ala Val Met Ile Ser Ile Leu Ala Val Thr Gly Cys
1               5                   10                  15

Gly Gly

<210> SEQ ID NO 784
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 784

Leu Ile Leu Leu Leu Thr Ser Ala Val Ala Leu Gly Gly Ala Trp Ala
1               5                   10                  15

Ala Pro Ala Ser Ser Ala Ala Pro Ala
            20                  25

<210> SEQ ID NO 785
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 785

Leu Arg Leu Val Cys Thr Ala Ala Leu Thr Ala Gly Ile Val Leu Ala
1               5                   10                  15

Pro Val Pro Ala Ala Ala
            20

<210> SEQ ID NO 786
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 786

Leu Pro Val Val Val Gly Ala Gly Pro Val Gly Leu Ala Ala Ala
1               5                   10                  15

Ala

<210> SEQ ID NO 787
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 787

Leu Ser Val Ala Val Ala Ala Ser Phe Met Ser Leu Thr Ile
1               5                   10

<210> SEQ ID NO 788
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 788

Leu Val Leu Ala Ala Gly Ala Ala Leu Thr Gly Ala Ala Thr Ala
1               5                   10                  15

<210> SEQ ID NO 789
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 789

Leu Val Leu Ser Val Thr Leu Ile Ala Met Ala Ala Ala Ser Val Trp
1               5                   10                  15

Ala Val Gly Gly Ser Val
            20

<210> SEQ ID NO 790
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 790
```

Met Ala Leu Ala Ala Leu Met Ile Ala Leu Gly Ser Leu Gly Leu
1               5                   10                  15

<210> SEQ ID NO 791
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 791

Met Phe Leu Ser Ala Val Leu Leu Leu Ser Ala Ala Ala Gln Thr Val
1               5                   10                  15

Trp Ala Asp Thr Val Phe
            20

<210> SEQ ID NO 792
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 792

Ile Ala Leu Ala Leu Leu Pro Leu Leu Phe Thr Pro Val Thr Lys
1               5                   10                  15

<210> SEQ ID NO 793
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 793

Met Lys Val Leu Leu Ala Ala Ala Leu Ile Ala Gly Ser Val Phe Phe
1               5                   10                  15

Leu Leu Leu Pro Gly
            20

<210> SEQ ID NO 794
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 794

Met Thr Ala Pro Ala Val Leu Thr Pro Pro Val Val Ile Gly Ala
1               5                   10                  15

Gly Pro Ile Gly Leu Ala Ala Ala Ala
            20                  25

<210> SEQ ID NO 795
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 795

```
Met Val Val Gly Leu Leu Val Ala Ala Leu Thr Thr Ile Thr Pro Thr
1               5                   10                  15

Ala Val Ala
```

<210> SEQ ID NO 796
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 796

```
Pro Ala His Ala Ala Ala Ala Ile Ala Ala Ala Ala Phe Leu Ala
1               5                   10                  15

Ala Gly Pro Gly Val Ala Val Gly Glu Pro Ala Ala Pro
            20                  25
```

<210> SEQ ID NO 797
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 797

```
Pro Ala Leu Cys Phe Leu Leu Ala Val Ala Met Ser Phe Phe Gly
1               5                   10                  15

Ser Ala Leu
```

<210> SEQ ID NO 798
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 798

```
Pro Ala Arg Pro Leu Gly Leu Ser Ile Leu Leu Leu Phe Leu Thr Glu
1               5                   10                  15

Ala Ala Leu
```

<210> SEQ ID NO 799
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 799

```
Pro Ala Ser Leu Leu Leu Leu Val Leu Ala Ser His Cys Cys Leu Gly
1               5                   10                  15

Ser Ala
```

<210> SEQ ID NO 800
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 800

Pro Leu Gly Leu Leu Leu Leu Pro Leu Ala Gly His Leu Ala Leu
1               5                   10                  15

<210> SEQ ID NO 801
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 801

Pro Leu Pro Trp Ser Leu Ala Leu Pro Leu Leu Leu Ser Trp Val Ala
1               5                   10                  15

Gly Gly

<210> SEQ ID NO 802
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 802

Pro Leu Arg Arg Ile Ala Leu Phe Cys Gly Leu Leu Val Leu Thr Leu
1               5                   10                  15

Leu Ile

<210> SEQ ID NO 803
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 803

Trp Ala Thr Leu Pro Leu Leu Cys Ala Ala Glu Leu Cys Val
1               5                   10

<210> SEQ ID NO 804
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 804

Val Leu Ala Val Val Val Cys Ala Ile Val Leu Ala Ala Pro
1               5                   10

<210> SEQ ID NO 805
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 805

Ala Ala Ala Pro Leu Ala Leu Leu Val Leu Leu Leu Leu Gly Pro Leu
1               5                   10                  15

Ala

<210> SEQ ID NO 806
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 806

Ala Ala Gly Leu Leu Leu Ala Phe Ala Leu Leu Cys Leu Pro
1               5                   10

<210> SEQ ID NO 807
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 807

Leu Leu Gly Ala Leu Ala Ala Val Leu Leu Ala Leu Ala
1               5                   10

<210> SEQ ID NO 808
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 808

Pro Val Leu Leu Ala Leu Gly Val Gly Leu Val Leu Leu Gly Leu Ala
1               5                   10                  15

Val

<210> SEQ ID NO 809
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 809

Ala Ala Ala Ala Val Leu Leu Ala Ala Gly Gly Ile Ala Val Ala
1               5                   10                  15

<210> SEQ ID NO 810
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 810

Leu Ala Leu Val Cys Gly Ile Val Val Ala Val Val Val Ile
1               5                   10

<210> SEQ ID NO 811
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 811

Ala Ala Leu Ile Gly Ala Val Leu Ala Pro Val Val Ala Val Leu Pro
1               5                   10                  15

Ala

<210> SEQ ID NO 812
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 812

Leu Ala Val Cys Gly Leu Pro Val Val Ala Leu Leu Ala Ala Leu Ala
1               5                   10                  15

Pro Leu Pro

<210> SEQ ID NO 813
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 813

Leu Leu Val Ala Leu Gly Gly Ala Val Val Ala Ala Pro Val Ala Ala
1               5                   10                  15

Ala Val Ala Pro
            20

<210> SEQ ID NO 814
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 814

Leu Leu Leu Val Leu Ala Val Leu Leu Ala Val Leu Pro Ala Pro Ala
1               5                   10                  15

Leu Ala

<210> SEQ ID NO 815
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 815

Leu Leu Ile Leu Leu Leu Leu Pro Leu Leu Ile Val Leu
1               5                   10

<210> SEQ ID NO 816
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 816

Val Leu Gly Leu Ala Ala Ala Ala Leu Ala Val Leu Pro Leu Val Pro
1               5                   10                  15

Ala

<210> SEQ ID NO 817
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 817

Phe Leu Met Leu Leu Leu Pro Leu Leu Leu Leu Val Ala Pro Val
1               5                   10                  15

Gly

<210> SEQ ID NO 818
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 818

Ala Leu Ala Ala Ala Ala Ala Ala Ala Leu Gly Leu Ala Ala Ala
1               5                   10                  15

Val Pro Ala

<210> SEQ ID NO 819
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 819

Leu Leu Leu Ala Ala Leu Leu Leu Ile Ala Phe Ala Ala Val Leu Val
1               5                   10                  15

Leu Leu

<210> SEQ ID NO 820
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 820

Met Ala Ala Leu Ala Ala Val Val Leu Ile Pro Leu Gly Ile Ala Ala
1               5                   10                  15

<210> SEQ ID NO 821
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 821
```

```
Ala Ala Leu Ile Gly Ala Val Leu Ala Pro Val Val Ala Val Leu Pro
1               5                   10                  15

Ala

<210> SEQ ID NO 822
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 822

Ala Ala Ala Val Ala Val Ala Gly Leu Ala Pro Leu Ala Leu
1               5                   10

<210> SEQ ID NO 823
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 823

Ala Ala Gly Ile Ala Val Ala Ile Ala Ala Ile Val Pro Leu Ala
1               5                   10                  15

<210> SEQ ID NO 824
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 824

Leu Ala Ala Val Ala Met Ala Ala Ala Val Leu Ala Ala Pro Ala
1               5                   10                  15

Leu Ala

<210> SEQ ID NO 825
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 825

Leu Ala Ala Val Gly Ala Ala Leu Ala Leu Gly Val Ala Ala Ala Pro
1               5                   10                  15

Ala Ala Ala Pro Ala
            20

<210> SEQ ID NO 826
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 826

Leu Leu Leu Ala Leu Leu Leu Ala Ala Gly Leu Val Leu Val Pro
1               5                   10                  15
```

<210> SEQ ID NO 827
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 827

Ala Leu Val Ala Val Ala Val Ala Val Val Ala Leu Leu Gly Val Ala
1               5                   10                  15

<210> SEQ ID NO 828
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 828

Leu Leu Leu Ile Ile Val Leu Leu Ile Val Pro Ala Leu Val Ile Ala
1               5                   10                  15

<210> SEQ ID NO 829
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 829

Ala Leu Val Leu Cys Leu Ala Leu Ala Ala Ala Val Val Pro Ala
1               5                   10                  15

<210> SEQ ID NO 830
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 830

Ala Ala Pro Val Pro Pro Ala Ala Leu Ala Leu Leu Leu Val Ala
1               5                   10                  15

<210> SEQ ID NO 831
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 831

Ile Val Ala Leu Leu Leu Val Pro Leu Val Leu Ala Ile Ala Ala Val
1               5                   10                  15

Leu

<210> SEQ ID NO 832
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 832

Ile Val Ala Leu Leu Val Pro Leu Val Leu Ala Ile Ala Ala Val
1               5                   10                  15
Leu

<210> SEQ ID NO 833
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 833

Leu Ala Val Leu Pro Val Val Ala Leu Leu Ala Ala Leu Phe Ala Pro
1               5                   10                  15

<210> SEQ ID NO 834
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 834

Pro Pro Leu Val Leu Ala Ala Leu Val Ala Cys Ile Ile Val Leu Ile
1               5                   10                  15

<210> SEQ ID NO 835
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 835

Leu Ala Leu Ala Val Leu Ala Ala Ala Leu Leu Ala Val Ala Pro Ala
1               5                   10                  15

<210> SEQ ID NO 836
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 836

Leu Gly Leu Pro Pro Leu Leu Leu Leu Ala Leu Ala Gly Gly Ala Ala
1               5                   10                  15

<210> SEQ ID NO 837
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 837

Leu Val Pro Leu Gly Ala Leu Ala Leu Val Val Ala Phe Pro Ala Ala
1               5                   10                  15

<210> SEQ ID NO 838
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 838

Pro Ala Val Ile Gly Val Ala Ala Val Val Ala Ala Ala Ala Ala
1               5                   10                  15

<210> SEQ ID NO 839
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 839

Ala Leu Pro Leu Leu Pro Leu Leu Leu Leu Val Gly Ala Leu Leu
1               5                   10                  15

<210> SEQ ID NO 840
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 840

Pro Ile Gly Val Val Leu Val Val Val Leu Gly Leu Ala Val Leu Ala
1               5                   10                  15

Leu

<210> SEQ ID NO 841
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 841

Val Leu Val Gly Ala Ala Ala Val Pro Val Leu Val Ala Ala Gly
1               5                   10                  15

<210> SEQ ID NO 842
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 842

Leu Ala Val Leu Val Leu Leu Val Leu Leu Pro Leu Val Pro Ala
1               5                   10                  15

<210> SEQ ID NO 843
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 843
```

```
Val Val Ala Val Leu Ala Pro Val Leu Phe Ala Leu
1               5                   10
```

<210> SEQ ID NO 844
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 844

```
Ala Ala Leu Leu Leu Pro Leu Leu Leu Leu Pro Leu
1               5                   10
```

<210> SEQ ID NO 845
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 845

```
Ala Leu Ala Val Gly Ala Ala Val Ala Ala Leu Leu Val Ile
1               5                   10
```

<210> SEQ ID NO 846
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 846

```
Leu Leu Ile Ala Ala Leu Leu Pro Leu
1               5
```

<210> SEQ ID NO 847
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 847

```
Leu Ala Ala Val Val Leu Leu Gly Leu Ala Ala Ala Pro Ala Ala
1               5                   10                  15
```

<210> SEQ ID NO 848
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 848

```
Trp Ala Ala Ala Ala Ala Ala Leu Leu Val Gly Ala Ala Pro Ala
1               5                   10                  15
```

<210> SEQ ID NO 849
<211> LENGTH: 13
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 849

Leu Ala Val Cys Gly Leu Pro Val Val Ala Leu Leu Ala
1               5                   10

<210> SEQ ID NO 850
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 850

Ala Ala Ala Val Ala Val Ala Gly Leu Ala Pro Leu Ala Leu
1               5                   10

<210> SEQ ID NO 851
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 851

Ala Leu Leu Pro Ala Leu Leu Leu Leu Leu Ala Ala Val Val
1               5                   10                  15

<210> SEQ ID NO 852
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 852

Ala Pro Pro Leu Ala Ile Leu Leu Leu Leu Ile Ala Pro Ala
1               5                   10                  15

<210> SEQ ID NO 853
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 853

Ala Pro Leu Leu Ala Leu Val Leu Leu Leu Ala Leu Ile Ala
1               5                   10

<210> SEQ ID NO 854
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 854

Ala Val Val Ala Val Leu Ala Leu Val Leu Ala Ala Leu Ile
1               5                   10

<210> SEQ ID NO 855
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 855

Leu Leu Ile Leu Pro Leu Leu Leu Leu Pro Ala Leu
1               5                   10

<210> SEQ ID NO 856
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 856

Leu Ala Ala Val Ala Ala Leu Ala Val Val Pro Val Ala
1               5                   10

<210> SEQ ID NO 857
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 857

Leu Leu Leu Leu Val Leu Ile Leu Pro Leu Ala Ala
1               5                   10

<210> SEQ ID NO 858
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 858

Leu Ala Val Val Val Val Ala Ala Val Leu Ala Ala Pro
1               5                   10

<210> SEQ ID NO 859
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 859

Val Leu Leu Ala Ala Ala Leu Ile Ala Val Leu Leu Leu Pro Pro
1               5                   10                  15

<210> SEQ ID NO 860
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 860

Leu Val Leu Ile Ala Leu Leu Ala Ala Pro Leu Ala Ala Ala
```

```
<210> SEQ ID NO 861
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 861

Leu Pro Leu Ala Leu Leu Leu Ala Ala Ala Ala Leu Val Pro
1               5                   10                  15

<210> SEQ ID NO 862
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 862

Pro Val Leu Leu Ala Ala Ala Leu Leu Leu Leu Leu Ala Leu Ala
1               5                   10                  15

<210> SEQ ID NO 863
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 863

Val Ile Ile Ala Leu Ile Val Ile Val Ala Val Val Leu Val Val Ala
1               5                   10                  15

Ala Val Leu Ala Leu
            20

<210> SEQ ID NO 864
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 864

Val Ile Ile Ala Leu Ile Val Ile Val Ala Val Val Leu Leu Val Val
1               5                   10                  15

Ala Ala Val Leu Ala Leu
            20

<210> SEQ ID NO 865
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 865

Val Pro Ile Ala Ala Val Ala Val Ala Ile Ala Val Val Leu
1               5                   10

<210> SEQ ID NO 866
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 866

Ala Ala Leu Leu Ala Leu Leu Leu Ala Ala Leu Pro Ala Ala Ala Leu
1               5                   10                  15

Leu Leu Ala Ala
            20

<210> SEQ ID NO 867
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 867

Leu Pro Leu Ala Val Ala Val Ala Ala Val Ala Ala Ala Val
1               5                   10

<210> SEQ ID NO 868
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 868

Leu Ala Ala Ile Ala Leu Val Ala Val Val Leu Ala Pro Ala Ala Ala
1               5                   10                  15

<210> SEQ ID NO 869
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 869

Ala Ala Ala Leu Ala Ala Ile Ala Val Ile Ala Ala Ala Pro Ala Val
1               5                   10                  15

Ala Ala

<210> SEQ ID NO 870
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 870

Ala Ala Ala Leu Ala Ala Ile Ala Val Ile Ala Ala Ala Pro Ala Val
1               5                   10                  15

Ala Ala

<210> SEQ ID NO 871
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 871

Pro Leu Ile Val Val Ala Ala Ala Val Val Ala Val Ala Leu Ala
1               5                   10                  15

Val Ala Ala Val
            20

<210> SEQ ID NO 872
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 872

Ala Val Val Ala Ala Ala Leu Ile Leu Ala Pro Ile
1               5                   10

<210> SEQ ID NO 873
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 873

Ala Val Val Val Val Leu Pro Ile Leu Leu Ala Ala
1               5                   10

<210> SEQ ID NO 874
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 874

Ala Leu Ala Leu Leu Leu Leu Val Leu Leu Pro Pro Ala
1               5                   10

<210> SEQ ID NO 875
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 875

Leu Val Val Leu Leu Ala Ala Leu Leu Val Leu
1               5                   10

<210> SEQ ID NO 876
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 876

Pro Ile Leu Val Leu Leu Leu Leu Ala
```

<210> SEQ ID NO 877
<211> LENGTH: 13
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 877

Leu Val Leu Ala Ala Leu Ala Val Val Ala Ala Pro Ala
1               5                   10

<210> SEQ ID NO 878
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 878

Val Ile Val Ala Leu Leu Ala Val Val Val Ala Val
1               5                   10

<210> SEQ ID NO 879
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 879

Pro Leu Leu Ala Leu Val Leu Pro Leu Ala Pro
1               5                   10

<210> SEQ ID NO 880
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 880

Ala Val Ala Leu Leu Ile Leu Ala Val
1               5

<210> SEQ ID NO 881
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 881

Val Leu Leu Ala Val Ile Ala Leu Ala Pro
1               5                   10

<210> SEQ ID NO 882
<211> LENGTH: 13
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 882

Leu Ile Val Ala Ala Val Val Val Ala Val Leu Ile
1               5                   10

<210> SEQ ID NO 883
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 883

Ala Val Val Val Ala Ala Leu Ala Leu Ala Pro
1               5                   10

<210> SEQ ID NO 884
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 884

Leu Ala Ala Val Leu Leu Leu Ile Pro Ala
1               5                   10

<210> SEQ ID NO 885
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 885

Ile Pro Leu Leu Leu Leu Leu Leu Ala Val Val Pro
1               5                   10

<210> SEQ ID NO 886
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 886

Pro Ala Val Ala Leu Val Ala Val Val Ala Val Ala Pro
1               5                   10

<210> SEQ ID NO 887
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 887

Leu Val Ala Ala Leu Leu Ala Val Leu Ile Ala Pro
1               5                   10

<210> SEQ ID NO 888
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 888

Ala Leu Leu Leu Ala Ala Val Ala Pro
1               5

<210> SEQ ID NO 889
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 889

Val Ala Ala Leu Leu Ala Val Leu Ala Ala Ala Pro
1               5                   10

<210> SEQ ID NO 890
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 890

Val Val Val Leu Leu Val Leu Leu Ala Leu Val Val Val
1               5                   10

<210> SEQ ID NO 891
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 891

Val Val Val Leu Leu Val Leu Leu Ala Leu Val Val Val
1               5                   10

<210> SEQ ID NO 892
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 892

Val Val Val Leu Leu Val Leu Leu Ala Leu Val Val Val
1               5                   10

<210> SEQ ID NO 893
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 893

Leu Ala Ala Val Ala Ala Leu Ala Val Val Val Pro
1               5                   10
```

```
<210> SEQ ID NO 894
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 894

Leu Gly Val Leu Val Gly Ala Val Gly Ala Ala
1               5                   10

<210> SEQ ID NO 895
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 895

Val Ala Ile Ala Ala Met Leu Gly Ala Leu Ala Leu Ala Leu Ala Pro
1               5                   10                  15

<210> SEQ ID NO 896
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 896

Phe Val Val Leu Gly Ala Ala Ala Ala Gly Ala Leu Ala Trp Ala Val
1               5                   10                  15

Leu Ala

<210> SEQ ID NO 897
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 897

Val Ile Val Leu Gly Val Leu Ala Ala Gly Ile Ala Leu Gly Trp Leu
1               5                   10                  15

Ala

<210> SEQ ID NO 898
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 898

Met Leu Val Leu Leu Leu Leu Phe Leu Leu Ile Met Gly Gly Phe Met
1               5                   10                  15

Phe Phe

<210> SEQ ID NO 899
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 899

Met Phe Leu Ala Ala Val Ala Ala Leu Ala Val Val Val Pro Val Ala
1               5                   10                  15

<210> SEQ ID NO 900
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 900

Leu Gly Gly Trp Ile Leu Val Leu Val Leu Pro Ile Ala Phe Pro Pro
1               5                   10                  15

<210> SEQ ID NO 901
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 901

Ile Leu Leu Gly Leu Leu Leu Gly Leu Val Gly Pro Ile Leu
1               5                   10                  15

<210> SEQ ID NO 902
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 902

Ile Ala Gly Ala Val Val Ala Ala Leu Gly Val Gly Ala Gly Leu Trp
1               5                   10                  15
Ala

<210> SEQ ID NO 903
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 903

Met Leu Leu Leu Val Ala Val Val Gly Cys Leu Leu Val Pro Pro Ala
1               5                   10                  15
Ala

<210> SEQ ID NO 904
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 904
```

```
Met Leu Met Leu Ile Leu Leu Leu Cys Ile Ile Gly Val
1               5                   10
```

<210> SEQ ID NO 905
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 905

```
Phe Ala Val Leu Ala Ala Ala Val Leu Val Gly Cys Gly Val
1               5                   10
```

<210> SEQ ID NO 906
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 906

```
Leu Leu Leu Gly Leu Leu Leu Cys Leu Ala Leu Val Leu Leu Leu Ala
1               5                   10                  15
```

<210> SEQ ID NO 907
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 907

```
Met Trp Leu Cys Leu Ala Leu Ala Leu Leu Leu Met Val Ile
1               5                   10
```

<210> SEQ ID NO 908
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 908

```
Ala Gly Val Ala Gly Val Cys Leu Leu Gly Val Val Ala Gly Ala Val
1               5                   10                  15

Ala Ala Val Ala
            20
```

<210> SEQ ID NO 909
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 909

```
Ala Val Ala Val Ala Gly Val Ala Ala Ala Val Leu Ala Pro Ala
1               5                   10                  15

Pro Ala
```

```
<210> SEQ ID NO 910
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 910

Ala Ala Ala Val Val Ala Ala Val Cys Ala Ala Leu Ala Gly Cys Ala
1               5                   10                  15

Ile

<210> SEQ ID NO 911
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 911

Ala Leu Leu Ala Ala Leu Leu Ala Leu Leu Ala Leu Leu Val Pro Ala
1               5                   10                  15

<210> SEQ ID NO 912
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 912

Ala Leu Leu Ala Ala Leu Leu Ala Leu Leu Ala Leu Leu Val Pro Ala
1               5                   10                  15

<210> SEQ ID NO 913
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 913

Ala Leu Leu Ala Ala Leu Leu Ala Leu Leu Ala Leu Leu Val Pro Ala
1               5                   10                  15

<210> SEQ ID NO 914
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 914

Ala Pro Leu Trp Ala Ala Ala Leu Leu Leu Val Leu Leu
1               5                   10

<210> SEQ ID NO 915
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 915

Ala Ala Ala Ala Val Ala Leu Ala Gly Val Ala Val Ala Ala Gly
1               5                   10                  15

Leu Ala

<210> SEQ ID NO 916
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 916

Ala Ala Leu Ala Val Ala Ala Leu Ala Ala Gly Cys Ala
1               5                   10

<210> SEQ ID NO 917
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 917

Ala Val Leu Ala Ala Val Ala Gly Val Ala Val Ala Pro Gly
1               5                   10                  15

Val Ala Ala Leu Pro Ala
            20

<210> SEQ ID NO 918
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 918

Ala Val Leu Ala Ala Val Ala Gly Val Ala Val Ala Pro Gly
1               5                   10                  15

Val Ala Ala Leu Pro Ala
            20

<210> SEQ ID NO 919
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 919

Ala Val Gly Ala Leu Ala Leu Ala Val Ala Val Leu Ala Cys Gly Gly
1               5                   10                  15

<210> SEQ ID NO 920
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 920
```

```
Cys Ala Ala Leu Leu Ala Ala Val Ala Val Leu Gly Ala Ala Gly Cys
1               5                   10                  15
```

<210> SEQ ID NO 921
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 921

```
Phe Ala Ile Gly Ala Val Val Ala Leu Ala Gly Met Gly Pro Trp
1               5                   10                  15

Leu
```

<210> SEQ ID NO 922
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 922

```
Gly Ala Ala Ala Val Ala Leu Ala Ala Ala Ala Leu Leu Ala Gly Cys
1               5                   10                  15
```

<210> SEQ ID NO 923
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 923

```
Leu Ala Val Val Leu Leu Ala Leu Val Ala Val Ala Gly Ala Ala Val
1               5                   10                  15

Ala
```

<210> SEQ ID NO 924
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 924

```
Gly Leu Val Ala Leu Leu Leu Gly Ala Cys Leu Ala Leu Ile Gly Leu
1               5                   10                  15

Leu Phe
```

<210> SEQ ID NO 925
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 925

```
Val Val Val Gly Leu Leu Leu Ile Val Gly Gly Phe Phe Leu Gly Leu
1               5                   10                  15

Val Ile
```

<210> SEQ ID NO 926
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 926

Val Ala Trp Leu Ala Val Val Leu Ala Val Cys Leu Ala Gly Cys Val
1               5                   10                  15

Gly Val

<210> SEQ ID NO 927
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 927

Leu Leu Ala Val Ile Leu Leu Val Leu Phe Trp Gly Val
1               5                   10

<210> SEQ ID NO 928
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 928

Leu Val Ala Leu Val Leu Leu Gly Val Gly Leu Leu Val Met Phe Leu
1               5                   10                  15

Ala

<210> SEQ ID NO 929
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 929

Pro Leu Val Leu Leu Leu Ala Val Leu Leu Ala Val Leu Cys Val
1               5                   10                  15

Leu

<210> SEQ ID NO 930
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 930

Leu Met Leu Leu Ala Met Val Val Ala Leu Val Ile Leu Pro Phe Phe
1               5                   10                  15

Ile Gly Gly

```
<210> SEQ ID NO 931
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 931

Gly Val Leu Ala Val Leu Ala Val Cys Val Leu Leu Gly Ala Gly
1               5                   10                  15

Cys Gly

<210> SEQ ID NO 932
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 932

Val Val Ile Ala Val Val Gly Val Val Val Leu Leu Val Leu Leu Ala
1               5                   10                  15

Leu Val Val Val
            20

<210> SEQ ID NO 933
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 933

Val Val Ile Ala Val Val Gly Val Val Val Leu Leu Val Leu Leu Ala
1               5                   10                  15

Leu Val Val Val
            20

<210> SEQ ID NO 934
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 934

Val Leu Leu Ala Leu Pro Val Cys Val Ala Ala Gly Val Ala Ile Val
1               5                   10                  15

Val Phe Gly

<210> SEQ ID NO 935
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 935

Val Leu Ala Val Val Val Ala Ile Val Leu Ala Ala Pro
1               5                   10
```

```
<210> SEQ ID NO 936
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 936

Pro Pro Val Leu Ala Gly Ile Gly Ala Ala Val Leu Val Ala Ala Ala
1               5                   10                  15

Leu Val Pro Gly
            20

<210> SEQ ID NO 937
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 937

Val Val Ala Ala Leu Leu Val Leu Gly Ala Gly Ala
1               5                   10

<210> SEQ ID NO 938
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 938

Ala Phe Ala Leu Ala Val Gly Gly Ala Ala Val Ala Leu Pro Gly Ala
1               5                   10                  15

Pro Ala Ala

<210> SEQ ID NO 939
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 939

Ala Leu Ile Ala Leu Leu Leu Gly Met Gly Leu Ala Leu Phe
1               5                   10

<210> SEQ ID NO 940
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 940

Met Ala Leu Leu Ala Leu Leu Val Gly Leu Val Leu Ala Leu
1               5                   10

<210> SEQ ID NO 941
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 941

Ile Val Pro Leu Leu Leu Ala Ala Phe Leu Leu Ile Gly Ala Gly Ala
1               5                   10                  15

<210> SEQ ID NO 942
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 942

Gly Leu Leu Leu Ala Cys Leu Leu Leu Ala Phe Ala Gly Leu Val Leu
1               5                   10                  15

Val Pro

<210> SEQ ID NO 943
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 943

Ala Leu Ala Ala Leu Val Ala Ala Val Cys Ala Ala Val Val Leu
1               5                   10                  15

<210> SEQ ID NO 944
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 944

Leu Ile Trp Ile Val Ile Ile Ala Leu Ala Val Ile Val Leu Val Leu
1               5                   10                  15

Leu

<210> SEQ ID NO 945
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 945

Ala Phe Cys Met Leu Ala Leu Leu Leu Ala Ala Leu Ile Phe Phe Ala
1               5                   10                  15

Ile Trp Ile Ile
            20

<210> SEQ ID NO 946
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 946

Val Phe Ala Leu Leu Phe Leu Leu Ala Val Val Leu Gly Val Ala Val
1               5                   10                  15

Ala Val Gly Ala
            20

<210> SEQ ID NO 947
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 947

Ala Leu Met Ala Ile Ala Val Val Leu Ala Ala Gly Val Leu Gly Val
1               5                   10                  15

<210> SEQ ID NO 948
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 948

Ala Ala Ala Pro Pro Gly Val Leu Leu Leu Leu Leu
1               5                   10

<210> SEQ ID NO 949
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 949

Ala Ala Ala Val Gly Ala Val Met Leu Ala Leu Ala Ala Ala Cys Gly
1               5                   10                  15

Gly Gly

<210> SEQ ID NO 950
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 950

Ala Ala Leu Ala Ala Leu Val Val Ala Ala Gly Leu Val Ala Gly Ala
1               5                   10                  15

Ala

<210> SEQ ID NO 951
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 951

Ala Ala Leu Ala Ala Val Leu Ala Leu Ala Ala Ala Cys Gly Gly
```

-continued

```
<210> SEQ ID NO 952
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 952

Ala Ala Leu Ala Val Ala Ala Ala Leu Ala Leu Leu Ala Ala Cys Gly
1               5                   10                  15

<210> SEQ ID NO 953
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 953

Ala Ala Leu Ala Ala Ala Val Ala Ala Val Gly Leu Ala Leu
1               5                   10

<210> SEQ ID NO 954
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 954

Ala Ala Leu Ala Ala Ala Val Ala Ala Val Gly Leu Ala Leu
1               5                   10

<210> SEQ ID NO 955
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 955

Leu Leu Ala Val Leu Leu Ala Leu Leu Gly Ala Trp Ala Val Trp Pro
1               5                   10                  15

Pro Leu

<210> SEQ ID NO 956
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 956

Val Val Leu Ala Leu Leu Val Ala Val Val Gly Leu Leu Cys Val Phe
1               5                   10                  15

Ala Ala

<210> SEQ ID NO 957
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 957

Ala Leu Val Val Gly Ala Cys Ala Ala Val Gly Val Leu Leu Gly Cys
1               5                   10                  15

Gly Gly Val

<210> SEQ ID NO 958
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 958

Ala Val Gly Val Ala Gly Ala Val Val Leu Gly Leu Leu Leu Trp Trp
1               5                   10                  15

Leu Leu Pro Leu
            20

<210> SEQ ID NO 959
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 959

Ala Trp Trp Leu Ile Leu Phe Ala Val Ile Gly Val Ala Val Leu Val
1               5                   10                  15

Ala Val Phe

<210> SEQ ID NO 960
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 960

Gly Met Leu Phe Gly Ala Ala Ala Val Ala Gly Ala Val Leu Ala Gly
1               5                   10                  15

<210> SEQ ID NO 961
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 961

Gly Val Ala Val Val Val Leu Ala Ile Leu Leu Pro Val Ala Ala Ala
1               5                   10                  15

Gly Leu Ala Leu
            20

<210> SEQ ID NO 962
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 962

Ile Ala Ile Ala Ala Ile Ala Ile Leu Ala Leu
1               5                   10

<210> SEQ ID NO 963
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 963

Ile Ile Ala Ala Leu Ile Ala Phe Ala Leu Ala Ala Cys
1               5                   10

<210> SEQ ID NO 964
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 964

Pro Ala Ala Ile Ala Leu Val Ala Met Ala Leu Val Leu Ala Pro Ala
1               5                   10                  15

Val Ala Ala Ala
            20

<210> SEQ ID NO 965
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 965

Pro Ala Ala Ile Ala Leu Val Ala Met Ala Leu Val Leu Ala Pro Ala
1               5                   10                  15

Val Ala Ala Ala
            20

<210> SEQ ID NO 966
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 966

Ala Val Ala Ile Ile Val Ala Val Val Ala Ile Ala Leu Ile Ile Gly
1               5                   10                  15

Gly Gly Val Trp
            20

<210> SEQ ID NO 967
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 967

Ala Val Ala Ile Ile Val Ala Val Val Ala Ile Ala Leu Ile Ile Gly
1               5                   10                  15

Gly Gly Val Trp
            20

<210> SEQ ID NO 968
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 968

Leu Ala Ala Val Ala Ala Ala Gly Ala Val Ala Ala Leu Gly Leu
1               5                   10                  15

Ala Ala Pro Ala Ala Ala Ala Pro
            20

<210> SEQ ID NO 969
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 969

Leu Ala Ala Val Ala Ala Ala Gly Ala Val Ala Ala Leu Gly Leu
1               5                   10                  15

Ala Ala Pro Ala Ala Ala Ala Pro
            20

<210> SEQ ID NO 970
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 970

Leu Ala Ala Val Ala Ala Ala Gly Ala Val Ala Ala Leu Gly Leu
1               5                   10                  15

Ala Ala Pro Ala Ala Ala Ala Pro
            20

<210> SEQ ID NO 971
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 971

Leu Ala Ala Val Val Gly Val Ala Ala Ala Val Gly Val Ala Ala Pro
1               5                   10                  15

Ala Ala Ala Ala Ala Val Pro Val Pro Val Pro Leu
            20                  25
```

```
<210> SEQ ID NO 972
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 972

Leu Ala Ala Val Val Gly Val Ala Ala Ala Val Gly Val Ala Ala Pro
1               5                   10                  15

Ala Ala Ala Ala Ala Val Pro Val Pro Val Pro Leu
            20                  25

<210> SEQ ID NO 973
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 973

Leu Ala Ala Val Val Gly Val Ala Ala Ala Val Gly Val Ala Ala Pro
1               5                   10                  15

Ala Ala Ala Ala Ala Val Pro Val Pro Val Pro Leu
            20                  25

<210> SEQ ID NO 974
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 974

Leu Ala Gly Cys Phe Leu Leu Ile Leu Gly Ile Val Leu Leu Pro Ala
1               5                   10                  15

<210> SEQ ID NO 975
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 975

Ala Leu Ala Ile Ala Pro Phe Ala Ala Gly Pro Ala Ala Val
1               5                   10

<210> SEQ ID NO 976
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 976

Leu Gly Leu Ala Val Met Ile Ile Leu Ala Val Gly Cys Gly Gly
1               5                   10                  15

<210> SEQ ID NO 977
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 977

Leu Ile Leu Leu Leu Ala Val Ala Leu Gly Gly Ala Trp Ala Ala Pro
1               5                   10                  15

Ala Ala Ala Pro Ala
            20

<210> SEQ ID NO 978
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 978

Leu Leu Val Cys Ala Ala Leu Ala Gly Ile Val Leu Ala Pro Val Pro
1               5                   10                  15

Ala Ala Ala

<210> SEQ ID NO 979
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 979

Leu Pro Val Val Val Val Gly Ala Gly Pro Val Leu Ala Ala Ala Ala
1               5                   10                  15

<210> SEQ ID NO 980
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 980

Leu Val Ala Val Ala Ala Met Leu Ile
1               5

<210> SEQ ID NO 981
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 981

Leu Val Leu Ala Ala Gly Ala Ala Leu Gly Ala Ala Ala
1               5                   10

<210> SEQ ID NO 982
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 982

Leu Val Leu Val Leu Ile Ala Met Ala Ala Ala Val Trp Ala Val Gly
1               5                   10                  15

Gly Val

<210> SEQ ID NO 983
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 983

Met Ala Leu Ala Ala Leu Met Ile Ala Leu Gly Leu Gly Leu
1               5                   10

<210> SEQ ID NO 984
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 984

Met Phe Leu Ala Val Leu Leu Leu Ala Ala Ala Val Trp Ala Val Phe
1               5                   10                  15

<210> SEQ ID NO 985
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 985

Ile Ala Leu Ala Leu Leu Pro Leu Leu Phe Pro Val
1               5                   10

<210> SEQ ID NO 986
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 986

Met Val Leu Leu Ala Ala Ala Leu Ile Ala Gly Val Phe Phe Leu Leu
1               5                   10                  15

Leu Pro Gly

<210> SEQ ID NO 987
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 987

Met Ala Pro Ala Val Leu Pro Pro Val Val Ile Gly Ala Gly Pro
1               5                   10                  15

Ile Gly Leu Ala Ala Ala Ala
```

<210> SEQ ID NO 988
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 988

Met Val Val Gly Leu Leu Val Ala Ala Leu Ile Pro Ala Val Ala
1               5                   10                  15

<210> SEQ ID NO 989
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 989

Pro Ala Ala Ala Ala Ala Ala Ile Ala Ala Ala Ala Phe Leu Ala Ala
1               5                   10                  15

<210> SEQ ID NO 990
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 990

Pro Ala Leu Cys Phe Leu Leu Leu Ala Val Ala Met Phe Phe Gly Ala
1               5                   10                  15

Leu

<210> SEQ ID NO 991
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 991

Pro Ala Pro Leu Gly Leu Ile Leu Leu Leu Phe Leu Ala Ala Leu
1               5                   10                  15

<210> SEQ ID NO 992
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 992

Pro Ala Leu Leu Leu Leu Val Leu Ala Cys Cys Leu Gly Ala
1               5                   10

<210> SEQ ID NO 993
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 993

Pro Leu Leu Leu Leu Leu Leu Pro Leu Ala Gly Leu Ala Leu
1               5                   10

<210> SEQ ID NO 994
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 994

Pro Leu Pro Trp Leu Ala Leu Pro Leu Leu Leu Trp Val Ala Gly Gly
1               5                   10                  15

<210> SEQ ID NO 995
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 995

Pro Leu Ile Ala Leu Phe Cys Gly Leu Leu Val Leu Leu Leu Ile
1               5                   10                  15

<210> SEQ ID NO 996
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 996

Trp Ala Leu Pro Leu Leu Cys Ala Ala Leu Cys Val
1               5                   10
```

MACROMOLECULE TRANSDUCTION DOMAINS AND METHODS FOR IDENTIFICATION AND USES THEREOF

TECHNICAL FIELD

The present invention relates to novel macromolecule transduction domain (MTD) peptides which facilitate the traverse of a biologically active molecule across the cell membrane, polynucleotides encoding the same, methods of identifying the same, methods of genetically engineering a biologically active molecule having cell permeability by using the same, methods of importing a biologically active molecule into a cell by using the same, and uses thereof.

BACKGROUND ART

Cellular internalization of macromolecules, such as DNA, RNA, proteins, oligonucleotides, and peptides, is still a challenging task because of the presence of the plasma membrane, which constitutes an impermeable barrier for such molecules. Numerous difficulties have been encountered in delivering such molecules to a desired target, including poor penetration into a tissue or cell, toxicity when delivered systemically due to the insufficient specificity of targeting to a particular tissue or cell, side effects when delivered in a high concentration in order to achieve an adequate local concentration at a particular target cell or tissue, and degradation such that inadequate amounts are delivered to the target and/or such that byproducts of degradation result in undesirable side effects.

In order to circumvent these problems, several carrier-mediated delivery systems have been developed. Among them, much attention has recently been given to the use of peptide-based delivery systems. The use of peptides with cell permeability has several advantages, which are mainly due to the various modifications that can be made to the peptide sequence. This allows the engineering of carriers that can address different cellular subdomains and/or are able to transport various types of cargo molecules.

Many cell permeable peptides are designed from sequences of membrane-interacting proteins, such as recombinant proteins, signal peptides, transmembrane domains, and antimicrobial peptides. Within these sequences, short sequences called protein transduction domains (PTDs) have been proved to efficiently cross biological membranes without the need of a carrier or a receptor and to deliver peptides or proteins into intracellular compartments. A number of studies have suggested that the use of PTD-based peptides could be of major importance for therapies against viral diseases or cancers. Among the PTD-based peptides, the third helix of the homeodomain of antennapedia called penetratin (Joliot, A. and A. Prochiantz, *Nat. Cell Biol.* 6(3):189-96 (2004)), the Tat peptide derived from the transactivating protein Tat of HIV-1 (Wadia, J. S. and S. F. Dowdy, *Curr. Opin. Biotechnol.* 13(1):52-6 (2002)), transportan (Pooga et al., *Faseb J.* 12(1):67-77 (1998)), and VP22 (Elliott, G and P. O'Hare, *Cell* 88(2):223-33 (1997)) have been shown to improve the cellular uptake of peptides, proteins, and oligonucleotides.

A second category of cell-penetrating peptides, called amphipathic peptides, has also been described. An amphipathic molecule can be defined, in short, as consisting of two domains: a hydrophilic (polar) domain and a hydrophobic (non-polar) domain. For peptides, the amphipathic character can arise from either the primary structure or the secondary structure. Primary amphipathic peptides can be defined as the sequential assembly of a domain of hydrophobic residues with a domain of hydrophilic residues. Secondary amphipathic peptides are generated by the conformational state which allows the positioning of the hydrophobic and hydrophilic residues on opposite sides of the molecule.

Other peptides, such as polyarginine-based peptides, calcitonin-derived peptides, and oligomers, have also been proposed as tools for intracellular delivery of therapeutics.

However, the currently known delivery systems appear to be limited due to their lack of efficiency and/or their toxicity, and little is known about the pathway of their cellular uptake, constituting a handicap for improving their efficiency. In addition, a number of delivery systems are limited in their ability to cross cellular and nuclear membranes. Even where such delivery peptides do cross cell membranes, they are often limited in their efficacies due to their entrapment in endosomes.

The present invention is directed to overcoming these deficiencies in the art.

DISCLOSURE

Technical Solution

The present invention relates to isolated macromolecule transduction domain (MTD) peptides capable of mediating the transport of a biologically active molecule into a cell.

Another aspect of the present invention relates to isolated polynucleotides encoding such MTD peptides.

The present invention also relates to a method of identifying a MTD peptide having cell permeability.

Another aspect of the present invention relates to a method of genetically engineering a biologically active molecule having cell permeability by attaching a MTD peptide to a biologically active molecule.

Still another aspect of the present invention relates to an isolated recombinant protein having cell permeability comprising a MTD peptide having cell permeability and a biologically active molecule.

The present invention also, relates to a pharmaceutical composition for delivery of a biologically active molecule to a cell comprising a cell permeable recombinant protein where a MTD is attached to a biologically active molecule.

Another aspect of the present invention relates to a method of transporting a biologically active molecule into a cell in a subject comprising administering to a subject a cell permeable recombinant protein comprising a MTD peptide attached to a biologically active molecule.

Other aspects of the present invention relate to the use of MTD peptides for drug delivery, vaccine administration, protein therapy, and gene therapy.

Advantageous Effects

The present invention provides MTD peptides having cell permeability which can facilitate the transport of a biologically active molecule into a cell and, thus, can be effectively used for drug delivery, vaccine administration, peptide therapy, and gene therapy.

DESCRIPTION OF DRAWINGS

FIGS. 1a to 1o show tables illustrating the amino acid sequences and structural characteristics of macromolecule transduction domain (MTD) peptides identified according to the method of the present invention.

FIG. 4a is a schematic diagram illustrating the subcloning of a DNA fragment encoding MTD-EGFP into the pGEM-Teasy vector according to the present invention, whereas

FIG. 5a is a schematic diagram illustrating the cloning of a DNA fragment encoding MTD-EGFP into the pET 28(+) vector according to the present invention, whereas

FIGS. 10a to 10i are photographs visualizing the cell permeabilities of His-MTD-EGFP recombinant proteins by confocal laser scanning microscopy according to the present invention.

FIGS. 12a to 12i are photographs visualizing the in vivo distribution of His-MTD-EGFP recombinant proteins by fluorescence microscopy according to the present invention.

FIGS. 13a to 13k show tables summarizing the characteristics of the MTD peptides identified according to the method of the present invention.

DETAILED DESCRIPTION

Figure 2:
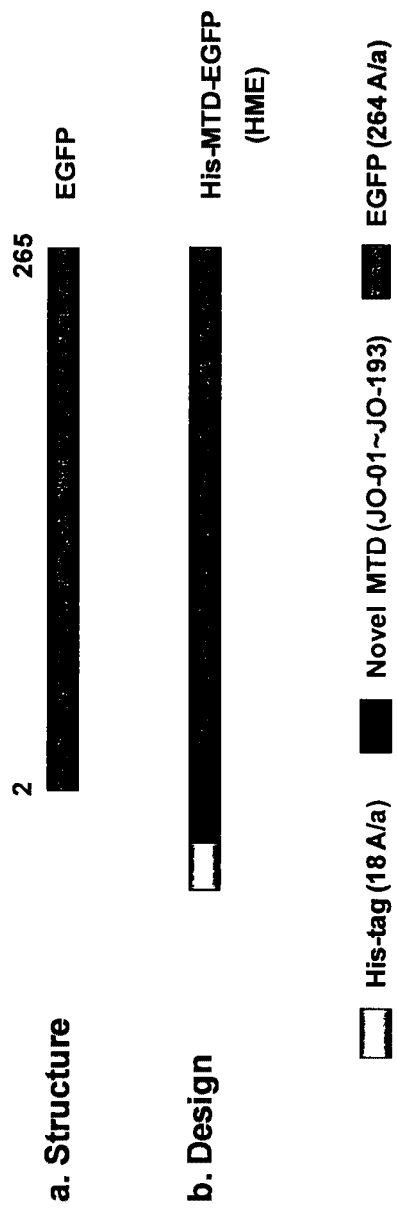
FIG. 2 is a schematic diagram illustrating the His-MTD-EGFP recombinant protein having cell permeability and constructed according to the present invention.

The present invention relates to novel macromolecule transduction domain (MTD) peptides having cell permeability that facilitate the traverse of a biologically active molecule across the cell membrane. The MTD peptides of the present invention are cell permeable polypeptides capable of mediating the import of a biologically active molecule, including polypeptides, protein domains, or full-length proteins, through the cell membrane. The MTD peptides of the present invention are characterized as having a single hydrophobic region at their N-terminus, forming a helix structure, exhibiting flexibility, and having relatively short amino acids (7 to 17 amino acids) in length (see FIGS. 1a to 1o).

One embodiment of the present invention relates to isolated MTD peptides having cell permeability, where the MTD peptide has an amino acid sequence selected from the group consisting of SEQ ID NOS: 1-193, analogs, derivatives, amidated variations, and conservative variations thereof.

A person having ordinary skill in the art can make similar substitutions to obtain peptides having greater cell permeability and a broader host range. For example, the present invention provides peptides corresponding to amino acid sequences SEQ ID NOS: 1 to 193, as well as analogues, derivatives, and amidated derivatives thereof, as long as the cell permeability of the peptide remains. Minor modifications to the primary amino acid sequence of the peptides of the present invention may result in peptides which have substantially equivalent or enhanced cell permeability, as compared to the specific peptides described herein. Such modifications may be deliberate, as by site-directed mutagenesis, or may be spontaneous. All of the peptides produced by these modifications are included herein, as long as the cell permeability of the original peptide still exists or, in the case of amidated versions of the peptide, the cell permeability of the original peptide is enhanced or altered such that the amidated peptide is therapeutically useful. It is envisioned that such modifications are useful for altering or enhancing the cell permeability of a particular peptide.

Further, the deletion of one or more amino acids can also result in a modification to the structure of the resultant molecule without any significant change in its cell permeability. This can lead to the development of a smaller active molecule which may also have utility. For example, amino- or carboxy-terminal amino acids which may not be required for the cell permeability of a particular peptide can be removed. The peptides of the present invention include any analog, homolog, mutant, isomer, or derivative of the peptides disclosed in the present application, so long as the cell permeability, as described herein, remains. All peptides were synthesized using L-amino acids; however, D forms of all of the peptides can be synthetically produced. In addition, C-terminal derivatives, such as C-terminal methyl esters and C-terminal amidates, can be produced, in order to increase the cell permeability of the peptide of the present invention.

A "peptide" of the present invention includes amino acid sequences that are conservative variations of those peptides specifically exemplified herein. The term "conservative variation" as used herein denotes the replacement of an amino acid residue by another, biologically similar residue. Examples of conservative variations include the substitution of one hydrophobic residue, such as isoleucine, valine, leucine, alanine, cysteine, glycine, phenylalanine, proline, tryptophan, tyrosine, norleucine, or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine, and threonine. The term "conservative variation" also includes the use of a substituted amino acid in place of an unsubstituted parent amino acid, provided that antibodies raised to the substituted polypeptide also immunoreact with the unsubstituted polypeptide. Such conservative substitutions are within the definition of the classes of the peptides of the present invention.

Another aspect of the present invention relates to isolated polynucleotides encoding the above MTD peptides of the present invention. Exemplary polynucleotides encode the MTD peptides having an amino acid sequence selected from the group consisting of SEQ ID NOS: 1 to 193 and analogs, derivatives, amidated variations, and conservative variations thereof. The polynucleotides encoding the MTD peptides of the present invention have nucleotide sequences represented by SEQ ID NOs: 194 to 386.

The polynucleotides of the present invention may be in the form of a RNA or DNA, where DNA includes cDNA and synthetic DNA. The DNA may be single stranded or double stranded. If it is single stranded, it may be the coding strand or non-coding (antisense) strand. The coding sequence may be identical to the nucleotide sequence selected from SEQ ID NOs: 194 to 386 or may be a different coding sequence, where the coding sequence, as a result of degeneracy or redundancy of the genetic code, encodes for the same polypeptide.

The polynucleotides of the present invention also include variants of the above-described polynucleotides, which encode fragments, analogs, and derivatives of the polynucleotides characterized by the deduced amino acid sequences of SEQ ID NOs: 1 to 193. The variant of the polynucleotide may be a naturally occurring allelic variant of the polynucleotide or a non-naturally occurring variant of the polynucleotide.

The polynucleotide of the present invention may have a coding sequence which is a naturally occurring allelic variant of the coding sequence characterized by the nucleotide sequence selected from SEQ ID NOs: 194 to 386. An allelic variant is an alternate form of a polynucleotide sequence which may have a substitution, deletion, or addition of one or more nucleotides, which does not substantially alter the function of the encoded polypeptide.

Sequences similar or homologous (e.g., at least about 70% sequence identity) to the sequences disclosed herein are also part of the present invention. In other embodiments of the present invention, the sequence identity at the amino acid level can be about 80%, 85%, 90%, 91%, 92%, 93%, 94%, 95%, 96%, 97%, 98%, 99%, or higher. At the polynucleotide level, the sequence identity can be about 70%, 75%, 80%, 85%, 90%, 91%, 92%, 93%, 94%, 95%, 96%, 97%, 98%, 99%, or higher. Alternatively, substantial identity exists when the polynucleotide segments hybridize under selective hybridization conditions (e.g., very high stringency hybridization conditions), to the complement of the strand. The polynucleotides may be present in whole cells, in a cell lysate, or in a partially purified or substantially pure form.

It is well known in the art that a single amino acid may be encoded by more than one nucleotide codon and that the polynucleotide may be easily modified to produce an alternate polynucleotide that encodes the same peptide. Therefore, other embodiments of the present invention include alternate nucleotide sequences encoding peptides containing the amino acid sequences as previously described. Nucleic acid molecules encoding peptides containing the claimed amino acid sequence include nucleotide sequences which encode any combination of the claimed sequence and any other amino acids located N-terminal or C-terminal to the claimed amino acid sequence.

It is to be understood that amino acid and nucleic acid sequences of the present invention may include additional residues, particularly N- or C-terminal amino acids or 5' or 3' polynucleotides, and still be essentially as set forth in the sequences disclosed herein, as long as the sequence confers membrane permeability upon the polypeptide or protein moiety of the recombinant protein.

The present invention also relates to a method of identifying the MTD peptides having cell permeability.

The method of the present invention involves the following steps:

1) identifying secreted proteins having a signal sequence-like domain from multiple amino acid sequence databases;

2) selecting from said identified secreted proteins hydrophobic peptides having a single hydrophobic region at their N-terminus and forming a helix structure; and 3) optimizing and minimizing said selected hydrophobic peptides under conditions effective to produce peptides suitable for use as an MTD peptide.

In order to identify certain candidate peptides that can potentially penetrate the plasma membrane, secreted proteins that have a signal sequence-like domain are identified from multiple amino acid sequence databases, as described in step 1). In a specific embodiment of the present invention, these secreted proteins are selected from the PubMed™ Entrez Protein Database by using several key words, such as "hydrophobic region of signal sequence," "signal sequence hydrophobic region," "signal sequence of secreted protein," "hydrophobic signal sequence," and "hydrophobic domain of secreted protein." As a result, more than 1,500 secreted proteins that have a signal sequence-like domain are identified.

As used herein, the term "signal sequence-like domain" refers to a peptide capable of mediating macromolecule translocation across the plasma membrane.

The term "signal peptide" as used herein is a short (3-60 amino acids long) peptide chain that directs the post-translational transport of a protein. Signal peptides may also be called targeting signals, signal sequences, transit peptides, or localization signals. The amino acid sequences of signal peptides direct proteins (which are synthesized in the cytoplasm) to certain organelles such as the nucleus, mitochondrial matrix, endoplasmic reticulum, chloroplast, apoplast and peroxisome. Some signal peptides are cleaved from the protein by signal peptidase after the proteins are transported. The N-terminal sequence of a secreted protein, which is required for transport through the cell membrane.

Examples of signal peptides may include, but are not limited to, transport to the nucleus (NLS: -Pro-Pro-Lys-Lys-Lys-Arg-Lys-Val-), transport to the endoplasmic reticulum ($H_2N$-Met-Met-Ser-Phe-Val-Ser-Leu-Leu-Leu-Val-Gly-Ile-Leu-Phe-Trp-Ala-Thr-Glu-Ala-Glu-Gln-Leu-Thr-Lys-Cys-Glu-Val-Phe-Gln-), retention to the endoplasmic reticulum (-Lys-Asp-Glu-Leu-COOH), transport to the mitochondrial matrix ($H_2N$-Met-Leu-Ser-Leu-Arg-Gln-Ser-Ile-Arg-Phe-Phe-Lys-Pro-Ala-Thr-Arg-Thr-Leu-Cys-Ser-Ser-Arg-Tyr-Leu-Leu-), transport to the peroxisome (PTS1: -Ser-Lys-Leu-COOH), transport to the peroxisome (PTS2: $H_2N$-Arg-Leu-X5-His-Leu-) (wherein, $H_2N$ is the N-terminus of a protein, and COOH is the C-Terminus of a protein).

Examples of signal sequence-like domains may include, but are not limited to, penetratin (Arg-Gln-Ile-Lys-Ile-Trp-Phe-Gln-Asn-Arg-Arg-Met-Lys-Trp-Lys-Lys), the Tat peptide derived from the transactivating protein Tat of HIV-1 (Arg-Lys-Lys-Arg-Arg-Gln-Arg-Arg-Pro), transportan (Gly-Trp-Thr-Leu-Asn-Ser-Ala-Gly-Tyr-Leu-Leu-Gly-Lys-Ile-Asn-Lys-Ala-Leu-Ala-Ala-Leu-Ala-Lys-Lys-Ile-Leu), Buforin II (Thr-Arg-Ser-Ser-Arg-Ala-Gly-Leu-Gln-Phe-Arg-Val-Gly-Arg-Val-His-Arg-Leu-Leu-Arg-Lys), MAP (model amphiphatic peptide: Lys-Leu-Ala-Leu-Lys-Ala-Ser-Leu-Lys-Ala-Leu-Lys-Ala-Ala-Leu-Lys-Leu-Ala), k-FGF (Ala-Ala-Val-Ala-Leu-Leu-Pro-Ala-Val-Leu-Leu-Ala-Leu-Leu-Ala-Pro), Ku 70 (Val-Pro-Met-Leu-Lys-Pro-Met-Leu-Lys-Glu), prion (Met-Ala-Asn-Leu-Gly-Tyr-Trp-Leu-Leu-Ala-Leu-Phe-Val-Thr-Met-Trp-Thr-Asp-Val-Gly-Leu-Cys-Lys-Lys-Arg-Pro-Lys-Pro), pVEC (Leu-Leu-Ile-Ile-Leu-Arg-Arg-Arg-Ile-Arg-Lys-Gln-Ala-His-Ala-His-Ser-Lys), pep-1 (Lys-Glu-Thr-Trp-Trp-Glu-Thr-Trp-Trp-Thr-Glu-Trp-Ser-Gln-Pro-Lys-Lys-Lys-Arg-Lys-Val), SynB1 (Arg-Gly-Gly-Arg-Leu-Ser-Tyr-Ser-Arg-Arg-Arg-Phe-Ser-Thr-Ser-Thr-Gly-Arg), pep-7 (Ser-Asp-Leu-Trp-Glu-Met-Met-Met-Val-Ser-Leu-Ala-Cys-Gln-Tyr), and HN-1 (Thr-Ser-Pro-Leu-Leu-Ile-His-Asn-Gly-Gln-Lys-Leu).

Next, as described in step 2), hydrophobic peptides that have a single hydrophobic region at their N-terminus and form a helix structure are selected from the secreted proteins identified in step 1). All of the secreted proteins having a signal sequence-like domain that were identified in step 1) are subjected to hydropathy analysis to determine whether they contain a single hydrophobic region (H-region) at their N-terminus, followed by computer-aided genomic and proteomic information analysis to determine whether they form a helix structure. The hydrophobic region usually forms a helix structure, which imparts the protein with membrane-translocating activity.

In one embodiment of the present invention, the SOSUI system, a classification and secondary prediction system for membrane proteins, can be used for the computer-aided genomic and proteomic information analysis. The SOSUI system is a useful tool for secondary structure prediction of membrane proteins from a protein sequence and is freely available on-line. Since the SOSUI system currently requires peptides to be analyzed to have at least about 20 amino acids in length, additional amino acids derived from the N-terminal domain of enhanced green fluorescent protein are added to the end of the signal sequence-like domain. When the SOSUI system is used, 220 hydrophobic peptides that have a single hydrophobic region at their N-terminus and form a transmembrane helix structure are selected.

Finally, the hydrophobic peptides selected in step 2) are optimized and minimized so that they are suitable for use as an MTD peptide, as described in step 3). To optimize the selected hydrophobic peptides, empirical modifications are made to them as follows: i) hydrophilic, nonpolar, and positively or negatively charged amino acids are removed from the selected hydrophobic peptides; and ii) various combinations of five hydrophobic amino acids, i.e., alanine (Ala or A), valine (Val or V), proline (Pro or P), leucine (Leu or L), and isoleucine (Ile or I) are created empirically. Said hydrophobic amino acids are known to provide flexibility to the H-region which may allow the hydrophobic region of the signal sequences to form a hairpin-like loop, resulting in destabilized conformational change of the phospholipid bilayer. Such local and transient formation of the non-bilayer lipid structure induced by contact with the flexible H-region leads to topological transformation.

To minimize the length of the hydrophobic peptides optimized as described above, the following principles are employed for determining which amino acids should be eliminated therefrom: i) non-hydrophobic amino acids at the left or the right side of the hydrophobic peptides are eliminated to minimize the size, while maintaining the hydrophobic region thereof; ii) non-hydrophobic amino acids at the middle or the right side of the hydrophobic peptides are replaced with a hydrophobic amino acid, proline (Pro or P) to provide flexibility or a bending potential; and iii) the number of repeated hydrophobic amino acids is minimized to reduce the size of the hydrophobic peptides. Thus, the MTD candidates are characterized as modified peptides exhibiting hydrophobicity and flexibility, having relatively short amino acids (7 to 17) in length, and forming a helix structure.

According to the method of the present invention described above, novel MTD peptides having an amino acid sequence selected from the group consisting of SEQ ID NOS: 1 to 193 and capable of facilitating the traverse of biologically active molecules across the cell membrane can be identified.

In another embodiment of the present invention, one of the novel MTDs, JO-98 (SEQ ID NO: 98) can be identified by the following process:

i) immunoglobulin domain containing 4 from *Homo sapiens* is selected from the PubMed™ Entrez Protein Database as a secreted protein having a signal sequence-like domain;

ii) through a hydropathy analysis, it is confirmed that said protein contains a single N-terminal hydrophobic region;

iii) the hydrophobic region (H-region) is selected from the full-length signal sequences of said protein, which has the amino acid sequence represented by MGILLGLLLLGHLTVDTY GRPIL (23 amino acids in length);

iv) through a structural analysis utilizing the SOSUI system, it is confirmed that the selected hydrophobic region forms a helix structure;

v) non-hydrophobic amino acids (methionine: M; glycine: G) at the left side of the hydrophobic region are deleted to make the first amino acid of the hydrophobic region a hydrophobic amino acid, hydrophobic peptide that has an amino acid sequence represented by ILLGLLLLGHLTVDTYGRPIL (21 amino acids in length);

vi) basic (histidine: H; arginine: R) and hydrophilic (threonine: T; aspartic acid: D; tyrosine: Y) amino acids are removed from the hydrophobic region to reduce the peptide length to no more than 15 amino acids, resulting in a peptide that has an amino acid sequence represented by ILLGLLLLGLVGPIL (15 amino acids in length);

vii) the structural analysis shows that the modified peptide, as described above, forms a helix structure;

viii) in order to impart flexibility to the peptide, nonpolar amino acids (glycine: G) at the middle and the right sides of the peptide are replaced with a hydrophobic amino acid, proline (P), respectively, resulting in a peptide has an amino acid sequence represented by ILLPLLLLGLVPPIL (15 amino acids in length); and ix) some of the repeated hydrophobic amino acids at the far right side of the peptide sequence are deleted to shorten the peptide length to 10 or less amino acids.

Therefore, the finally optimized peptide as a macromolecule transduction domain has an amino acid sequence represented by ILLPLLLLP (9 amino acids in length; SEQ ID NO: 98) and forms a helix structure, which has been designated as "JO-98." The last amino acid, proline, of the JO-98 peptide is a flexible site for interaction with a biologically active molecule to form a recombinant protein.

A further aspect of the present invention relates to a method of genetically engineering a biologically active molecule to have cell permeability by using the MTD peptides.

The therapeutic use of biologically active molecules is often hindered by their low cell permeability. Although biologically active molecules have been shown to be taken up by cells via an endocytic process, the molecules that enter the cell in this manner are usually trapped in endocytic vesicles and degraded in lysosomes.

The MTD of the present invention provides efficient transport of biologically active molecules having a high molecular weight across the cell membrane, whereas other membrane transport peptides previously tested have not been shown to transport molecules of a size greater than approximately 25 amino acids. The MTD of the present invention can be attached to a peptide or polypeptide using conventional methods in the art to enhance the peptide's or polypeptide's membrane permeability. The MTD can be provided in the form of a kit, which includes the necessary components known to those skilled in the art to facilitate linkage of a peptide to a target polypeptide. A target protein attached to the MTD in this manner can then be delivered to the cell either in vitro or in vivo for intracellular import.

According to the method of the present invention, the polynucleotide described above can be inserted into a protein expression vector to produce a protein which can be imported from the exterior to the interior of a cell by the action of the MTD peptides described herein.

An expression vector is genetically engineered to incorporate a nucleic acid sequence encoding a MTD in an orientation either N-terminal and/or C-terminal to a nucleic acid sequence encoding a peptide, polypeptide, protein domain, or full-length protein of interest as a biologically active molecule, and in the correct reading frame so that a recombinant protein consisting of the macromolecule transduction domain and the target biologically active molecule may be expressed. Expression vectors may be chosen from among those readily available for use in prokaryotic or eukaryotic expression systems.

As used herein, an MTD is a macromolecule transduction domain of the present invention, which directs cellular transport of a target protein from the exterior to the interior of a cell. In another embodiment of the present invention, the MTD may comprise an alternate sequence which mediates the import of a peptide or polypeptide through the cell membrane to the interior of a cell.

A target protein is a protein which normally exhibits less than optimal permeability through the cell membrane, but which, when attached either N-terminal and/or C-terminal to an MTD of the present invention, is transported from the exterior to the interior of the cell.

In another embodiment of the present invention, a cleavage site is located between the MTD and the target polypeptide, protein domain, or full-length protein. This site may alternatively be a factor X site or another site that is known to those skilled in the art to relate to the cleavage of the recombinant protein to physically remove the MTD from the subject peptide or polypeptide.

The method of the present invention provides a means for producing proteins having cell permeability for introduction into the interior of the cell, where their actions help to further elucidate cellular control and biosynthesis mechanisms. This method also provides a means for introducing intracellular proteins into cells to produce targeted cellular changes, such as the inhibition of apoptosis by the introduction of Bcl-2. Cell cycle control, for example, can be altered by the introduction of a functional p53 protein product into those cells that have become tumorigenic due to an abnormal p53 protein.

As used herein, the term "biologically active molecule" includes any molecule which, if imported into a cell, is capable of exhibiting a biological effect. Since very large proteins having molecular weights ranging from about 100,000 to about 1 million are exported by cells (e.g., antibodies, fibrinogen, and macroglobulin), very large proteins can be imported into cells by the method of the present invention. Therefore, proteins having sizes ranging from a few amino acids to about a thousand amino acids can be used. A preferable size range for proteins is from a few amino acids to about 250 amino acids. For any molecule, the size can be up to a molecular weight of about 1 million, specifically up to a molecular weight of about 25,000, and more specifically up to a molecular weight of about 3,000. In addition, only those molecules which can be attached to an MTD peptide as a signal peptide, either directly or indirectly, are within the scope of the present invention.

Examples of biologically active molecules include, but are not limited to, proteins, polypeptides, and peptides, which include functional domains of biologically active molecules, such as growth factors, enzymes, transcription factors, toxins, antigenic peptides (for vaccines), antibodies, and antibody fragments. Additional examples of biologically active molecules include nucleic acids, such as plasmids, coding nucleic acid sequences, mRNAs and antisense RNA molecules, carbohydrates, lipids, and glycolipids. Further examples of biologically active molecules include therapeutic agents, in particular those with low cell membrane permeability. Some examples of these therapeutic agents include cancer drugs, such as Daunorubicin, and toxic chemicals which, because of the lower dosage that can be used when administered by this method, can now be more safely administered. Yet another example of a biologically active molecule is an antigenic peptide. Antigenic peptides can be administered to provide immunological protection when imported by cells involved in the immune response. Other examples include immunosuppressive peptides (e.g., peptides that block autoreactive T cells, which are known in the art). Numerous other examples will be apparent to the skilled artisan.

Representative examples of biologically active molecules suitable for the present invention may include enzymes, hormones, transport proteins, immunoglobulin or antibodies, structural proteins, motor function proteins, receptors, signaling proteins and storage proteins in terms of their function; and membrane or transmembrane proteins, internal proteins, external or secret proteins, virus proteins, native proteins, glicoproteins, cleaved proteins, proteins with disulfide bonds, protein complexes, chemically modified proteins and prions in terms of their location and roles.

Standard recombinant nucleic acid methods can be used to express a genetically engineered recombinant protein. In one embodiment of the present invention, a nucleic acid sequence encoding the macromolecule transduction domain is cloned into a nucleic acid expression vector, e.g., with appropriate signal and processing sequences and regulatory sequences for transcription and translation. In another embodiment, the protein can be synthesized using automated organic synthetic methods. Synthetic methods for producing proteins are described, for example, in Methods in Enzymology, Volume 289: Solid-Phase Peptide Synthesis by Gregg B. Fields (Editor), Sidney P. Colowick, Melvin I. Simon (Editor), Academic Press (1997).

In order to obtain high level expression of a cloned gene or nucleic acid, such as a cDNA encoding a MTD peptide, a MTD sequence is typically subcloned into an expression vector that contains a strong promoter for directing transcription, a transcription/translation terminator, and, in the case of a nucleic acid encoding a protein, a ribosome binding site for translational initiation. Suitable bacterial promoters are well known in the art and are described, e.g., in Sambrook & Russell, Molecular Cloning: A Laboratory Manual, 3d Edition, Cold Spring Harbor Laboratory, N.Y. (2001) and Ausubel et al., Current Protocols in Molecular Biology, Greene Publishing Associates and Wiley Interscience, N.Y. (1989). Bacterial expression systems for expressing the MTD peptide of the present invention are available in, e.g., *E. coli*, *Bacillus* sp., and *Salmonella* (Palva et al., Gene 22: 229-235 (1983); Mosbach et al., Nature 302: 543-545 (1983)). Kits for such expression systems are commercially available. Eukaryotic expression systems for mammalian cells, yeast, and insect cells are well known in the art and are also commercially available. In another embodiment of the present invention, the eukaryotic expression vector is an adenoviral vector, an adeno-associated vector, or a retroviral vector.

The expression vector for expressing the cell permeable recombinant protein can include regulatory sequences, including for example, a promoter, operably attached to a sequence encoding the macromolecule transduction domain. Non-limiting examples of inducible promoters that can be used include steroid-hormone responsive promoters (e.g., ecdysone-responsive, estrogen-responsive, and glutacorticoid-responsive promoters), the tetracycline "Tet-On" and "Tet-Off" systems, and metal-responsive promoters. The construct can be introduced into an appropriate host cell, e.g., a bacterial cell, yeast cell, insect cell, or tissue culture cell. The construct can also be introduced into embryonic stem cells to generate a transgenic organism as a model subject. Large numbers of suitable vectors and promoters are known to those skilled in the art and are commercially available for generating the recombinant constructs of the present invention.

Known methods can be used to construct vectors containing the polynucleotide of the present invention and appropriate transcriptional/translational control signals. These methods include in vitro recombinant DNA techniques, synthetic techniques, and in vivo recombination/genetic recombination. See, for example, the techniques described in Sambrook & Russell, Molecular Cloning: A Laboratory Manual, 3d Edition, Cold Spring Harbor Laboratory, N.Y. (2001) and Ausubel et al., Current Protocols in Molecular Biology Greene Publishing Associates and Wiley Interscience, N.Y. (1989).

Host cells suitable for producing a cell permeable recombinant protein include bacterial cells and eukaryotic cells (e.g., fungal, insect, plant, and mammalian cells). Host cells can be disrupted by any convenient method, including freeze-thaw cycling, sonication, mechanical disruption, or the use of cell lysing agents. Scopes, Protein Purification: Principles and Practice, New York: Springer-Verlag (1994) describes a number of general methods for purifying recombinant (and non-recombinant) proteins. The methods can include, e.g., ion-exchange chromatography, size-exclusion chromatography, affinity chromatography, selective precipitation, dialysis, and hydrophobic interaction chromatography. These methods can be adapted to devise a purification strategy for the cell permeable recombinant protein. If the cell permeable recombinant protein includes a purification handle, such as an epitope tag or a metal chelating sequence, affinity chromatography can be used to purify the protein greatly.

The amount of protein produced can be evaluated by detecting the macromolecule transduction domain directly (e.g., using Western analysis) or indirectly (e.g., by assaying materials from, the cells for specific DNA binding activity, such as by electrophoretic mobility shift assay). Proteins can be detected prior to purification, during any stage of purification, or after purification. In some implementations, purification or complete purification may not be necessary.

In a specific embodiment of the present invention, the expression vector is pEGFP-C1 (Clontech™, Mountain View, Calif.), which comprises a polynucleotide encoding a recombinant protein including an enhanced green fluorescent protein (EGFP). The insertion of a polynucleotide encoding an MTD according to the present invention into vector pEGFP-C1, 5' and/or 3' to the EGFP gene of the vector enables the expression of a recombinant protein incorporating both the MTD and the EGFP. The MTD, connected N-terminal and/or C-terminal to the EGFP, carries the EGFP protein to the interior of the cell.

The genetically engineered recombinant proteins prepared by the method of the present invention are cell permeable proteins and can be used as protein-based vaccines, particularly where killed or attenuated whole organism vaccines are impractical. The cell permeable proteins prepared by the method of the present invention can also be used for the treatment of diseases, particularly cancer. Cell permeable proteins can be delivered to the interior of the cell, eliminating the need to transfect or transform the cell with a recombinant vector. The cell permeable proteins of the present invention can be used in vitro to investigate protein function or can be used to maintain cells in a desired state.

The MTD of the present invention can be used to deliver peptides, polypeptides, protein domains, or proteins to the interior of a target cell either in vitro or in vivo. The MTD can be attached to the target protein through a peptide linkage formed by the expression of the recombinant protein from a recombinant DNA or RNA molecule or can be attached to the target protein by means of a linker covalently attached to the MTD. A covalent linkage can be used to attach the MTD of the present invention to a non-protein molecule, such as a polynucleotide, for import into the cell.

Another aspect of the present invention relates to a pharmaceutical composition comprising the cell permeable recombinant proteins of the present invention, where the MTD peptide is operably attached to a biologically active molecule.

The cell permeable recombinant protein produced by the method of the present invention may be administered in vitro by any of the standard methods known to those skilled in the art, such as by addition of the recombinant protein to culture medium. Furthermore, it will be appreciated by those skilled in the art that recombinant proteins produced by this method may be delivered in vivo by standard methods utilized for protein/drug delivery, including parenteral administration, intravenous administration, topical administration, aerosol administration or inhalation, oral administration (particularly when provided in an encapsulated form), or by rectal or vaginal administration (particularly when provided in a suppository form).

Examples of administration include, but are not limited to, parenteral administration, e.g., by intravenous injection including regional perfusion, inhalation of an aerosol, subcutaneous or intramuscular injection, topical administration, such as to skin wounds and lesions, direct transfection into, e.g., bone marrow cells prepared for transplantation and subsequent transplantation into the subject, and direct transfection into an organ that is subsequently transplanted into the subject. Parenteral administration, e.g., regional perfusion, if used, is generally characterized by injection. Injectables can be prepared in conventional forms, such as liquid solutions, suspensions, or emulsions. A slow release or sustained release system can also be used, allowing the maintenance of a constant level of dosage.

Further administration methods include oral administration, particularly when the complex is encapsulated, or rectal administration, particularly when the complex is in a suppository form. A pharmaceutically acceptable carrier includes any material that is not biologically or otherwise undesirable, i.e., the material may be administered to an individual along with the selected complex without causing any undesirable biological effects or interacting in a deleterious manner with any of the other components of the pharmaceutical composition in which it is administered.

Depending on the intended mode of administration (e.g., including, but not limited to, intravenous, parenteral, transcutaneous, subcutaneous, intramuscular, intracranial, intraorbital, ophthalmic, intraventricular, intracapsular, intraspinal, intracisternal, intraperitoneal, intranasal, intrarectal, intravaginal, aerosol, or oral), the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The pharmaceutical compositions of the present invention will include, as noted above, an effective amount of the cell permeable recombinant protein in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving or dispersing an active compound as described herein, and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances, such as wetting or emulsifying agents, pH buffering agents, and the like. Actual methods of preparing such dosage forms are known, or will be apparent, to those skilled in the art.

Administration of a cell permeable recombinant protein produced by the method of the present invention may be performed for a period of time ranging from 10 minutes to 72 hours, particularly when the administration is carried out by the addition of recombinant protein to culture media for in vitro use. For in vivo or in vitro use, the effective administration time for a cell permeable recombinant protein produced by the method of the present invention may be readily determined by those skilled in the relevant art.

For either in vitro or in vivo use, the cell permeable recombinant protein can be administered at any effective concentration. An effective concentration is that amount that results in the importation of the biologically active molecule into the cell. Such a concentration—culture medium concentration (in vitro) or blood serum concentration (in vivo)—will typically be from about 0.1 nM to about 500 µM. Optimal concentrations for the specific recombinant protein and/or the specific target cell can be readily determined according to the teachings herein. Thus, the in vivo dosage for the recombinant protein is the concentration which will cause the blood serum concentration of the recombinant protein to be, about 0.1 nM to about 500 µM, more specifically, about 0.5 nM to about 100 µM. The amount of the recombinant protein administered will, of course, depend upon the subject being treated, the subject's age and weight, the manner of administration, and the judgment of the skilled administrator. The exact amount of the complex will further depend upon the general condition of the subject, the severity of the disease/condition being treated by the administration, and the particular complex chosen. However, the appropriate amount can be determined by one of ordinary skill in the art, using routine optimization, given the teachings provided herein.

Further, the cell permeable recombinant proteins produced by the method of the present invention can be used for vaccine administration (Lingnan et al., *Expert. Rev. Vaccines* 6: 741-746, 2007; O'Hagan et al., *Methods* 40: 10-19, 2009).

Vaccines using cell permeable recombinant proteins provide an advantage over the typical peptide vaccines. The immune system recognition of an antigen depends upon appropriate antigen processing. Previously, entire proteins or protein domains could not be delivered to the interior of the cell for processing to occur. As a consequence, peptides representing antigenic epitopes had to be identified prior to the delivery to the cell of small peptides representing those epitopes. The method of the present invention allows whole proteins or protein domains to be imported into the cell, where antigenic processing can occur. This provides multiple antigenic epitopes in one administration, and eliminates the need for experimental identification of specific epitopes for vaccine development.

Typically, such vaccines are prepared for injection into a human or mammalian subject. Injectable vaccines can be prepared as liquid solutions or suspensions. Solid forms can be prepared which are suitable for solution in, or suspension in, a liquid, prior to injection. The preparation may also be emulsified. The active immunogenic ingredient is often mixed with a pharmaceutically acceptable carrier which is compatible with the active ingredient. Suitable carriers include, but are not limited to, water, dextrose, glycerol, saline, ethanol, and combinations thereof. The vaccine may contain additional agents, such as wetting or emulsifying agents, pH buffering agents, or adjuvants which enhance the effectiveness of the vaccine.

The vaccine may be conventionally administered parenterally. Either subcutaneous or intramuscular injection is appropriate. Other modes of administration may include oral administration, nasal administration, rectal administration, and vaginal administration, which may involve combining the peptide immunogen with pharmaceutically acceptable carriers, such as mannitol, lactose, starch, magnesium stearate, sodium saccharine, cellulose, magnesium carbonate, or other carriers. Compositions for oral administration may form solutions, suspensions, tablets, pills, capsules, sustained release formulations, or powders. A protein-based vaccine of the present invention can be administered by an enteric-coated capsule for release of the polypeptide into the lumen of the intestine.

The cell permeable recombinant proteins of the present invention may be formulated into the vaccine as neutral or salt forms. Pharmaceutically acceptable salts include the acid addition salts (formed with the free amino groups of the polypeptide) and which are formed with inorganic acids, such as, for example, hydrochloric or phosphoric acids, or such organic acids as acetic, mandelic, oxalic, and tartaric acids. Salts formed with the free carboxyl groups of the polypeptide may also be derived from inorganic bases such as, for example, sodium, potassium ammonium, calcium, or ferric hydroxides, and such organic bases as isopropylamine, trimethylamine, 2-ethylamino ethanol, and histidine.

The vaccine is administered in a manner compatible with the dosage formulation, and in such an amount as will be therapeutically effective and immunogenic. The quantity to be administered depends on the subject to be treated, taking into account, for example, the capacity of the individual's immune system to synthesize antibodies and the degree of protection desired. The precise amounts of the active ingredient (peptide immunogen) to be administered depend on the judgment of the practitioner. Suitable dosage ranges generally require several hundred micrograms of active ingredient per vaccination. Also variable are the regimes for initial administration and booster vaccinations, which should be determined according to the judgment of the practitioner. The dosage of the vaccine will depend on the route of administration and will vary according to the size of the host.

Furthermore, the cell permeable recombinant proteins of the present invention can be effectively used in drug delivery systems (Spencer and Verma, *Proc. Natl. Acad. Sci. USA* 104: 7594-7599, 2007; Choi et al., *Nat. Med.* 12: 574-579, 2006; Vives et al., *J. Biol. Chem.* 272: 16010-16017, 1997; Kumar et al., *Nature* 448: 39-43, 2007; Jo et al., *Nat. Med.* 11: 892-898, 2005).

The method of genetically engineering proteins with cell membrane permeability according to the present invention provides a means for delivering therapeutic protein products into a cell. Combination of the present invention with previously described methods of extracellular protein delivery provides a method of delivering proteins for import into a cell in a stabilized, functional form in a controlled-release fashion.

Polypeptides are produced using an appropriate expression vector and an expression system. Cell permeability is conferred upon the protein or polypeptide by the expression of a recombinant protein with the MTD located N-terminal and/or C-terminal to the expressed polypeptide. The less stable proteins are stabilized by methods known to those skilled in the art and described previously. Delivery to the extracellular environment is accomplished by providing the stabilized recombinant protein in an appropriate carrier, such as microsphere carriers. The protein of choice will dictate the appropriate vector and expression system, as well as the appropriate stabilization and delivery techniques. A person of ordinary skill in the art of drug delivery systems can choose the appropriate techniques from among those described.

The method of the present invention provides a means for producing cell permeable proteins for the treatment of cancer. Regulators of apoptosis and cell cycle control have been found to play a key role in oncogenesis, while gene therapy techniques (Balaggan et al., *Gene Therapy* 13(15): 1153-1165, 2006; Kuo et al., *Proc. Natl. Acad. Sci. USA* 10; 98(8): 4605-4610, 2001), using intratumoral injection of an adenoviral expression vector encoding the p53 gene, have shown promise for the control of some tumors. However, the delivery of specific protein products through the use of viral vectors has proven to be problematic. The MTDs and methods of the present invention provide a means for producing cell permeable proteins from among the cell cycle regulators and regulators of apoptosis, as well as other proteins identified to play a role in the development of the cancer state.

For example, in one embodiment of the present invention, the polynucleotide encoding the p53 gene can be inserted into a suitable vector, either 5' or 3' to the sequence of the MTD of the present invention. Under expression conditions appropriate for the vector of choice and known to those skilled in the art, a recombinant protein comprising an MTD and the p53 protein can be expressed. The attachment of the MTD to the p53 protein renders the p53 protein cell permeable, and protein can be administered to tumor cells to inhibit tumor development. Administration of cell permeable proteins can be accomplished in various ways, including, but not limited to, intratumoral injection, infusion, and intravenous administration. Bax and Bcl-$x_L$ are other examples of proteins from among a wide variety of proteins that have been determined to affect cell cycle control and apoptosis and, therefore, be effective for cancer therapy. The method of the present invention provides a more efficient, less labor-intensive, and less costly method for the delivery of anti-oncogenic proteins to tumor cells.

The term "cell membrane" as used herein refers to a lipid-containing barrier which separates cells or groups of cells from the extracellular space. Cell membranes include, but are not limited to, plasma membranes, cell walls, intracellular organelle membranes, such as the mitochondrial membrane, nuclear membranes, and the like.

The term "biologically active molecule" as used herein refers to compounds or molecules that are capable of eliciting or modifying a biological response in a system. Non-limiting examples of biologically active molecules include antibodies (e.g., monoclonal, chimeric, humanized etc.), cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, siRNA, miRNA, RNAi inhibitors, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers. In certain embodiments, the term biologically active molecule is used interchangeably with the term "macromolecule".

The term "macromolecule" as used herein refers to large molecules (molecular weight greater than 1000 daltons) exemplified by, but not limited to, peptides, proteins, and oligonucleotides and polynucleotides of biological or synthetic origin.

The term "peptide" as used herein refers to a compound made up of a single chain of D- or L-amino acids or a mixture of D- and L-amino acids joined by peptide bonds. Preferably, peptides contain at least two amino acid residues and are less than about 50 amino acids in length.

The term "protein" as used herein refers to a compound that is composed of linearly arranged amino acids attached by peptide bonds, but in contrast to peptides, has a well-defined conformation. Proteins, as opposed to peptides, preferably contain chains of 50 or more amino acids.

The term "polypeptide" as used herein refers to a polymer of at least two amino acid residues and which contains one or more peptide bonds. Polypeptides encompass peptides and proteins, regardless of whether the polypeptide has a well-defined conformation.

The term "nucleic acid" as used herein refers to oligonucleotides or polynucleotides, such as deoxyribonucleic acid (DNA) and ribonucleic acid (RNA), as well as analogs of either RNA or DNA, for example made from nucleotide analogs any of which are in single or double stranded form.

Amino acid residues are herein referred to by their standard single-letter or three-letter notations or by their full names: A, Ala, alanine; C, Cys, cysteine; D, Asp, aspartic acid; E, Glu, glutamic acid; F, Phe, phenylalanine; G, Gly, glycine; H, His, histidine; I, Ile, isoleucine; K, Lys, lysine; L, Leu, leucine; M, Met, methionine; N, Asn, asparagine; P, Pro, proline; Q, Gln, glutamine; R, Arg, arginine; S, Ser, serine; T, Thr, threonine; V, Val, valine; W, Trp, tryptophan; X, Hyp, hydroxyproline; and Y, Tyr, tyrosine.

The term "macromolecule transduction domain (MTD)" as used herein refers to a peptide that facilitates the transport of macromolecules into a cell.

The term "isolated" polynucleotide as used herein refers to a polynucleotide that is substantially free of the sequences with which it is associated in nature. By substantially free is meant at least 50%, preferably at least 70%, more preferably at least 80%, and even more preferably at least 90% free of the materials with which it is associated in nature. As used herein, an "isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature.

The term "operatively attached" as used herein means that DNA fragments of a promoter, a MTD peptide or other genes are sufficiently connected to direct and regulate the expression of genes.

The term "homology" or "similarity" as used herein refers to the likeness or the percentage of identity between two sequences (e.g., polynucleotide or polypeptide sequences). Typically, a higher similarity in sequences means more similarity in the physical or chemical properties or biological activities.

Unless defined otherwise, all technical and scientific terms used herein have the same meaning as commonly understood by one of ordinary skill in the art to which this invention belongs. Although any method and material similar or equivalent to those described herein can also be used in the practice or testing of the present invention, specific methods and materials are now described. All publications mentioned herein are incorporated herein by reference in their entirety to disclose and describe the methods and/or materials in connection with which the publications are cited.

It must be noted that as used herein and in the appended claims, the singular forms "a," "an," and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are presented to aid practitioners of the invention, provide experimental support for the invention, and to provide model protocols. In no way are these examples to be understood to limit the invention.

Example 1

Identification of Novel Macromolecule Transduction Domain Peptides

In order to identify novel macromolecule transduction domain (MTD) candidates that can potentially penetrate the plasma membrane of live cells, secreted proteins having a signal sequence-like domain were selected from the PubMed™ Entrez Protein Database by using several key words, including "hydrophobic region of signal sequence," "signal sequence hydrophobic region," "signal sequence of secreted protein," "hydrophobic signal sequence," and "hydrophobic domain of secreted protein." As a result, more than 1,500 secreted proteins having a signal sequence-like domain were selected.

All of the selected secreted proteins having a signal sequence-like domain were subjected to hydropathy analysis to determine whether they contain a single hydrophobic region at their N-terminus. Subsequently, they were subjected to a computer-aided genomic and proteomic information analysis, i.e., the SOSUI system, to determine whether they form a helix structure. Since the SOSUI system currently requires peptides to be analyzed to have at least about 20 amino acids in length, additional amino acids derived from the N-terminal domain of enhanced green fluorescent protein were added to the end of the signal sequence-liked domain. When the SOSUI system is used, 220 peptide sequences having a single hydrophobic region at their N-terminus and forming a transmembrane helix structure were selected.

To optimize the selected peptide sequences as a signal sequence, empirical modifications were made to them as follows: first, hydrophilic, nonpolar, and positively or negatively charged amino acids were removed from the selected peptide sequences and, then, various combinations of five hydrophobic amino acids (i.e., alanine: A, valine: V, proline: P, leucine: L, isoleucine: I) were created empirically.

After that, non-hydrophobic amino acids at the left or right side of the peptide sequences were eliminated to minimize the size while maintaining their hydrophobic region, followed by adding or replacing non-hydrophobic amino acids at the middle or right side of the peptide sequences with proline, to thereby provide flexibility to the peptide. Finally, the number of repeated hydrophobic amino acids was minimized to reduce the length of the peptide sequence. The resulting peptides as MTD candidates exhibited hydrophobicity and flexibility, have relatively short amino acids (7 to 17 in length), and form a helix structure.

According to the method described above, novel 193 MTD peptides having amino acid sequences represented by SEQ ID NOs: 1 to 193, respectively, and are capable of facilitating the traverse of biologically active molecules across the cell membrane were identified. The 193 MTDs were designated as JO-001 to JO-193, respectively, and their structural characteristics and sequences are shown in FIGS. 1a to 1o.

Example 2

Expression of Recombinant Proteins Fused to MTDs

Having demonstrated the feasibility of the cellular import of MTD peptides identified in Example 1 above, the enhanced green fluorescent protein (EGFP) was used as a full-length protein cargo molecule. Green fluorescent protein (GFP) is a protein cloned from the jellyfish, *Aquorea Victoria*. GFP is one of the most widely used reporter proteins and produces a green light when illuminated with blue or UV light (Inouye et al., *FEBS Letters* 351(2): 211-14 (1994)). In one embodiment of the present invention, a commercially available GFP expression vector, pEGFP-C1 (Clontech™), is used. The EGFP protein encoded by pEGFP-C1 is a mutant of wild-type GFP, which has been modified to produce a stronger green light. Further, when a foreign gene is inserted into the multiple cloning sites of the pEGFP-C1 vector, the inserted foreign gene is expressed in the form of a recombinant protein with EGFP.

Figure 3A:
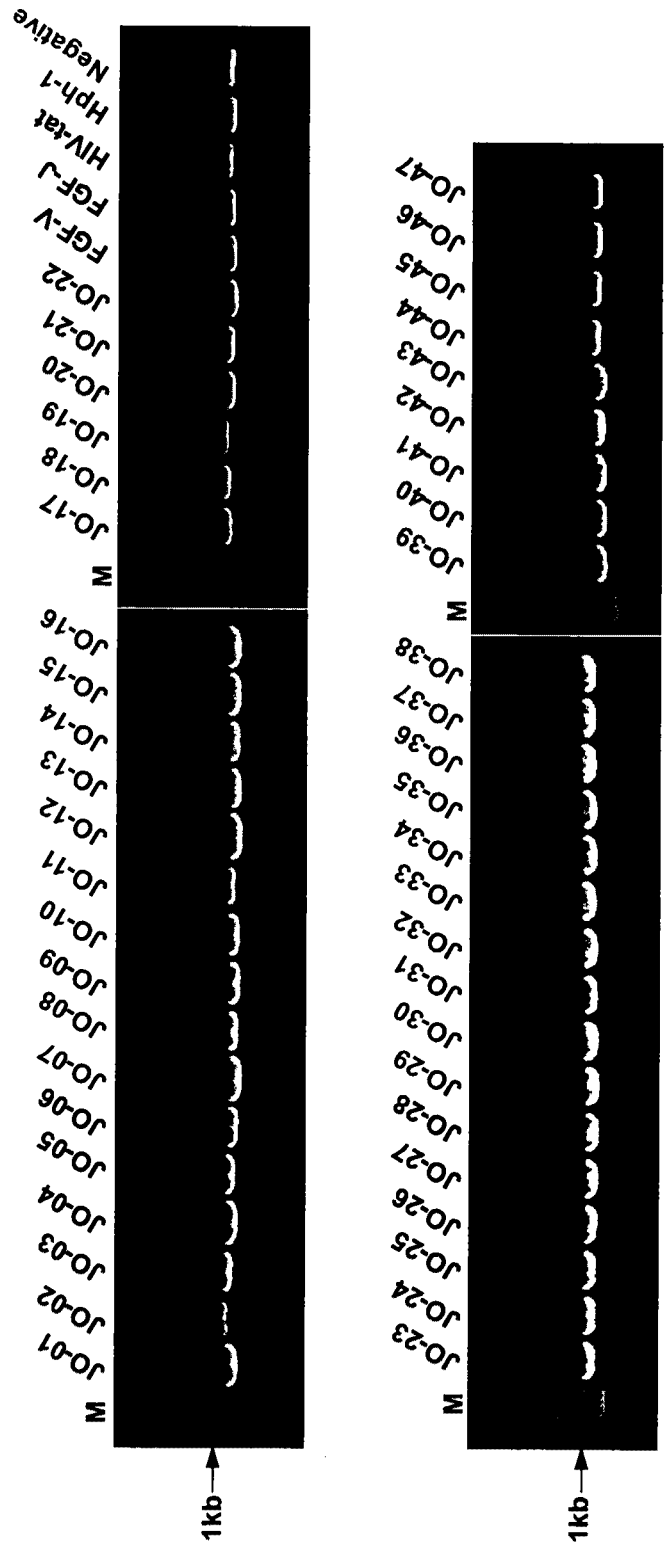
FIGS. 3a to 3c are photographs of an agarose gel electrophoresis analysis showing DNA fragments encoding MTDs-EGFP amplified by PCR according to the present invention.
Figure 3B:
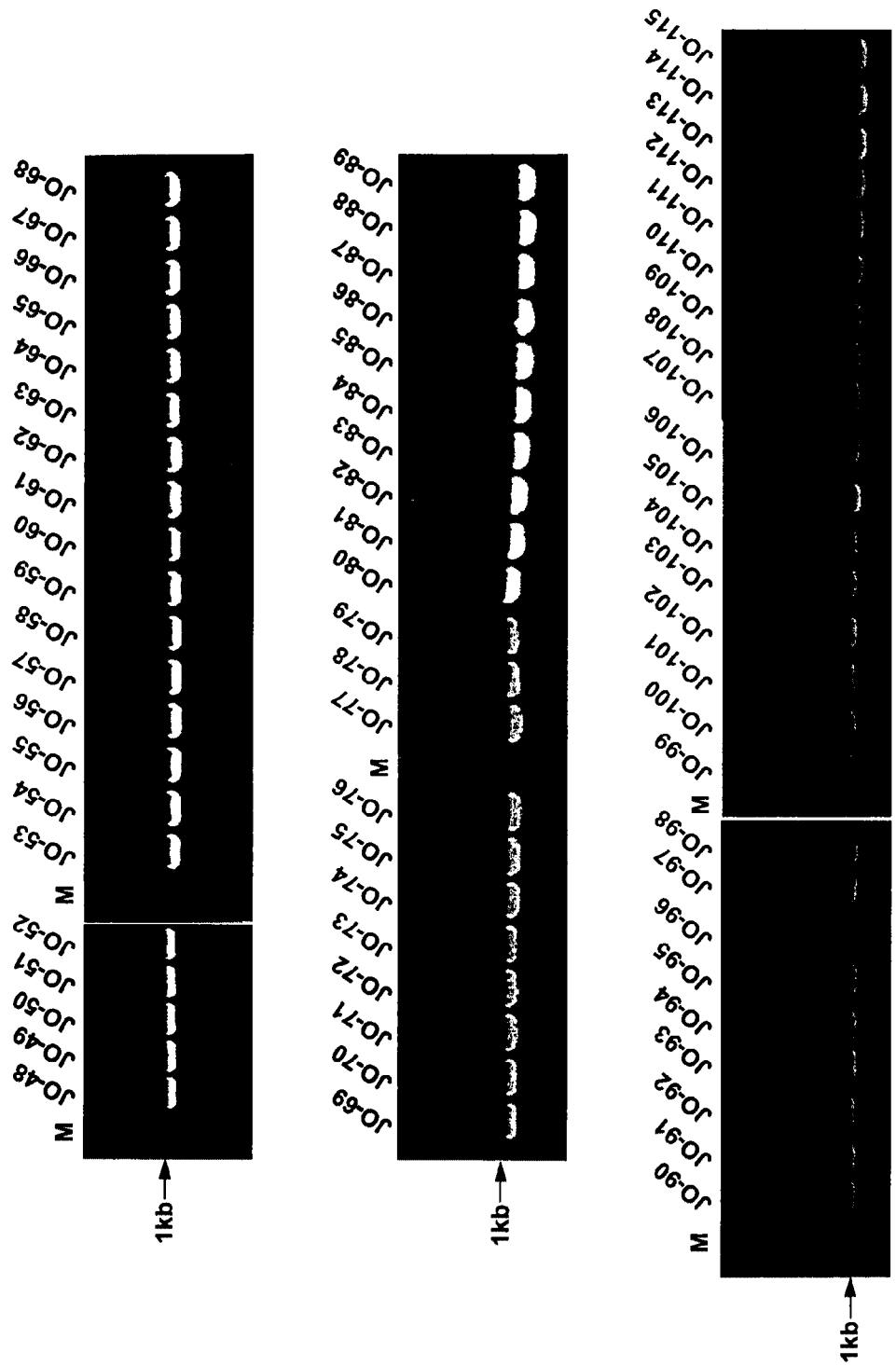
Figure 3C:
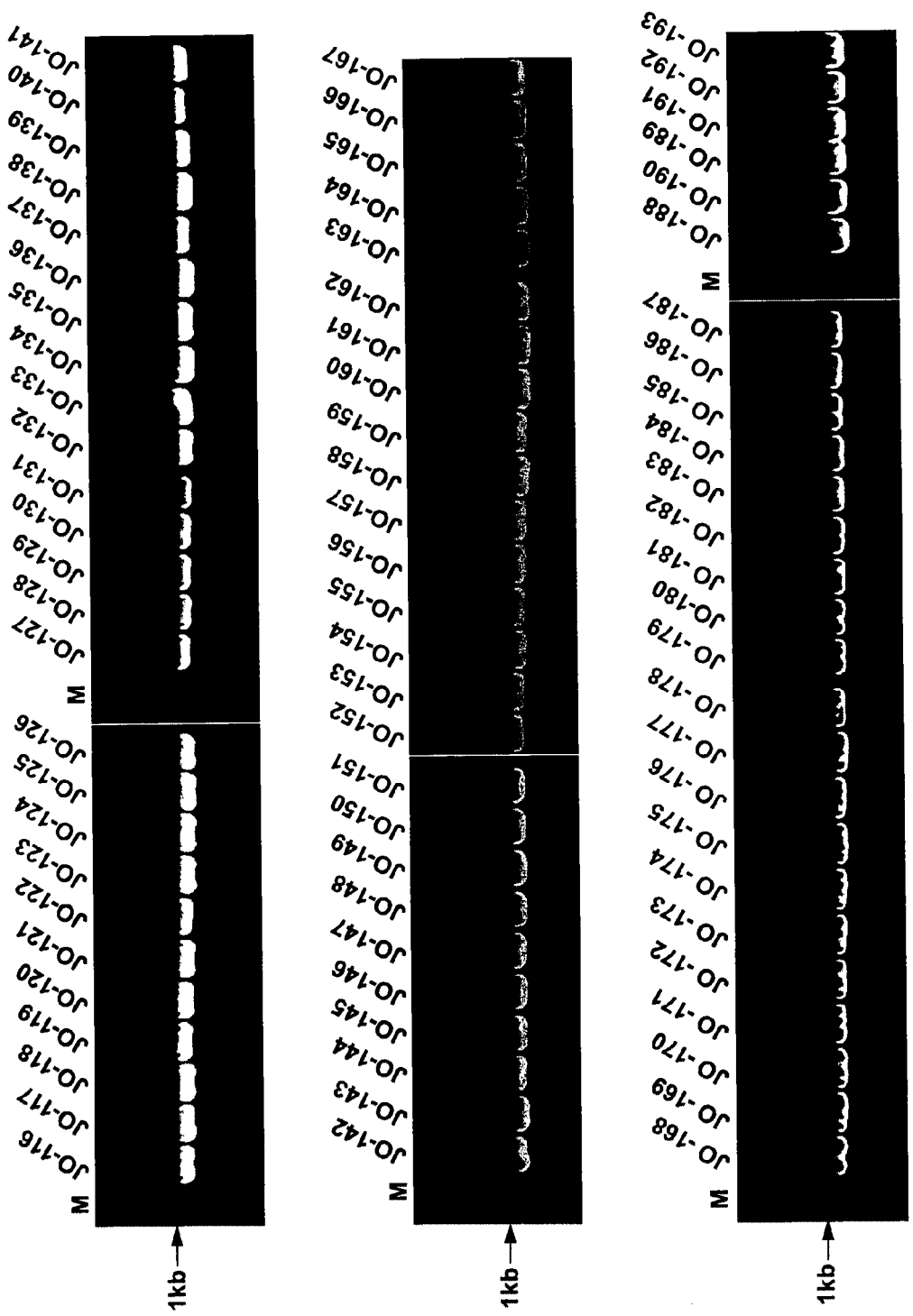

In order to construct expression vectors for EGFP proteins fused to each novel MTD (His-MTD-EGFP: HME)(FIG. 2), a polymerase chain reaction (PCR) was conducted by using the oligonucleotides described in Tables 1 and 2 below as a primer set (forward primers SEQ ID NOs: 393 to 585 for MTD JO-1 to JO-193, respectively; reverse primer SEQ ID NO: 586 for MTD JO-1 to JO-193) and the pEGFP-C1 plasmid as a template. The conditions for the PCR were 30 cycles of 45 seconds at 95° C., 45 seconds at 68, and 1 minute at 72° C. after initial denaturation of 5 minutes at 95, and final extension of 5 minutes at 72° C. The amplified PCR product was digested with restriction enzyme NdeI and subjected to agarose gel electrophoresis. An MTD-derived from kFGF-4 16 mer (FGF-V, AAVALLPAVLLALLAP, Lin et al., *J. Biol. Chem.* 275: 16774-16778, 2000; Veach et al., *J. Biol. Chem.* 279: 11425-11431, 2004), an MTD-derived from kFGF-4 12 mer (FGF-J, AAVLLPVLLAAP, Jo et al., Nat. Biotech. 19: 929-933, 2001; Jo et al., *Nat. Med.* 11: 892-898, 2005 (SEQ ID NO: 389), a protein transduction domain derived from HIV-Tat (HIV-Tat, YGRKKRRQRRR, Schwarze et al., *Science* 285: 1569-1572, 1999), and HIV-Tat homologous (Hph-1, YARVRRRGPRR) were used as positive controls, and a scramble peptide (SEQ ID NO: 387) was used as a negative control. As shown in FIGS. 3a to 3c, it was confirmed that the DNA fragments encoding MTDs-EGFP were successfully amplified.

TABLE 1

PCR forward primer sequences for each MTD-EGFP protein

| MTD | Sequence | SEQ ID NO |
|---|---|---|
| JO-01 | 5'-CCGCATATGGCGGTGGTGGTGTGCGCGATTGTGC TGGCGGCGCCGGTGAGCAAGGGCGAGGAGCTG-3' | 393 |
| JO-02 | 5'-CCGCATATGCCGGTGGCGCTGCTGGTGCTGGTGC TGCTGGGCCCGGTGAGCAAGGGCGAGGAGCTG-3' | 394 |
| JO-03 | 5'CCGGATATGCTGCTGCTGGCGTTTGCGCTGCTGTG CCTGGCGGTGAGCAAGGGCGAGGAGGTG-3' | 395 |
| JO-04 | 5'-CCGCATATGCTGCTGGGCGCACTGGCGGCGGTGC TGCTGGCGCTGGCGGTGAGCAAGGGCGAGGAGCT G-3' | 396 |
| JO-05 | 5'-CCGCATATGCCGGTGCTGCTGGCGCTGGGCGTGG GCCTGGTGCTGCTGGGCCTGGCGGTGGTGAGCAAGGG CGAGGAGCTG-3' | 397 |
| JO-06 | 5'-CCGCATATGGCGGCGGCGGCGGTGCTGCTGGCGG CGGTGAGCAAGGGCGAGGAGCTG-3' | 398 |
| JO-07 | 5-CCGCATATGATTGTGGTGGCGGTGGTGGTGATTGT GAGCAAGGGCGAGGAGCTG-3' | 399 |
| JO-08 | 5'-CCGCATATGGCGGTGCTGGGGCCGGTGGTGGCGG TGGTGAGCAAGGGCGAGGAGCTG-3' | 400 |
| JO-09 | 5'-CCGGATATGCTGGCGGTGTGCGGCCTGCCGGTGG TGGCGCTGCTGGCGGTGAGCAAGGGCGAGGAGGT G-3' | 401 |
| JO-10 | 5'-CCGCATATGCTGGGCGGCGCGG348TGGTGGCGG CGCCGGTGGCGCGGGGTGGCGGCGGTGAGCAAGGGC GAGGAGCTG-3' | 402 |
| JO-11 | 5'-CCGCATATGGTGCTGCTGGTGCTGGCGGTGCTGC TGGCGGTGCTGGCGGTGAGCAAGGGCGAGGAGCT G-3' | 403 |
| JO-12 | 5'-CCGCATATGCTGCTGATTCTGCTGCTGCTGCCGC TGCTGATTGTGGTGAGCAAGGGCGAGGAGCTG-3' | 404 |
| JO-13 | 5'-CCGCATATGGTGGCGGCGGCGGCGCTGGCGGTGC TGCCGCTGGTGAGGAAGGGCGAGGAGCTG-3' | 405 |
| JO-14 | 5'-CCGCATATGTTTCTGATGCTGCTGCTGCCGCTGC TGCTGCTGCTGGTGGCGGTGAGCAAGGGCGAGGAGCT G-3' | 406 |
| JO-15 | 5'-GCGCATATGGCGGCGGCGGCGGCGGCGCTGGGTC TGGGGGCGGCGGTGCCGGGGGTGAGCAAGGGCGAGGA GCTG-3' | 407 |
| JO-16 | 5'-CCGCATATGCTGCTGCTGGCGGCGCTGCTGCTGA TTGCGTTTGCGGCGGTGGTGAGCAAGGGCGAGGAGCT G-3' | 408 |
| JO-17 | 5'-GCGCATATGGCGCTGGCGGCGGTGGTGCTGATTC GCTGGGCATTGCGGCGGTGAGCAAGGGCGAGGAGCT G-3' | 409 |
| JO-18 | 5'-CCGCATATGGCGGCGCTGATTGGCGCGGTGCTGG CGCCGGTGGTGGCGGTGGTGAGCAAGGGCGAGGAGCT G-3' | 410 |
| JO-19 | 5'-CCGCATATGGCGGCGGCGGTGGCGGTGGCGGGCC TGGCGGCGCTGGCGCTGGTGAGCAAGGGCGAGGAGCT G-3' | 411 |
| JO-20 | 5'-CCGCATATGATTGCGGTGGCGATTGCGGCGATTG TGCCGCTGGCGGTGAGCAAGGGCGAGGAGCTG-3' | 412 |
| JO-21 | 5'-CCGCATATGGCGGCGGCGGCGGTGCTGGCGGCGC GGCGCTGGCGGTGAGCAAGGGCGAGGAGCTG-3' | 413 |
| JO-22 | 5'-CCGGATATGGCGGCGCTGGCGCTGGGCGTGGCGG CGGCGCCGGCGGCGGCGCCGGCGGTGAGCAAGGGCGA GGAGCTG-3' | 414 |
| JO-23 | 5'-CCGCATATGCTGGCGGTGCTGGTGGTGCTGGTGC TGCTGCCGGTGAGCAAGGGGGAGGAGCTG-3' | 415 |
| JO-24 | 5'-CCGCATATGGTGGTGGCGGTGCTGGCGCCGGTGC TGGTGAGCAAGGGCGAGGAGCTG-3' | 416 |
| JO-25 | 5'-CCGCATATGGCGGCGCTGCTGCTGCCGCTGGTGC TGCTGCTGCCGGTGAGCAAGGGCGAGGAGCTG-3' | 417 |
| JO-26 | 5'-CCGCATATGCCGGCGGCGGTGGCGGGGGCTGGTGG TGATTGTGAGCAAGGGCGAGGAGCTG-3' | 418 |
| JO-27 | 5'-CCGGATATGCTGCTGATTGGGGCGCTGCTGCCGG TGAGCAAGGGCGAGGAGCTG-3' | 419 |
| JO-28 | 5'-CCGCATATGGCGGCGGTGGTGCTGCTGCCGCTGG CGGCGGcGcCGGTGAGCAAGGGCGAGGAGCTG-3' | 420 |
| JO-29 | 5'-GCGCATATGGGGGCGGCGGCGGCGGCGCTGCTGG TGCCGGTGAGCAAGGGCGAGGAGCTG-3' | 421 |
| JO-30 | 5'-GGGCATATGCTGCCGGTGGTGGCGCTGCTGGCGG TGAGCAAGGGCGAGGAGCTG-3' | 422 |
| JO-31 | 5'-GCGCATATGGCGGCGGCGCTGGCGGCGCCGCTGG CGCTGGCGGTGAGCAAGGGCGAGGAGCTG-3' | 423 |
| JO-32 | 5'-CCGCATATGCTGCTGCTGGCGCTGCTGCTGGCGG CGGTGAGCAAGGGCGAGGAGGTG-3' | 424 |
| JO-33 | 5'-CCGCATATGGCGGTGGCGGTGGTGGGGCTGCTGG TGAGCAAGGGCGAGGAGCTG-3' | 425 |
| JO-34 | 5'-CCGCATATGCTGCTGCTGATTATTGTGCTGCTGA TTGTGCCGGTGAGCAAGGGCGAGGAGCTG-3' | 426 |
| JO-35 | 5'-CCGCATATGGTGGCGCTGGCGGCGGCGGTGGTGC CGGTGAGCAAGGGCGAGGAGCTG-3' | 427 |
| JO-36 | 5'CCGCATATGCCGGCGGCGCTGGCGCTGCTGCTGGT GGCGGTGAGCAAGGGCGAGGAGCTG-3' | 428 |
| JO-37 | 5'-CCGCATATGATTGTGGCGCTGCTGCTGGTGCCGC TGGTGCTGGCGATTGCGGCGGTGCTGGTGAGCAAGGG CGAGGAGCTG-3' | 429 |
| JO-38 | 5'-CCGCATATGATTGTGGCGCTGCTGCTGGTGCCGG TGAGCAAGGGCGAGGAGCTG-3' | 430 |
| JO-39 | 5'-CCGCATATGGCGCTGGTGCTGGCGGATTGCGGGGG TGCTGGTGAGCAAGGGGAGGAGCTG-3' | 431 |
| JO-40 | 5'-CCGCATATGGCGCTGGTGCTGGCGGCGCTGGTGG GGGTGAGCAAGGGCGAGGAGCTG-3' | 432 |
| JO-41 | 5'-CCGCATATGGCGGCGGCGCTGCTGGCGGTGGCGG TGAGCAAGGGCGAGGAGCTG-3' | 433 |
| JO-42 | 5'-CCGCATATGCCGCTGCTGCTGCTGGCGCTGGCGG TGAGCAGGGCGAGGAGCTG-3' | 434 |
| JO-43 | 5'-CCGCATATGGCGCTGGCGCTGGTGGTGGCGGTGA GCAAGGGCGAGGAGCTG-3' | 435 |
| JO-44 | 5'-CCGCATATGGTGGCGGCGGTGGTGGTGGGGGCGG TGAGCAAGGGCGAGGAGCTG-3' | 436 |
| JO-45 | 5'-CCGCATATGCCGCTGGTGGCGCTGCTGCTGCTGG TGGTGAGCAAGGGCGAGGAGCTG-3' | 437 |

TABLE 1-continued

PCR forward primer sequences for each MTD-EGFP protein

| MTD | Sequence | SEQ ID NO |
|---|---|---|
| JO-46 | 5'-CCGCATATGGTGGTGCTGGTGGTGGTGCTGCCGCTGGCGGTGCTGGCGGTGAGCAAGGGGGAGGAGGTG-3' | 438 |
| JO-47 | 5'-CCGCATATGGCGGCGGCGGTGCCGGTGCTGGTGGCGGCGGTGAGCAAGGGCGAGGAGCTG-3' | 439 |
| JO-48 | 5'-CCGCATATGCCGGCGCTGCTGCTGCTGCTGCTGGCGGCGGTGGTGGTGAGCAAGGGCGAGGAGCTG-3' | 440 |
| JO-49 | 5'-CCGCATATGGGGCTGGCGATTCTGCTGCTGCTGCTGATTGCGCCGGTGAGGAAGGGCGAGGAGCTG-3' | 441 |
| JO-50 | 5'-CCGCATATGCCGCTGCTGGGGCTGGTGCTGCTGCTGGCGCTGATTGCGGTGAGCAAGGGCGAGGAGCTG-3' | 442 |
| JO-51 | 5'-CCGCATATGGTGGTGGCGGTGCTGGCGCTGGTGCTGGCGGCGCTGGTGAGCAAGGGCGAGGAGCTG-3' | 443 |
| JO-52 | 5'-CCGCATATGCCGCTGCTGCTGCTGGTGCGGGCGCTGGTGAGCAAGGGCGAGGAGCTG-3' | 444 |
| JO-53 | 5'-CCGCATATGCTGGCGGCGGTGGCGGCGCTGGGGGTGGTGGCGGTGAGCAAGGGCGAGGAGCTG-3' | 445 |
| JO-54 | 5'-CCGCATATGCTGCTGCTGCTGGTGCTGATTCTGCCGCTGGCGGCGGTGAGCAAGGGCGAGGAGCTG-3' | 446 |
| JO-55 | 5'-CCGCATATGCTGGCGGTGGTGGTGGTGGCGGCGGTGGTGAGCAAGGGCGAGGAGCTG-3' | 447 |
| JO-56 | 5'CCGCATATGGTGCTGCTGGCGGCGGGGCTGATTGCGGTGAGCAAGGGCGAGGAGCTG-3' | 448 |
| JO-57 | 5'-CCGCATATGCTGATTGCGCTGCTGGCGGCGCCGCTGGCGGTGAGCAAGGGCGAGGAGCTG-3' | 449 |
| JO-58 | 5'-CCGCATATGCTGGCGCTGCTGGTGCTGGGGGCGGTGAGCAAGGGGGAGGAGCTG-3' | 450 |
| JO-59 | 5'-CCGCATATGCTGCTGGCGGCGGCGCTGCTGCTGCTGCTGCTGGCGGTGAGCAAGGGCGAGGAGGTG-3' | 451 |
| JO-60 | 5'-CCGCATATGGTGATTATTGCGCTGATTGTGATTGTGGCGGTGAGCAAGGGCGAGGAGCTG-3' | 452 |
| JO-61 | 5'-CCGCATATGGTGGTGCTGGTGGTGGCGGCGGTGCTGGCGCTGGTGAGCAAGGGCGAGGAGCTG-3' | 453 |
| JO-62 | 5'-CCGCATATGGTGGCGGTGGCGATTGCGGTGGTGCTGGTGAGCAAGGGCGAGGAGGTG-3' | 454 |
| JO-63 | 5'-CCGCATATGCCGCTGATTGTGGTGGCGGCGGCGGTGGTGGCGGTGGTGAGGAAGGGCGAGGAGCTG-3 | 455 |
| JO-64 | 5'-CCGCATATGCCGCTGGGGGTGGCGGTGGCGGCGGTGGCGGCGGTGAGCAAGGGCGAGGAGCTG -3' | 456 |
| JO-65 | 5'-CCGCATATGGCGGCGATTGCGCTGGTGGCGGTGGTGCTGGTGAGCAAGGGCGAGGAGCTG-3' | 457 |
| JO-66 | 5'-CCGCATATGGCGGCGGCGCTGGCGGCGATTGCGGTGATTGTGAGCAAGGGCGAGGAGCTG-3' | 458 |
| JO-67 | 5'-CCGCATATGGCGGCGGGGCCGGCGGTGGCGGCGGTGAGCAAGGGCGAGGAGCTG-3' | 459 |
| JO-68 | 5'-CCGCATATGGTGCTGCTGGCGGCGCTGCCGGTGAGCAAGGGCGAGGAGCTG-3' | 460 |
| JO-69 | 5'-CGGCATATGGCGCTGCTGGCGGTGGTGGCGGCGGTGAGCAAGGGCGAGGAGGTG-3' | 461 |
| JO-70 | 5'-GCGGATATGGCGGTGGTGGTGGCTGCCGATTCTGGTGGTGAGCAAGGGCGAGGAGCTG-3' | 462 |
| JO-71 | 5'-CCGCATATGGCGCTGGCGCTGCTGCTGCTGGTGCCGGTGAGCAAGGGCGAGGAGCTG-3' | 463 |
| JO-72 | 5'-GCGCATATGCTGGTGGTGCTGCTGGCGGCGCTGCTGGTGGTGGTGAGCAAGGGCGAGGAGCTG-3' | 464 |
| JO-73 | 5'-CCGCATATGCCGGTGCTGCTGCTGCTGGCGCCGGTGAGGAAGGGCGAGGAGCTG-3' | 465 |
| JO-74 | 5'-GCGCATATGGCGCTGGCGGTGGTGGCGGCGCCGGTGAGCAAGGGCGAGGAGCTG-3' | 466 |
| JO-75 | 5'-CCGCATATGGTGATTGTGGCGCTGCTGGCGGTGGTGAGGAAGGGGGGGAGCTG-3' | 467 |
| JO-76 | 5'-CCGCATATGGGGGTGGTGCTGGCGGTGGCGCCGGTGAGCAAGGGCGAGGAGCTG-3' | 468 |
| JO-77 | 5'-CCGCATATGGCGGTGGCGCTGCTGATTCTGGCGGTGGTGAGGAAGGGCGAGGAGCTG-3' | 469 |
| JO-78 | 5'-CCGCATATGGTGCTGCTGGCGGTGATTCCGGTGAGCAAGGGCGAGGAGCTG-3' | 470 |
| JO-79 | 5'-CCGCATATGCTGATTGTGGCGGCGGTGGTGGTGGTGGCGGTGCTGATTGTGAGCAAGGGCGAGGAGCTG-3' | 471 |
| JO-80 | 5'-CCGCATATGGCGGTGGTGGTGGGGGCGCCGGTGAGCAAGGGCGAGGAGCTG-3' | 472 |
| JO-81 | 5'-CCGCATATGCTGGCGGCGGTGCTGGTGCTGATTCGGGTGAGGAAGGGCGAGGAGCTG-3' | 473 |
| JO-82 | 5'-CCGCATATGCTGCTGCTGCTGCTGCTGGCGGTGGTGCCGGTGAGCAAGGGCGAGGAGCTG-3' | 474 |
| JO-83 | 5'-CCGCATATGGCGGTGGCGCTGGTGGGGGTGGTGGCGGTGGCGGTGAGCAAGGGCGAGGAGCTG -3' | 475 |
| JO-84 | 5'-CCGCATATGCTGGTGGCGGCGCTGCTGGCGGTGCTGGTGAGCAAGGGCGAGGAGCTG-3' | 476 |
| JO-85 | 5'-CCGCATATGCTGCTGGCGGCGGCGGCGGCGCTGCTGGCGGTGAGCAAGGGCGAGGAGCTG -3' | 477 |
| JO-86 | 5'-CCGCATATGCTGGCGGTGCTGGCGGCGGCGCCGGTGAGCAAGGGCGAGGAGCTG-3' | 478 |
| JO-87 | 5'-CCGCATATGGTGGTGGTGCTGCTGGTGCTGCTGGCGCTGGTGGTGGTGAGCAAGGGCGAGGAGCTG-3' | 479 |
| JO-88 | 5'-CCGCATATGGTGGTGATTGCGGTGGTGCCGGTGAGCAAGGGCGAGGAGCTG-3' | 480 |
| JO-89 | 5'-GCGCATATGGTGCTGCTGGTGCTGCTGGCGCTGGTGGTGAGCAAGGGCGAGGAGCTG-3' | 481 |
| JO-90 | 5'-CCGCATATGGTGCTGCTGGTGCTGCTGGGGCTGGTGGTGAGCAAGGGCGAGGAGGTG-3' | 482 |
| JO-91 | 5'-CCGCATATGCCGGTGCTGGTGCCGGCGGTGCCGGTGAGCAAGGGCGAGGAGCTG-3' | 483 |
| JO-92 | 5'-CCGCATATGGCGGCGCTGGCGCTGGCGCTGGCGGTGAGCAAGGGCGAGGAGCTG-3' | 484 |
| JO-93 | 5'-CCGCATATGGCGGGGGCGGCGCCGGCGCTGGCGGTGAGCAAGGGCGAGGAGCTG-3' | 485 |

TABLE 1-continued

PCR forward primer sequences for each MTD-EGFP protein

| MTD | Sequence | SEQ ID NO |
|---|---|---|
| JO-94 | 5'-CCGCATATGATTGTGCTGCCGGTGCTGGCGGCGCCGGTGAGCAAGGGCGAGGAGCTG-3' | 486 |
| JO-95 | 5'-CCGCATATGCTGGTGCTGCTGCTGCTGCCGCTGCTGATTGTGAGCAAGGGCGAGGAGGTG-3' | 487 |
| JO-96 | 5'-CCGCATATGCTGGCGGCGGTGGCGCCGGCGCTGGCGGTGGTGGTGAGCAAGGGCGAGGAGCTG-3' | 488 |
| JO-97 | 5'-CCGCATATGATTCTGGTGCTGGTGCTGCCGATTGTGAGCAAGGGCGAGGAGCTG-3' | 489 |
| JO-98 | 5'-CCGCATATGATTCTGCTGCCGCTGCTGCTGCTGCCGGTGAGCAAGGGCGAGGAGCTG-3' | 490 |
| JO-99 | 5'-CCGGATATGATTGCGCCGGCGGTGGTGGCGGGGCTGCCGGTGAGCAAGGGGGAGGAGCTG-3' | 491 |
| JO-100 | 5'-CCGCATATGCTGCTGCTGGTGGCGGTGGTGCCGCTGCTGGTGCCGGTGAGCAAGGGCGAGGAGCTG-3' | 492 |
| JO-101 | 5'-CCGCATATGCTGATTCTGCTGCTGCTGCCGATTATTGTGAGGAAGGGCGAGGAGCTG-3' | 493 |
| JO-102 | 5'-CCGCATATGGCGGTGCTGGCGGCGCCGGCGGTGCTGGTGGTGAGCAAGGGCGAGGAGCTG-3' | 494 |
| JO-103 | 5'-CCGCATATGCTGGCGCTGCCGGTGCTGCTGCTGGCGGTGAGCAAGGGCGAGGAGCTG-3' | 495 |
| JO-104 | 5'-CCGCATATGGTGGCGCTGGCGCTGCTGCTGGTGAGCAAGGGCGAGGAGGTG-3' | 496 |
| JO-105 | 5'-CCGGATATGGTGGCGGTGCCGCTGCTGGTGGTGGGGTGAGGAAGGGCGAGGAGCTG-3' | 497 |
| JO-106 | 5'-CCGCATATGGCGGTGGCGGTGGCGCGGGTGGCGGCGGCGGTGAGGAAGGGGGAGGAGCTG-3' | 498 |
| JO-107 | 5'-CCCATATGGCGGCGCGGTGGTGGCGGCGGTGCCGGCGGCGGTGAGCAAGGGCGAGGAGCTG-3' | 499 |
| JO-108 | 5'-CCCATATGGCGCTGCTGGCGGCGCTGCTGGCGCCGGTGAGcAAGGGCGAGGAGCTG-3' | 500 |
| JO-109 | 5'-CCCATTGCGCTGGCGCTGCTGGTGCCGGTGAGCAAGGGCGAGGAGCTG-3' | 501 |
| JO-110 | 5'-CCGCATATGGCGCTGCTGGCGGCGCTGCTGGCGCTGCTGGCGCTGCTGGTGGTGAGCAAGGGCGAGGAGCTG-3' | 502 |
| JO-111 | 5'-CCGCATATGGCGGCGGCGCTGCCGCTGCTGGTGCTGCTGCCGGTGAGCAAGGGGGAGGAGCTG-3' | 503 |
| JO-112 | 5'-CCCATATGGCGGCGGCGGTGGCGGCGGCGCTGGCGCCGGTGAGCAAGGGCGAGGAGCTG-3' | 504 |
| JO-113 | 5'-CCCATTGGCGGCGCTGGCGGTGGCGGCGCTGGCGGCGGTGAGCAAGGGCGAGGAGCTG-3' | 505 |
| JO-114 | 5'-CCCATTGGCGGTGCTGGCGGCGGCGGTGCCGGTGAGCAAGGGCGAGGAGCTG-3' | 506 |
| JO-115 | 5'-CCGCATATGGTGGCGGCGCTGCCGGCGCCGGGGGTGAGCAAGGGCGAGGAGCTG-3' | 507 |
| JO-116 | 5'-CCGCATATGGCGCTGGCGCTGGCGGTGCCGGCGGTGCTGCCGGTGAGCAAGGGCGAGGAGCTG-3' | 508 |
| JO-117 | 5'-CCGCATATGGCGGCGCTGCTGCCGGCGGCGGTGGCGGTGCCGGTGAGCAAGGGCGAGGAGCTG-3' | 509 |
| JO-118 | 5'-CCGCATATGGCGGTGGTGGTGGCGCTGGCGCCGGTGAGCAAGGGCGAGGAGCTG-3' | 510 |
| JO-119 | 5'-CCGCATATGGCGGCGGCGGTGGCGGTGCCGGCGGCGGCGCTGCTGGCGGTGAGCAAGGGCGAGGAGCTG-3' | 511 |
| JO-120 | 5'-CCGCATATGGCGGTGGTGCTGCCGCTGGCGCTGGTGGCGGTGGCGCCGGTGAGCAAGGGCGAGGAGCTG-3' | 512 |
| JO-121 | 5'-CCGCATATGCTGGTGGCGCTGCCGGTGCTGCCGGTGAGGAAGGGCGAGGAGCTG-3' | 513 |
| JO-122 | 5'-CCGCATATGGTGGTGGTGCCGCTGCTGCTGATTGTGCCGGTGAGCAAGGGCGAGGAGCTG-3' | 514 |
| JO-123 | 5'-CCGCATATGCTGGCGGTGGTGCTGGCGGTGGCGGTGAGCAAGGGCGAGGAGCTG-3' | 515 |
| JO-124 | 5'-CCGCATATGCTGCTGGCGGTGCCGATTCTGCTGGGGCTGCCGGTGAGCAAGAGGAGCTG-3' | 516 |
| JO-125 | 5'-CCGGATATGCTGGTGGGGCTGGTGCTGGTGCCGGTGAGCAAGGGCGGGAGCTG-3' | 517 |
| Jo-126 | 5'-CCGCATATGCTGGTGCTGCTGCTGGCGGTGCTGCTGGCGGTGCTGCCGGTGAGCAAGGGCGAGGAGCTG-3' | 518 |
| JO-127 | 5'-CCGCATATGCTGCTGGCGCCGGTGGTGGCGCTGGTGATTCTGCCGGTGAGGAAGGGCGAGGAGCTG-3' | 519 |
| JO-128 | 5'-CCGCATATGGTGCTGGCGGTGCTGGCGGTGCCGGTGCTGCTGCTGCCGGTGAGCAAGGGCGAGGAGCTG-3' | 520 |
| JO-129 | 5'-CCGCATATGGTGGTGATTGCGGTGGTGCCGGTGGTGGTGAGCAAGGGCGAGGAGCTG-3' | 521 |
| JO-130 | 5'-CCGCATATGCTGCTGGTGCTGCTGGCGCTGGTGGTGGTGCCGGTGAGCAAGGGCGAGGAGCTG-3' | 522 |
| JO-131 | 5'-CCGCATATGGTGCTGCTGGCGCTGCCGGTGGTGGCGGCGCCGGTGAGCAAGGGCGAGGAGCTG-3' | 523 |
| JO-132 | 5'-CCGCATATGGCGGTGGTGGTGCCGGCGATTGTGCTGGCGGCGCCGGTGAGCAAGGGCGAGGAGCTG-3' | 524 |
| JO-133 | 5'-CCGCATATGGCGGTGCTGGTGCCGGCGGCGGCGCTGGTGCCGGTGAGGAAGGGCGAGGAGCTG-3' | 525 |
| JO-134 | 5'-CCGCATATGGTGGTGGCGGCGCTGCCGCTGGTGCTGCCGGTGAGCAAGGGCGAGGAGCTG-3' | 526 |
| JO-135 | 5'-CCGCATATGGCGGCGGTGGCGCTGCCGGCGGCGGCGCCGGTGAGCAAGGGCGAGGAGCTG-3' | 527 |
| JO-136 | 5'-CCGCATATGGTGATTGCGCTGCCGCTGCTGCCGGTGAGCAAGGGCGAGGAGCTG-3' | 528 |
| JO-137 | 5'-CCGCATATGCTGCTGGCGCTGCCGCTGGTGCTGGTGCTGGCGCTGCCGGTGAGCAAGGGCGAGGAGGTG-3' | 529 |
| JO-138 | 5'-CCGGATATGATTGTGCCGCTGCTGCTGGCGGCGCCGGTGAGCAAGGGCGAGGAGCTG-3' | 530 |
| JO-139 | 5'-CCGCATATGCTGCTGCTGGCGCCGCTGCTGCTGGCCGGTGAGCAGGGGCGAGGAGCTG-3' | 531 |
| JO-140 | 5'-CCGCATATGCTGGGGGCGCTGCCGGTGGCGGGGGTGCCGGTGAGCAAGGGCGAGGAGCTG-3' | 532 |

TABLE 1-continued

PCR forward primer sequences for each MTD-EGFP protein

| MTD | Sequence | SEQ ID NO |
|---|---|---|
| JO-141 | 5'-CCGCATATGGCGCTGGCGGTGATTGTGCTGGTGC TGCTGGTGAGCAAGGGCGAGGAGCTG-3' | 533 |
| JO-142 | 5'-CGGCATATGCTGGCGCTGCTGCTGCCGGCGGCGC TGATTCCGGTGAGCAAGGGCGAGGAGCTG-3' | 534 |
| JO-143 | 5'-CCGCATATGGCGCTGCTGCCGCTGCTGGCGGTGG TGCTGCCGCCGGTGAGCAAGGGCGAGGAGCTG-3' | 535 |
| JO-144 | 5'-CCGCATATGGCGATTGCGGTGCCGGTGCTGGCGG CGCCGGTGAGCAAGGGCGAGGAGCTG-3' | 536 |
| JO-245 | 5'-CCGCATATGGCGGCGGCGCGGGTGCTGCTGCTGC TGCTGCCGGTGAGCAAGGGCGAGGAGCTG-3' | 537 |
| JO-146 | 5'-CCGCATATGGCGGCGGCGCCGGTGCTGCTGCTGC TGCTGCGGGTGAGCAAGGGCGAGGAGCTG-3' | 538 |
| JO-147 | 5'-CCGCATATGGCGGCGCTGGCGGCGCTGGTGGTGG CGGCGCCGCCGGTGAGCAAGGGCGAGGAGCTG-3' | 539 |
| JO-148 | 5'-CCGCATATGGCGGCGCTGGCGGCGGTGCCGCTGG GGCTGGCGCCGGTGAGCAAGGGCGAGGAGCTG-3' | 540 |
| JO-149 | 5'-CGGCATATGGCGCTGGCGGTGGCGGCGCCGGCGC TGGCGCTGCTGCCGCCGGTGAGCAAGGGCGAGGAGCT G-3' | 541 |
| JO-150 | 5'-CCGCATATGCTGGTGGCGCTGGTGCTGCTGCCGG TGAGCAAGGGGGAGGAGCTG-3' | 542 |
| Jo-151 | 5'-GCGCATATGCTGGTGCTGCTGCTGGCGGTGCTG CTGCTGGGGGTGCTGCCGGTGAGCAAGGGCGAGGAG CTG-3' | 543 |
| JO-152 | 5'-CCGCATATGCTGCTGGCGCCGGTGGTGGCGCTG GTGATTCTGCCGGTGAGCAAGGGCGAGGAGCT G-3' | 544 |
| JO-153 | 5'-CCGCATATGGTGCTGGCGGTGCTGGCGGTGGCG GTGCTGCTGCTGCCGGTGAGCAAGGGCGAGGAGCT G-3' | 545 |
| JO-154 | 5'-CCGCATATGGTGGTGATTGCGGTGGTGCCGGTG GTGGTGAGCAGGGCGAGGAGCTG-3' | 546 |
| JO-155 | 5'-CCGGATATGCTGCTGGTGCTGCTGGCGCTGGTG GTGGTGCCGGTGAGCAAGGGCGAGGAGCTG-3' | 547 |
| JO-156 | 5'-CCGCATATGGTGCTGCTGGCGCTGCCGGTGGTG GCGGCGCCGGTGAGCAAGGGCGAGGAGCTG-3' | 548 |
| JO-157 | 5'-CCGCATATGGCGGTGGTGGTGCCGGCGATTGTG CTGGCGGCGCCGGTGAGCAAGGGCGAGGAGCTG-3' | 549 |
| JO-158 | 5'-CCGCATATGGCGGTGCTGGTGCCGGCGGCGGCG CTGGTGCCGGTGAGCAAGGGCGAGGAGCTG-3' | 550 |
| JO-159 | 5'-CCGCATATGGTGGTGGCGGCGCTGCCGCTGGTG CTGCCGGTGAGCAAGGGCGAGGAGCTG-3' | 551 |
| JO-160 | 5'-CCGCATATGGCGGCGGTGGCGCTGCCGGCGGCG GCcICCGGTGAGCAAGGGCGAGGAGCTG-3' | 552 |
| JO-161 | 5'-CCGCATATGCTGATTGCGCTGCCGCTGCTGCCG AGTGAGCAAGGGCGGGAGCTG-3' | 553 |
| JO-162 | 5'-CCGCATATGCTGCTGGCGCTGCCGCTGGTGGTG CGGTGCTGGCGCTGCGTGAGCAAGGGCGAGGAGCT G-3' | 554 |
| JO-163 | 5'-CCGCATATGATTGTGCCGCTGCTGCTGGCGGCG GCCGGTGAGCAAGGGCGAGGAGCTG-3' | 555 |
| JO-164 | 5'-CCGCATATGCTGCTGCTGGCGCCGCTGGTGCTG AGGGCCGGTGAGCAGGGCGAGGAGCTG-3' | 556 |
| JO-165 | 5'-CGGCATATGCTGGCGGCGCTGCCGGTGGCGGCG AGTGCCGGTGAGCAGGGCGAGGAGCTG-3' | 557 |
| JO-166 | 5'-CCGCATATGGCGCTGGCGGTGATTGTGCTGGTG AGTGCTGGTGAGCAGGGCGAGGAGCTG-3' | 558 |
| JO-167 | 5'-CCGCATATGCTGGGGCTGCTGCTGCCGGCGGCG CTGATTCCGGTGAGCAAGGGCGAGGAGCTG-3' | 559 |
| JO-168 | 5'-GCGGATATGCTGGCGGCGGTGGTGCCGGTGGCG GCGGCGGTGCCGGTGAGCAAGGGCGAGGAGCTG-3' | 560 |
| JO-169 | 5'-CCGCATATGGTGGCGGCGCCGGGGGCGGCGGCG CCGGTGAGCAAGGGCGAGGAGCTG-3' | 561 |
| JO-170 | 5'-GCGGATATGGCGGTGCCGGTGCCGGTGCCGCTG GTGAGCAAGGGCGAGGAGCTG-3' | 562 |
| JO-171 | 5'-CCGCATATGCTGCTGATTCTGCCGATTGTGCTG CTGCGGGTGAGCAAGGGCGAGGAGCTG-3' | 563 |
| JO-172 | 5'-CCGCATATGGCGCTGGCGCTGCCGGCGCTGGCG ATTGCGCCGGTGAGCAAGGGCGAGGAGCTG-3' | 564 |
| JO-173 | 5'-CCGCATATGGCGGTGATTCCGATTCTGGCGGTG CCGGTGAGCAAGGGCGAGGAGCTG-3' | 565 |
| JO-174 | 5'-CCGCATATGCTGATTCTGCTGCTGCCGGCGGTG GCGCGCTGCCGGTGAAAGGGCGAGGAGCTG-3' | 566 |
| JO-175 | 5'-CCGCATATGATTGTGCTGGCGCCGGTGCCGGCG GCGGCGGTGAGCAAGGGCGAGGAGCTG-3' | 567 |
| JO-176 | 5'-CCGCATATGGTGGTGGTGGTGCCGGTGCTGGCG GCGGCGGCGGTGAGCAAGGGCGAGGAGCTG-3' | 568 |
| JO-177 | 5'-GCGCATATGGTGGTGGCGGTGGCGGCGCCGGTG AGCAAGGGCGAGGAGCTG-3' | 569 |
| JO-178 | 5'-CCGCATATGCTGGTGCTGGCGGCGCCGGCGGCG CTGCCGGTGAGCAAGGGCGAGGAGCTG-3' | 570 |
| JO-179 | 5'-CCGCATATGCTGATTGCGCCGGCGGCGGCGGTG CCGGTGAGCAAGGGCGAGGAGCTG-3' | 571 |
| JO-180 | 5'-CGGCATATGGCGCTGGCGGCGCTGCCGATTGGG CTGCGGGTGAGCAAGGGCGAGGAGGTG-3' | 572 |
| JO-181 | 5'-CCGCATATGGCGGTGCTGCTGCTGCCGGGGGCG GCGGTGAGCAAGGGGGAGGAGCTG-3' | 573 |
| Jo-182 | 5'-CCGCATATGATTGCGCTGGCGCTGCTGCCGCTGC TGGTGAGCAAGGGCGAGGAGCTG-3' | 574 |
| JO-183 | 5'-CCGCATATGGTGCTGCTGGCGGCGGCGGTGATT GCGCCGGTGAGCAAGGGCGAGGAGCTG-3' | 575 |
| JO-184 | 5'-CCGCATATGGCGCCGGCGGTGCTGCCGCCGGTG GTGGTGATTGTGAGCAAGGGCGAGGAGCTG-3' | 576 |
| JO-185 | 5'-CCGCATATGGTGGTGGGCCTGCTGGTGGCGGCG CTGGTGAGCAAGGGCGAGGAGCTG-3' | 577 |
| JO-186 | 5'-CCGCATATGGCGGCGATTGCGGCGGCGGCGCCG CTGGCGGCGGTGAGCAAGGGCGAGGAGCTG-3' | 578 |
| JO-187 | 5'-CCGCATATGCTGCTGCTGGCGGTGGCGCGGGTG AGCAAGGGCGAGGAGCTG-3' | 579 |
| JO-188 | 5'-CCGCATATGCTGATTCTGCTGCTGCCGCTGGCG GCGCTGGTGAGCAAGGGCGAGGAGCTG-3' | 580 |

TABLE 1-continued

PCR forward primer sequences
for each MTD-EGFP protein

| MTD | Sequence | SEQ ID NO |
|---|---|---|
| JO-189 | 5'-CCGCATATGGCGCTGCTGCTGCTGGTGCTGGCG GTGAGCAAGGGCGAGGAGCTG-3' | 581 |
| JO-190 | 5'-CGGCATATGGTGGTGCTGCTGCTGCTGCCGCTG GCGGTGAGCAAGGGCGAGGAGCTG-3' | 582 |
| JO-191 | 5'-GCGCATATGCTGGCGCTGCCGCTGCTGCTGCCG GTGAGCAAGGGCGAGGAGCTG-3' | 583 |
| JO-192 | 5'-CCGCATATGCTGCTGGTGCTGCCGCTGCTGATT GTGAGCAAGGGGGAGGAGCTG-3' | 584 |
| JO-193 | 5'-CCGCATATGCTGCGGCTGCTGCCGGCGGCGCTG GTGGTGAGCAAGGGCGAGGAGCTG-3' | 585 |

TABLE 2

PCR reverse primer sequence
for each MTD-EGFP protein

| MTD | Sequence | SEQ ID NO |
|---|---|---|
| JO-1~ JO-193 | 3'-TTA TCT AGA TCC GGT GGA TCC CGG GCC-5' | 586 |

Figure 4A:
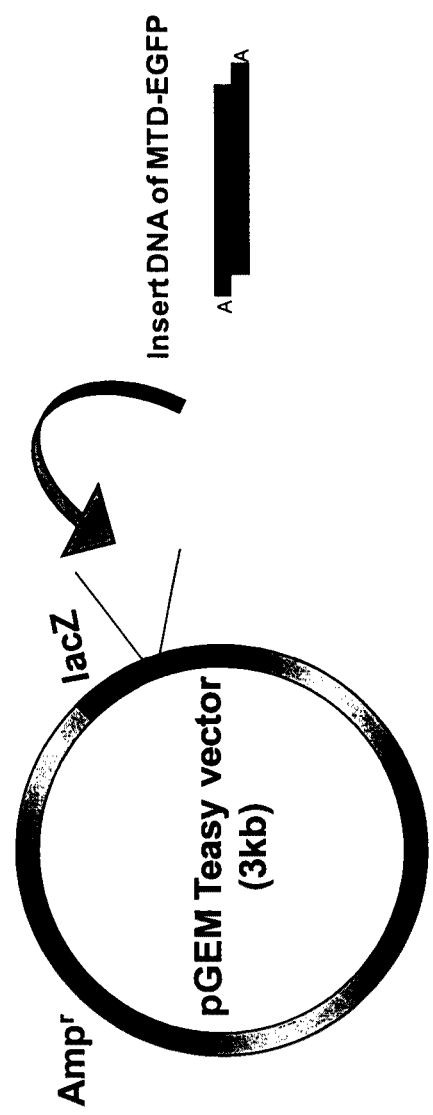
Figure 4B:
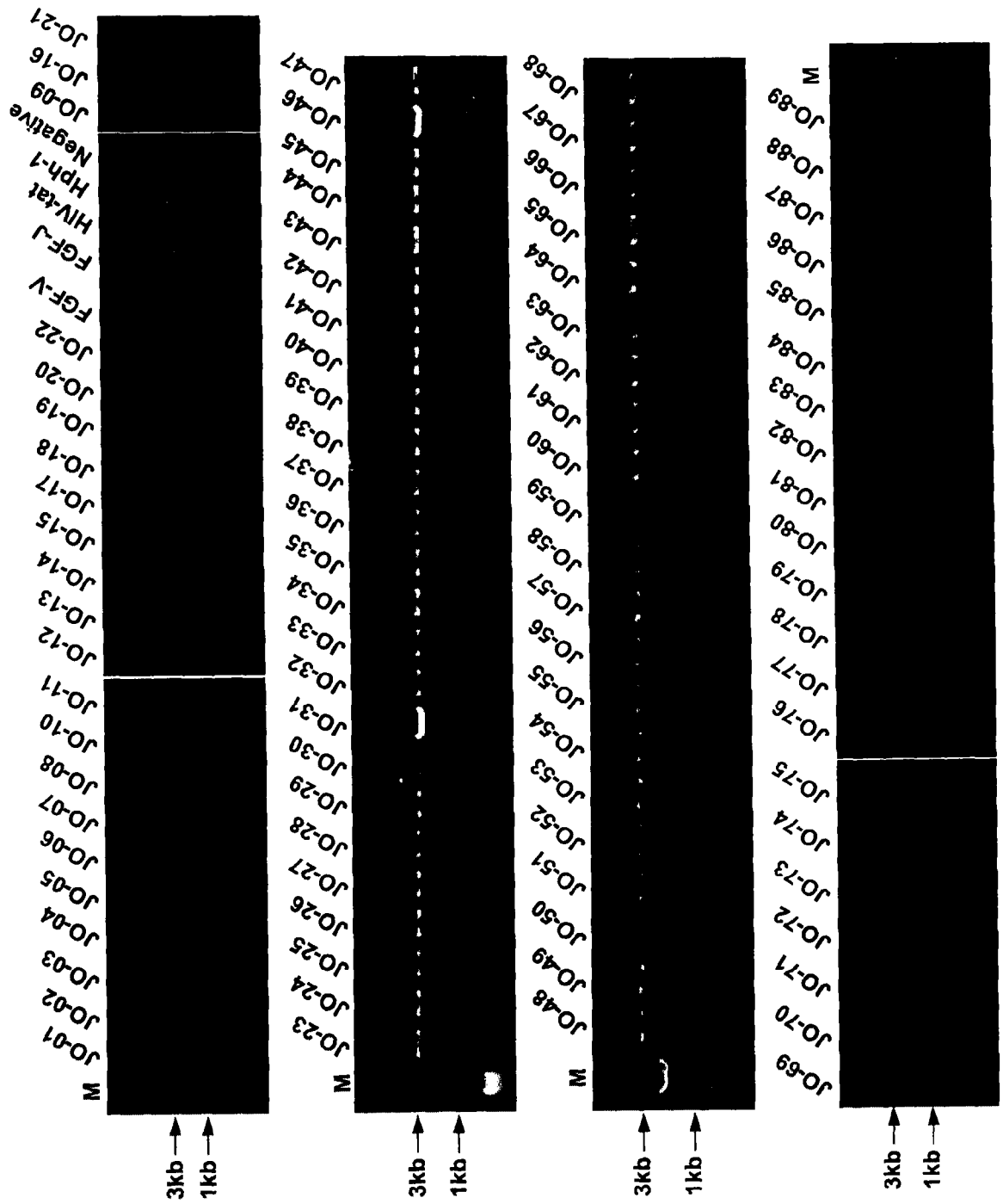
FIGS. 4b to 4d are photographs of an agarose gel electrophoresis analysis showing DNA fragments encoding MTDs-EGFP subcloned into pGEM-Teasy vector according to the present invention.
Figure 4C:
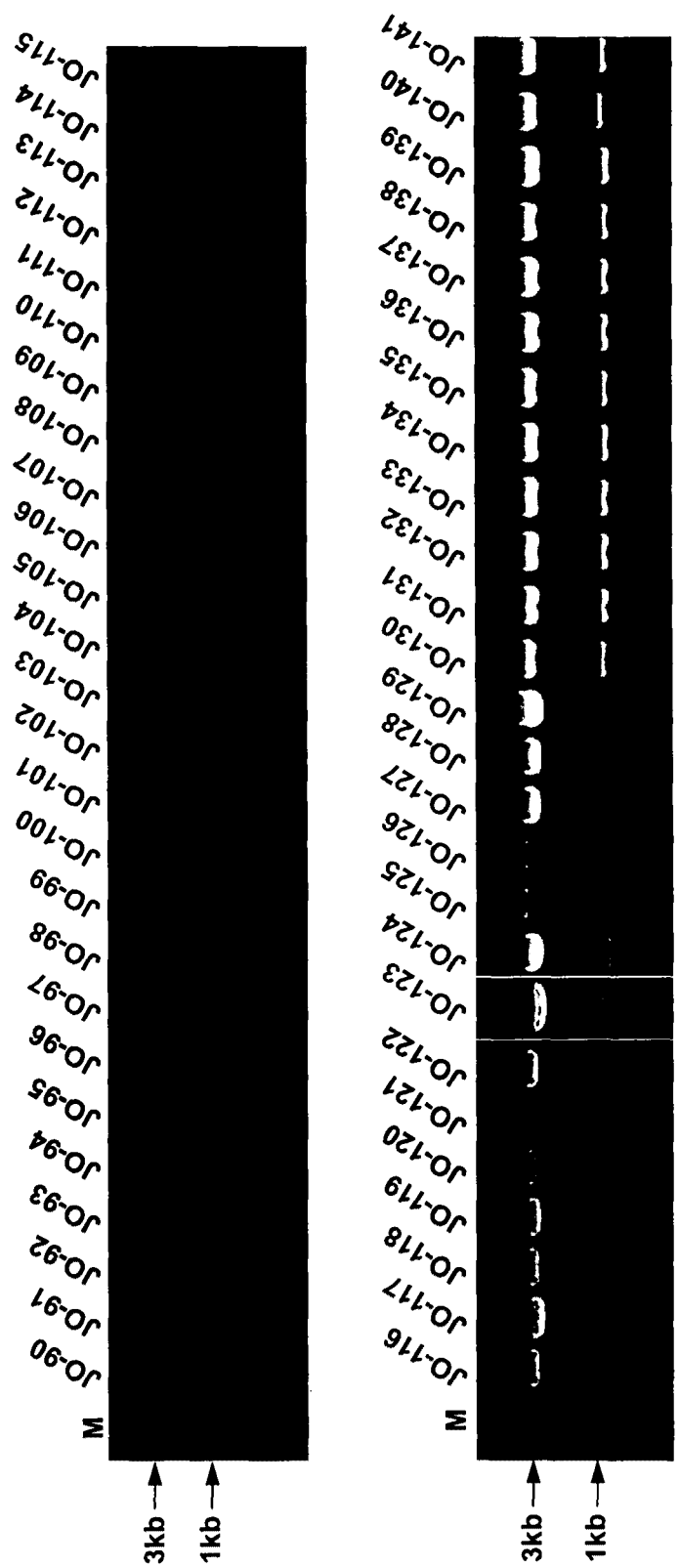
Figure 4D:
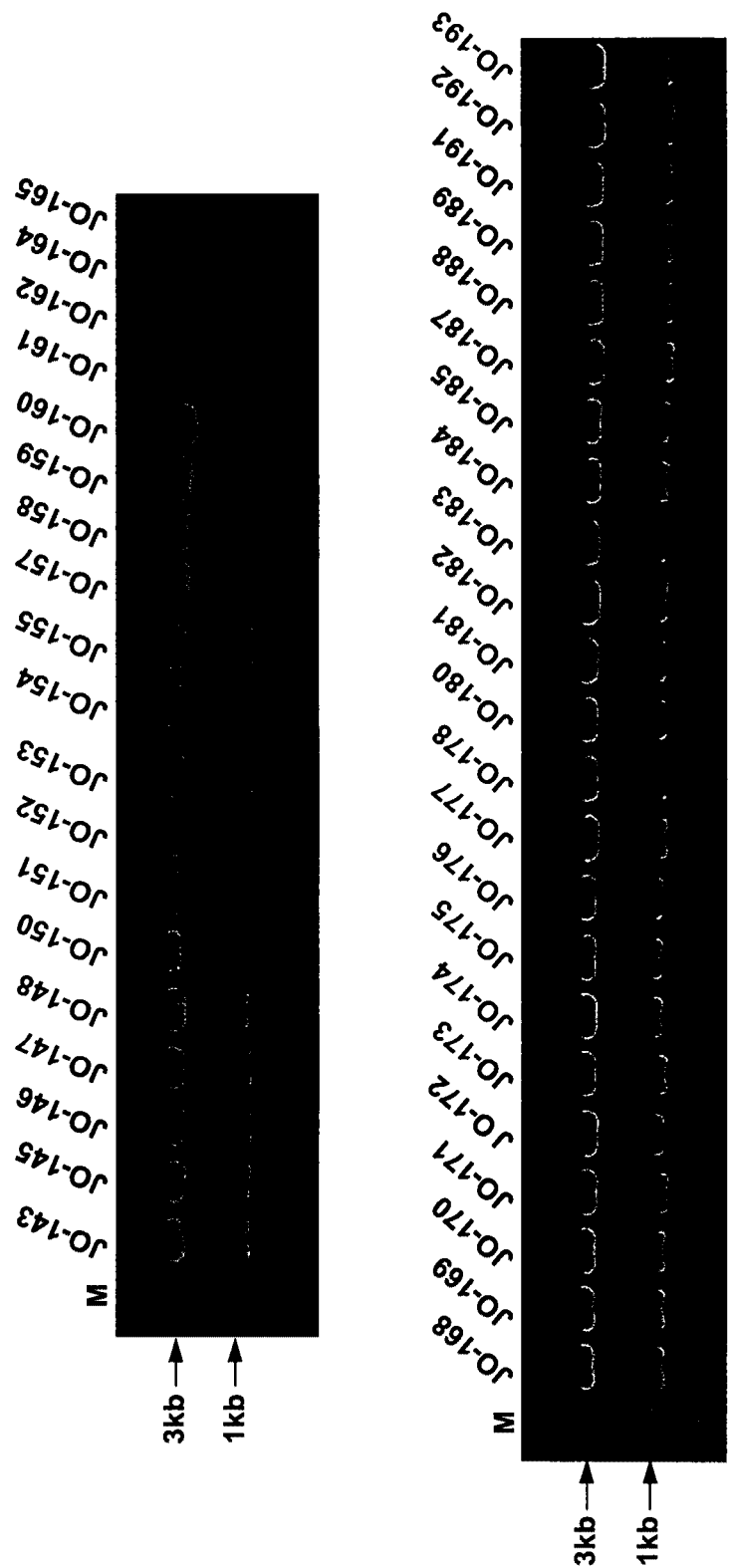

Referring to FIG. 4a, each of the PCR amplified products was subcloned into the pGEM-Teasy vector (Promega™, Madison Wis., USA) with a T4 DNA ligase, according to the TA cloning method and then E. coli DH5α was transformed, where transformants were selected on LB plate media containing 50 µg/mL ampicillin, IPTG and X-gal. After the recombinant fragment inserted into pGEM-Teasy vector was isolated by treating with the restriction enzyme NdeI, it was subjected to 0.8% agarose gel electrophoresis. As a result, DNA fragments of about 1 kb and vector fragments of about 3 kb were detected, which confirms that the insert DNA of MTD-EGFP was appropriately subcloned into pGEM-Teasy vector (FIGS. 4b to 4d).

Figure 5A:
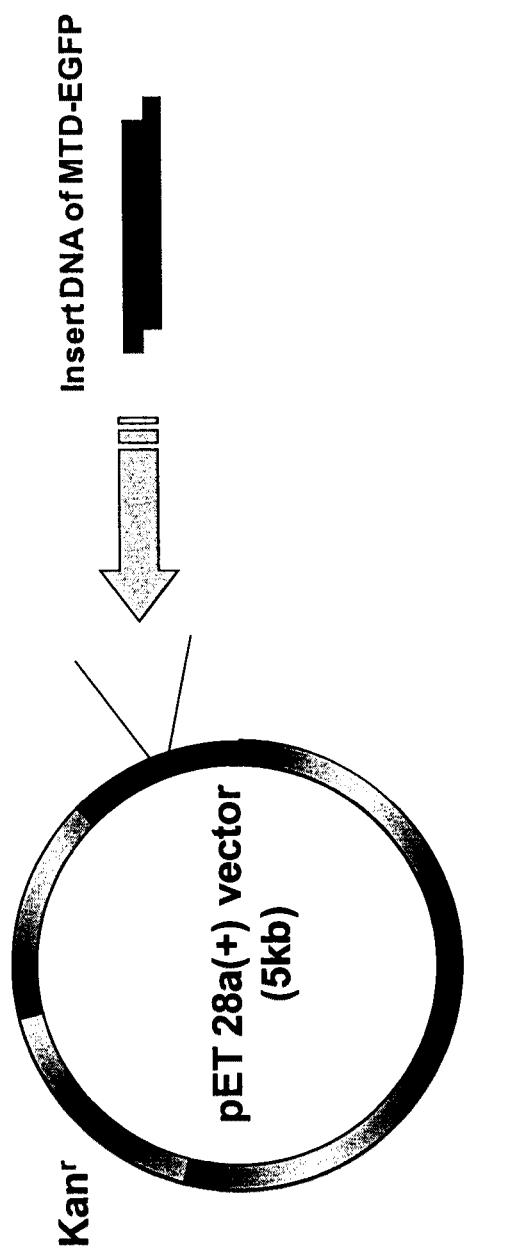

As described in FIG. 5a, each of the isolated insert DNA fragments encoding MTDs-EGFP was cloned into the E. coli expression plasmid pET-28a(+) (commercially available from Novagen™, Madison, Wis.). The pET-28a(+) plasmids are designed to facilitate His-tag fusions at either the N- or C-terminus and to provide strong expression of the genes in E. coli from the T7 phage promoter. At the 3' end of each MTD-EGFP encoding gene, the coding sequence was fused in frame at the NdeI site to the His-tag sequence followed by a translation stop codon, which results in the production of MTD-EGFP recombinant proteins with six histidine residues added to the C-terminus for the sake of easy purification on nickel columns.

Figure 5B:
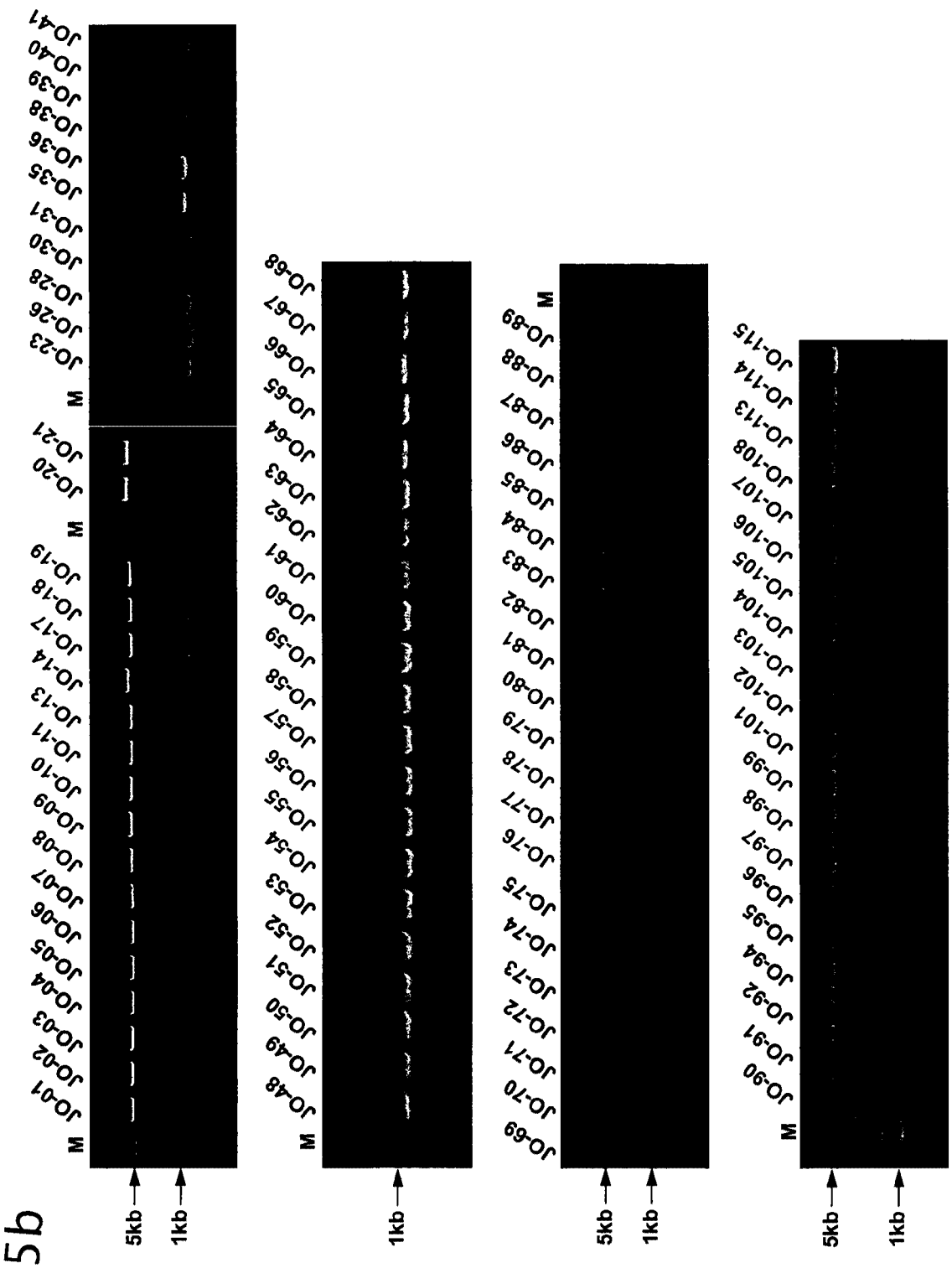
FIGS. 5b to 5c are photographs of an agarose gel electrophoresis analysis showing DNA fragments encoding MTDs-EGFP cloned into the pET 28(+) vector according to the present invention.
Figure 5C:
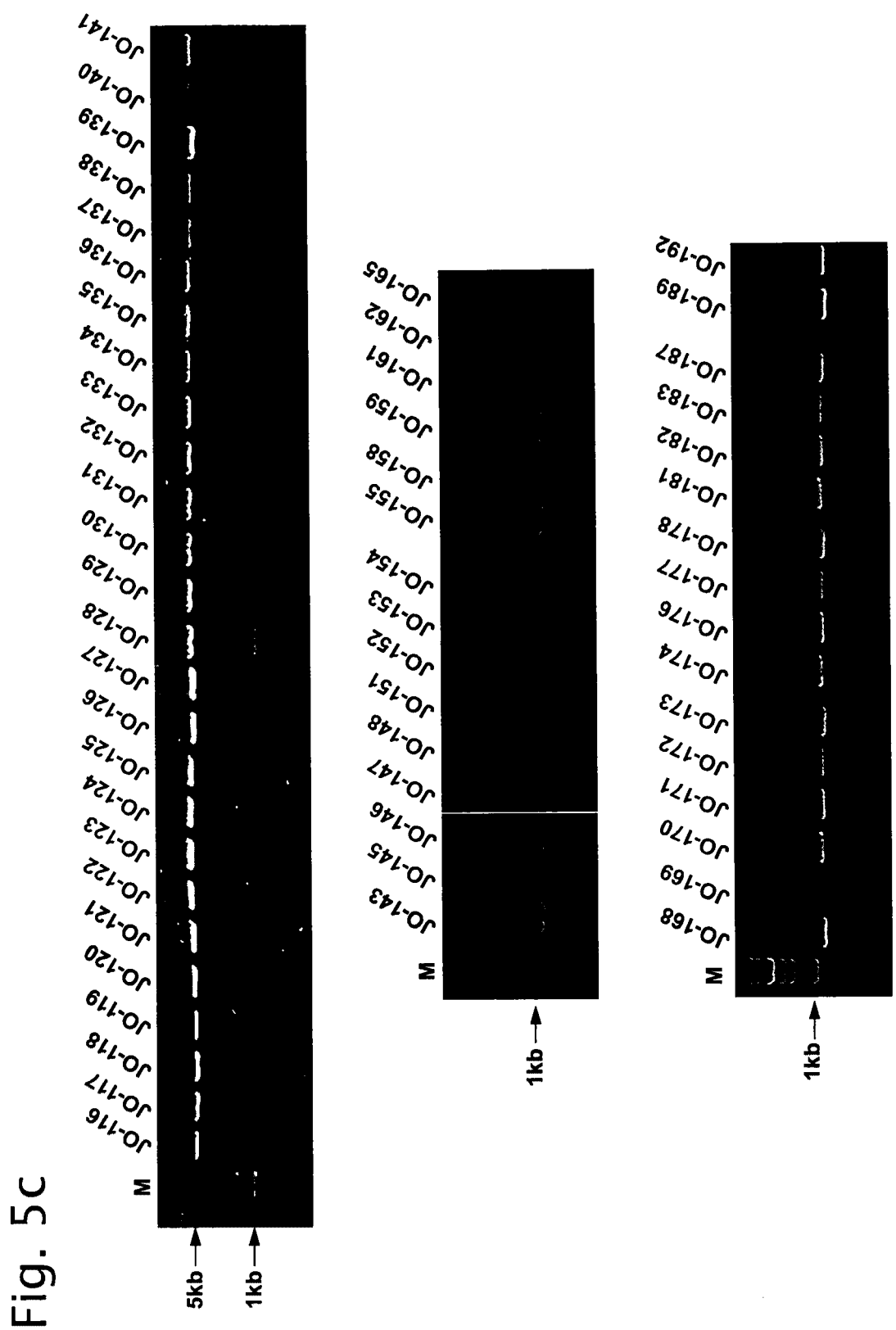

After the clones were treated with the restriction enzyme NdeI and subjected to agarose gel electrophoresis, it was verified that DNA fragments of about 1 kb and vector fragments of about 5 kb were detected, which confirms the cloning of the insert DNA of MTD-EGFP into pET-28a(+) vector, as shown in FIGS. 5b to 5c. Further, out of the 193 novel MTDs, 148 MTDs were found to be successfully cloned for the expression of His-MTD-EGFP recombinant proteins.

Example 3

Inducible Expression and Purification of Recombinant Proteins Fused to MTDs

To express the cell permeable recombinant proteins fused to MTDs prepared as described in Example 2 above, the expression vectors comprising the His-MTD-EGFP recombinant proteins were transfected in the BL21 (DE3), BL21-Gold (DE3), BL21-CodonPlus (DE3) and BL21-GoldpLysS (DE3) strains, respectively. An EGFP expression vector including kFGF4-derived MTD (SEQ ID NO: 387) was used as a positive control, while an EGFP expression vector fused to a scramble peptide (SEQ ID NO: 389) having no function was used as a negative control.

Figure 6A:
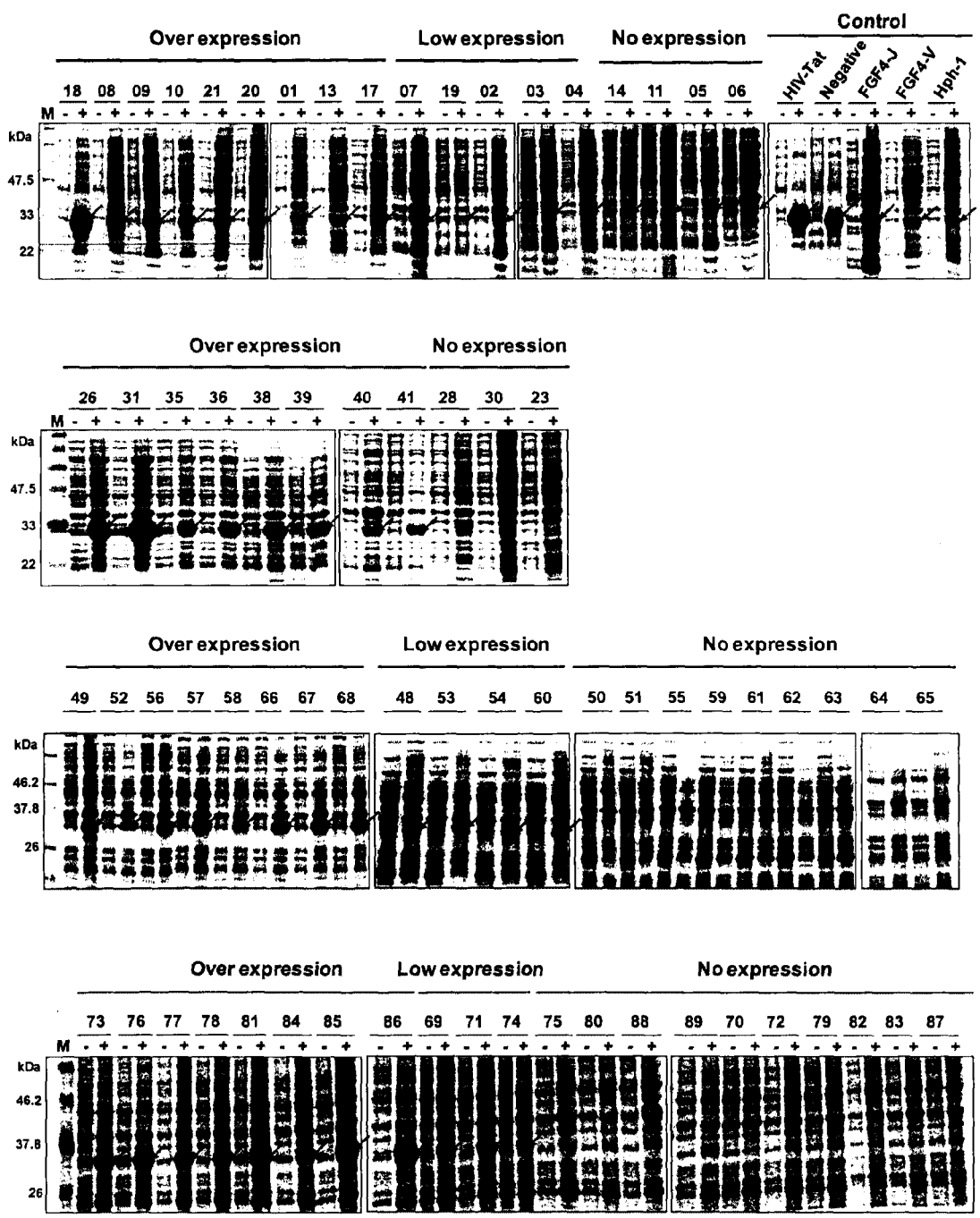
FIGS. 6a and 6b are photographs of a SDS-PAGE analysis illustrating the inducible expression of His-MTD-EGFP recombinant proteins according to the present invention.
Figure 6B:
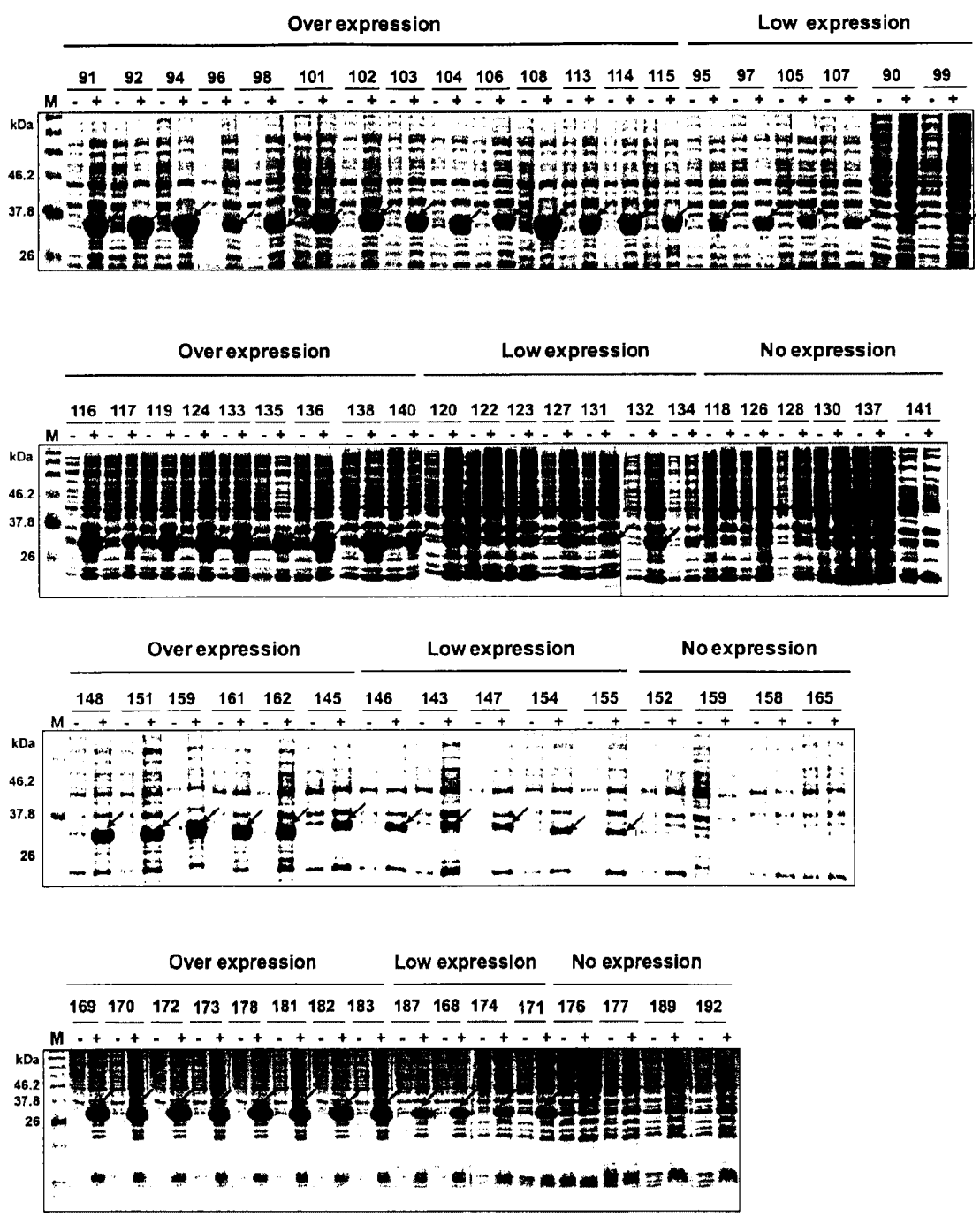

After the transfection, cells were grown at 37° C. in an LB medium containing kanamycin (30 µg/ml) with vigorous shaking until the optical density 600 ($OD_{600}$) reached between 0.4 and 0.6. IPTG (isoprophyl-β-D-thiogalactoside) was then added thereto at a final concentration of 0.6 mM to induce the expression of the His-MTD-EGFP recombinant proteins. Protein induction was prolonged for 3 hours at 37° C. His-MTD-EGFP recombinant proteins expressed in E. coli, with IPTG were loaded on a SDS-PAGE gel, stained with Coomassie Brilliant Blue, and then destained. As illustrated in FIGS. 6a and 6b, except for some His-MTD-EGFP recombinant proteins expressed in BL21-GoldpLysS (DE3) strains, most His-MTD-EGFP recombinant proteins were expressed at a high level in BL21-CodonPlus (DE3). Several His-MTD-EGFP recombinant proteins were not expressed.

The inducible expression of His-MTD-EGFP recombinant proteins in an E. coli system leads to the formation of insoluble aggregates, which are known as inclusion bodies. To completely solubilize these inclusion bodies, all of the above expressed proteins were denatured by dissolving them in 8 M urea. Denatured His-MTD-EGFP recombinant proteins were purified by histidine tag affinity chromatography, using a nickel nitrilotriacetate resin (Qiagen™, Hilden, Germany). Since strong denaturants, such as 8 M urea, completely solubilize the inclusion bodies, the purification method was carried out under pH-dependent denaturing conditions.

Figure 7A:
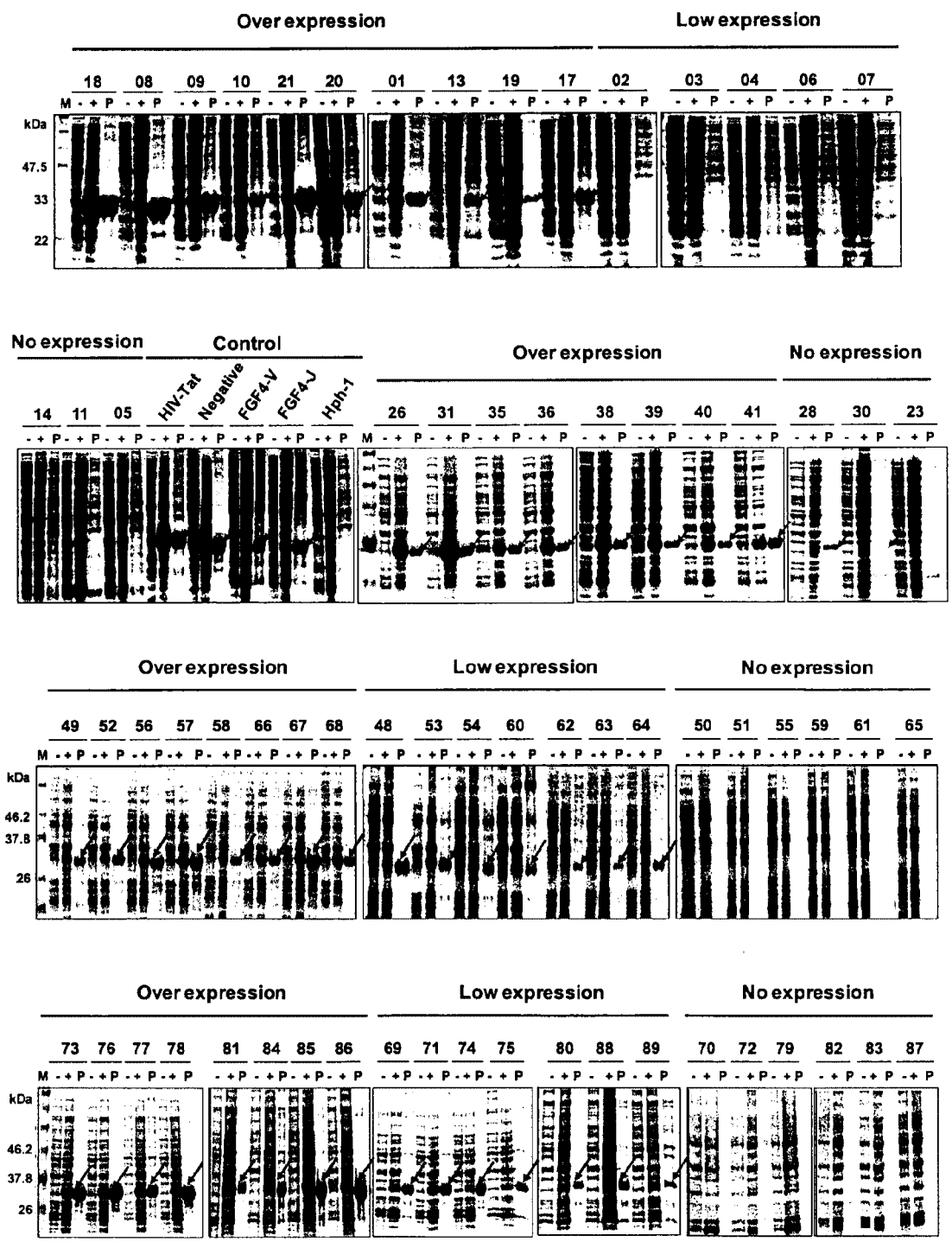
FIGS. 7a and 7b are photographs of a SDS-PAGE analysis showing the purity of His-MTD-EGFP recombinant proteins under denaturing conditions according to the present invention.
Figure 7B:
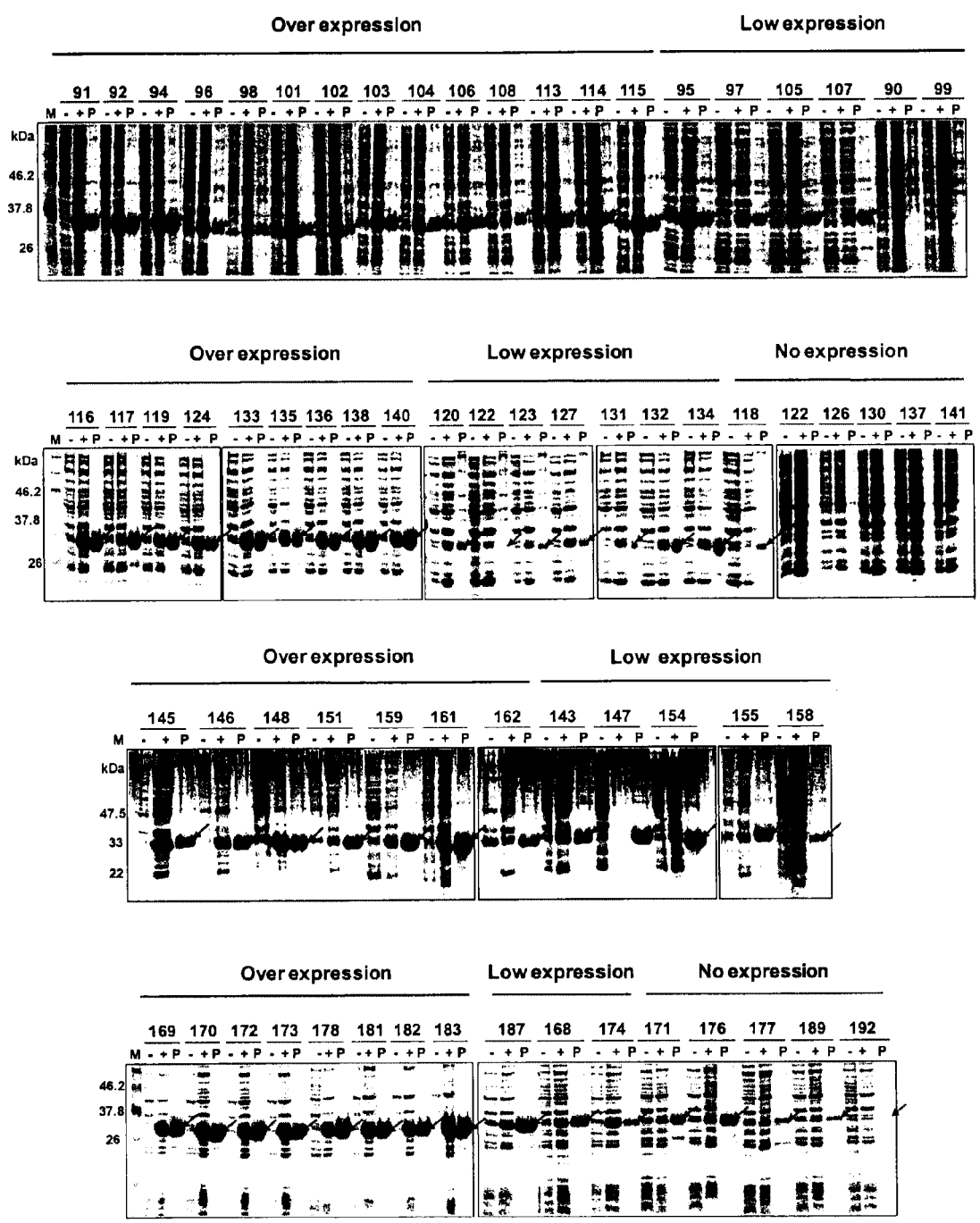

The E. coli culture solutions were harvested by centrifugation at 4,000×g for 20 minutes, re-suspended in a lysis buffer (100 mM $NaH_2PO_4$, 10 mM Tris.Cl, 8 M urea, pH 8.0), and subjected to ultrasonication on ice using a sonicator equipped with a probe. The cell lysates were centrifuged at 7,000×g for 20 minutes, so as to separate the supernatant and the cellular debris pellet. The supernatant was taken out and then incubated with a Ni-NTA resin equilibrated with the lysis buffer by gently shaking (using a rotary shaker) for 2 hours to overnight. After washing with a washing buffer (100 mM $NaH_2PO_4$, 10 mM Tris.Cl, 8 M urea, pH 6.3) five times, the proteins bound to the resin were eluted with an elution buffer (100 mM $NaH_2PO_4$, 10 mM Tris.Cl, 8 M urea, pH 4.5). The His-MTD-EGFP proteins purified under the denaturing conditions described above were analyzed on a SDS-PAGE gel and stained with Coomassie Brilliant Blue, where the results thereof are shown in FIGS. 7a and 7b.

Figure 8:
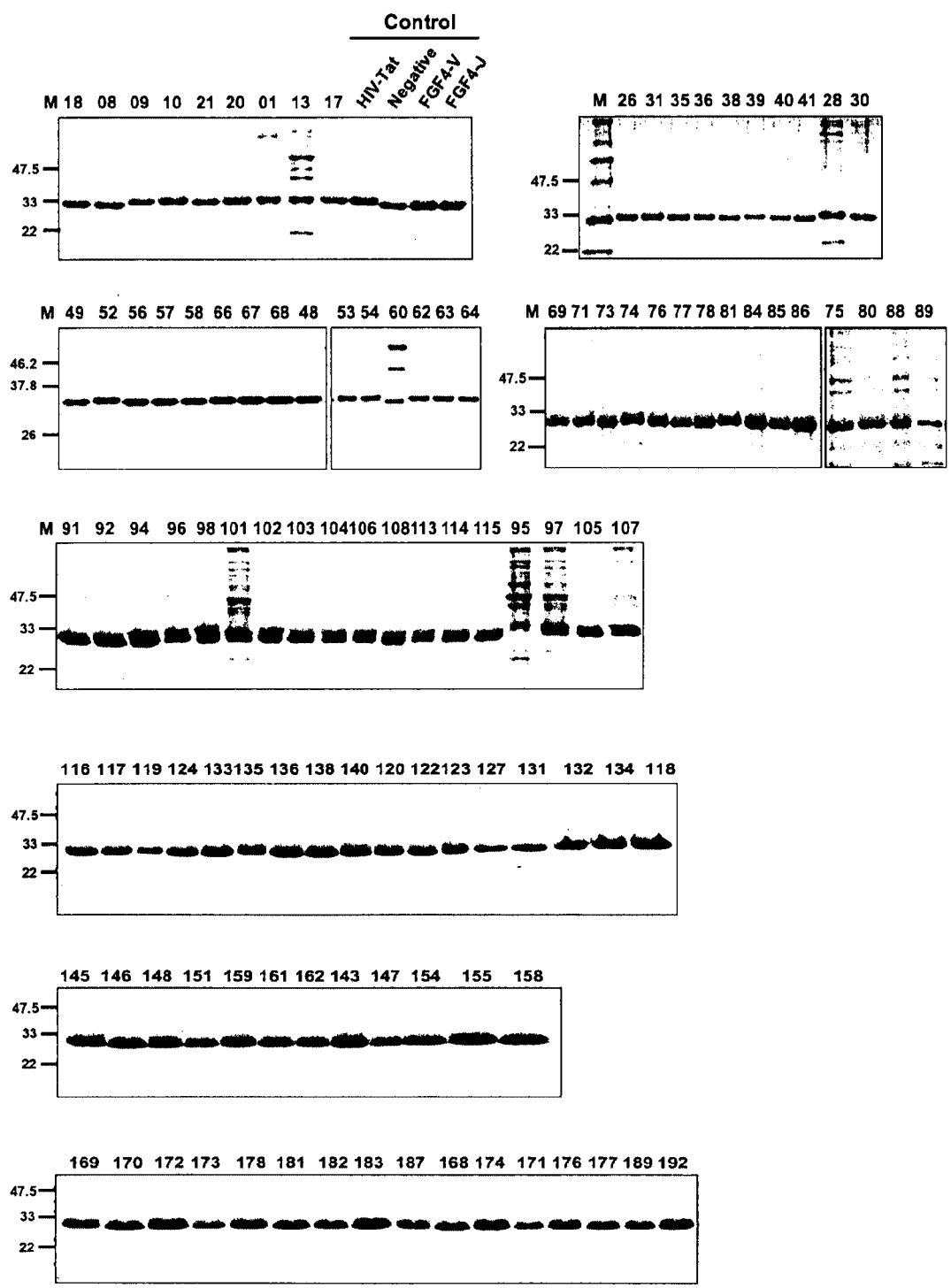
FIG. 8 is a photograph of a SDS-PAGE analysis showing the purification of His-MTD-EGFP recombinant proteins under renaturing conditions according to the present invention.
Figure 9A:
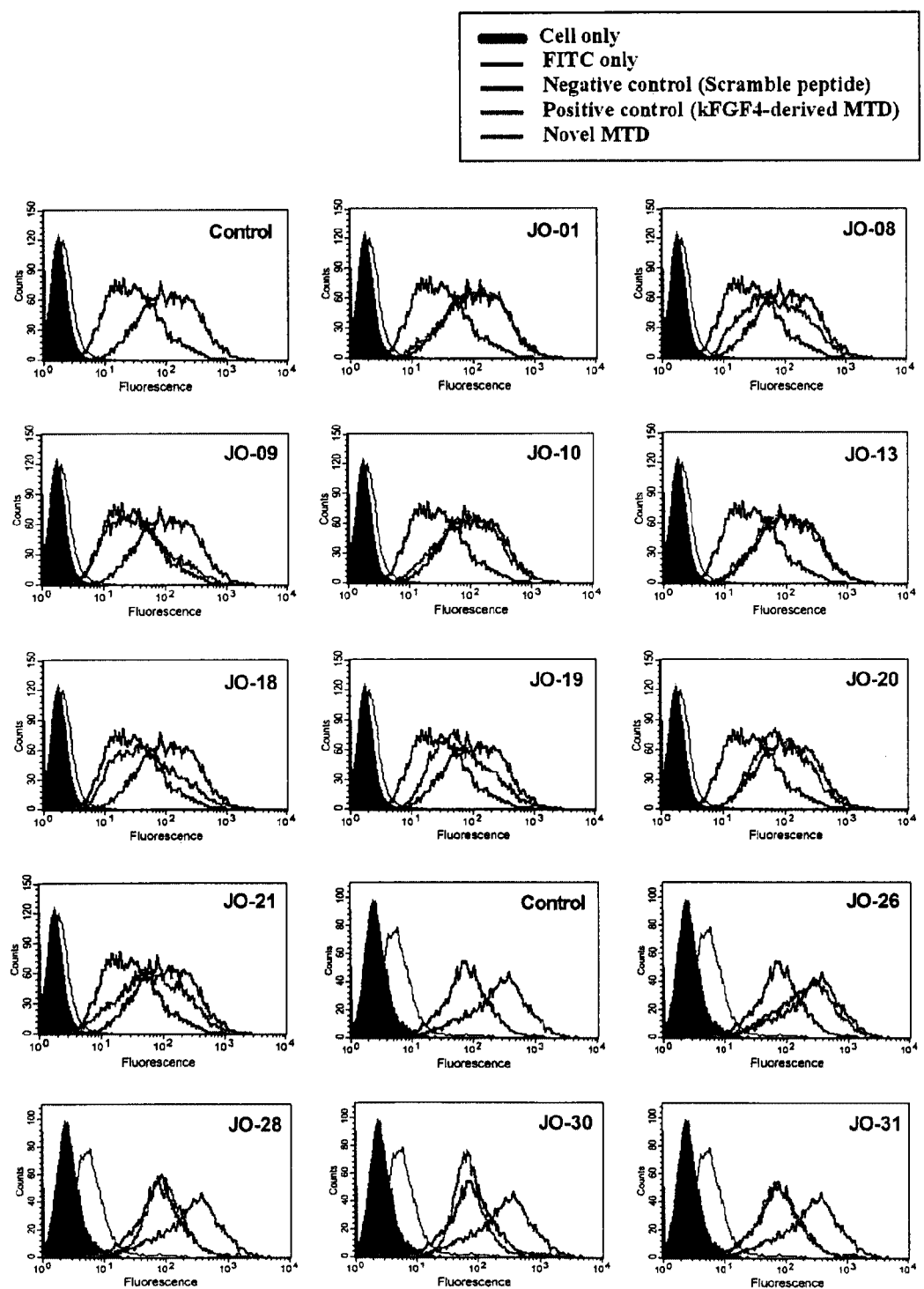
FIGS. 9a to 9g are graphs illustrating the cell permeabilities of His-MTD-EGFP recombinant proteins analyzed by flow cytometry according to the present invention.
Figure 9B:
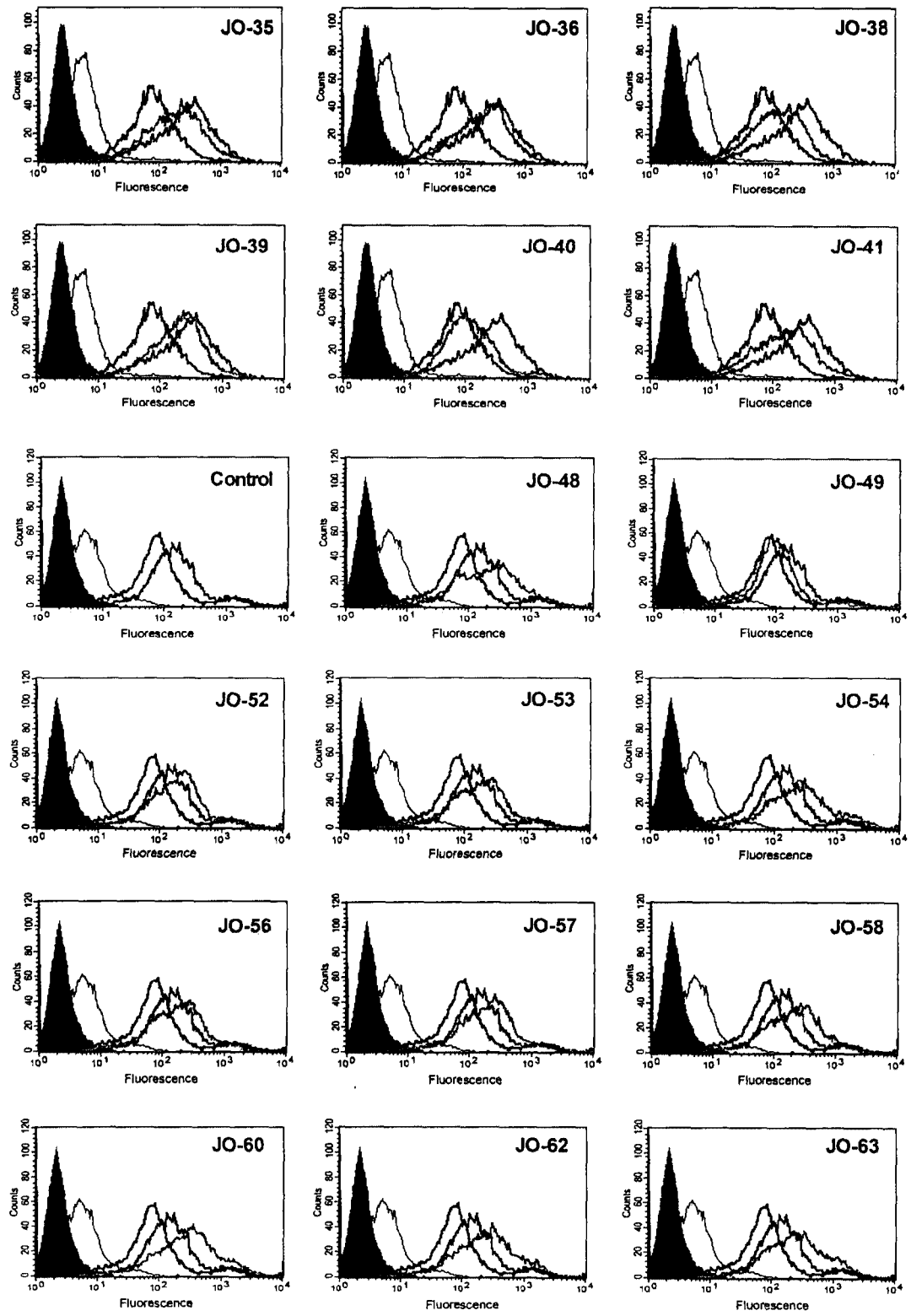
Figure 9C:
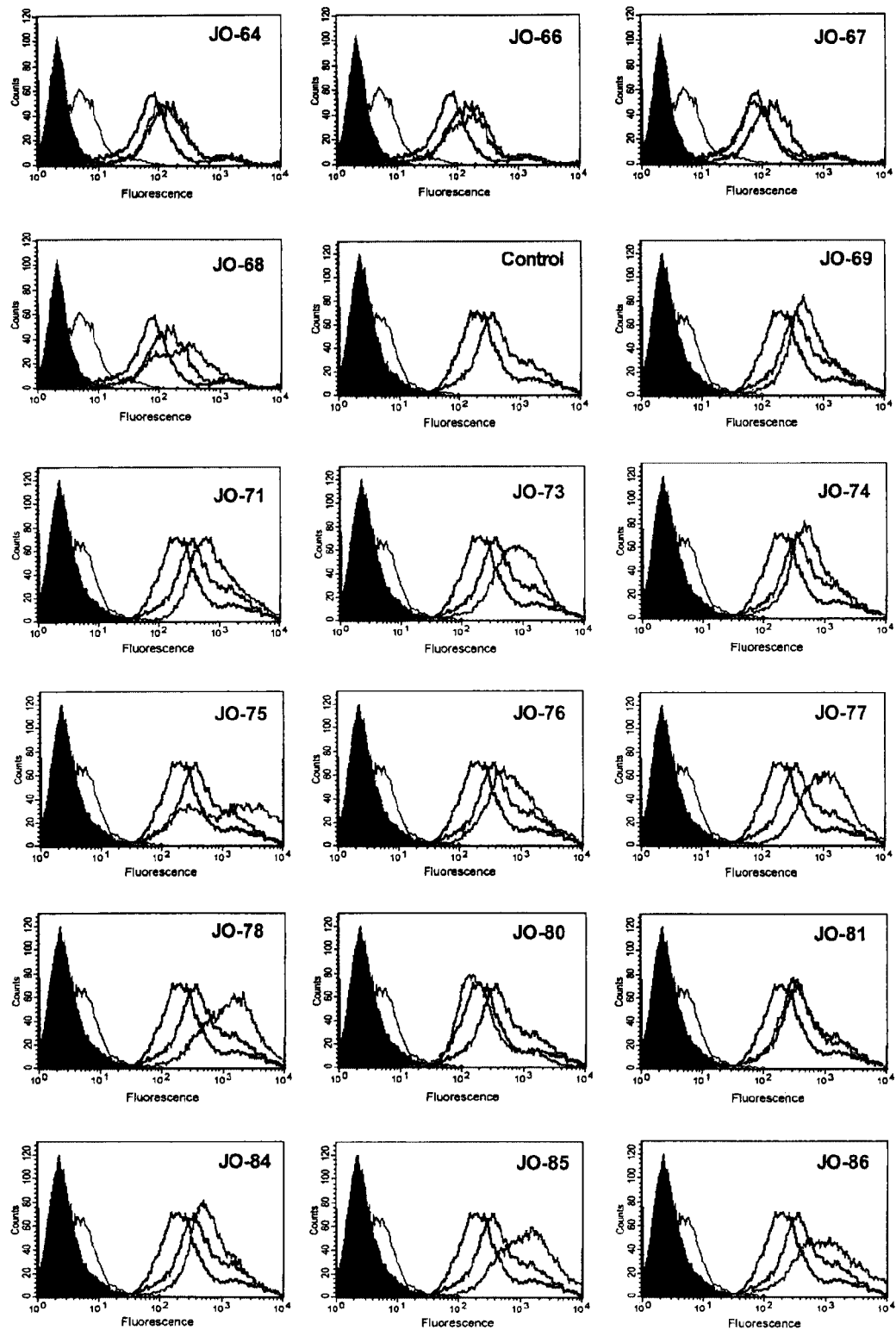
Figure 9D:
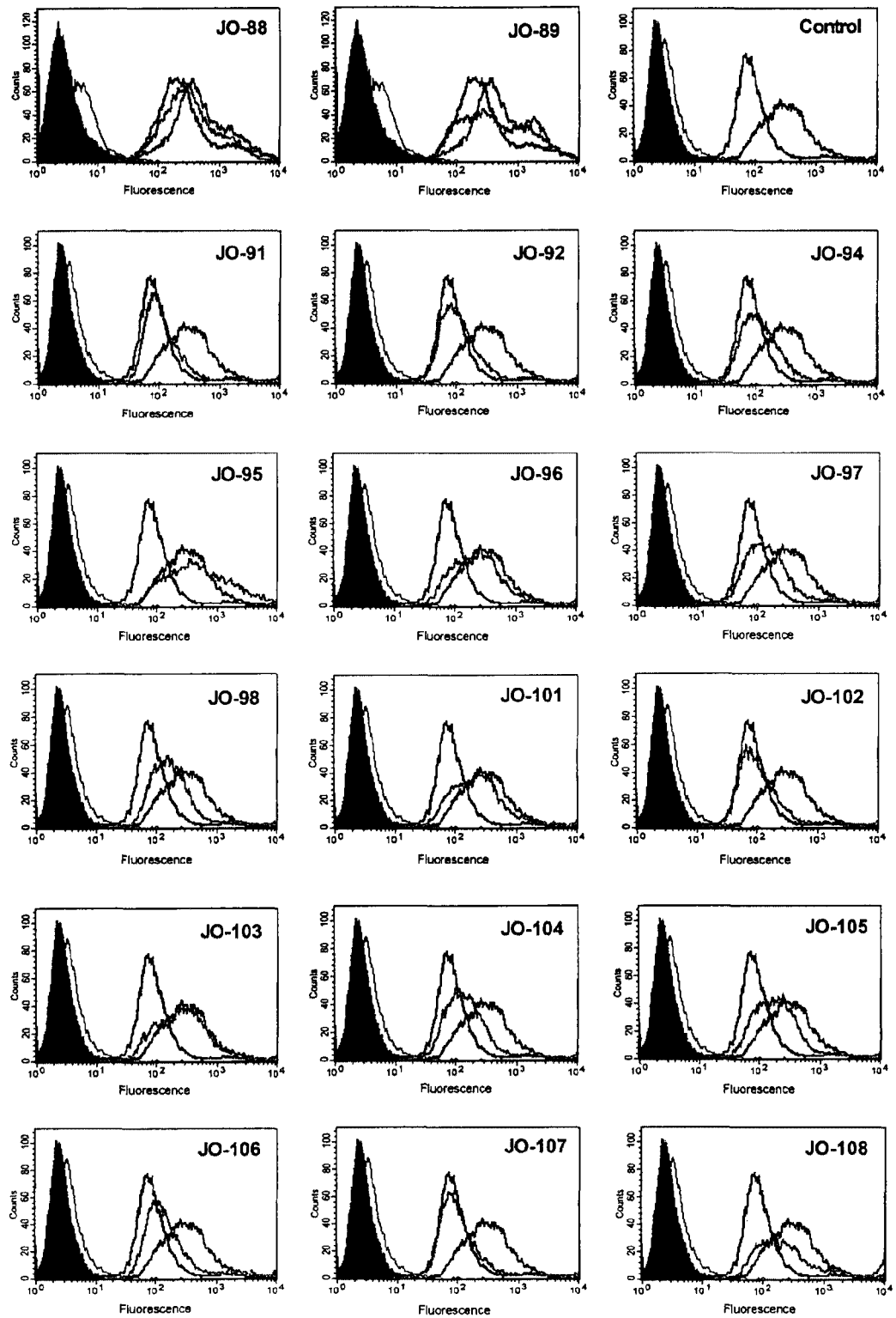
Figure 9E:
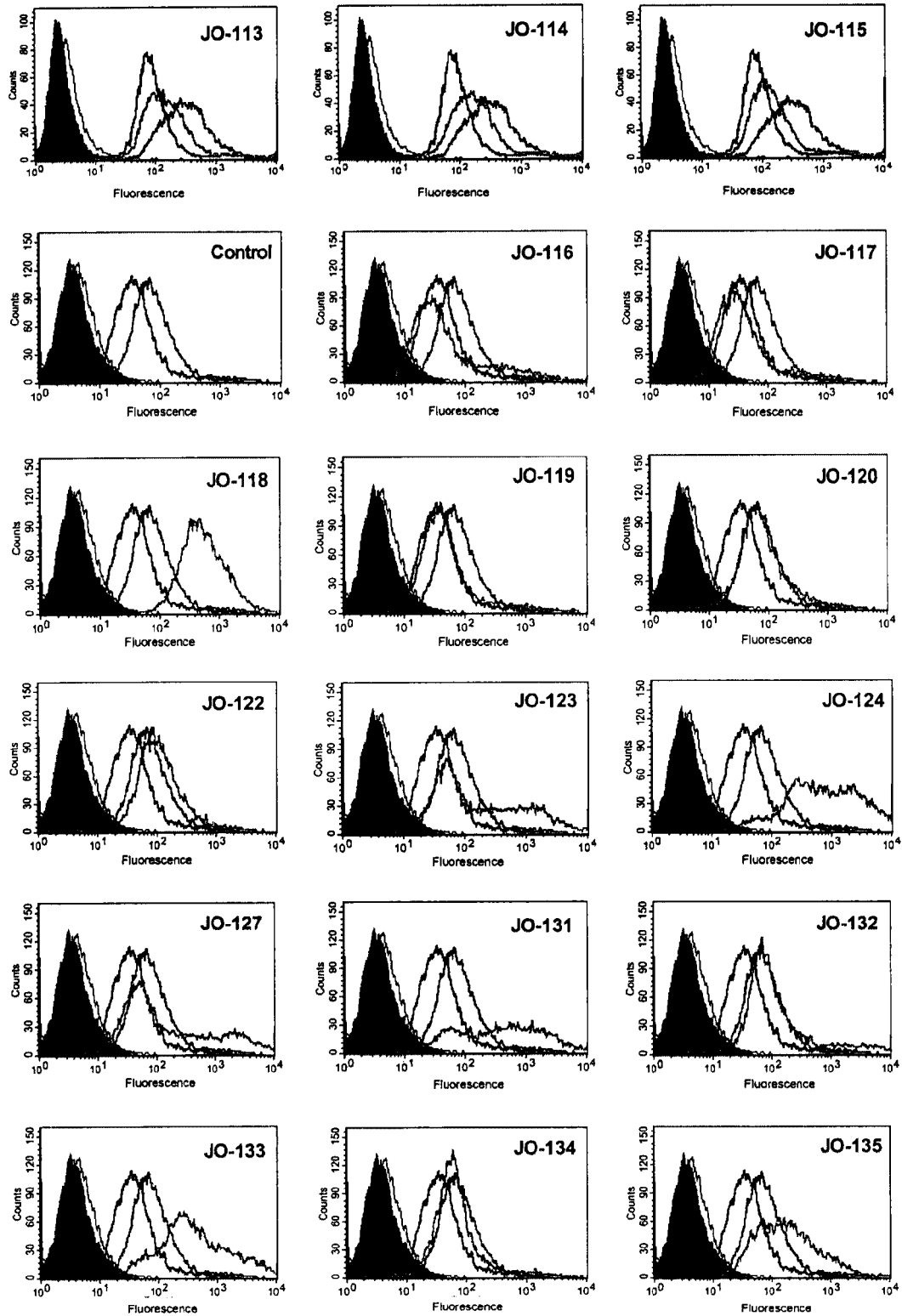
Figure 9F:
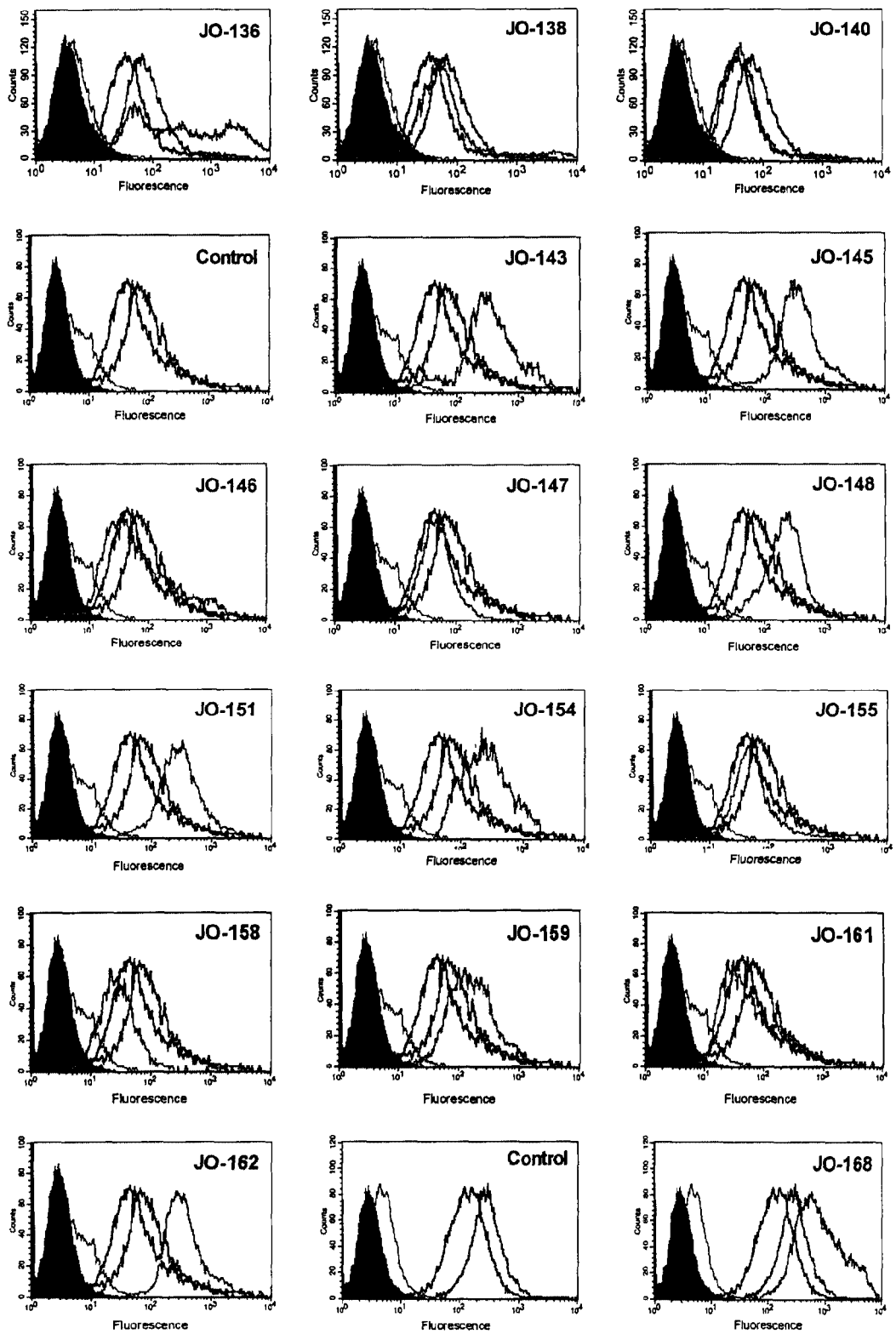
Figure 9G:
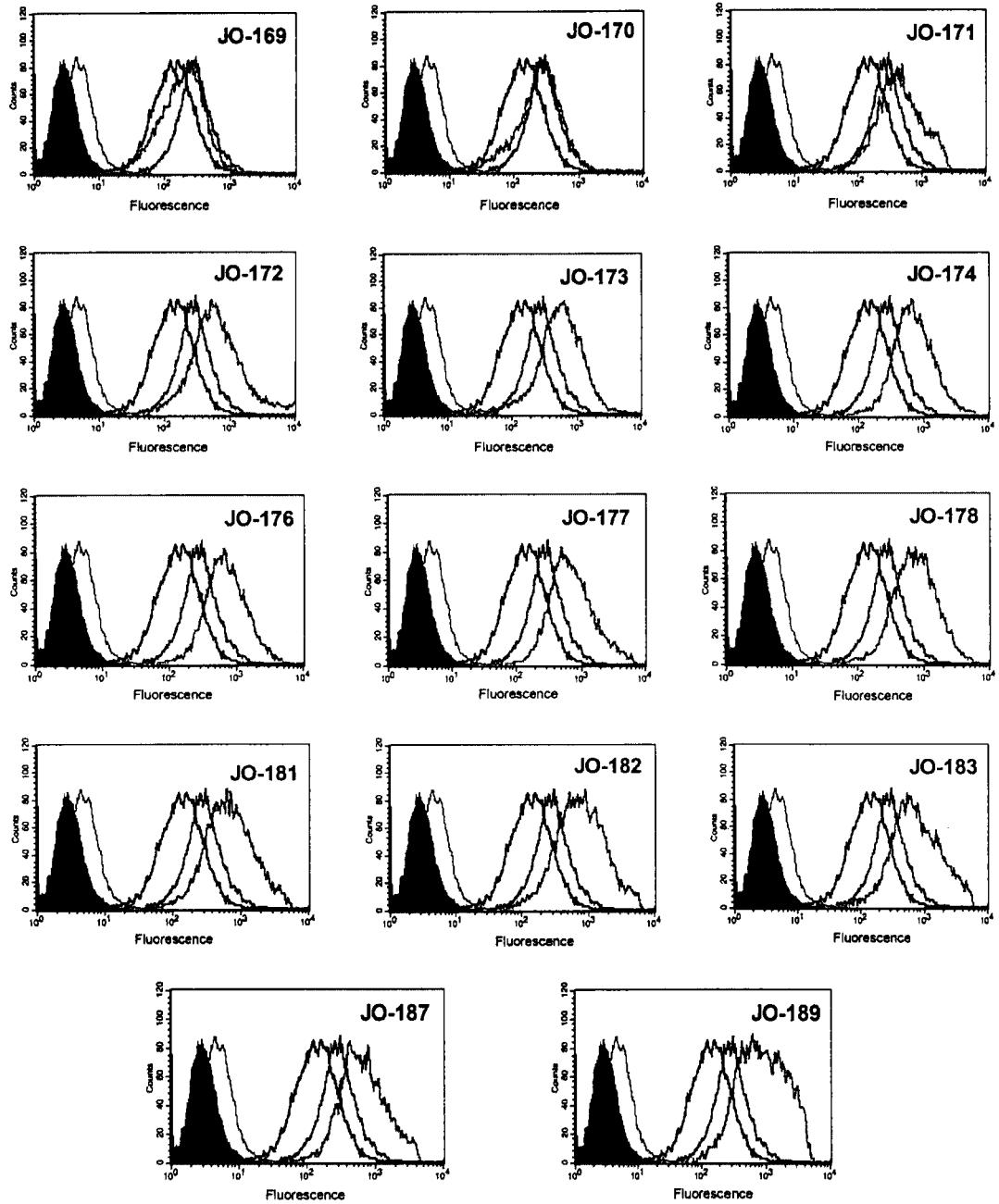
Figure 10A:
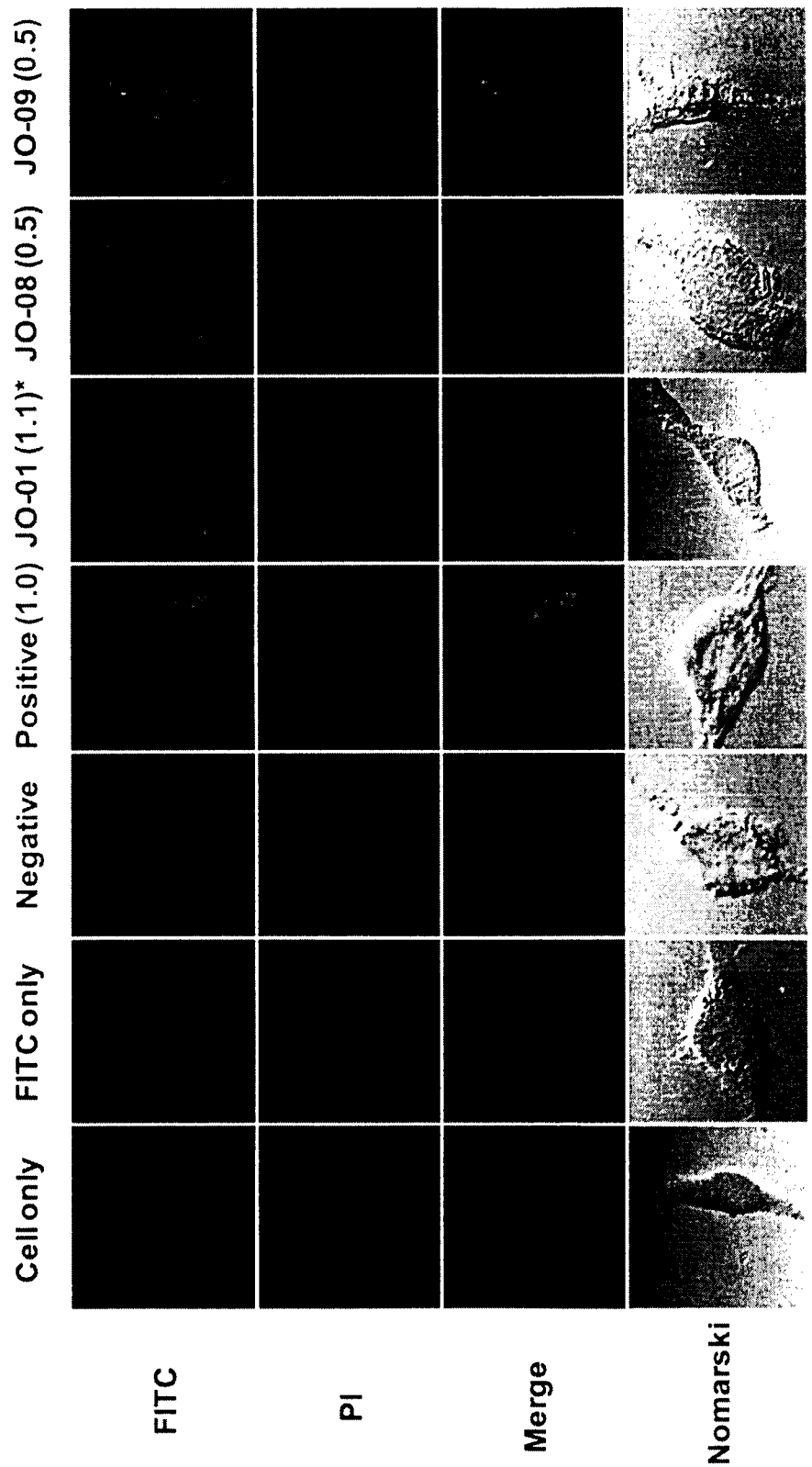
Figure 10B:
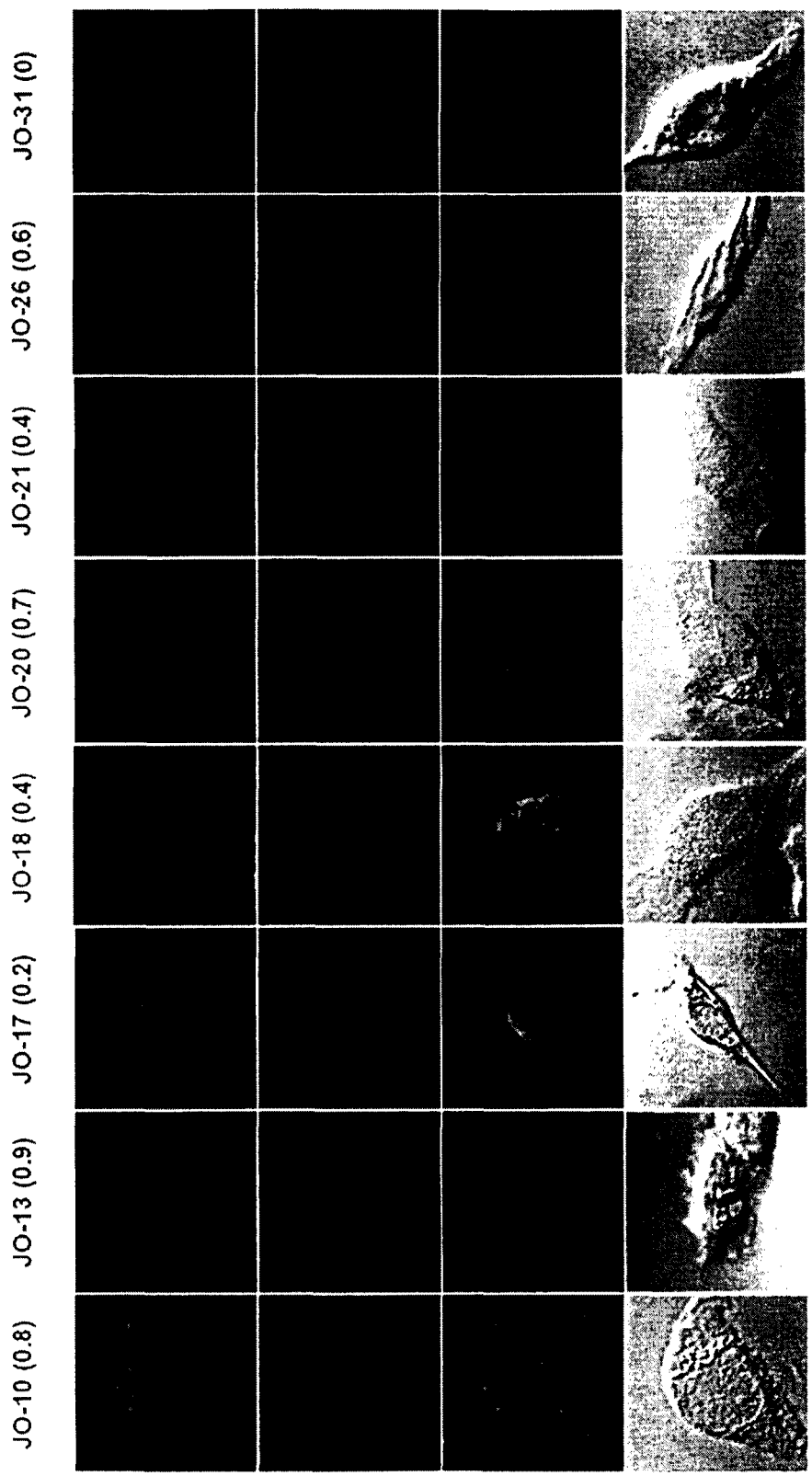
Figure 10C:
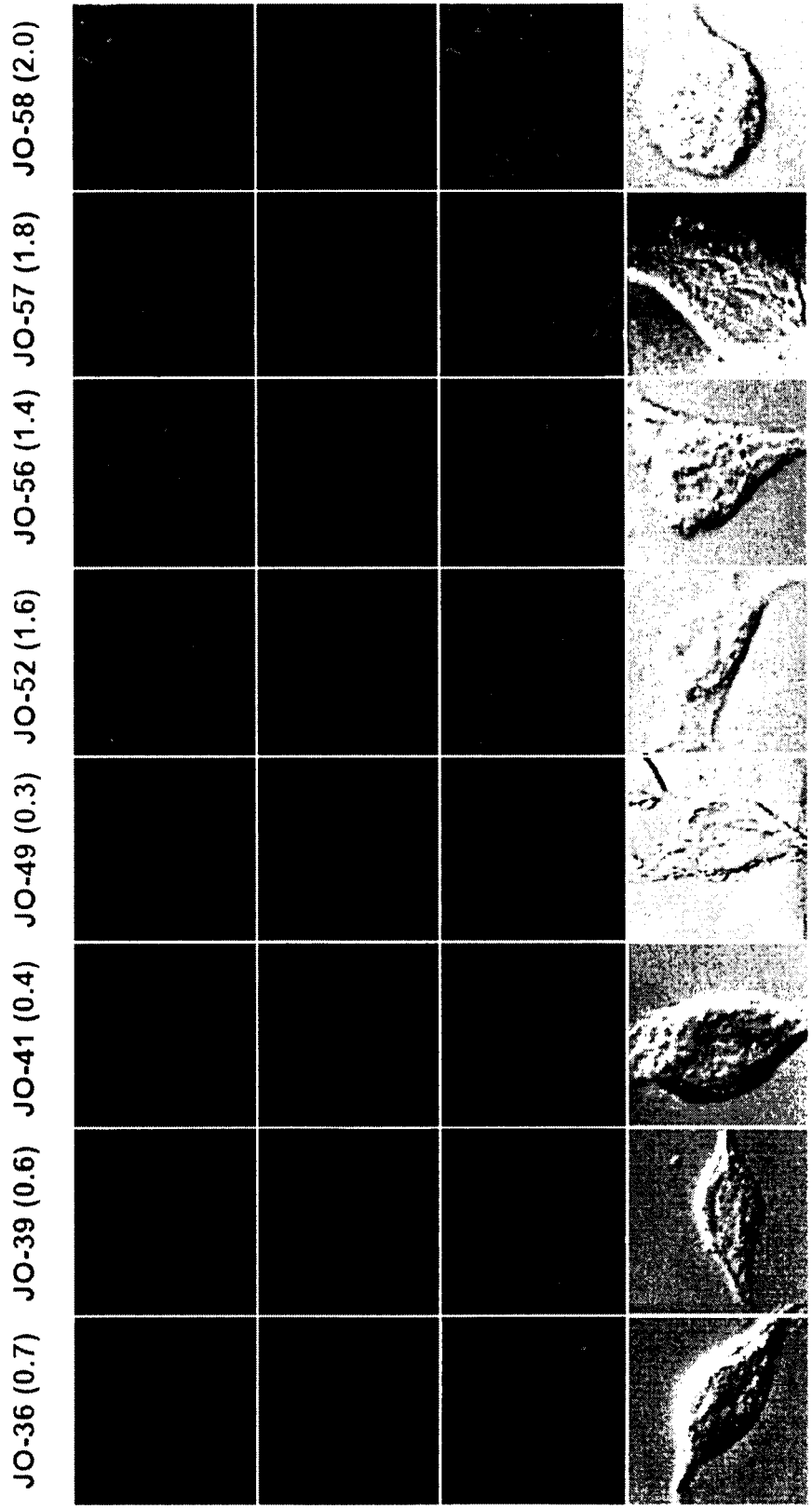
Figure 10D:
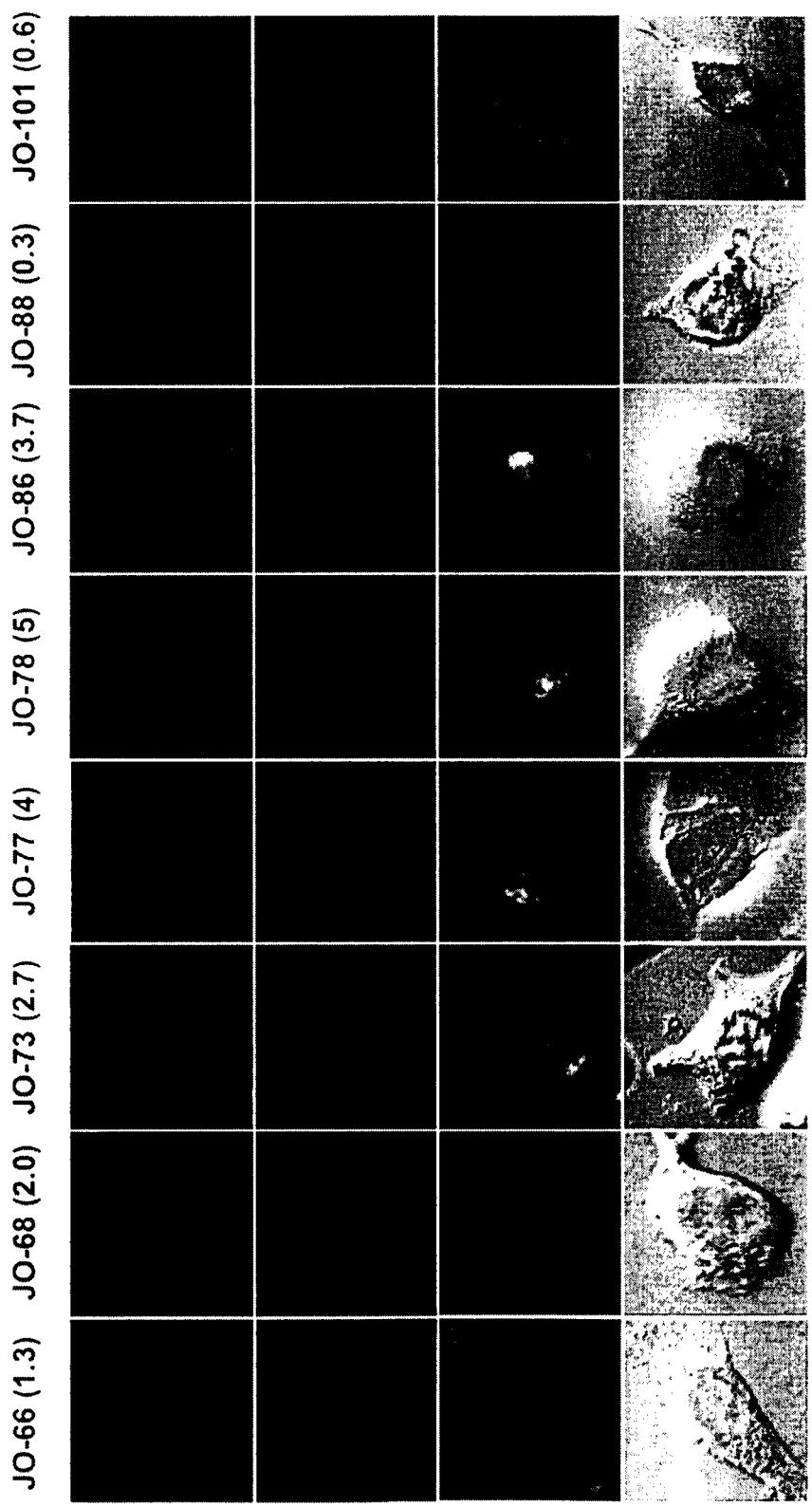
Figure 10E:
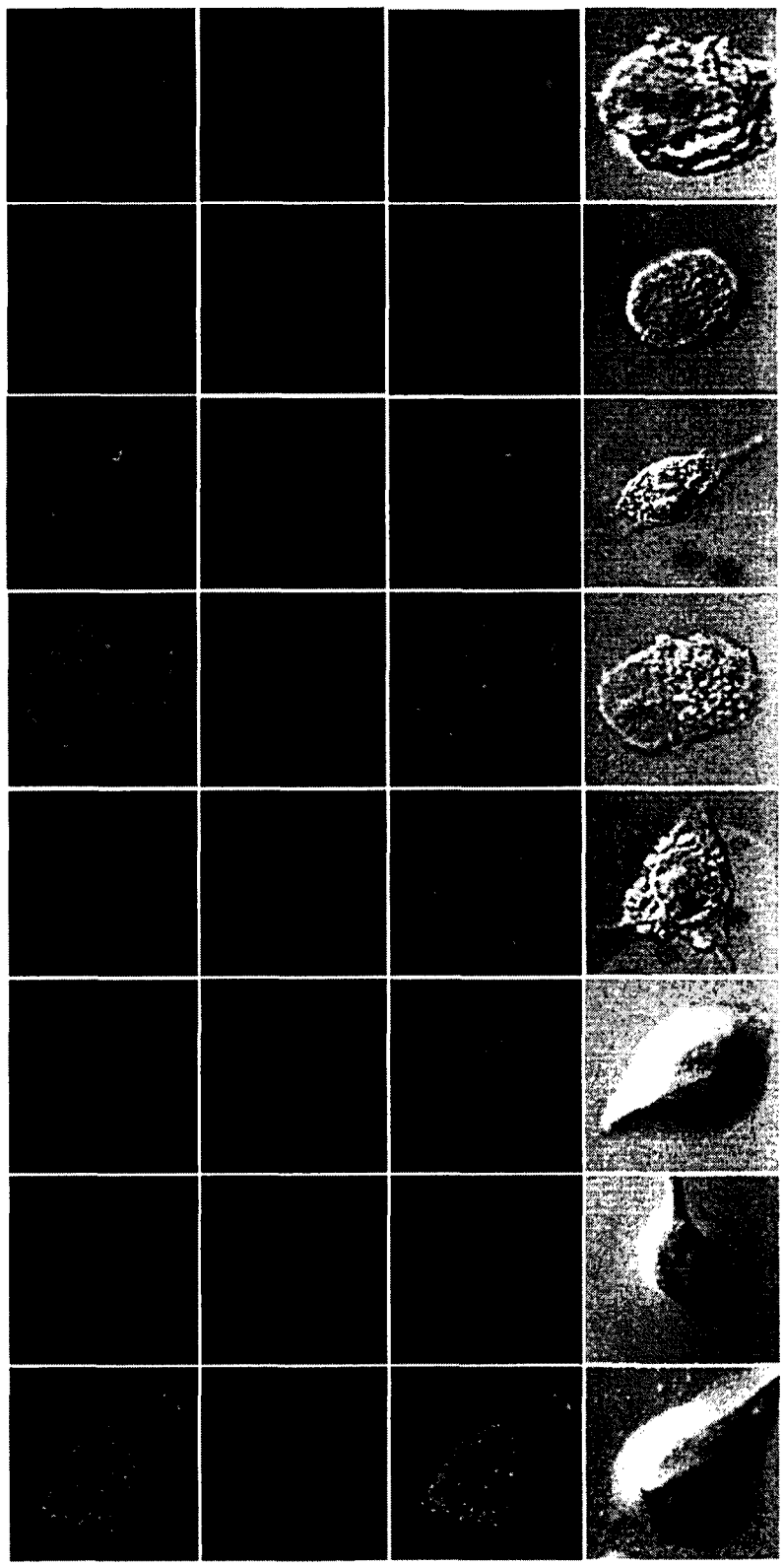
Figure 10F:
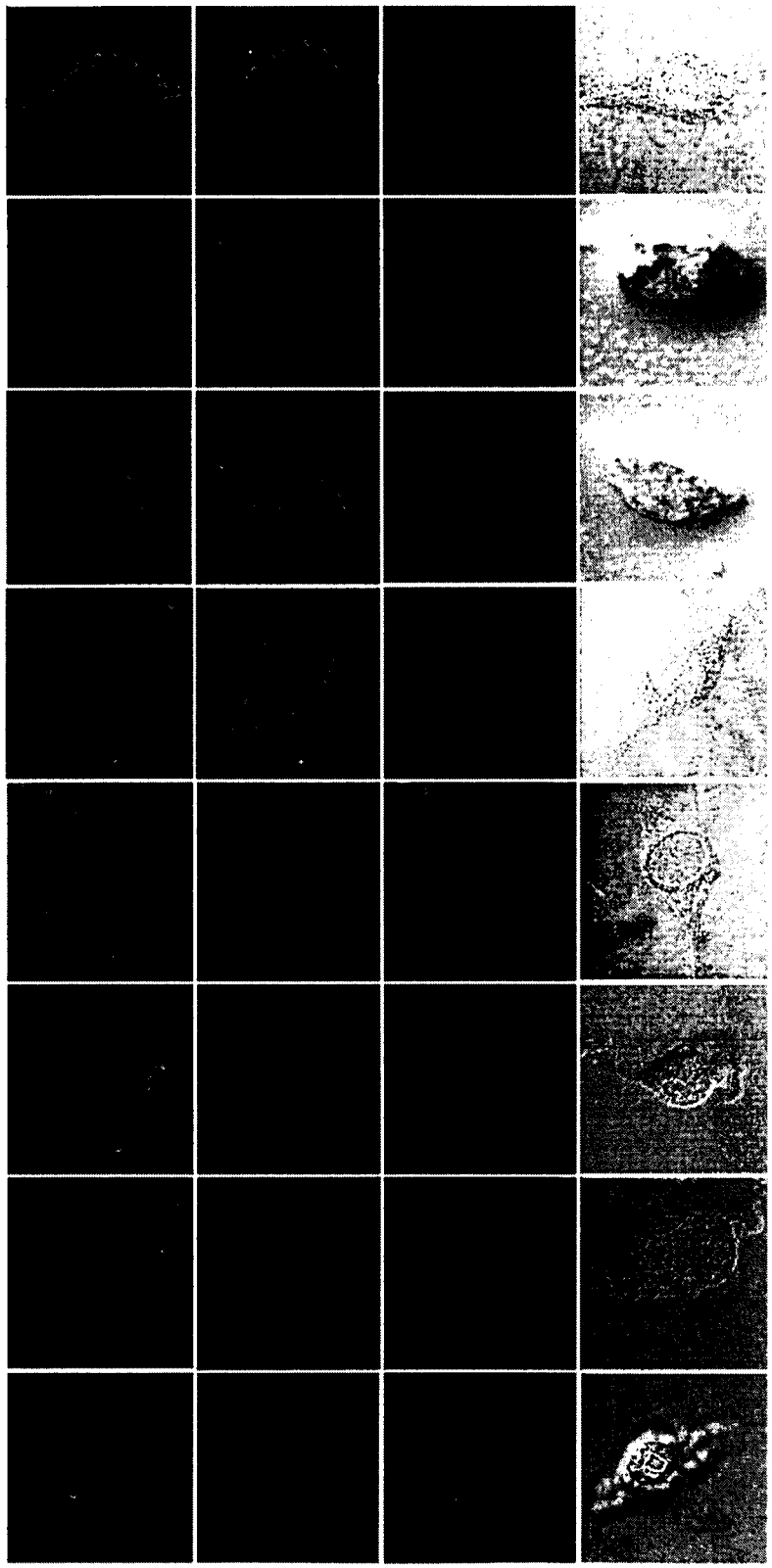
Figure 10G:
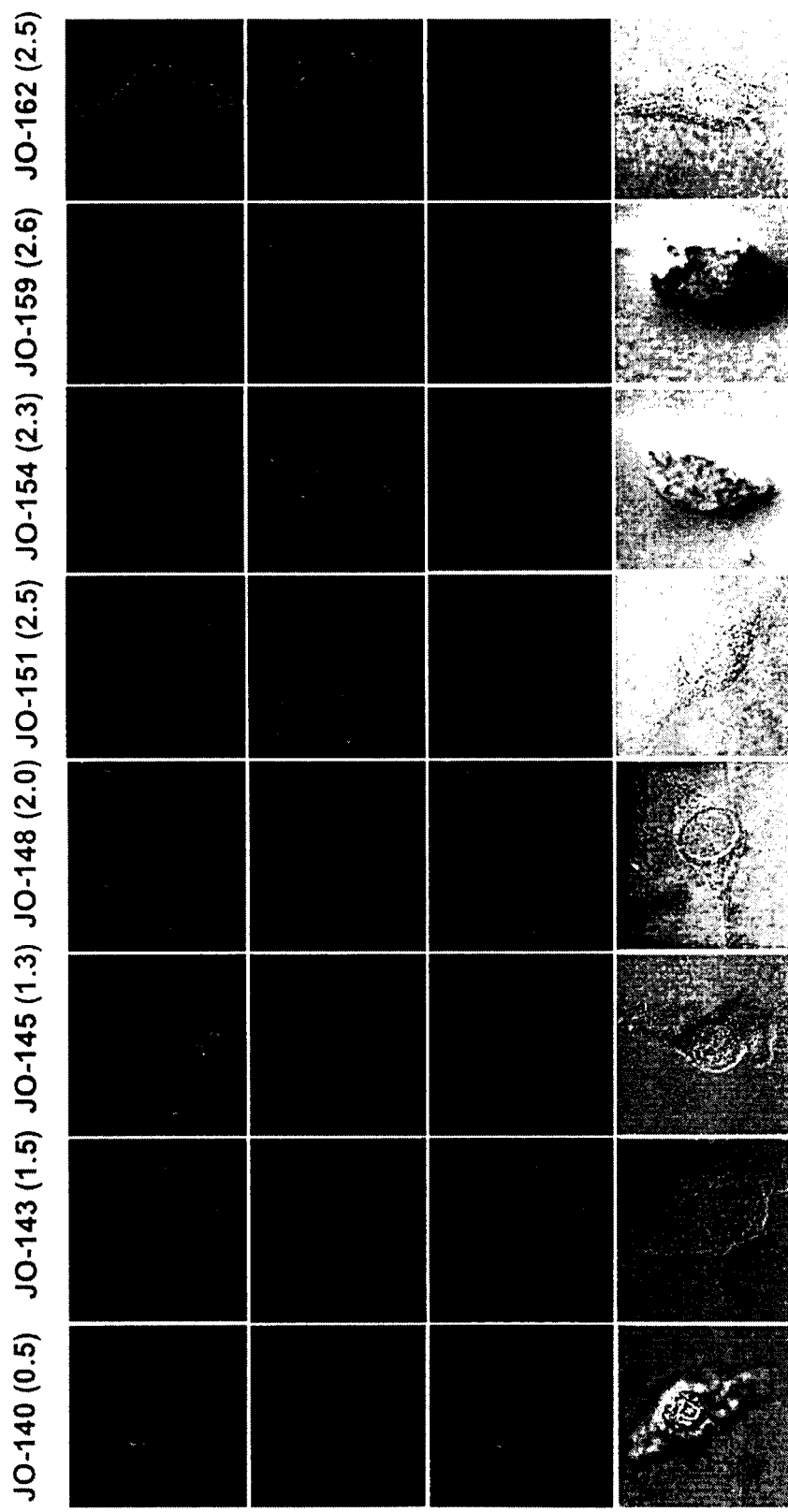
Figure 10H:
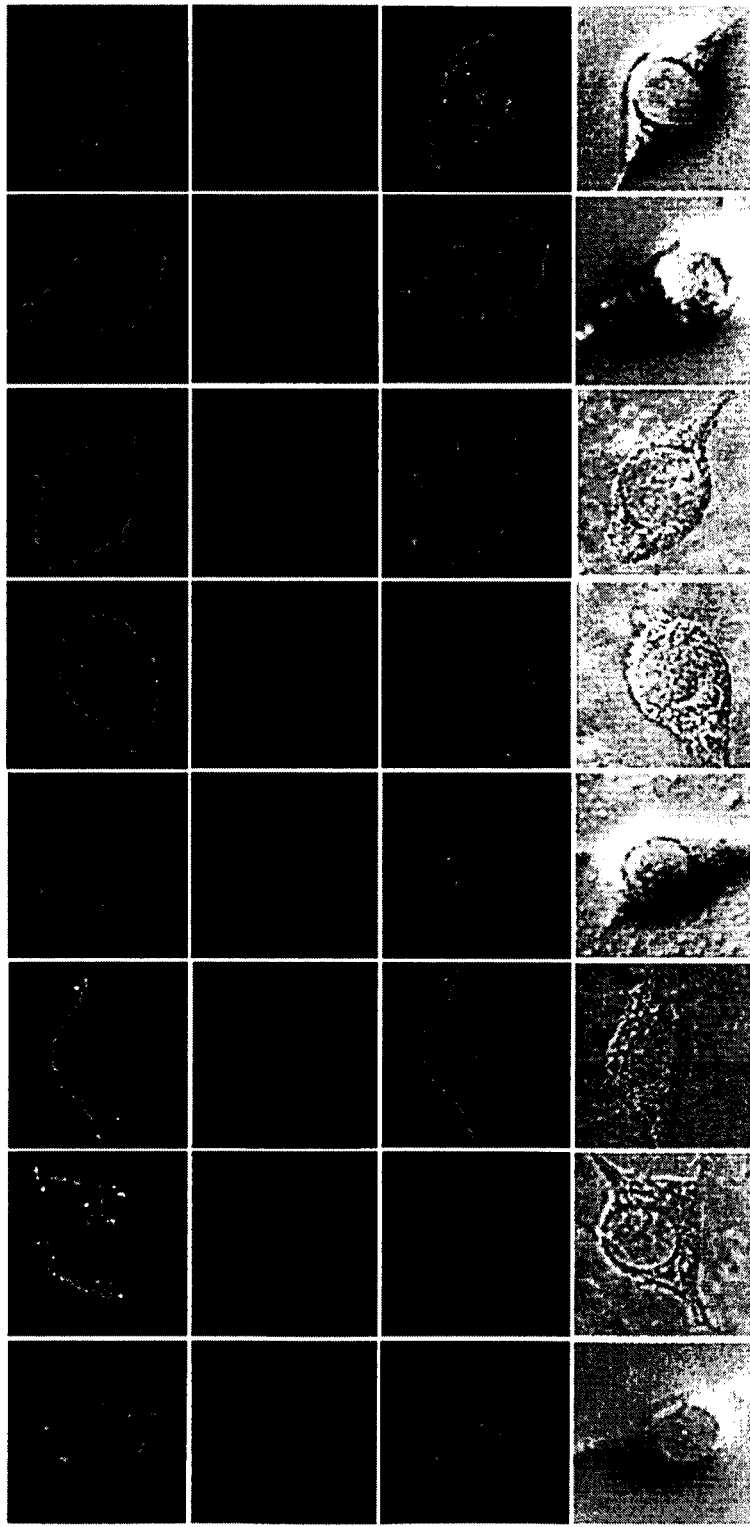
Figure 11A:
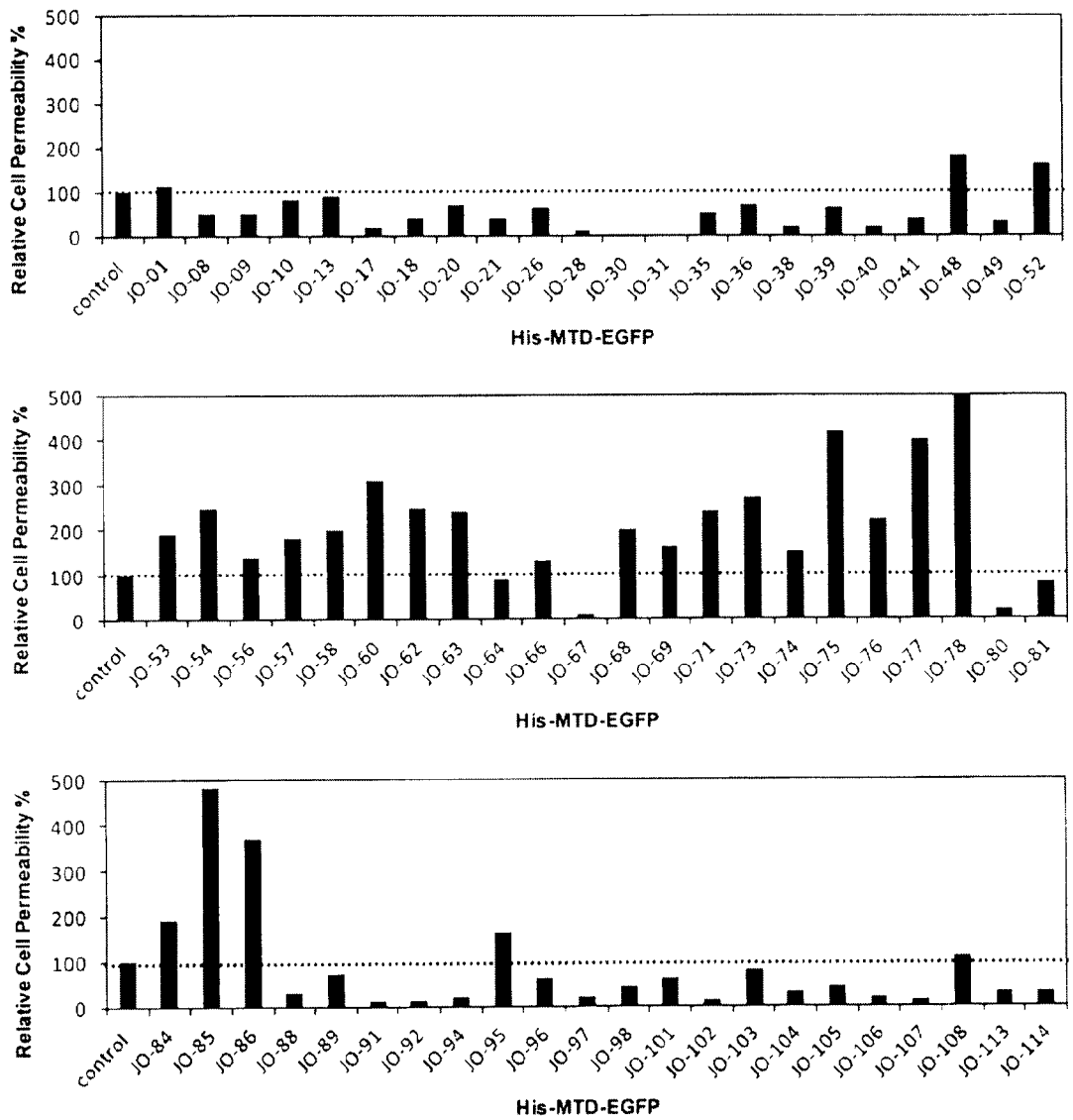
FIGS. 11a and 11b are graphs comparing the cell permeabilities of His-MTD-EGFP recombinant proteins according to the present invention with a positive control.
Figure 11B:
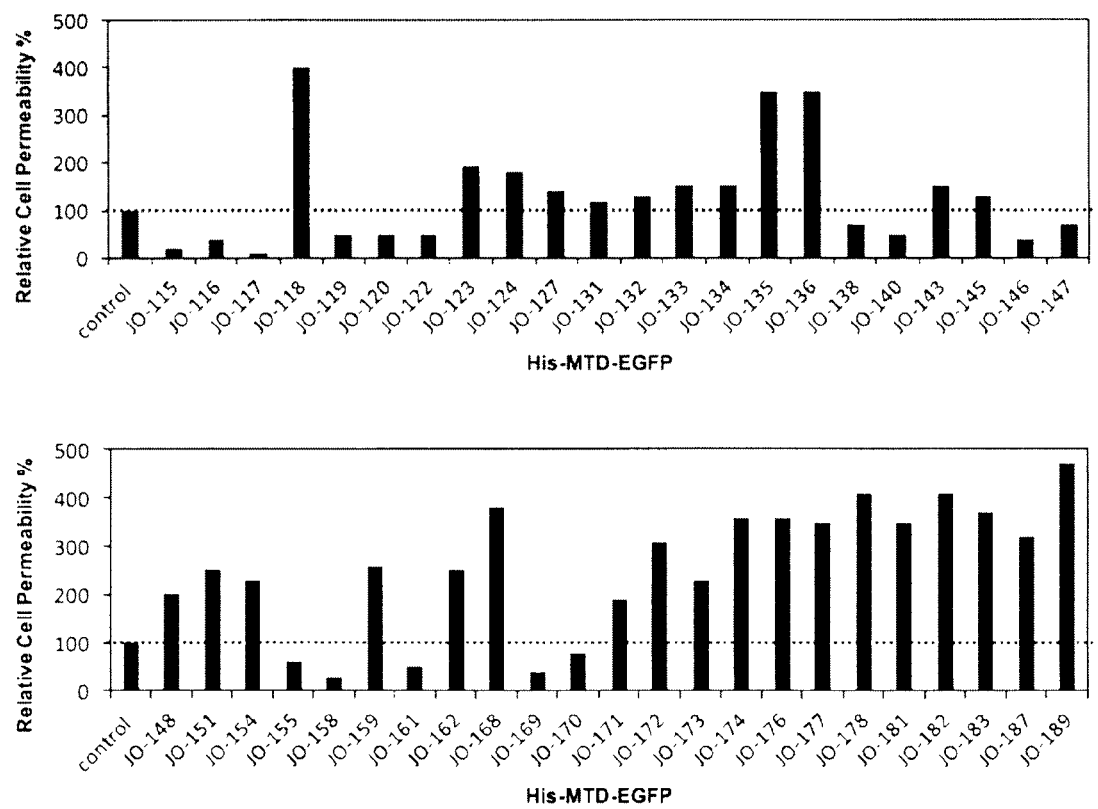
Figure 12H:
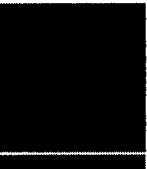

In order to renature the His-MTD-EGFP recombinant proteins purified above, the denatured proteins were refolded by removing the denaturant. Urea was removed from the proteins by dialyzing them against a refolding buffer (0.55 M Guanidine HCl, 0.44 M L-Arginine, 50 mM Tris-HCl, 150 mM NaCl, 1 mM EDTA, 100 mM NDSB, 2 mM Glutathione Oxidized, and 0.2 mM Glutathione Reduced). All of the refolded recombinant proteins were dialyzed for 9 hours against a physiological buffer, such as a cell culture medium (e.g., Dulbecco's modified Eagle's Medium: DMEM). After the replacement of the refolding buffer with DMEM, the cell permeabilities of all of the purified recombinant proteins were ready to be determined in vitro and in vivo. According to the SDS-PAGE analysis results shown in FIG. 8, out of the 148 transformants established as described in Example 2 above, the inducible expression of His-MTD-EGFP recombinant proteins was visually detected in 112 transformants, whereas 4 His-MTD-EGFP recombinant proteins were not expressed enough to be visually detected but were sufficiently purified for cell permeability analysis. The 116 His-MTD-EGFP recombinant proteins were prepared in a soluble form.

Example 4

Determination of Quantitative Cell Permeability of Recombinant Proteins Fused to MTDs In order to quantitatively determine the cell permeability of the His-MTD-EGFP recombinant proteins, the 116 recombinant proteins purified in a soluble form as described in Example 3 above were mixed with 0.7 µg/µl of fluorescein isothiocyanate (FITC) and reacted at room temperature for 1 hours by stirring. The reaction solution was subjected to a dialysis against Dulbecco's modified Eagle's medium (DMEM; WelGENE Inc., Korea) for 2 days until the FITC was completely removed to thereby obtain FITC-conjugated recombinant proteins. RAW 264.7 cells derived from mouse macrophage were treated with 10 µM of the FITC-labeled protein. The RAW 264.7 cells were maintained in DMEM supplemented with 10% fetal bovine serum and 1% penicillin (500 mg/ml, WelGENE Inc.), and incubated at 37° C. in a humidified atmosphere of 5% $CO_2$ in air. After the incubation, the cells were incubated with 10 µM of each of the FITC-conjugated recombinant protein prepared above for 1 hour at 37° C., followed by treating them with Trypsin/EDTA (T/E, Invitrogen™, Carlsbad Calif., USA) to remove cell surface bound proteins and washing with cold PBS three times.

The FITC-conjugated His-MTD-EGFP recombinant proteins were subjected to fluorescence-activated cell sorting (FACS) analysis (FACS Calibur, Beckton-Dickinson, San Diego Calif., USA). For each sample, the cells ($1\times10^4$) were analyzed by using the CellQuest™ Pro cytometric analysis software. Each experiment was conducted at least twice. The cell permeable potency of each His-MTD-EGFP recombinant protein fused to novel MTDs (JO-1 to JO-193) was visually compared to that of a positive control protein fused to kFGF4-derived MTD.

FIGS. 9a to 9g show the results of a flow cytometry analysis where the gray filled curve represents cell only, the black curve represents FITC only, the blue curve represents the cell permeability of a negative control (scramble peptide), the red curve represents the cell permeability of a positive control (kFGF4-derived MTD), and the green curve represents the cell permeability of each recombinant protein.

In order to evaluate the cell permeability of each MTD in mammalian cells, the cellular uptake efficiencies of the His-MTD-EGFP recombinant proteins were compared with those of the positive control protein fused to kFGF4-derived MTD and the negative control protein fused to a scramble peptide, by evaluating the change in median fluorescence after incubation with each FITC-conjugated His-MTD-EGFP recombinant protein.

Referring to the results shown in FIGS. 9a to 9g, none of the cells treated with 10 µM of the FITC-conjugated His-MTD-EGFP proteins for 1 hour at 37° C. underwent a change in median fluorescence such that the median fluorescence after treatment was significantly lower than that of the cells treated with the negative control. In contrast, 80 His-MTD-EGFP recombinant proteins, out of the 111 proteins that were tested, exhibited 0.5-fold (50%) or higher fluorescence signal than that of the positive control. These results suggest that some of the newly developed novel MTDs fused with the cargo molecule EGFP exhibit significantly high levels of plasma membrane-penetrating ability which is enough to deliver macromolecules, such as protein, into live cells.

Example 5

Determination of Cell Permeability and Intracellular Localization of Recombinant Proteins Fused to MTDs Out of the 111 FITC-conjugated His-MTD-EGFP recombinant proteins tested by flow cytometry, 60 His-MTD-EGFP recombinant proteins were selected for visualization of cell permeability and intracellular localization thereof. Among them, 50 His-MTD-EGFP recombinant proteins exhibited higher cell permeability than 0.5-fold as compared with the positive control protein fused to kFGF4-derived MTD.

NIH 3T3 cells were treated without (cell only) or with FITC (FITC only), or FITC-conjugated recombinant proteins such as a negative control (His-scramble peptide-EGFP), a positive control (His-kFGF4-derived MTD-EGFP) or the recombinant proteins fused to novel MTDs (His-MTDs-EGFP), and visualized by confocal laser scanning microscopy. NIH 3T3 cells were cultured for 24 hours in an 8-well chamber slide (LabTek, Nalgen Nunc, Rochester N.Y., USA). Cells were maintained in DMEM supplemented with 10% fetal bovine serum, 1% penicillin and streptomycin in 5% $CO_2$ at 37° C. The cells were washed with PBS three times, and then treated for 1 hour with DMEM, DMEM plus free FITC, or DMEM containing 10 µM FITC-conjugated recombinant proteins in 5% $CO_2$ at 37° C. One hour after the treatment, the cells were fixed in 4% paraformaldehyde (PFA) for 20 minutes at room temperature for observation.

For the direct detection of FITC-conjugated recombinant proteins that were internalized, the cells were washed with PBS three times and counterstained with a nuclear fluorescent stain solution, propidium iodide (PI, Sigma-Aldrich™, St Louis Mo., USA), at a concentration of 1 µg/ml. After PI staining for 5 minutes, the cells were washed with PBS three times and fixed by polyvinyl alcohol mountain medium with DABCO (Fluca™, St Louis Mo., USA). The intracellular distribution of the fluorescence was determined at the middle of a single cell analyzed by confocal laser scanning microscopy, where the results are shown in FIGS. 10a to 10i. Parameters specific for each fluorochrome were followed as FITC: excited at 488 nm light, detected with a 530 nm bandpass filter.

Surprisingly, as shown in FIGS. 10a to 10i, 11a, and 11b, the FITC-conjugated His-MTD-EGFP recombinant proteins were well distributed largely in either the cytoplasm or the nucleus (JO-13, -18, -49, -58, -68, -101, -108, -116, -118, -122, -123, -127, -132, -133, -136, -138, -140, -148, -162, -169, -170, and -172) or both, as compared with the negative control protein fused to a scramble peptide. Ten MTDs (JO-17, -18, -21, -31, -41, -49, -88, -107, -116, and -169), which exhibited lower cell permeability than 0.5-fold as compared with the positive control (1.0-fold), showed weak intracellular localization ability after an 1 hour treatment. These results completely coincided with those from the flow cytometry analysis.

Example 6

Determination of In Vivo Tissue Distribution of Recombinant Proteins Fused to MTDs Forty-three recombinant proteins were selected from 111 FITC-conjugated recombinant proteins tested by flow cytometry for the analysis of in vivo tissue distribution ability. FITC only (DMEM plus free FITC), a negative control (FITC-conjugated recombinant protein fused to a scramble peptide), a positive control (FITC-conjugated recombinant protein fused to a kFGF4-derived MTD), or the His-MTD-EGFP recombinant proteins (FITC-conjugated recombinant proteins fused to selected novel MTDs) were intraperitoneally injected into Balb/c mice (6 weeks, female, Central Lab. Animal Inc., Korea) at a dose of 300 μg/500 μl/mouse, respectively. After 2 hours, six organs (i.e., liver, kidney, spleen, lung, heart, and brain) of each mouse were extracted, washed with PBS, and quickly frozen with an O.C.T. compound (Sakura™, Japan) on dry ice. Cryosections (20 μm thickness) of each organ were prepared by a microtome cryostat (Sakura), placed on glass slides and, then, mounted in a Vectashield™ mounting medium (Vecta lab, Burlingame Calif., USA). In vivo tissue distribution of selected novel MTDs was analyzed by using a fluorescence microscope (Nikon™, Japan), where the results are shown in FIGS. 12a to 12i.

In the negative control, there was no significant level of fluorescence. In contrast, the positive control protein fused to kFGF4-derived MTD showed well distributed fluorescence activity in all of the organs. With respect to the mice injected with the recombinant proteins fused to selected novel MTDs, most MTDs having 0.5-fold or higher cell permeability than the positive control as determined by flow cytometry showed relatively strong in vivo tissue distribution ability in all of the organs, although there were some minor differences among the organs. In particular, JO-13 (1.3-fold) and JO-133 (1.5-fold) MTDs were distributed well in all of the organs except the brain. These results indicate that the novel MTDs demonstrated their strong cell permeability and/or intracellular localization ability by flow cytometry and confocal laser scanning microscopy and can effectively mediate macromolecule intracellular transduction in vitro and in vivo.

In summary, the macromolecule transduction domain (MTD) peptides identified according to the method of the present invention have the characteristics of inducible protein expression, purification and cell permeability as represented in FIGS. 13a to 13k.

The present invention has been described in detail with reference to specific embodiments thereof. However, it will be appreciated by those skilled in the art that changes may be made in these embodiments without departing from the principles and spirit of the invention, the scope of which is defined in the appended claims and their equivalents.

The invention claimed is:

1. An isolated macromolecule transduction domain (MTD) peptide capable of mediating the transport of a biologically active molecule into a cell, wherein the MTD peptide comprises the amino acid sequence SEQ ID NO:159.

2. An isolated polynucleotide encoding the macromolecule transduction domain (MTD) peptide according to claim 1, wherein the isolated polynucleotide comprises the nucleotide sequence SEQ ID NO:352.

3. A method of identifying a macromolecule transduction domain (MTD) peptide capable of mediating the transport of a biologically active molecule into a cell, comprising:
  identifying secreted proteins having a signal sequence-like domain from multiple amino acid sequence databases;
  selecting from said identified secreted proteins hydrophobic peptides having a single hydrophobic region at their N-terminus and forming a helix structure;
  eliminating non-hydrophobic amino acids at the left or right side of the selected hydrophobic peptide to minimize the peptide length while maintaining the hydrophobic region thereof;
  replacing non-hydrophobic amino acids at the middle or right side of the selected hydrophobic peptide with a hydrophobic amino acid, proline, to provide flexibility;
  minimizing the number of repeated hydrophobic amino acids to reduce the length of the selected hydrophobic peptide;
  contacting a cell with the biologically active molecule and the selected hydrophobic peptide; and
  determining transport of the biologically active molecule in the presence of the selected hydrophobic peptide by determining the presence of the biologically active molecule in the cell compared to a control in which the biologically active molecule is contacted with a cell in the absence of the selected hydrophobic peptide.

4. The method according to claim 3, wherein the signal sequence-like domain is selected from the group consisting of penetratin (Arg-Gln-Ile-Lys-Ile-Trp-Phe-Gln-Asn-Arg-Arg-Met-Lys-Trp-Lys-Lys (SEQ ID NO: 592)), the Tat peptide derived from the transactivating protein Tat of HIV-1 (Arg-Lys-Lys-Arg-Arg-Gln-Arg-Arg-Pro (SEQ ID NO: 593)), transportan (Gly-Trp-Thr-Leu-Asn-Ser-Ala-Gly-Tyr-Leu-Leu-Gly-Lys-Ile-Asn-Lys-Ala-Leu-Ala-Ala-Leu-Ala-Lys-Lys-Ile-Leu (SEQ ID NO: 594)), Buforin II (Thr-Arg-Ser-Ser-Arg-Ala-Gly-Leu-Gln-Phe-Arg-Val-Gly-Arg-Val-His-Arg-Leu-Leu-Arg-Lys (SEQ ID NO: 595)), MAP (model amphipathic peptide: Lys-Leu-Ala-Leu-Lys-Ala-Ser-Leu- Lys-Ala-Leu-Lys-Ala-Ala-Leu-Lys-Leu-Ala (SEQ ID NO: 596)), k-FGF (Ala-Ala-Val-Ala-Leu-Leu-Pro-Ala-Val-Leu-Leu-Ala-Leu-Leu-Ala-Pro (SEQ ID NO: 597)), Ku 70 (Val-Pro-Met-Leu-Lys-Pro-Met-Leu-Lys-Glu (SEQ ID NO: 598)), prion (Met-Ala-Asn-Leu-Gly-Tyr-Trp-Leu-Leu-Ala-Leu-Phe-Val-Thr-Met-Trp-Thr-Asp-Val-Gly-Leu-Cys-Lys-Lys-Arg-Pro-Lys-Pro (SEQ ID NO: 599)), pVEC (Leu-Leu-Ile-Ile-Leu-Arg-Arg-Arg-Ile-Arg-Lys-Gln-Ala-His-Ala-His-Ser-Lys (SEQ ID NO: 600)), pep-1 (Lys-Glu-Thr-Trp-Trp-Glu-Thr-Trp-Trp-Thr-Glu-Trp-Ser-Gln-Pro-Lys-Lys-Lys-Arg-Lys-Val (SEQ ID NO: 601)), SynB1 (Arg-Gly-Gly-Arg-Leu-Ser-Tyr-Ser-Arg-Arg-Arg-Phe-Ser-Thr-Ser-Thr-Gly-Arg (SEQ ID NO: 602)), pep-7 (Ser-Asp-Leu-Trp-Glu-Met-Met-Met-Val-Ser-Leu-Ala-Cys-Gln-Tyr (SEQ ID NO: 603)), and HN-1 (Thr-Ser-Pro-Leu-Leu-Ile-His-Asn-Gly-Gln-Lys-Leu (SEQ ID NO: 604)).

5. The method according to claim 3, wherein the MTD peptide produced as a result of said optimizing and minimizing exhibits cell permeability, hydrophobicity, and flexibility, is about 7 to about 17 amino acids in length, and forms a helix structure.

6. The method according to claim 5, wherein the MTD peptide comprises the amino acid sequence SEQ ID NO:159.

7. An isolated recombinant protein having cell permeability comprising:
a macromolecule transduction domain (MTD) peptide comprises the amino acid sequence SEQ ID NO:159; and
a biologically active molecule.

8. The isolated recombinant protein according to claim 7, wherein the biologically active molecule is selected from the group consisting of a protein, a polypeptide and a peptide.

9. The isolated recombinant protein according to claim 7, wherein the biologically active molecule is selected from the group consisting of a growth factor, an enzyme, a transcription factor, a toxin, an antigenic peptide, an antibody, and an antibody fragment.

10. The isolated recombinant protein according to claim 7, wherein the biologically active molecule is selected from the group consisting of an enzyme, a hormone, a transport protein, an immunoglobulin, an antibody, a structural protein, a motor function protein, a receptor, a signaling protein, a storage protein, a membrane protein, a transmembrane protein, an internal protein, an external protein, a secreted protein, a viral protein, a native protein, a glycoprotein, a cleaved protein, a protein with a disulfide bond, a protein complex, a chemically modified protein and a prion.

11. The isolated recombinant protein according to claim 7, wherein the biologically active molecule is selected from the group consisting of a nucleic acid, a coding nucleic acid sequence, a mRNA, an antisense RNA molecule, a carbohydrate, a lipid, and a glycolipid.

12. The isolated recombinant protein according to claim 7, wherein the biologically active molecule is a therapeutic agent.

13. The isolated recombinant protein according to claim 12, wherein the biologically active molecule is selected from the group consisting of a therapeutic drug and a toxic chemical.

14. A method of making a biologically active molecule having cell permeability comprising attaching a macromolecule transduction domain (MTD) peptide to a biologically active molecule under conditions effective to produce a biologically active molecule having cell permeability, wherein the MTD peptide comprises the amino acid sequence SEQ ID NO:159.

15. The method according to claim 14, wherein said attaching comprises attaching a MTD peptide to the N-terminal, C-terminal, both or middle of the biologically active molecule, wherein the biologically active molecule is a peptide, polypeptide or protein.

16. The method according to claim 14, wherein said attaching comprises attaching a MTD peptide to the biologically active molecule by a peptide bond.

17. The method according to claim 14, wherein said attaching comprises attaching a MTD peptide to the biologically active molecule by a covalent bond.

18. A method of transporting a biologically active molecule into a cell in a subject comprising administering to a subject a cell permeable recombinant protein comprising a macromolecule transduction domain (MTD) peptide attached to a biologically active molecule, wherein the MTD peptide comprises the amino acid sequence SEQ ID NO:159.

19. A method of delivering a drug to a subject, the method comprising administering the drug in combination with a macromolecule transduction domain (MTD) peptide, wherein the MTD peptide comprises the amino acid sequence SEQ ID NO:159.

* * * * *